US006281352B1

(12) United States Patent
Xue et al.

(10) Patent No.: US 6,281,352 B1
(45) Date of Patent: Aug. 28, 2001

(54) MACROCYCLIC COMPOUNDS AS METALLOPROTEASE INHIBITORS

(75) Inventors: Chu-Bio Xue, Hockessin; Carl P. Decicco; Robert J. Cherney, both of Newark, all of DE (US); Elizabeth Arner, West Grove; William F. DeGrado, Moylan, both of PA (US); Jingwu Duan, Newark; Xiaohua He, Hockessin, both of DE (US); Irina Cipora Jacobson, Boothwyn; Ronald L. Magolda, Wallington, both of PA (US); David Nelson, Newark, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 08/856,223

(22) Filed: May 14, 1997

Related U.S. Application Data

(63) Continuation-in-part of application No. 08/743,439, filed on Nov. 1, 1996, now abandoned.
(60) Provisional application No. 60/006,684, filed on Nov. 14, 1995.

(51) Int. Cl.⁷ ........................ A61K 31/33; C07D 225/04; C07D 225/00
(52) U.S. Cl. .................... 540/451; 540/454; 540/453; 514/183
(58) Field of Search .................. 540/451, 454, 540/453; 514/183

(56) References Cited

U.S. PATENT DOCUMENTS 5,427,954   6/1995   Sandy et al. .

FOREIGN PATENT DOCUMENTS

| 574758 | 12/1993 | (EP) . |
| 2268934 | 1/1994 | (GB) . |
| WO9005716 | 5/1990 | (WO) . |
| WO9213831 | 8/1992 | (WO) . |
| WO9221360 | 12/1992 | (WO) . |
| WO9402446 | 2/1994 | (WO) . |
| WO9424140 | 10/1994 | (WO) . |
| WO9509841 | 4/1995 | (WO) . |
| WO9718207 | 5/1997 | (WO) . |

OTHER PUBLICATIONS

Ksander et al., 1997, J. Med. Chem. 40, (4) 495–505.
Mankin et al. 1970, J. Bone Joint Surg.. 52A, 424–434.
Mankin et al. 1978, Arthritis Rheum., 21, 761–766.
Woessner et al. 1983, Arthritis Rheum., 26, 63–68.
Woessner et al. 1984, Arthritis Rheum., 27, 305–312.
Lohmander et al. 1993, Arthritis Rheum., 36, 1214–1222.
Wahl et al. 1990, Ann. Rep. Med. Chem., 25, 177–184.
Feldman et al. 1994, Lancet, 344, 1105.
MacDonald et al. 1990, Clin. Exp. Immunol., 81, 301.
Gearing et al., 1994, Nature, 370, 555.
Robert & Vellaccio 1983, The Peptides 5, 342–429.
Kogan et al. 1990, Tetrahedron, 46, 6623.
Wernic et al. 1989, J. Organ Chem, 54, 4224.
Hughes D. 1992, Org. React, 42, 335.
Bennion et al. 1991, J. Med. Chem. 34, 439.
Stetler–Stevenson, 1990, Cancer & Metastases Review 9, 289–303.
Tortotella et al. 1995, Trans Ortho Res. Soc. 20, 341.
Remington's Pharm. Sci. 1985, 17th Ed., Mack Pub. Co., p.1418.

Primary Examiner—Sabiha N. Qazi
(74) Attorney, Agent, or Firm—Karen H. Kondrad

(57) ABSTRACT

This invention relates to macrocyclic molecules which inhibit metalloproteinases, including aggrecanase, and the production of tumor necrosis factor (TNF). In particular, the compounds are inhibitors of metalloproteinases involved in tissue degradation and inhibitors of the release of tumor necrosis factor. The present invention also relates to pharmaceutical compositions comprising such compounds and to methods of using these compounds for the treatment of inflammatory diseases.

50 Claims, No Drawings

MACROCYCLIC COMPOUNDS AS METALLOPROTEASE INHIBITORS

CROSS-REFERENCE TO EARLIER FILED APPLICATION

This application is a continuation-in-part of U.S. patent application Ser. No. 08/743,439 (now abandoned) filed Nov. 1, 1996 which is a continuation-in-part of U.S. Provisional Patent Application Ser. No. 60/006,684 filed Nov. 14, 1995. The disclosure of this earlier filed application is hereby incorporated by reference.

FIELD OF THE INVENTION

The present invention relates to macrocyclic molecules which inhibit metalloproteinases, including aggrecanase, and the production of tumor necrosis factor (TNF), pharmaceutical preparations containing them and to their use as pharmaceutical agents. In particular the compounds are inhibitors of metalloproteinases involved in tissue degradation and inhibitors of the release of tumor necrosis factor.

BACKGROUND OF THE INVENTION

There is now a body of evidence that metalloproteinases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMP (tissue inhibitor of metalloproteinase), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A, 1970, 424–434). There are four classes of protein degradative enzymes in mammalian cells: serine, cysteine, aspartic and metalloproteinases. The available evidence supports that it is the metalloproteinases which are responsible for the degradation of the extracellular matrix of articullar cartillage in OA and RA. Increased activities of collagenases and stromelysin have been found in OA cartilage and the activity correlates with severity of the lesion (Mankin et al. Arthritis Rheum. 21, 1978, 761–766, Woessner et al. Arthritis Rheum. 26, 1983, 63–68 and Ibid. 27, 1984, 305–312). In addition, aggrecanase (a newly identified metalloproteinase enzymatic activity) has been identified that provides the specific cleavage product of proteoglycan, found in RA and OA patients (Lohmander L. S. et al. Arthritis Rheum. 36, 1993, 1214–22).

Therefore metalloproteinases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175–184, AP, San Diego, 1990).

This invention describes macrocyclic molecules that inhibit aggrecanase and other metalloproteinases. These novel molecules are provided as cartilage protecting therapeutics. The inhibiton of aggrecanase and other metalloproteinases by these novel molecules prevent the degradation of cartilage by these enzymes, thereby alleviating the pathological conditions of osteo- and rheumatoid arthritis.

Tumor necrosis factor (TNF) is a cell associated cytokine that is processed from a 26 kd precursor form to a 17 kd active form. TNF has been shown to be a primary mediator in humans and in animals, of inflammation, fever, and acute phase responses, similar to those observed during acute infection and shock. Excess TNF has been shown to be lethal. There is now considerable evidence that blocking the effects of TNF with specific antibodies can be beneficial in a variety of circumsatnces including autoimmune diseases such as rheumatoid arthritis (Feldman et al, Lancet, 1994, 344, 1105) and non-insulin dependent diabetes melitus. (Lohmander L. S. et al. Arthritis Rheum. 36, 1993, 1214–22) and Crohn's disease (Macdonald T. et al. Clin. Exp. Immunol. 81, 1990, 301)

Compounds which inhibit the production of TNF are therefore of therapeutic importance for the treatment of inflammatory disorders. Recently it has been shown that a matrix metalloproteinase or family of metalloproteinases, hereafter known as TNF-convertases (TNF-C), as well as other MP's are capable of cleaving TNF from its inactive to active form (Gearing et al Nature, 1994, 370, 555). This invention describes macrocyclic molecules that inhibit this conversion and hence the secretion of active TNF-a from cells. These novel molecules provide a means of mechanism based therapeutic intervention for diseases including but not restricted to septic shock, haemodynamic shock, sepsis syndrom, post ischaemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, rheumatoid arthritis, multiple sclerosis, radiation damage, hyperoxic alveolar injury, HIV and non-insulin dependent diabetes melitus.

Since excessive TNF production has been noted in several disease conditions also characterized by MMP-mediated tissue degradation, compounds which inhibit both MMPs and TNF production may also have a particular advantage in diseases where both mechansisms are involved.

There are several patents which disclose hydroxamate and carboxylate based MMP inhibitors.

PCT International Publication No. WO 92/213260 describes N-carboxyalkylpeptidyl compounds of general formula:

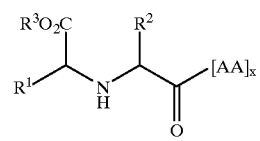

wherein AA is an amino acid, as inhibitors of matrix metallproteinase mediated diseases.

PCT International Publication No. WO 90/05716 discloses hydroxamic acid based collagenase inhibitors having the general formula:

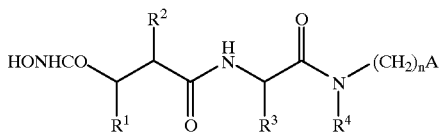

PCT International Publication No. WO 92/13831 describes related hydroxamic acids having collagenase inhibiting activity with the general formula:

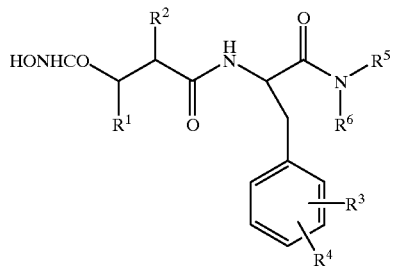

PCT International Publication No. WO 94/02446 discloses metaloproteinase inhibitors which are natural amino acid derivatives of general formula:

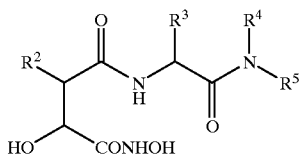

WO95/09841 d e scribes compounds that are hydroxamic acid derivatives and are inhibitors of cytokine production.

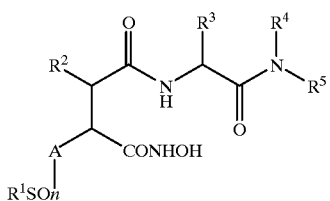

European Patent Application Publication No. 574,758 A1, discloses hydroxamic acid derivatives as collagenase inhibitors having the general formula:

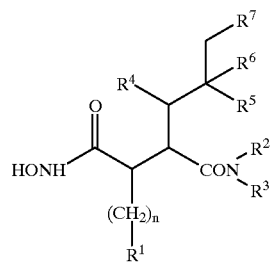

GB 2 268 934 A and WO 94/24140 claim hydroxamate inhibitors of MMPs as inhibitors of TNF production.

The compounds of the current invention act as inhibitors of MMPs, in particular aggrecanase and TNF-C, thereby preventing cartilage loss and destruction and inflammatory disorders involving TNF. The hydroxamic and carboxylic acids and derivatives are cyclic, and thus non-peptide in nature, which offers a distinct advantage over existing inhibitors because they have superior pharmacokinetic parameters. A selection of these molecules are water soluble and are orally bioavailable.

SUMMARY OF THE INVENTION

This invention provides novel hydroxamic acids and carboxylic acids and derivatives thereof of formula (I) (described below) which are useful as inhibitors of metalloproteinases, such as aggrecanase and TNF-C. The present invention also includes pharmaceutical compositions comprising such compounds of formula (I) and methods of using such compounds for the treatment of arthritis and other inflammatory disorders as described previously, in a patient.

Also included in the present invention are pharmaceutical kits comprising one or more containers containing pharmaceutical dosage units comprising a compound of formula (I), for the treatment of arthritis and other inflammatory disorders as described previously.

The present invention also includes methods of inhibiting metalloproteinases, such as aggrecanase and TNF-C, and for the treatment of arthritis by administering a compound of formula (I) in combination with one or more second therapeutic agents selected from other inhibitors of metalloproteinases, such as aggrecanase and TNF-C and/or therapeutic agents for the treatment of arthritis and inflammation.

DETAILED DESCRIPTION OF THE INVENTION

This invention provides novel hydroxamic acids and carboxylic acids and derivatives thereof of formula (I) (described below) which are useful as inhibitors of metalloproteinases, such as aggrecanase and TNF-C. The present invention also includes pharmaceutical compositions comprising such compounds of formula (I) and methods of using such compounds for the treatment of arthritis and other inflammatory disorders as described previously, in a patient.

Also included in the present invention are pharmaceutical kits comprising one or more containers containing pharmaceutical dosage units comprising a compound of formula (I), for the treatment of arthritis and other inflammatory disorders as described previously.

The present invention also includes methods of inhibiting metalloproteinases, such as aggrecanase and tumor necrosis factor alpha, and for the treatment of arthritis by administering a compound of formula (I) in combination with one or more second therapeutic agents selected from other inhibitors of metalloproteinases, such as aggrecanase and tumor necrosis factor alpha and/or therapeutic agents for the treatment of arthritis and inflammation.

In the following description a (–) symbolizes the point of attachment.

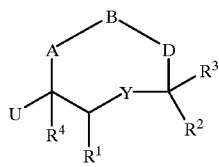

Formula I or pharmaceutically acceptable salts or prodrug forms thereof, wherein:

U is selected from: —$CO_2H$, —CONHOH, —$CONHOR^{11}$, —SH, —NH—$COR^{11}$, —N(OH)$COR^{11}$, —$SN_2H_2R^6$, —$SONHR^6$, $CH_2CO_2H$, PO(OH)$_2$, PO(OH)$NHR^6$, $CH_2SH$, —C(O)$NHOR^{12}$, —$CO_2R^{12}$, and common prodrug derivatives;

$R^1$ is selected from:
H,
—($C_0$–$C_6$)alkyl-S(O)p-($C_1$–$C_6$)alkyl,
—($C_0$–$C_6$)alkyl-O—($C_1$–$C_6$)alkyl,
—($C_0$–$C_6$)alkyl-S(O)p-($C_0$–$C_6$)alkyl-aryl,
—($C_0$–$C_6$)alkyl-O—($C_0$–$C_6$)alkyl-aryl,
alkyl of from 1 to 20 carbon atoms which include branched, cyclic and unsaturated alkyl groups, substituted alkyl
wherein the substituent is selected from;
hydrogen, halo, hydroxy, alkoxy, aryloxy, (such as phenoxy), amino, mono-alkylamino, di-alkylamino, acylamino (such as acetamido and benzamido), arylamino, guanidino, N-methyl imidazolyl, imidazolyl, indolyl, mercapto, alkylthio, arylthio (such as phenylthio), carboxy, carboxamido, carbo alkoxy, or sulfonamido,
—($C_0$–$C_8$)alkyl-aryl,
—($C_0$–$C_8$)alkyl-substituted aryl,
—($C_0$–$C_8$)aryl-($C_1$–$C_4$)alkyl-aryl,
—($C_1$–$C_8$)alkyl-biaryl,
—($C_0$–$C_8$)alkyl-S(O)p-($C_0$–$C_8$)alkyl-aryl,
—($C_0$–$C_8$)alkyl-S(O)p-($C_0$–$C_8$)alkyl-substituted aryl,
—($C_1$–$C_4$)alkyl-aryl-($C_0$–$C_8$)alkyl-aryl-[S(O)p-($C_0$–$C_8$)alkyl],
—($C_0$–$C_8$)alkyl-S(O)p-($C_0$–$C_8$)alkyl-biaryl,
—($C_0$–$C_8$)alkyl-O—($C_0$–$C_8$)alkyl-aryl,
—($C_0$–$C_8$)alkyl-S(O)p-($C_0$–$C_8$)alkyl-substituted aryl,
—($C_1$–$C_4$)alkyl-aryl-($C_0$–$C_8$)alkyl-aryl-[O—($C_0$–$C_8$)alkyl],
—($C_0$–$C_8$)alkyl-O—($C_0$–$C_8$)alkyl-biaryl,
—($C_0$–$C_8$)alkyl-O—($C_0$–$C_8$)alkyl-substituted aryl,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl;

$R^2$ is selected from H, —$CO_2R^5$, —$CONR^6R^5$, —$CONR^6$(OR$^5$), -alkyl, -alkylaryl, -alkylheteroaryl, -alkylheterocyclic, -aryl, -heteroaryl or -heterocyclic which is substituted with one or more substituents selected from:
hydrogen, halo, hydroxy, alkoxy, aryloxy, (such as phenoxy), amino, mono-alkylamino, di-alkylamino, acylamino (such as acetamido and benzamido), arylamino, guanidino, N-methyl imidazolyl, imidazolyl, indolyl, mercapto, lower alkylthio, arylthio (such as phenylthio), carboxy, sulfonamido, carboxamido, or carboalkoxy;

$R^3$ is selected from:
—H, —OH, —$OR^6$ —$NH_2$, —$NHR^6$, —$N(R^6)_2$, —($C_1$–$C_6$)alkyl, —($C_1$–$C_6$)alkyl-aryl, —$SR^6$, halide, or nitrile;

Alternatively $R^2$ and $R^3$ can form a 3 to 8 membered saturated, unsaturated, aryl, heteroaryl or heterocyclic ring;

$R^4$ is selected from:
H, —OH, —$OR^6$ —$NH_2$, —$NHR^6$, —$N(R^6)_2$, —($C_1$–$C_6$)alkyl, —($C_1$–$C_6$)alkyl-aryl, —S(O)p-($C_1$–$C_6$)alkyl, halide, or nitrile;

$R^5$ is selected from:
—(CHR$^1$Y)$_n$—R$^9$, —C(R$^7$R$^8$)$_n$—W—C(R$^7$R$^8$)$_m$—R$^9$,
—C(R$^7$R$^8$)$_m$—R$^9$, —C(R$^7$R$^8$)$_m$-aryl,
—C(R$^7$R$^8$)$_m$CONR$^7$R$^8$,
—C(R$^7$R$^8$)$_m$-substituted heteroaryl,
—C(R$^7$R$^8$)$_m$-substituted heterocyclic,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboxamido or aryl;

$R^6$ is selected from:
H, alkyl, —($C_1$–$C_6$)alkyl-aryl,
—($C_1$–$C_6$)alkyl-heteroaryl,
—($C_1$–$C_6$)alkyl-heterocyclic,
—($C_1$–$C_6$)alkyl-acyl;

Alternatively, $R^5$ and $R^6$ may form a 3 to 8 membered ring optionally unsaturated containing from 1 to 3 heteroatoms selected from —O, —$NR^6$, —S(O)p, or an acyl group, optionally fused to an aryl ring;

$R^7$ and $R^8$ may be selected independently from:
H, $R^1$, or form a 3 to 7 membered substituted ring with 0–3 unsaturations,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl,
optionally containing —O—, —S(O)p, —$NR^6$, optionally fused to a substituted aryl ring,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboxamido or aryl;

$R^9$ is H, alkyl, cycloalkyl 5 or 6 membered ring optionally containing from 1 to 2 N, O or S(O)p, optionally substituted with —OH, —O—($C_1$–$C_6$)alkyl, —O-acyl-alkyl, $NHR^{10}$, or aryl;

$R^{10}$ is H or an optionally substituted alkyl group;

$R^{11}$ is hydrogen, alkyl of from 1 to 10 C atoms which include branched, cyclic and unsaturated alkyl groups, substituted alkyl
wherein the substituent is selected from:
hydrogen, halo, hydroxy, alkoxy, aryloxy, such as phenoxy, amino, di-alkylamino, acylamino such as acetamido and benzamido, arylamino, guanidino, imidazolyl, indolyl, mercapto, alkylthio, arylthio (such as phenylthio) carboxy, carboxamido, carbo-alkoxy, or sulfonamide,
—($C_1$–$C_4$)alkyl-aryl,
—($C_1$–$C_4$)alkyl-($C_1$–$C_8$)alkyl-aryl
—($C_1$–$C_8$)alkyl-biaryl,
substituted —($C_1$–$C_8$)alkyl-aryl,
wherein the substituent is selected from:

hydrogen, halo, hydroxy, alkoxy, aryloxy, such as phenoxy, amino, di-alkylamino, acylamino such as acetamido and benzamido, arylamino, guanidino, imidazolyl, indolyl, mercapto, alkylthio, arylthio (such as phenylthio) carboxy, carboxamido, carboalkoxy, or sulfonamide;

$R_{11a}$ is H, —$SO_2$—$C_1$–$C_6$-alkyl, —$SO_2$—$C_1$–$C_6$-alkyl-substituted aryl, —$SO_2$-aryl, —$SO_2$-substituted heteroaryl, —$COR^9$, —$CO_2$t-Bu, —$CO_2$Bn, or -alkyl-substituted aryl wherein the substituent is selected from:
hydrogen, $C_1$–$C_5$ alkyl, hydroxy, halo, alkoxy, amino, mono-alkylamino, di-alkylamino, acylamino, thio, thioalkyl, carboxy, carboxamido or aryl;

$R^{12}$ is selected from: H, aryl, ($C_1$ to $C_{10}$)alkyl-, aryl ($C_1$ to $C_6$)alkyl-,
$C_3$ to $C_{11}$ cycloalkyl,
$C_3$ to $C_{10}$ alkylcarbonyloxyalkyl,
$C_3$ to $C_{10}$ alkoxycarbonyloxyalkyl,
$C_2$ to $C_{10}$ alkoxycarbonyl,
$C_5$ to $C_{10}$ cycloalkylcarbonyloxyalkyl,
$C_5$ to $C_{10}$ cycloalkoxycarbonyloxyalkyl,
$C_5$ to $C_{10}$ cycloalkoxycarbonyl,
aryloxycarbonyl, aryloxycarbonyloxy($C_1$ to $C_6$ alkyl)-, arylcarbonyloxy($C_1$ to $C_6$ alkyl)-,
$C_5$ to $C_{12}$ alkoxyalkylcarbonyloxyalkyl,
[5-($C_1$–$C_5$ alkyl)-1,3-dioxa-cyclopenten-2-one-yl] methyl,
(5-aryl-1,3-dioxa-cyclopenten-2-one-yl)methyl,
$(R^{17})(R^{17a})N$—($C_1$–$C_{10}$ alkyl)—, —$CH(R^{13})OC(=O)R^{14}$, —$CH(R^{13})OC(=O)OR^{15}$, or

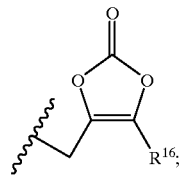

wherein
$R^{13}$ is H or $C_1$–$C_4$ linear alkyl;
$R^{14}$ is selected from:
H,
$C_1$–$C_8$ alkyl or $C_3$–$C_8$ cycloalkyl, said alkyl or cycloalkyl being substituted with 1–2 groups independently selected from:
$C_1$–$C_4$ alkyl,
$C_3$–$C_8$ cycloalkyl
$C_1$–$C_5$ alkoxy,
aryl substituted with 0–2 groups independently selected from:
halogen, phenyl, $C_1$–$C_6$ alkyl, $C_1$–$C_6$ alkoxy, $NO_2$, —$S(C_1$–$C_5$ alkyl), —$S(=O)(C_1$–$C_5$ alkyl), —$SO_2(C_1$–$C_5$ alkyl), —OH, —$N(R^{17})(R^{17a})$, —$CO_2R^{17a}$, —$C(=O)N(R^{17})(R^{17a})$, or —$C_vF_w$ where v=1 to and w=1 to (2v+1),
aryl substituted with 0–2 groups independently selected from:
halogen, phenyl, $C_1$–$C_6$ alkyl, $C_1$–$C_6$ alkoxy, $NO_2$, —$S(C_1$–$C_5$ alkyl), —$S(=O)(C_1$–$C_5$ alkyl), —$SO_2(C_1$–$C_5$ alkyl), —OH, —$N(R^{17})(R_{17a})$, $CO_2R^{17a}$, —$C(=O)N(R^{17})(R^{17a})$, or —$C_vF_w$ where v=1 to 3 and w=1 to (2v+1);
$R^{15}$ is selected from:

$C_1$–$C_8$ alkyl, $C_3$–$C_8$ cycloalkyl, said alkyl or cycloalkyl being substituted with 1–2 groups independently selected from:
$C_1$–$C_4$ alkyl,
$C_3$–$C_8$ cycloalkyl,
$C_1$–$C_5$ alkoxy,
aryl substituted with 0–2 groups independently selected from:
halogen, phenyl, $C_1$–$C_6$ alkyl, $C_1$–$C_6$ alkoxy, $NO_2$, —$S(C_1$–$C_5$ alkyl), —$S(=O)(C_1$–$C_5$ alkyl), —$SO_2(C_1$–$C_5$ alkyl), —OH, —$N(R^{17})(R^{17a})$, —$CO_2R^{17a}$, —$C(=O)N(R^{17})(R^{17a})$, or —$C_vF_w$ where v=1 to 3 and w=1 to (2v+1),
aryl substituted with 0–2 groups independently selected from:
halogen, phenyl, $C_1$–$C_6$ alkyl, $C_1$–$C_6$ alkoxy, $NO_2$, —$S(C_1$–$C_5$ alkyl), —$S(=O)(C_1$–$C_5$ alkyl), —$SO_2(C_1$–$C_5$ alkyl), —OH, —$N(R^{17})(R_{17a})$, —$CO_2R^{17a}$, —$C(=O)N(R^{17})(R^{17a})$, or —$C_vF_w$ where v=1 to 3 and w=1 to (2v+1);
$R^{16}$ is $C_1$–$C_4$ alkyl, benzyl, or phenyl,
$R^{17}$ and $R^{17a}$ is independently selected from: H, $C_1$–$C_{10}$ alkyl, $C_2$–$C_6$ alkenyl, $C_4$–$C_{11}$ cycloalkylalkyl, and aryl ($C_1$–$C_6$ alkyl);

Combinations of A, B and D, and/or variables are permissable only if such combinations result in stable compounds (as defined herein)

A can be absent, —$(CHR^6)_m$—, —$O(CHR^6)_m$—, —$NR^6(CHR^6)_m$—, —$S(O)p(CHR^6)_m$—, or selected from an alkyl from 1 to 10 carbon atoms which include branched, cyclic and unsaturated alkyl groups or —($C_1$–$C_6$)alkyl-aryl;

B can be a bond or selected from —NH—, —$NR^{11}$—, —$NR^{11a}$— —O—, —$S(O)p$-($C_1$–$C_6$)alkyl-NH—($C_1$–$C_6$)alkyl-, ($C_1$–$C_6$)alkyl-$NR^{11}$—($C_1$–$C_6$)alky-, —$C_1$–$C_6$—NH-aryl-, —O—($C_1$–$C_6$)alkyl-, —($C_1$–$C_6$) alkyl-O-aryl-, —S—($C_1$–$C_6$)alkyl-, —($C_1$–$C_6$)alkyl-S-aryl-, —($C_1$–$C_6$)alkyl-, —($C_1$–$C_6$)alkenyl-, —($C_1$–$C_6$)alkynyl-, —CONH—, —$CONR^{11}$, —NHCO—, —$NR^{11}CO$—, —OCO—, —COO—, —$OCO_2$—$R^{11}NCONR^{11}$—, HNCONH—, —$OCONR^{11}$—, —$NR^{11}COO$—, —$HNSO_2$—, —$SO_2NH$—, aryl, cycloalkyl, heterocycloalkyl, —$R^{11}NCSNR^{11}$—, —HNCSNH, —$OCSNR^{11}$—, —$NR^{11}CSO$—, —HNCNNH—, and a peptide bond mimic;

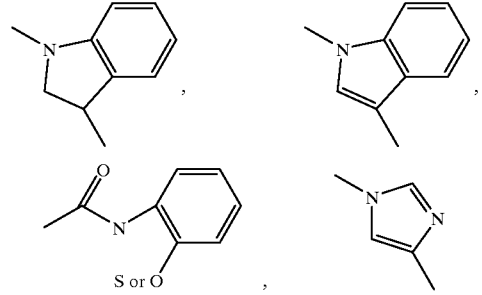

D can be absent or an alkyl from 1 to 10 carbon atoms optionally containing O, S or $NR^6$, which include branched and cyclic and unsaturated alkyl groups and aryl $C_1$–$C_6$ alkyl-;
p can be 0, 1 or 2;
m is an integer from 0 to 5;
n is an integer from 1 to 5;

W is —O—, —S(O)p- or —NR$^{10}$—;

Y is selected from: —CONR$^{10}$—, —NR$^{10}$CO—, —SO$_2$NR$^{10}$—, —NR$^{10}$SO$_2$—, a peptide bond mimic, a 5 membered heterocyclic ring saturated, unsaturated or partially unsaturated containing from 1 to 4 heteroatoms selected from N,O or S, with the proviso that the size of the macrocycle encompased in formula I by —A—B—D—C(R$^2$)(R$^3$)—Y—C(R$^1$)—C(U)(R$^4$)—, be connected by no less than 11 atoms and no more than 22 atoms to form the cycle.

[2] There is provided by this invention compounds of the formula(II):

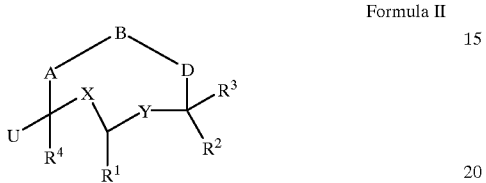

Formula II or pharmaceutically acceptable salts or prodrug forms thereof, wherein;

X is selected from CH$_2$, NH, NR$^5$, S(O)p, or O;

U, Y, R$^1$, R$^2$, R$^3$, R$^4$, R$^5$ R$^6$, R$^7$, R$^8$, R$^9$, R$^{10}$, R$^{11}$, R$^{11a}$ R$^{12}$, R$^{13}$, R$^{14}$, R$^{15}$, R$^{16}$ R$^{17}$ R$^{17a}$ and p, m, n, A, B, D and W are as specified previously in Formula I and defined as stable compounds;

with the proviso that the size of the macrocycle encompased in formula I by —A—B—D—C(R$^2$)(R$^3$)—Y—C(R$^1$)—X—C(U)(R$^4$)—, be connected by no less than 11 atoms and no more than 22 atoms to form the cycle.

[3] There is provided by this invention compounds of the formula (III):

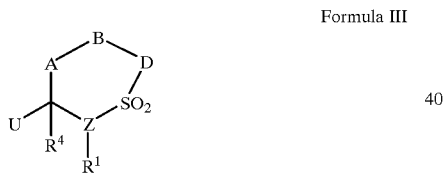

Formula III

U is selected from; —CO$_2$H, —CONHOH, —CONHOR$^{11}$, —SH, —NH—COR$^{11}$, —N(OH)COR$^{11}$, —SN$_2$H$_2$R$^6$, —SONHR$^6$, CH$_2$CO$_2$H, PO(OH)$_2$, PO(OH)NHR$^6$, CH$_2$SH, and common prodrug derivatives —C(O)NHOR$^{12}$ and —CO$_2$R$^{12}$;

Z is selected from: N or CH;

R$^1$, R$^4$, R$^6$, R$^{11}$, R$^{11a}$, R$^{12}$, R$^{13}$, R$^{14}$, R$^{15}$, R$^{16}$, R$^{17}$ R$^{17a}$, A, B, C, are as specified previously in Formula I and defined as stable compounds;

[4] Preferred compounds of the present invention are compounds of formula I where;

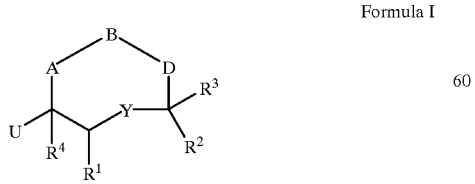

Formula I or pharmaceutically acceptable salts or prodrug forms thereof, wherein;

U is selected from; —CONHOH, —CONHOR$^{11}$, N(OH) COR$^{11}$, —SN$_2$H$_2$R$^6$, —SONHR$^6$, —CO$_2$H, —CH$_2$SH, —C(O)NHOR$^{12}$; and common prodrug derivatives;

R$^1$ is selected from:
H,
—(C$_0$–C$_6$)alkyl-S(O)p-(C$_1$–C$_6$)alkyl,
—(C$_0$–C$_6$)alkyl-O—(C$_1$–C$_6$)alkyl,
—(C$_0$–C$_6$)alkyl-S(O)p-(C$_0$–C$_6$)alkyl-aryl,
—(C$_0$–C$_6$)alkyl-O—(C$_0$–C$_6$)alkyl-aryl,
alkyl of from 1 to 20 carbon atoms which include branched, cyclic and unsaturated alkyl groups, substituted alkyl
wherein the substituent is selected from;
hydrogen, halo, hydroxy, alkoxy, aryloxy, (such as phenoxy), amino, mono-alkylamino, di-alkylamino, acylamino (such as acetamido and benzamido), arylamino, guanidino, N-methyl imidazolyl, imidazolyl, indolyl, mercapto, alkylthio, arylthio (such as phenylthio), carboxy, carboxamido, carbo alkoxy, or sulfonamido,
—(C$_0$–C$_8$)alkyl-aryl,
—(C$_0$–C$_8$)alkyl-substituted aryl,
—(C$_0$–C$_8$)aryl-(C$_1$–C$_4$)alkyl-aryl,
—(C$_1$–C$_8$)alkyl-biaryl,
—(C$_0$–C$_8$)alkyl-S(O)p-(C$_0$–C$_8$)alkyl-aryl,
—(C$_0$–C$_8$)alkyl-S(O)p-(C$_0$–C$_8$)alkyl-substituted aryl,
—(C$_1$–C$_4$)alkyl-aryl-(C$_0$–C$_8$)alkyl-aryl-[S(O)p-(C$_0$–C$_8$)alkyl],
—(C$_0$–C$_8$)alkyl-S(O)p-(C$_0$–C$_8$)alkyl-biaryl,
—(C$_0$–C$_8$)alkyl-O—(C$_0$–C$_8$)alkyl-aryl,
—(C$_0$–C$_8$)alkyl-S(O)p-(C$_0$–C$_8$)alkyl-substituted aryl,
—(C$_1$–C$_4$)alkyl-aryl—(C$_0$–C$_8$)alkyl-aryl-[O—(C$_0$–C$_8$) alkyl],
—(C$_0$–C$_8$)alkyl-O—(C$_0$–C$_8$)alkyl-biaryl,
—(C$_0$–C$_8$)alkyl-O—C$_0$–C$_8$)alkyl-substituted aryl,
wherein the substituent is selected from;
hydrogen, C$_1$–C$_5$ alkyl, hydroxy, halo, alkoxy, amino, mono-alkylamino, di-alkylamino, acylamino, thio, thioalkyl, carboxy, carboamido or aryl;

R$^2$ is selected from H, —CO$_2$R$^5$, —CONR$^6$R$^5$, —CONR$^6$ (OR$^5$), -alkyl, -alkylaryl, -alkylheteroaryl, -alkylheterocyclic, -aryl, -heteroaryl or -heterocyclic which is substituted with one or more substituents selected from:
hydrogen, halo, hydroxy, alkoxy, aryloxy, (such as phenoxy), amino, mono-alkylamino, di-alkylamino, acylamino (such as acetamido and benzamido), arylamino, guanidino, N-methyl imidazolyl, imidazolyl, indolyl, mercapto, lower alkylthio, arylthio (such as phenylthio), carboxy, sulfonamido, carboxamido, or carboalkoxy;

R$^3$ is selected from
H, —OH, and —NH$_2$;

Alternatively R$^2$ and R$^3$ can form a 3 to 6 membered saturated, unsaturated, aryl, heteroaryl or heterocyclic ring;

R$^4$ is selected from:
H, —OH, and —NH$_2$;

R$^5$ is selected from:
—(CHR$^1$Y)$_n$—R$^9$, —C(R$^7$R$^8$)$_n$—W—C(R$^7$R$^8$)$_m$—R$^9$,
—C(R$^7$R$^8$)$_m$—R$^9$, —C(R$^7$R$^8$)$_m$-aryl,
—C(R$^7$R$^8$)$_m$CONR$^7$R$^8$,
—C(R$^7$R$^8$)$_m$-substituted heteroaryl,
—C(R$^7$R$^8$)$_m$-substituted heterocyclic wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboxamido or aryl;

$R^6$ is selected from:
H, alkyl-, —($C_1$–$C_6$)alkyl-aryl,
—($C_1$–$C_6$)alkyl-heteroaryl,
—($C_1$–$C_6$)alkyl-heterocyclic,
—($C_1$–$C_6$)alkyl-acyl;

Alternatively, $R^5$ and $R^6$ may form a 3 to 8 membered ring optionally unsaturated containing from 1 to 3 heteroatoms selected from —O, —$NR^6$, —S(O)p, or an acyl group, optionally fused to an aryl ring;

$R^7$ and $R^8$ may be selected independently from:
H, $R^1$, or form a 3 to 7 membered substituted ring with 0–3 unsaturations,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl,
optionally containing —O—, —S(O)p, —$NR^6$, optionally fused to a substituted aryl ring,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboxamido or aryl;

$R^9$ is H, alkyl, cycloalkyl, 5 or 6 membered ring optionally containing from 1 to 2 N, O or S(O)p, optionally substituted with —OH, —O—($C_1$–$C_6$)alkyl, —O-acyl-alkyl, $NHR^{10}$, or aryl;

$R^{10}$ is H or an optionally substituted alkyl group;

$R^{11}$ is hydrogen, alkyl of from 1 to 10 C atoms which include branched, cyclic and unsaturated alkyl groups, substituted alkyl
wherein the substituent is selected from:
hydrogen, halo, hydroxy, alkoxy, aryloxy, such as phenoxy, amino, di-alkylamino, acylamino such as acetamido and benzamido, arylamino, guanidino, imidazolyl, indolyl, mercapto, alkylthio, arylthio (such as phenylthio) carboxy, carboxamido, carboalkoxy, or sulfonamide,
—($C_1$–$C_4$)alkyl-aryl,
—($C_1$–$C_4$)alkyl-($C_1$–$C_8$)alkyl-aryl,
—($C_1$–$C_8$)alkyl-biaryl,
substituted —($C_1$–$C_8$)alkyl-aryl,
wherein the substituent is selected from:
hydrogen, halo, hydroxy, alkoxy, aryloxy, such as phenoxy, amino, di-alkylamino, acylamino such as acetamido and benzamido, arylamino, guanidino, imidazolyl, indolyl, mercapto, alkylthio, arylthio (such as phenylthio) carboxy, carboxamido, carboalkoxy, or sulfonamide;

$R^{11a}$ is H, —$SO_2$—$C_1$–$C_6$-alkyl, —$SO_2$—$C_1$–$C_6$-alkyl-substituted aryl, —$SO_2$-aryl, —$SO_2$-substituted heteroaryl, —$COR^9$, —$CO_2$t-Bu, —$CO_2$Bn, or -alkyl-substituted aryl
wherein the substituent is selected from:
hydrogen, $C_1$–$C_5$ alkyl, hydroxy, halo, alkoxy, amino, mono-alkylamino, di-alkylamino, acylamino, thio, thioalkyl, carboxy, carboxamido or aryl;

$R^{12}$ is selected from: H, aryl, ($C_1$ to $C_{10}$)alkyl-, aryl ($C_1$ to $C_6$)alkyl-,
$C_3$ to $C_{11}$ cycloalkyl,
$C_3$ to $C_{10}$ alkylcarbonyloxyalkyl,
$C_3$ to $C_{10}$ alkoxycarbonyloxyalkyl,
$C_2$ to $C_{10}$ alkoxycarbonyl,
$C_5$ to $C_{10}$ cycloalkylcarbonyloxyalkyl,
$C_5$ to $C_{10}$ cycloalkoxycarbonyloxyalkyl,
$C_5$ to $C_{10}$ cycloalkoxycarbonyl,
aryloxycarbonyl, aryloxycarbonyloxy($C_1$ to $C_6$ alkyl)-, arylcarbonyloxy($C_1$ to $C_6$ alkyl)-,
$C_5$ to $C_{12}$ alkoxyalkylcarbonyloxyalkyl,
[5-($C_1$–$C_5$ alkyl)-1,3-dioxa-cyclopenten-2-one-yl] methyl,
(5-aryl-1,3-dioxa-cyclopenten-2-one-yl)methyl,
$(R^{17})(R^{17a})N$—($C_1$–$C_{10}$ alkyl)-, —$CH(R^{13})OC(=O)R^{14}$,
—$CH(R^{13})OC(=O)OR^{15}$, or

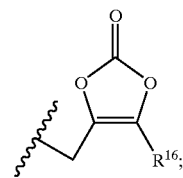

wherein
$R^{13}$ is H or $C_1$–$C_4$ linear alkyl;
$R^{14}$ is selected from:
H, $C_1$–$C_8$ alkyl or $C_3$–$C_8$ cycloalkyl, said alkyl or cycloalkyl being substituted with 1–2 groups independently selected from:
$C_1$–$C_4$ alkyl,
$C_3$–$C_8$ cycloalkyl
$C_1$–$C_5$ alkoxy,
aryl substituted with 0–2 groups independently selected from:
halogen, phenyl, $C_1$–$C_6$ alkyl, $C_1$–$C_6$ alkoxy, $NO_2$, —$S(C_1$–$C_5$ alkyl), —$S(=O)(C_1$–$C_5$ alkyl), —$SO_2(C_1$–$C_5$ alkyl), —OH, —$N(R^{17})(R^{17a})$, —$CO_2R^{17a}$, —$C(=O)N(R^{17})(R^{17a})$, or —$C_vF_w$ where v=1 to 3 and w=1 to (2v+1),
aryl substituted with 0–2 groups independently selected from:
halogen, phenyl, $C_1$–$C_6$ alkyl, $C_1$–$C_6$ alkoxy, $NO_2$, —$S(C_1$–$C_5$ alkyl), —$S(=O)(C_1$–$C_5$ alkyl), —$SO_2(C_1$–$C_5$ alkyl), —OH, —$N(R^{17})(R^{17a})$, —$CO_2R^{17a}$, —$C(=O)N(R^{17})(R^{17a})$, or —$C_vF_w$ where v=1 to 3 and w=1 to (2v+1);

$R^{15}$ is selected from:
$C_1$–$C_8$ alkyl, $C_3$–$C_8$ cycloalkyl, said alkyl or cycloalkyl being substituted with 1–2 groups independently selected from:
$C_1$–$C_4$ alkyl,
$C_3$–$C_8$ cycloalkyl,
$C_1$–$C_5$ alkoxy,
aryl substituted with 0–2 groups independently selected from:
halogen, phenyl, $C_1$–$C_6$ alkyl, $C_1$–$C_6$ alkoxy, $NO_2$, —$S(C_1$–$C_5$ alkyl), —$S(=O)(C_1$–$C_5$ alkyl), —$SO_2(C_1$–$C_5$ alkyl), —OH, —$N(R^{17})(R^{17a})$, —$CO_2R^{17a}$, —$C(=O)N(R^{17})(R^{17a})$, or —$C_vF_w$ where v=1 to 3 and w=1 to (2v+1),
aryl substituted with 0–2 groups independently selected from:
halogen, phenyl, $C_1$–$C_6$ alkyl, $C_1$–$C_6$ alkoxy, $NO_2$, —$S(C_1$–$C_5$ alkyl), —$S(=O)(C_1$–$C_5$ alkyl), —$SO_2(C_1$–$C_5$ alkyl), —OH, —$N(R^{17})(R^{17a})$, —$CO_2R^{17a}$, —$C(=O)N(R^{17})(R^{17a})$, or —$C_vF_w$ where v=1 to 3 and w=1 to (2v+1);

$R^{16}$ is $C_1$–$C_4$ alkyl, benzyl, or phenyl;

$R^{17}$ and $R^{17a}$ is independently selected from: H, $C_1$–$C_{10}$ alkyl, $C_2$–$C_6$ alkenyl, $C_4$–$C_{11}$ cycloalkylalkyl, and aryl ($C_1$–$C_6$ alkyl);

Combinations of A, B and D, and/or variables are permissable only if such combinations result in stable compounds (as defined herein).

A can be absent, —$(CHR^6)_m$—, —$O(CHR^6)_m$—, —$NR^6(CHR^6)_m$—, —$S(O)p(CHR^6)_m$—, or selected from an alkyl from 1 to 10 carbon atoms which include branched, cyclic and unsaturated alkyl groups or —($C_1$–$C_6$)alkyl-aryl;

B can be a bond or selected from —NH—, —$NR^{11}$—, —$NR^{11a}$— —O—, —S(O)p-($C_1$–$C_6$)alkyl-NH—($C_1$–$C_6$)alkyl-, ($C_1$–$C_6$)alkyl-$NR^{11}$—($C_1$–$C_6$)alky-, —$C_1$–$C_6$—NH-aryl-, —O—($C_1$–$C_6$)alkyl-, —($C_1$–$C_6$)alkyl-O-aryl-, —S—($C_1$–$C_6$)alkyl-, —($C_1$–$C_6$)alkyl-S-aryl-, —($C_1$–$C_6$)alkyl-, —($C_1$–$C_6$)alkenyl-, —($C_1$–$C_6$)alkynyl-, —CONH—, —$CONR^{11}$, —NHCO—, —$NR^{11}CO$—, —OCO—, —COO—, —$OCO_2$—, —$R^{11}NCONR^{11}$—, HNCONH—, —$OCONR^{11}$—, —$NR^{11}COO$—, —$HNSO_2$—, —$SO_2NH$—, aryl, cycloalkyl, heterocycloalkyl, —$R^{11}NCSNR^{11}$—, —HNCSNH, —$OCSNR^{11}$—, —$NR^{11}CSO$—, —HNCNNH—, and a peptide bond mimic;

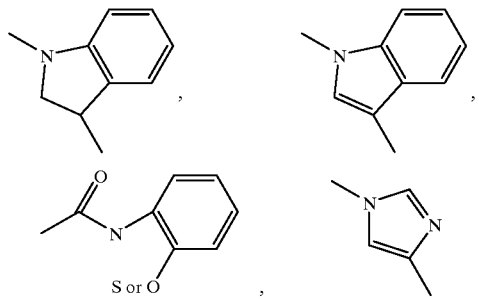

D can be absent or an alkyl from 1 to 10 carbon atoms optionally interupted by O, S or $NR^{6}$ which include branched and cyclic and unsaturated alkyl groups and —($C_1$–$C_6$)-alkyl-aryl;

p can be 0, 1 or 2;

m is an integer from 0 to 5;

n is an integer from 1 to 5;

W is —O—, —S(O)p- or —$NR^{10}$—;

Y is selected from: —$CONR^{10}$—, —$NR^{10}CO$—, —$SO_2NR^{10}$—, —$NR^{10}SO_2$—, a peptide bond mimic, a 5 membered heterocyclic ring saturated, unsaturated or partially unsaturated containing from 1 to 4 heteroatoms selected from N,O or S, with the proviso that the size of the macrocycle encompased in formula I by —A—B—D—$C(R^2)(R^3)$—Y—$C(R^1)$—C(U)($R^4$)—, be connected by no less than 11 atoms and no more than 22 atoms to form the cycle.

[5] Preferred compounds of the present invention are compounds of formula II where;

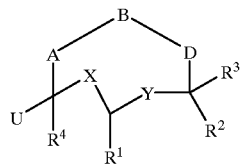

Formula II or pharmaceutically acceptable salts or prodrug forms thereof, wherein;

X is selected from $CH_2$, NH, S and O;

U, Y, $R^1$, $R^2$, $R^3$, $R^4$, $R^5$, $R^6$, $R^7$, $R^8$, $R^9$, $R^{10}$, $R^{11}$, $R^{11a}$, $R^{12}$, $R^{13}$, $R^{14}$, $R^{15}$, $R^{16}$, $R^{17}$, $R^{17a}$ and p, m, n, A, B, D and W are as specified previously in Formula I and defined as stable compounds;

with the proviso that the size of the macrocycle encompased in formula I by —A—B—D—$C(R^2)(R^3)$—Y—$C(R^1)$—X—C(U)($R^4$)—, be connected by no less than 11 atoms and no more than 22 atoms to form the cycle.

[6] More preferred compounds of the present invention are compounds of formula I where,

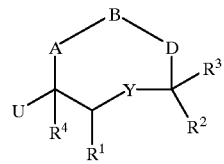

Formula I or pharmaceutically acceptable salts or prodrug forms thereof, wherein;

U is selected from: —CONHOH, —$C(O)NHOR^{12}$, —$CO_2H$ and common prodrug derivatives;

$R^1$ is selected from:

H, —($C_0$–$C_6$)alkyl-S(O)p-($C_1$–$C_6$)alkyl,
—($C_0$–$C_6$)alkyl-O—($C_1$–$C_6$)alkyl,
—($C_0$–$C_6$)alkyl-S(O)p-($C_0$–$C_6$)alkyl-aryl,
—($C_0$–$C_6$)alkyl-O—($C_0$–$C_6$)alkyl-aryl, alkyl of from 1 to 20 carbon atoms which include branched, cyclic and unsaturated alkyl groups, substituted alkyl wherein the substituent is selected from;
    hydrogen, halo, hydroxy, alkoxy, aryloxy, (such as phenoxy), amino, mono-alkylamino, di-alkylamino, acylamino (such as acetamido and benzamido), arylamino, guanidino, N-methyl imidazolyl, imidazolyl, indolyl, mercapto, alkylthio, arylthio (such as phenylthio), carboxy, carboxamido, carbo alkoxy, or sulfonamido,
—($C_0$–$C_8$)alkyl-aryl,
—($C_0$–$C_8$)alkyl-substituted aryl,
—($C_0$–$C_8$)aryl-($C_1$–$C_4$)alkyl-aryl,
—($C_1$–$C_8$)alkyl-biaryl,
—($C_0$–$C_8$)alkyl-S(O)p-($C_0$–$C_8$)alkyl-aryl,
—($C_0$–$C_8$)alkyl-S(O)p-($C_0$–$C_8$)alkyl-substituted aryl,
—($C_1$–$C_4$)alkyl-aryl-($C_0$–$C_8$)alkyl-aryl-[S(O)p-($C_0$–$C_8$)alkyl],
—($C_0$–$C_8$)alkyl-S(O)p-($C_0$–$C_8$)alkyl-biaryl,
—($C_0$–$C_8$)alkyl-O—($C_0$–$C_8$)alkyl-aryl,
—($C_0$–$C_8$)alkyl-S(O)p-($C_0$–$C_8$)alkyl-substituted aryl,
—($C_1$–$C_4$)alkyl-aryl-($C_0$–$C_8$)alkyl-aryl-[O—($C_0$–$C_8$) alkyl],
—($C_0$–$C_8$)alkyl-O—($C_0$–$C_8$)alkyl-biaryl,
—($C_0$–$C_8$)alkyl-O—($C_0$–$C_8$)alkyl-substituted aryl, wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl;

$R^2$ is selected from H, —$CO_2R^5$, —$CONR^6R^5$, —$CONR^6$ ($OR^5$), -alkyl, -alkylaryl, -alkylheteroaryl, -alkylheterocyclic, -aryl, -heteroaryl or -heterocyclic which is substituted with one or more substituents selected from:
hydrogen, halo, hydroxy, alkoxy, aryloxy, (such as phenoxy), amino, mono-alkylamino, di-alkylamino, acylamino (such as acetamido and benzamido), arylamino, guanidino, N-methyl imidazolyl, imidazolyl, indolyl, mercapto, lower alkylthio, arylthio (such as phenylthio), carboxy, sulfonamido, carboxamido, or carboalkoxy;

$R^3$ and $R^4$ are H;

$R^5$ is selected from:
—$(CHR^1Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
—$C(R^7R^8)_m CONR^7R^8$,
—$C(R^7R^8)_m$-substituted heteroaryl,
—$C(R^7R^8)_m$-substituted heterocyclic,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboxamido or aryl;

$R^6$ is selected from:
H, alkyl-, —$(C_1$–$C_6)$alkyl-aryl,
—$(C_1$–$C_6)$alkyl-heteroaryl,
—$(C_1$–$C_6)$alkyl-heterocyclic,
—$(C_1$–$C_6)$alkyl-acyl;

Alternatively, $R^5$ and $R^6$ may form a 3 to 8 membered ring optionally unsaturated containing from 1 to 3 heteroatoms selected from —O, —$NR^6$, —S(O)p, or an acyl group, optionally fused to an aryl ring;

$R^7$ and $R^8$ may be selected independently from:
H, $R^1$, or form a 3 to 7 membered substituted ring with 0–3 unsaturations,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl,
optionally containing —O—, —S(O)p, —$NR^6$, optionally fused to a substituted aryl ring,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboxamido or aryl;

$R^9$ is H, alkyl, cycloalkyl, 5 or 6 membered ring optionally containing from 1 to 2 N, O or S(O)p, optionally substituted with —OH, —O—$(C_1$–$C_6)$alkyl, —O-acyl-alkyl, $NHR^{10}$, or aryl;

$R^{10}$ is H or an optionally substituted alkyl group;

$R^{11}$ is hydrogen, alkyl of from 1 to 6 C atoms which include branched, cyclic and unsaturated alkyl groups, substituted alkyl;
wherein the substituent is selected from:
hydrogen, halo, hydroxy, alkoxy, aryloxy, such as phenoxy, amino, di-alkylamino, acylamino such as aceatamido and benzamido, arylamino, guanidino, imidazolyl, indolyl, mercapto, loweralkylthio, arylthio (such as phenylthio) carboxy, carboxamido, carbo-alkoxy, and sulfonamide;

—$(C_1$–$C_4)$alkyl-aryl,
—$(C_1$–$C_8)$alkyl-substituted aryl,
wherein the substituent is selected from:
hydrogen, halo, hydroxy, alkoxy, aryloxy, such as phenoxy, amino, di-alkylamino, acylamino such as acetamido and benzamido, arylamino, guanidino, imidazolyl, indolyl, mercapto, loweralkylthio, arylthio (such as phenylthio) carboxy, carboxamido, carbo-alkoxy, and sulfonamide;

$R^{11a}$ is H, —$SO_2$—$C_1$–$C_6$-alkyl, —$SO_2$—$C_1$–$C_6$-alkyl-substituted aryl, —$SO_2$-aryl, —$SO_2$-substituted heteroaryl, —$COR^9$, —$CO_2$t-Bu, —$CO_2$Bn,
wherein the substituent is selected from:
hydrogen, $C_1$–$C_5$ alkyl, hydroxy, halo, alkoxy, amino, mono-alkylamino, di-alkylamino, acylamino, thio, thioalkyl, carboxy, carboxamido or aryl;

$R^{12}$ is selected from: H, aryl, ($C_1$ to $C_{10}$)alkyl-, aryl ($C_1$ to $C_6$)alkyl-,
$C_3$ to $C_{11}$ cycloalkyl,
$C_3$ to $C_{10}$ alkylcarbonyloxyalkyl,
$C_3$ to $C_{10}$ alkoxycarbonyloxyalkyl,
$C_2$ to $C_{10}$ alkoxycarbonyl,
$C_5$ to $C_{10}$ cycloalkylcarbonyloxyalkyl,
$C_5$ to $C_{10}$ cycloalkoxycarbonyloxyalkyl,
$C_5$ to $C_{10}$ cycloalkoxycarbonyl,
aryloxycarbonyl, aryloxycarbonyloxy($C_1$ to $C_6$ alkyl)-, arylcarbonyloxy($C_1$ to $C_6$ alkyl)-,
$C_5$ to $C_{12}$ alkoxyalkylcarbonyloxyalkyl,
[5-($C_1$–$C_5$ alkyl)-1,3-dioxa-cyclopenten-2-one-yl]methyl,
(5-aryl-1,3-dioxa-cyclopenten-2-one-yl)methyl,
$(R^{17})(R^{17a})N$—$(C_1$–$C_{10}$ alkyl)-, —$CH(R^{13})OC(=O)R^{14}$,
—$CH(R^{13})OC(=O)OR^{15}$, or

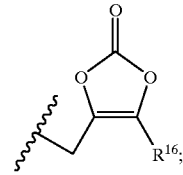

wherein
$R^{13}$ is H or $C_1$–$C_4$ linear alkyl;
$R^{14}$ is selected from:
H, $C_1$–$C_8$ alkyl or $C_3$–$C_8$ cycloalkyl, said alkyl or cycloalkyl being substituted with 1–2 groups independently selected from:
$C_1$–$C_4$ alkyl,
$C_3$–$C_8$ cycloalkyl
$C_1$–$C_5$ alkoxy,
aryl substituted with 0–2 groups independently selected from:
halogen, phenyl, $C_1$–$C_6$ alkyl, $C_1$–$C_6$ alkoxy, $NO_2$, —$S(C_1$–$C_5$ alkyl), —$S(=O)(C_1$–$C_5$ alkyl), —$SO_2(C_1$–$C_5$ alkyl), —OH, —$N(R^{17})(R^{17a})$, —$CO_2R^{17a}$, —$C(=O)N(R^{17})(R^{17a})$, or —$C_vF_w$ where v=1 to 3 and w=1 to (2v+1),
aryl substituted with 0–2 groups independently selected from:
halogen, phenyl, $C_1$–$C_6$ alkyl, $C_1$–$C_6$ alkoxy, $NO_2$, —$S(C_1$–$C_5$ alkyl), —$S(=O)(C_1$–$C_5$ alkyl), —SO$_2$(C$_1$–C$_5$ alkyl), —OH, —N(R$^{17}$)(R$^{17a}$), —CO$_2$R$^{17a}$, C(=O)N(R$^{17}$)(R$^{17a}$), or —C$_v$F$_w$ where v=1 to 3 and w=1 to (2v+1);

R$^{15}$ is selected from:
C$_1$–C$_8$ alkyl, C$_3$–C$_8$ cycloalkyl, said alkyl or cycloalkyl being substituted with 1–2 groups independently selected from:
C$_1$–C$_4$ alkyl,
C$_3$–C$_8$ cycloalkyl,
C$_1$–C$_5$ alkoxy,
aryl substituted with 0–2 groups independently selected from:
halogen, phenyl, C$_1$–C$_6$ alkyl, C$_1$–C$_6$ alkoxy, NO$_2$, —S(C$_1$–C$_5$ alkyl), —S(=O)(C$_1$–C$_5$ alkyl), —SO$_2$(C$_1$–C$_5$ alkyl), —OH, —N(R$^{17}$)(R$^{17a}$), —CO$_2$R$^{17a}$, —C(=O)N(R$^{17}$)(R$^{17a}$), or —C$_v$F$_w$ where v=1 to 3 and w=1 to (2v+1),
aryl substituted with 0–2 groups independently selected from:
halogen, phenyl, C$_1$–C$_6$ alkyl, C$_1$–C$_6$ alkoxy, NO$_2$, —S(C$_1$–C$_5$ alkyl), —S(=O)(C$_1$–C$_5$ alkyl), —SO$_2$(C$_1$–C$_5$ alkyl), —OH, —N(R$^{17}$)(R$^{17a}$), —CO$_2$R$^{17a}$, —C(=O)N(R$^{17}$)(R$^{17a}$), or —C$_v$F$_w$ where v=1 to 3 and w=1 to (2v+1);

R$^{16}$ is C$_1$–C$_4$ alkyl, benzyl, or phenyl;
R$^{17}$ and R$^{17a}$ is independently selected from: H, C$_1$–C$_{10}$ alkyl, C$_2$–C$_6$ alkenyl, C$_4$–C$_{11}$ cycloalkylalkyl, and aryl (C$_1$–C$_6$ alkyl);

Combinations of A, B and D, and/or variables are permissable only if such combinations result in stable compounds (as defined herein).

A can be absent, —(CHR$^6$)$_m$—, —O(CHR$^6$)$_m$—, —NR$^6$(CHR$^6$)$_m$—, —S(O)p(CHR$^6$)$_m$—, or selected from an alkyl from 1 to 10 carbon atoms which include branched, cyclic and unsaturated alkyl groups or —(C$_1$–C$_6$)alkyl-aryl;

B can be a bond or selected from —NH—, —NR$^{11}$—, —NR$^{11a}$—, —O—, —S(O)p-C$_1$–C$_6$alkyl-NH—C$_1$–C$_6$alkyl-, C$_1$–C$_6$alkyl-NR$^{11}$—C$_1$–C$_6$alky-, C$_1$–C$_6$—NH-aryl-, —O—C$_1$–C$_6$alkyl-, C$_1$–C$_6$alkyl-O-aryl-, —S—C1–C6alkyl-, C1–C6alkyl-S-aryl-, C$_1$–C$_6$alkyl-, C$_1$–C$_6$alkenyl-, C$_1$–C$_6$alkynyl-, —CONH—, —CONR$^{11}$, —NHCO—, —NR$^{11}$CO—, —OCO—, —COO—, —OCO2—, —R$^{11}$NCONR$^{11}$—, HNCONH—, —OCONR$^{11}$—, —NR$^{11}$COO—, —HNSO$_2$—, —SO$_2$NH—, aryl, cycloalkyl, heterocycloalkyl, —R$^{11}$NCSNR$^{11}$—, —HNCSNH, —OCSNR$^{11}$—, —NR$^{11}$CSO—, —HNCNNH—, and a peptide bond mimic;

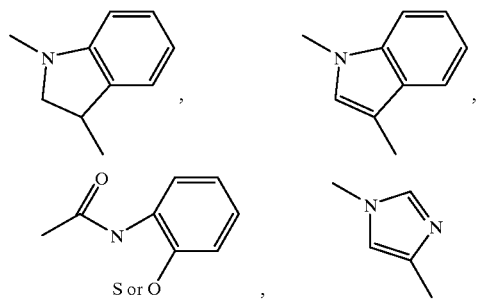

D can be absent or an alkyl of from 1 to 6 carbon atoms which include branched and cyclic and unsaturated alkyl groups or —(C$_1$–C$_6$)alkyl-aryl;

p can be 0, 1 or 2;
m is an integer from 0 to 3;
n is an integer from 1 to 4;
W is —O—, S(O)p or NR$^{10}$;
Y is selected from: —CONR$^{10}$—, —NR$^{10}$CO—, —SO$_2$NR$^{10}$—, —NR$^{10}$SO$_2$—, a peptide bond mimic, a 5 membered heterocyclic ring saturated, unsaturated or partially unsaturated containing from 1 to 4 heteroatoms selected from N,O or S,
with the proviso that the size of the macrocycle encompased in formula I by —A—B—D—C(R$^2$)(R$^3$)—Y—C(R$^1$)—C(U)(R$^4$)—, be connected by no less than 11 atoms and no more than 22 atoms to form the cycle.

Only substituents that form stable compounds are claimed for formula I.

[7] More preferred compounds of the present invention are compounds of formula II where,

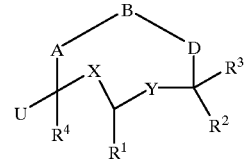

Formula II or pharmaceutically acceptable salts or prodrug forms thereof, wherein;
X is selected from CH$_2$, NH, S and O;
U is selected from; —CO$_2$H, —CO$_2$R$^{12}$ and common prodrug derivatives;
Y, R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{17a}$ and p, m, n, A, B, D and W are as specified previously in Formula I and defined as stable compounds;
with the proviso that the size of the macrocycle encompased in formula I by —A—B—D—C(R$^2$)(R$^3$)—Y—C(R$^1$)—X—C(U)(R$^4$)—, be connected by no less than 11 atoms and no more than 22 atoms to form the cycle.

[8] More preferred compounds of the present invention are compounds of formula I where,

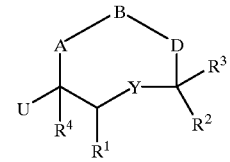

Formula I or pharmaceutically acceptable salts or prodrug forms thereof, wherein;
U is selected from: —CONHOH, —C(O)NHOR$^{12}$, —CO$_2$H, and common prodrug derivatives;
R$^1$ is selected from:
H, —(C$_0$–C$_6$)alkyl-S(O)p-(C$_1$–C$_6$)alkyl,
—(C$_0$–C$_6$)alkyl-O—(C$_1$–C$_6$)alkyl,
—(C$_0$–C$_6$)alkyl-S(O)p-(C$_0$–C$_6$)alkyl-aryl,
—(C$_0$–C$_6$)alkyl-O—(C$_0$–C$_6$)alkyl-aryl,
alkyl of from 1 to 20 carbon atoms which include branched, cyclic and unsaturated alkyl groups, substituted alkyl
wherein the substituent is selected from;
hydrogen, halo, hydroxy, alkoxy, aryloxy, (such as phenoxy), amino, mono-alkylamino, di-alkylamino, acylamino (such as acetamido and benzamido), arylamino, guanidino, N-methyl imidazolyl, imidazolyl, indolyl, mercapto, alkylthio, arylthio (such as phenylthio), carboxy, carboxamido, carbo alkoxy, or sulfonamido,
—($C_0$–$C_8$)alkyl-aryl,
—($C_0$–$C_8$)alkyl-substituted aryl,
—($C_0$–$C_8$)aryl-($C_1$–$C_4$)alkyl-aryl,
—($C_1$–$C_8$)alkyl-biaryl,
—($C_0$–$C_8$)alkyl-S(O)p-($C_0$–$C_8$)alkyl-aryl,
—($C_0$–$C_8$)alkyl-S(O)p-($C_0$–$C_8$)alkyl-substituted aryl,
—($C_1$–$C_4$)alkyl-aryl-($C_0$–$C_8$)alkyl-aryl-[S(O)p-($C_0$–$C_8$)alkyl],
—($C_0$–$C_8$)alkyl-S(O)p-($C_0$–$C_8$)alkyl-biaryl,
—($C_0$–$C_8$)alkyl-O—($C_0$–$C_8$)alkyl-aryl,
—($C_0$–$C_8$)alkyl-S(O)p-($C_0$–$C_8$)alkyl-substituted aryl,
—($C_1$–$C_4$)alkyl-aryl-($C_0$–$C_8$)alkyl-aryl-[O—($C_0$–$C_8$)alkyl],
—($C_0$–$C_8$)alkyl-O—($C_0$–$C_8$)alkyl-biaryl,
—($C_0$–$C_8$)alkyl-O—($C_0$–$C_8$)alkyl-substituted aryl,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl;
$R^2$ is selected from H, —$CO_2R^5$, —$CONR^6R^5$, —$CONR^6$($OR^5$), -alkyl, -alkylaryl, -alkylheteroaryl, -alkylheterocyclic, -aryl, -heteroaryl or -heterocyclic which is substituted with one or more substituents selected from:
hydrogen, halo, hydroxy, alkoxy, aryloxy, (such as phenoxy), amino, mono-alkylamino, di-alkylamino, acylamino (such as acetamido and benzamido), arylamino, guanidino, N-methyl imidazolyl, imidazolyl, indolyl, mercapto, lower alkylthio, arylthio (such as phenylthio), carboxy, sulfonamido, carboxamido, or carboalkoxy;
$R^3$ and $R^4$ are H;
$R^5$ is selected from:
—($CHR^1Y$)$_n$—$R^9$, —$C(R^7R^8)_n$—W—$C(R^7R^8)_m$—$R^9$,
—$C(R^7R^8)_m$—$R^9$, $C(R^7R^8)_m$—aryl,
—$C(R^7R^8)_m$-heteroaryl,
—$C(R^7R^8)_m$-heterocyclic;
$R^6$ is selected from:
H, alkyl-, —($C_1$–$C_6$)alkyl-aryl,
—($C_1$–$C_6$)alkyl-heteroaryl,
—($C_1$–$C_6$)alkyl-heterocyclic,
—($C_1$–$C_6$)alkyl-acyl;
Alternatively, $R^5$ and $R^6$ may form a 3 to 8 membered ring optionally unsaturated containing from 1 to 3 heteroatoms selected from —O, —$NR^6$, —S(O)p, or an acyl group, optionally fused to an aryl ring;
$R^7$ and $R^8$ may be selected independently from:
H, $R^1$, or form a 3 to 7 membered substituted ring with 0–3 unsaturations,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl,
optionally containing —O—, —S(O)p, —$NR^6$, optionally fused to a substituted aryl ring,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboxamido or aryl;

$R^9$ is H, alkyl, cycloalkyl, 5 or 6 membered ring optionally containing from 1 to 2 N, O or S(O)p, optionally substituted with —OH, —O—($C_1$–$C_6$)alkyl, —O-acyl-alkyl, $NHR^{10}$, or aryl;
$R^{10}$ is H or an optionally substituted alkyl group;
$R^{11}$ is hydrogen, alkyl of from 1 to 6 C atoms which include branched, cyclic and unsaturated alkyl groups, substituted lower alkyl;
wherein the substituent is selected from:
hydrogen, halo, hydroxy, alkoxy, aryloxy, such as phenoxy, amino, di-alkylamino, acylamino such as acetamido and benzamido, arylamino, guanidino, imidazolyl, indolyl, mercapto, loweralkylthio, arylthio (such as phenylthio) carboxy, carboxamido, carbo-alkoxy, and sulfonamide;
—($C_1$–$C_4$)alkyl-aryl,
—($C_1$–$C_8$)alkyl-substituted aryl,
wherein the substituent is selected from:
hydrogen, halo, hydroxy, alkoxy, aryloxy, such as phenoxy, amino, di-alkylamino, acylamino such as acetamido and benzamido, arylamino, guanidino, imidazolyl, indolyl, mercapto, loweralkylthio, arylthio (such as phenylthio) carboxy, carboxamido, carbo-alkoxy, and sulfonamide;
$R^{11a}$ is H, —$SO_2$—($C_1$–$C_6$)alkyl, —$SO_2$—($C_1$–$C_6$)alkyl substituted aryl, —$SO_2$-aryl, —$SO_2$-substituted heteroaryl, —$COR^9$, —$CO_2$t—Bu, —$CO_2$Bn,
wherein the substituent is selected from:
hydrogen, $C_1$–$C_5$ alkyl, hydroxy, halo, alkoxy, amino, mono-alkylamino, di-alkylamino, acylamino, thio, thioalkyl, carboxy, carboxamido or aryl;
$R^{12}$ is selected from: H, aryl, ($C_1$ to $C_{10}$)alkyl-, aryl—($C_1$ to $C_6$)alkyl,
$C_3$ to $C_{11}$ cycloalkyl,
$C_3$ to $C_{10}$ alkylcarbonyloxyalkyl,
$C_3$ to $C_{10}$ alkoxycarbonyloxyalkyl,
$C_2$ to $C_{10}$ alkoxycarbonyl,
$C_5$ to $C_{10}$ cycloalkylcarbonyloxyalkyl,
$C_5$ to $C_{10}$ cycloalkoxycarbonyloxyalkyl,
$C_5$ to $C_{10}$ cycloalkoxycarbonyl,
aryloxycarbonyl, aryloxycarbonyloxy($C_1$ to $C_6$ alkyl), arylcarbonyloxy($C_1$ to $C_6$ alkyl),
$C_5$ to $C_{12}$ alkoxyalkylcarbonyloxyalkyl,
[5-($C_1$–$C_5$ alkyl)-1,3-dioxa-cyclopenten-2-one-yl] methyl,
(5-aryl-1,3-dioxa-cyclopenten-2-one-yl)methyl,
($R^{17}$)($R^{17a}$)N-($C_1$–$C_{10}$ alkyl)-, —$CH(R^{13})OC(=O)R^{14}$, —$CH(R^{13})OC(=O)OR^{15}$, or

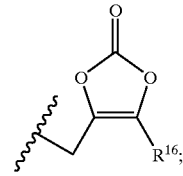

wherein
$R^{13}$ is H or $C_1$–$C_4$ linear alkyl;
$R^{14}$ is selected from:
H,
$C_1$–$C_8$ alkyl or $C_3$–$C_8$ cycloalkyl, said alkyl or cycloalkyl being substituted with 1–2 groups independently selected from:

$C_1$-$C_4$ alkyl,
$C_3$-$C_8$ cycloalkyl
$C_1$-$C_5$ alkoxy,
aryl substituted with 0–2 groups independently selected from:
  halogen, phenyl, $C_1$-$C_6$ alkyl, $C_1$-$C_6$ alkoxy, $NO_2$, —S($C_1$-$C_5$ alkyl), —S(=O)($C_1$-$C_5$ alkyl), —$SO_2$($C_1$-$C_5$ alkyl), —OH, —N($R^{17}$)($R_{17a}$), —$CO_2R^{17a}$, —C(=O)N($R^{17}$)($R^{17a}$), or —$C_vF_w$ where v=1 to 3 and w=1 to (2v+1),
aryl substituted with 0–2 groups independently selected from:
  halogen, phenyl, $C_1$-$C_6$ alkyl, $C_1$-$C_6$ alkoxy, $NO_2$, —S($C_1$-$C_5$ alkyl), —S(=O)($C_1$-$C_5$ alkyl), —$SO_2$($C_1$-$C_5$ alkyl), —OH, —N($R^{17}$)($R^{17a}$), $CO_2R^{17a}$, —C(=O)N($R^{17}$)($R^{17a}$), or —$C_vF_w$ where v=1 to 3 and w=1 to (2v+1);

$R^{15}$ is selected from:
$C_1$-$C_8$ alkyl, $C_3$-$C_8$ cycloalkyl, said alkyl or cyzloalkyl being substituted with 1 2 groups independently selected from:
  $C_1$-$C_4$ alkyl,
  $C_3$-$C_8$ cycloalkyl,
  $C_1$-$C_5$ alkoxy,
  aryl substituted with 0–2 groups independently selected from:
    halogen, phenyl, $C_1$-$C_6$ alkyl, $C_1$-$C_6$ alkoxy, $NO_2$, —S($C_1$-$C_5$ alkyl), —S(=O)($C_1$-$C_5$ alkyl), —$SO_2$($C_1$-$C_5$ alkyl), —OH, —N($R^{17}$)($R^{17a}$), —$CO_2R^{17a}$, —C(=O)N($R^{17}$)($R^{17a}$), or —$C_vF_w$ where v=1 to 3 and w=1 to (2v+1),
  aryl substituted with 0–2 groups independently selected from:
    halogen, phenyl, $C_1$-$C_6$ alkyl, $C_1$-$C_6$ alkoxy, $NO_2$, —S($C_1$-$C_5$ alkyl), —S(=O)($C_1$-$C_5$ alkyl), —$SO_2$($C_1$-$C_5$ alkyl), —OH, —N($R^{17}$)($R^{17a}$), —$CO_2R^{17a}$, —C(=O)N($R^{17}$)($R^{17a}$), or —$C_vF_w$ where v=1 to 3 and w=1 to (2v+1);

$R^{16}$ is $C_1$-$C_4$ alkyl, benzyl, or phenyl;

Combinations of A, B and D, and/or variables are permissable only if such combinations result in stable compounds (as defined herein).

A can be; —$(CH_2)_m$—, —O—$(CH_2)_m$—, —S—$(CH_2)_m$—, —$NR^6$—$(CH_2)_m$—;
B can be a bond or selected from —NH—, —$NR^{11}$—, —$NR^{11a}$—, —O—, —S(O)p-$C_1$-$C_6$alkyl-NH— $C_1$-$C_6$alkyl-, $C_1$-$C_6$alkyl-$NR^{11}$—$C_1$-$C_6$alky-, $C_1$-$C_6$—NH-aryl-, —O—$C_1$-$C_6$alkyl-, $C_1$-$C_6$alkyl-O-aryl-, —S—C1-C6alkyl-, C1-C6alkyl-S-aryl-, $C_1$-$C_6$alkyl-, $C_1$-$C_6$alkenyl-, $C_1$-$C_6$alkynyl-, —CONH—, —$CONR^{11}$, —NHCO—, —$NR^{11}CO$—, —OCO—, —COO—, —OCO2—, —$R^{11}NCONR^{11}$—, HNCONH—, —$OCONR^{11}$—, —$NR^{11}COO$—, —$HNSO_2$—, —$SO_2NH$—, aryl, cycloalkyl, heterocycloalkyl, —$R^{11}NCSNR^{11}$—, —HNCSNH, —$OCSNR^{11}$—, —$NR^{11}CSO$—, —HNCNNH—, and a peptide bond mimic;

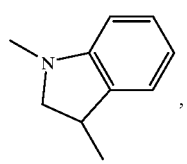 , 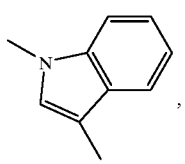 ,

-continued

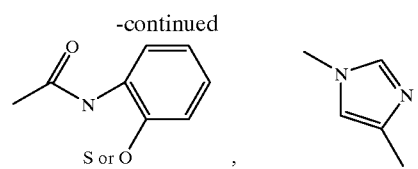

S or O

D is —$(CH_2)m$—;
p can be 0, 1 or 2;
m is an integer from 0 to 3;
n is an integer from 1 to 4;
W is —O—, S(O)p or $NR^{10}$;
Y is selected from: —$CONR^{10}$—, —$NR^{10}CO$—, —$SO_2NR^{10}$—, —$NR^{10}SO_2$—, a peptide bond mimic, a 5 membered heterocyclic ring saturated, unsaturated or partially unsaturated containing from 1 to 4 heteroatoms selected from N,O or S, with the proviso that the size of the macrocycle encompased in formula I by —A—B—D—C($R^2$)($R^3$)—Y—C($R^1$)—C(U)($R^4$)—, be connected by no less than 11 atoms and no more than 22 atoms to form the cycle.

Only substituents that form stable compounds are claimed for formula I.

[9] The most preferred compounds of the present invention are compounds of formula Ia, Ib, Ic and Id where, Formula IV IVa

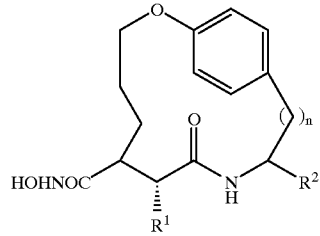

IVb

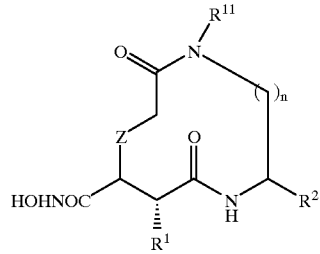

IVc

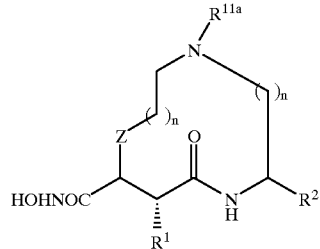

-continued

IVd

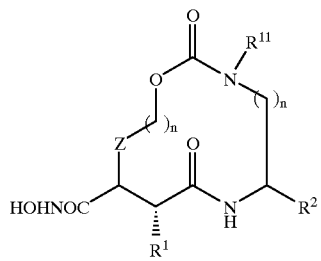

or pharmaceutically acceptable salts or prodrug forms thereof, wherein;

$R^1$ is selected from:
H, —$(C_0-C_6)$alkyl-S(O)p-$(C_1-C_6)$alkyl,
—$(C_0-C_6)$alkyl-O—$(C_1-C_6)$alkyl,
—$(C_0-C_6)$alkyl-S(O)p-$(C_0-C_6)$alkyl-aryl,
—$(C_0-C_6)$alkyl-O—$(C_0-C_6)$alkyl-aryl,
alkyl of from 1 to 20 carbon atoms which include branched, cyclic and unsaturated alkyl groups, substituted alkyl
wherein the substituent is selected from;
hydrogen, halo, hydroxy, alkoxy, aryloxy, (such as phenoxy), amino, mono- alkylamino, di-alkylamino, acylamino (such as acetamido and benzamido), arylamino, guanidino, N-methyl imidazolyl, imidazolyl, indolyl, mercapto, alkylthio, arylthio (such as phenylthio), carboxy, carboxamido, carbo alkoxy, or sulfonamido,
—$(C_0-C_8)$alkyl-aryl,
—$(C_0-C_8)$alkyl-substituted aryl,
—$(C_0-C_8)$aryl-$(C_1-C_4)$alkyl-aryl,
—$(C_1-C_8)$alkyl-biaryl,
—$(C_0-C_8)$alkyl-S(O)p-$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[S(O)p-$(C_0-C_8)$alkyl],
—$(C_0-C_8)$alkyl-S(O)p-$(C_0-C_8)$alkyl-biaryl,
—$(C_0-C_8)$alkyl-O—$(C_0-C_8)$alkyl-aryl,
—$(C_0-C_8)$alkyl-S(O)p-$(C_0-C_8)$alkyl-substituted aryl,
—$(C_0-C_4)$alkyl-aryl-$(C_0-C_8)$alkyl-aryl-[O—$(C_0-C_8)$alkyl],
—$(C_0-C_8)$alkyl-O—$(C_0-C_8)$alkyl-biaryl,
—$(C_0-C_8)$alkyl-O—$(C_0-C_8)$alkyl-substituted aryl,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;

$R^2$ is selected from H, —$CO_2R^5$, —$CONR^6R^5$, —$CONR^6$($OR^5$), -alkyl, -alkylaryl, -alkylheteroaryl, -alkylheterocyclic, -aryl, -heteroaryl or -heterocyclic which is substituted with one or more substituents selected from:
hydrogen, halo, hydroxy, alkoxy, aryloxy, (such as phenoxy), amino, mono-alkylamino, di-alkylamino, acylamino (such as acetamido and benzamido), arylamino, guanidino, N-methyl imidazolyl, imidazolyl, indolyl, mercapto, lower alkylthio, arylthio (such as phenylthio), carboxy, sulfonamido, carboxamido, or carboalkoxy;

$R^5$ is selected from:
—$(CHR^1Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
—$C(R^7R^8)_m CONR^7R^8$,
—$C(R^7R^8)_m$-heteroaryl,
—$C(R^7R^8)_m$-heterocyclic;

$R^6$ is selected from:
H, alkyl-, —[$(C_1-C_6)$alkyl-aryl,
—$(C_1-C_6)$alkyl-heteroaryl,
—$(C_1-C_6)$alkyl-heterocyclic,
—$(C_1-C_6)$alkyl-acyl;

Alternatively, $R^5$ and $R^6$ may form a 3 to 8 membered ring optionally unsaturated containing from 1 to 3 heteroatoms selected from —O, —$NR^6$, —S(O)p, or an acyl group, optionally fused to an aryl ring;

$R^7$ and $R^8$ may be selected independently from:
H, $R^1$, or form a 3 to 7 membered substituted ring with 0–3 unsaturations,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl,
optionally containing —O—, —S(O)p, —$NR^6$, optionally fused to a substituted aryl ring,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboxamido or aryl;

$R^9$ is H, alkyl, cycloalkyl, 5 or 6 membered ring optionally containing from 1 to 2 N, O or S(O)p, optionally substituted with —OH, —O—$(C_1-C_6)$alkyl, —O-acyl-alkyl, $NHR^{10}$, or aryl;

$R^{10}$ is H or an optionally substituted alkyl group;

$R^{11}$ is hydrogen, alkyl of from 1 to 6 C atoms which include branched, cyclic and unsaturated alkyl groups, substituted lower alkyl;
wherein the substituent is selected from:
hydrogen, halo, hydroxy, alkoxy, aryloxy, such as phenoxy, amino, di-alkylamino, acylamino such as acetamido and benzamido, arylamino, guanidino, imidazolyl, indolyl, mercapto, loweralkylthio, arylthio (such as phenylthio) carboxy, carboxamido, carbo-alkoxy, and sulfonamide;
—$(C_1-C_4)$alkyl-aryl,
—$(C_1-C_8)$alkyl-substituted aryl,
wherein the substituent is selected from:
hydrogen, halo, hydroxy, alkoxy, aryloxy, such as phenoxy, amino, di-alkylamino, acylamino such as acetamido and benzamido, arylamino, guanidino, imidazolyl, indolyl, mercapto, loweralkylthio, arylthio (such as phenylthio) carboxy, carboxamido, carbo-alkoxy, and sulfonamide;

$R^{11a}$ is H, —$SO_2$—$(C_1-C_6)$alkyl, —$SO_2$—$(C_1-C_6)$alkyl substituted aryl, —$SO_2$-aryl, —$SO_2$-substituted heteroaryl, —$COR^9$, —$CO_2$t-Bu, —$CO_2$Bn,
wherein the substituent is selected from:
hydrogen, $C_1-C_5$ alkyl, hydroxy, halo, alkoxy, amino, mono-alkylamino, di-alkylamino, acylamino, thio, thioalkyl, carboxy, carboxamido or aryl;

m is an integer from 0 to 5;
n is an integer from 1 to 5;
p can be 0, or 2;
W is —O—, S(O)p or $NR^{10}$;
Z is $CH_2$ or O Y is selected from: —CONR$^{10}$—, —NR$^{10}$CO—, —SO$_2$NR$^{10}$—, —NR$^{10}$SO$_2$—, a peptide bond mimic, a 5 membered heterocyclic ring saturated, unsaturated or partially unsaturated containing from 1 to 4 heteroatoms selected from N,O or S, Only substituents that form stable compounds are claimed for formula Ia to Id.

[10] Most preferred compounds of the present invention include compounds of formula I, or a pharmaceutically acceptable salt or prodrug form thereof, selected from the following:

2S,5R,6S-3-aza-4-oxo-10-oxa-5-isobutyl-2-(N-methylcarboxamido)-[10]paracyclophane-6-N-hydroxycarboxamide;

2S,5R,6S-3-aza-4-oxo-10-oxa-5-isobutyl-2-(carboxymethyl)-[10]paracyclophane-6-N-hydroxycarboxamide;

2S,5R,6S-3-aza-4-oxo-10-oxa-5-isobutyl-2-(N-benzylcarboxamido)-[10]paracyclophane-6-N-hydroxycarboxamide;

2S,5R,6S-3-aza-4-oxo-10-oxa-5-isobutyl-2-(hydroxymethyl)-[10]paracyclophane-6-N-hydroxycarboxamide;

2S,5R,6S-3-aza-4-oxo-10-oxa-5-isobutyl-2-(L-alanine-N-methylamide)-[10]paracyclophane-6-N-hydroxycarboxamide;

2S,5R,6S-3-aza-4-oxo-10-oxa-5-isobutyl-2-[L-(O-methyl)tyrosine-N-methylamide]-[10]paracyclophane-6-N-hydroxycarboxamide;

2S,5R,6S-3-aza-4-oxo-10-oxa-5-isobutyl-2-[L-(O-tert-butyl)serine-N-methylamide]-[10]paracyclophane-6-N-hydroxycarboxamide;

2S,5R,6S-3-aza-4-oxo-10-oxa-5-isobutyl-2-(L-serine-N-methylamide)-[10]paracyclophane-6-N-hydroxycarboxamide;

2S,5R,6S-3-aza-4-oxo-10-oxa-5-isobutyl-2-(glycine-N-methylamide)-[10]paracyclophane-6-N-hydroxycarboxamide;

2S,5R,6S-3-aza-4-oxo-10-oxa-5-isobutyl-2-(D-alanine-N-methylamide)-[10]paracyclophane-6-N-hydroxycarboxamide;

2S,5R,6S-3-aza-4-oxo-10-oxa-5-isobutyl-2-(beta-alanine-N-methylamide)-[10]paracyclophane-6-N-hydroxycarboxamide;

2S,5R,6S-3-aza-4-oxo-10-oxa-5-isobutyl-2-[D-(O-tert-butyl)serine-N-methylamide]-[10]paracyclophane-6-N-hydroxycarboxamide;

2S,5R,6S-3-aza-4-oxo-10-oxa-5-isobutyl-2-(D-serine-N-methylamide)-[10]paracyclophane-6-N-hydroxycarboxamide;

2S,5R,6S-3-aza-4-oxo-10-oxa-5-isobutyl-2-(L-lysine-N-methylamide)-[10]paracyclophane-6-N-hydroxycarboxamide;

2S,5R,6S-3-aza-4-oxo-10-oxa-5-isobutyl-2-(L-valine-N-methylamide)-[10]paracyclophane-6-N-hydroxycarboxamide;

2S,5R,6S-3-aza-4-oxo-10-oxa-5-isobutyl-2-[(2-pyridyl)ethylcarboxamido]-[10]paracyclophane-6-N-hydroxycarboxamide trifluoroacetate;

2S,5R,6S-3-aza-4-oxo-10-oxa-5-isobutyl-2-[(4-methyl)piperazinylcarboxamido]-[10]paracyclophane-6-N-hydroxycarboxamide;

2S,5R,6S-3-aza-4-oxo-10-oxa-5-isobutyl-2-(2-benzimidazolyl)-[10]paracyclophane-6-N-hydroxycarboxamide;

2S,5R,6S-3-aza-4-oxo-10-oxa-5-isobutyl-2-[(2-imidazolyl)carboxamido]-[10]paracyclophane-6-N-hydroxycarboxamide;

2S,5R,6S-3-aza-4-oxo-10-oxa-5-isobutyl-2-[(2-benzimidazolyl)methylcarboxamido]-[10]paracyclophane-6-N-hydroxycarboxamide;

2S,5R,6S-3-aza-4-oxo-10-oxa-5-isobutyl-2-[(3-imidazolyl)propylcarboxamido]-[10]paracyclophane-6-N-hydroxycarboxamide;

2S,5R,6S-3-aza-4-oxo-10-oxa-5-isobutyl-2-[2-(4-aminosulfonyLphenyl)ethylcarboxamido]-[10]paracyclophane-6-N-hydroxycarboxamide;

2S,5R,6S-3-aza-4-oxo-10-oxa-5-isobutyl-2-(glycine-N,N-dimethylamide)-[10]paracyclophane-6-N-hydroxycarboxamide;

2S,5R,6S-3-aza-4-oxo-10-oxa-5-isobutyl-2-(1-adamantylcarboxamido)-[10]paracyclophane-6-N-hydroxycarboxamide;

2S,5R,6S-3-aza-4-oxo-10-oxa-5-isobutyl-2-[(4-aminoindazolyl)carboxamido]-[10]paracyclophane-6-N-hydroxycarboxamide;

2S,5R,6S-3-aza-4-oxo-10-oxa-5-isobutyl-2-(N,N-diethylcarboxamido)-[10]paracyclophane-6-N-hydroxycarboxamide;

2S,5R,6S-3-aza-4-oxo-10-oxa-5-isobutyl-2-(N-isopropylcarboxamido)-[10]paracyclophane-6-N-hydroxycarboxamide;

2S,5R,6S-3-aza-4-oxo-10-oxa-5-isobutyl-2-(N-cyclopropylcarboxamido)-[10]paracyclophane-6-N-hydroxycarboxamide;

2S,5R,6S-3-aza-4-oxo-10-oxa-5-isobutyl-2-(N-tert-butylcarboxaimido)-[10]paracyclophane-6-N-hydroxycarboxamide;

2S,5R,6S-3-aza-4-oxo-10-oxa-5-isobutyl-2-[glycine-(N-isopropyl)amide]-[10]paracyclophane-6-N-hydroxycarboxamide;

2S,5R,6S-3-aza-4-oxo-10-oxa-5-isobutyl-2-[glycine-(N-ethyl)amide]-[10]paracyclophane-6-N-hydroxycarboxarmide;

2S,5R,6S-3-aza-4-oxo-10-oxa-5-isobutyl-2-[glycine-(N-cyclopropyl)amide]-[10]paracyclophane-6-N-hydroxycarboxamide;

2S,5R,6S-3-aza-4-oxo-10-oxa-5-isobutyl-2-[glycine-(N-tert-butyl)amide]-[10]paracyclophane-6-N-hydroxycarboxamide;

2S,5R,6S-3-aza-4-oxo-10-oxa-5-isobutyl-2-[glycine-(N-cyclobutyl)amide]-[10]paracyclophane-6-N-hydroxycarboxcamide;

2S,5R,6S-3-aza-4-oxo-10-oxa-5-isobutyl-2-[glycine-(N-morpholino)amide]-[10]paracyclophane-6-N-hydroxycarboxamide;

2S,5R,6S-3-aza-4-oxo-10-oxa-5-isobutyl-2-[glycine-(N-2-hydroxydimethylethyl)amide]-[10]paracyclophane-6-N-hydroxycarboxamide;

2S,5R,6S-3-aza-4-oxo-10-oxa-5-isobutyl-2-[glycine-(N-ethylmethylpropyl)amide]-[10]paracyclophane-6-N-hydroxycarboxamide;

2S,5R,6S-3-aza-4-oxo-10-oxa-5-isobutyl-2-[glycine-(N-dimethylpropyl)amide]-[10]paracyclophane-6-N-hydroxycarboxamide;

2S,5R,6S-3-aza-4-oxo-10-oxa-5-isobutyl-2-[glycine-(N-(di-2-hydroxymethyl)ethylamide]-[10]paracyclophane-6-N-hydroxycarboxarmide;

2S,5R,6S-3-aza-4-oxo-10-oxa-5-isobutyl-2-[glycine-(4-hydroxypiperidine)amide]-[10]paracyclophane-6-N-hydroxycarboxamide;

2S,5R,6S-3-aza-4-oxo-10-oxa-5-isobutyl-2-(2-benzimidazolecarboxamido)-[10]paracyclophane-6-N-hydroxycarboxamide;

2S,5R,6S-3-aza-4-oxo-10-oxa-5-isobutyl-2-[S-(methyl)-2-phenylmethylcarboxamido]-[10]paracyclophane-6-N-hydroxycarboxamide;

4S,7R,8S-5-aza-6-oxo-12-oxa-7-isobutyl-2-(carboxymethyl)-[12]paracyclophane-8-N-hydroxycarboxamide;

4S,7R,8S-5-aza-6-oxo-12-oxa-7-isobutyl-2-(N-methylcarboxamido)-[12]paracyclophane-8-N-hydroxycarboxamide;

4S,7R,8S-5-aza-6-oxo-12-oxa-7-isobutyl-2-(glycine-N-methlamide)-[12]paracyclophane-8-N-hydroxycarboxamide;

2S,3R,6S-10-t-Butoxycarbonyl-5,10-diaza-2-(N-hydroxycarboxanmido)-6-(N-methylcarboxamido)-1-oxa-4-oxo-3-(3-phenylprop-1-yl)cyclotetradecane;

2S,3R,6S-5,10-Diaza-2-(N-hydroxycarboxarmide)-6-(N-methylcarboxamido)-1-oxa-4-oxo-3-(3-phenylprop-1-yl)cyclotetradecane hydrochloride;

2S,3R,6S-10-Acetyl-5,10-diaza-2-(N-hydroxycarboxarmide)-6-(N-methylcarboxamido)-1-oxa-4-oxo-3-(3-phenylprop-1-yl)cyclotetradecane;

2S,3R,6S-10-Benzenesulfonyl-5,10-diaza-2-(N-hydroxycarboxarmide)-6-(N-methylcarboxamido)-1-oxa-4-oxo-3-(3-phenylprop-1-yl)cyclotetradecane;

2S,3R,6S,12(R,S)-10-Acetyl-5,10-diaza-2-(N-hydroxycarboxamido)-6-(N-methylcarboxamido)-12-methyl-1-oxa-4-oxo-3-(3-phenylprop-1-yl)cyclotridecane;

2S,3R,6S-3-aza-4-oxo-10-oxa-5-hexyl-2-(carboxymethyl)-[10]paracyclophane-6-N-hydroxycarboxamide;

2S,3R,6S-3-aza-4-oxo-10-oxa-5-hexyl-2-(hydroxycarboxyl)-[10]paracyclophane-6-N-hydroxycarboxamide;

2S,3R,6S-3-aza-4-oxo-10-oxa-5-hexyl-2-((2-methoxylethyloxy)carboxyl)-[10]paracyclophane-6-N-hydroxycarboxamide;

2S,3R,6S-3-aza-4-oxo-10-oxa-5-hexyl-2-((2-phenylethyloxy)carboxy)-[10]paracyclophane-6-N-hydroxycarboxamide;

2S,3R,6S-3-aza-4-oxo-10-oxa-5-hexyl-2-(1-(n-methylcarboximido)methylcarboxyl)-[10]paracyclophane-6-N-hydroxycarboxamide;

2S,3R,6S-3-aza-4-oxo-10-oxa-5-hexyl-2-(2-(N-methylaminosulfonyl)ethylcarboxamido)-[10]paracyclophane-6-N-hydroxycarboxamide;

2S,3R,6S-3-aza-4-oxo-10-oxa-5-hexyl-2-(4-(N-methylaminosulfonyl)butylcarboxamido)-[10]paracyclophane-6-N-hydroxycarboxamide;

2S,3R,6S-3-aza-4-oxo-10-oxa-5-hexyl-2-(2-(N-methylaminosulfonyl)hexyllcarboxamido)-[10]paracyclophane-6-N-hydroxycarboxamide;

2S,3R,6S-3-aza-4-oxo-10-oxa-5-hexyl-2-(2-(carbomethoxy)ethylcarboxamido)-[10]paracyclophane-6-N-hydroxycarboxamide;

2S,3R,6S-3-aza-4-oxo-10-oxa-5-hexyl-2-(2-(hydroxycarbonyl)ethylcarboxamido)-[10]paracyclophane-6-N-hydroxycarboxamide;

2S,3R,6S-3-aza-4-oxo-10-oxa-5-hexyl-2-(L-ornithine(4-t-butoxycarbonyl)carboxymethyl)-[10]paracyclophane-6-N-hydroxycarboxamide;

2S,3R,6S-3-aza-4-oxo-10-oxa-5-hexyl-2-(L-ornithinecarboxymethyl)-[10]paracyclophane-6-N-hydroxycarboxamide hydrochloride;

2S,3R,6S-3-aza-4-oxo-10-oxa-5-hexyl-2-(L-ornithine(4-t-butoxycarbonyl)-N-methylamide)-[10]paracyclophane-6-N-hydroxycarboxamide;

2S,3R,6S-3-aza-4-oxo-10-oxa-5-hexyl-2-(L-ornithine-N-methylamide)-[10]paracyclophane-6-N-hydroxycarboxamide hydrochloride;

2S,3R,6S-3-aza-4-oxo-10-oxa-5-hexyl-2-(L-lysine carboxamide)-[10]paracyclophane-6-N-hydroxycarboxamide;

2S,3R,6S-3-aza-4-oxo-10-oxa-5-hexyl-2-(L-serine(O-tert-butyl)-N-methylamide)-[10]paracyclophane-6-N-hydroxycarboxamide;

2S,3R,6S-3-aza-4-oxo-10-oxa-5-hexyl-2-(L-alanine-N-methylamide)-[10]paracyclophane-6-N-hydroxycarboxamide;

2S,3R,6S-3-aza-4-oxo-10-oxa-5-hexyl-2-(D-alanine-N-methylamide)-[10]paracyclophane-6-N-hydroxycarboxamide;

2S,3R,6S-3-aza-4-oxo-10-oxa-5-hexyl-2-(glycine-N-methylamide)-[10]paracyclophane-6-N-hydroxycarboxamide;

2S,3R,6S-3-aza-4-oxo-10-oxa-5-hexyl-2-(benzylcarboxamido)-[10]paracyclophane-6-N-hydroxycarboxamide;

2S,3R,6S-3-aza-4-oxo-10-oxa-5-hexyl-2-(phenylmethylcarboxamido)-[10]paracyclophane-6-N-hydroxycarboxamide;

2S,3R,6S-3-aza-4-oxo-10-oxa-5-hexyl-2-(diphenylethyl carboxamido)-[10]paracyclophane-6-N-hydroxycarboxamide;

2S,3R,6S-3-aza-4-oxo-10-oxa-5-hexyl-2-(2-(2-pyridyl)ethycarboxamido)-[10]paracyclophane-6-N-hydroxycarboxcamide;

2S,3R,6S-3-aza-4-oxo-10-oxa-5-hexyl-2-(2-(4-sulfonylaminophenyl)ethylcarboxamido)-[10]paracyclophane-6-N-hydroxycarboxamide;

2S,3R,6S-3-aza-4-oxo-10-oxa-5-hexyl-2-(2-(3,4-dimethoxyphenyl)ethylcarboxamido)-[10]paracyclophane-6-N-hydroxycarboxamide;

2S,3R,6S-3-aza-4-oxo-10-oxa-5-hexyl-2-(2-(4-morpholino)ethylcarboxamido)-[10]paracyclophane-6-N-hydroxycarboxamide;

2S,3R,6S-3-aza-4-oxo-10-oxa-5-hexyl-2-(3-(4-morpholino)propylcarboxamido)-[10]paracyclophane-6-N-hydroxycarboxamide hydrochloride;

2S,3R,6S-3-aza-4-oxo-10-oxa-5-hexyl-2-(3-(1-imidazolyl)propylcarboxamido)-[10]paracyclophane-6-N-hydroxycarboxamide;

2S,3R,6S-3-aza-4-oxo-10-oxa-5-hexyl-2-(3-(1-imidazolyl)propylcarboxamido)-[10]paracyclophane-6-N-hydroxycarboxamide trifluoroacetate;

2S,3R,6S-3-aza-4-oxo-10-oxa-5-hexyl-2-(cyclohexylcarboxamido)-[10]paracyclophane-6-N-hydroxycarboxamide;

2S,3R,6S-3-aza-4-oxo-10-oxa-5-hexyl-2-(4methyl-piperazine-1-ylcarboxamido))-[10]paracyclophane-6-N-hydroxycarboxamide;

2S,3R,6S-3-aza-4-oxo-10-oxa-5-hexyl-2-(dimethylcarboxamido)-[10]paracyclophane-6-N-hydroxycarboxamide;

2S,13S,14R-1,7-diaza-8,15-dioxo-9-oxa-14-isobutyl-7-methyl-2-(N-methylcarboxamido)-cyclopentadecane-13-N-hydroxycarboxamide;

2S,13S,14R-1,7-diaza-8,15-dioxo-9-oxa-14-isobutyl-7-methyl-2-[N-(2-pyridyl)methylcarboxamido]-cyclopentadecane-13-N-hydroxycarboxamide trifluoroacetate;

2S,13S,14R-1,7-diaza-8,15-dioxo-9-oxa-14-isobutyl-7-methyl-2-[2-(5-methylthiazolyl)carboxamido]-cyclopentadecane-13-N-hydroxycarboxamide;

2S,13S,14R-1,7-diaza-8,15-dioxo-9-oxa-14-isobutyl-7-methyl-2-[(2-pyridyl)carboxamido]-cyclopentadecane-13-N-hydroxycarboxamide;

2S,13S,14R-1,7-diaza-8,15-dioxo-9-oxa-14-isobutyl-7-methyl-2-[(3-pyridyl)carboxamido]-cyclopentadecane-13-N-hydroxycarboxamide;

2S,13S,14R-1,7-diaza-8,15-dioxo-9-oxa-14-isobutyl-7-methyl-2-[(4-pyridyl)carboxamido]-cyclopentadecane-13-N-hydroxycarboxamide;

2S,13S,14R-1,7-diaza-8,15-dioxo-9-oxa-14-isobutyl-7-methyl-2-[4-(N-ethoxycarbonyl)piperidinecarboxamido]-cyclopentadecane-13-N-hydroxycarboxamide;

2S,13S,14R-1,7-diaza-8,15-dioxo-9-oxa-14-isobutyl-7-methyl-2-[4-hydroxcyclohexylcarboxamido]-cycloentadecane-13-N-hydroxycarboxamide;

2S,13S,14R-1,7-diaza-8,15-dioxo-9-oxa-14-isobutyl-7-methyl-2-(glycine-N-methylamide)-cyclopentadecane-13-N-hydroxycarboxamide;

2S,13S,14R-1,7-diaza-8,15-dioxo-9-oxa-14-isobutyl-7-methyl-2-(glycine-N,N-dimethylamide)-cyclopentadecane-13-N-hydroxycarboxamide;

2S,13S,14R-1,7-diaza-8,15-dioxo-9-oxa-14-isobutyl-7-methyl-2-(glycine-2-pyridylamide)-cyclopentadecane-13-N-hydroxycarboxamide;

2S,13S,14R-1,7-diaza-8,15-dioxo-9-oxa-14-isobutyl-7-methyl-2-[glycine-2-(3,4,5,6-tetrahydropyridyl)amide]-cyclopentadecane-13-N-hydroxycarboxamide;

2S,13S,14R-1,7-diaza-8,15-dioxo-9-oxa-14-isobutyl-7-methyl-2-[glycine-N-(4-hydroxy)piperidineamide]-cyclopentadecane-13-N-hydroxyarboxamide;

2S,13S,14R-1,7-diaza-8,15-dioxo-9-oxa-14-isobutyl-7-methyl-2-[glycine-N-pyrolidineamide]-cyclopentadecane-13-N-hydroxycarboxamide;

2S,13S,14R-1,7-diaza-8,15-dioxo-9-oxa-14-isobutyl-7-methyl-2-[glycine-N-morpholinoamide]-cyclopentadecane-13-N-hydroxycarboxamide;

2S,13S,14R-1,7-diaza-8,15-dioxo-9-oxa-14-isobutyl-7-methyl-2-[glycine-(4-methyl)N-piperazinylamide]-cyclopentadecane-13-N-hydroxycarboxamide trifluoroacetate;

2S,13S,14R-1,7-diaza-8,15-dioxo-9-oxa-14-isobutyl-7-methyl-2-[glycine-2-(5-methyl)thiazolylamide]-cyclopentadecane-13-N-hydroxycarboxamide trifluoroacetate;

2S,13S,14R-1,7-diaza-8,15-dioxo-9-oxa-14-isobutyl-2-[glycine-N-morpholinoamide]-cyclopentadecane-13-N-hydroxycarboxamide;

2S,11S,12R-1,7-Diaza-8,13-dioxo-2-(N-methylcarboxamido)-12-isobutylcyclotridecane-11-(N-hydroxycarboxamide);

2S,11S,12R-1,7-Diaza-8,13-dioxo-12-isobutylcyclotridecane-2-(glycine N-methyl amide)-11-(N-hydroxycarboxamide);

2S,11S,12R-1,7-Diaza-8,13-dioxo-12-isobutylcyclotridecane-2-(N$^e$—H—L-lycine-a-N—H-amide trifluoroacetate)-11-(N-hydroxycarboxarmide);

2S,11S,12R-1,7-Diaza-8,13-dioxo-12-isobutylcyclotridecane-2-(L-alanine-a-N-methyl amide)-11-(N-hydroxycarboxamide);

2S,11S,12R-1,7-Diaza-8,13-dioxo-12-isobutylcyclotridecane-2-(b-alanine N-methyl amide)-11-(N-hydroxycarboxamide);

2S,11S,12R-1,7-Diaza-8,13-dioxo-2-(N-methylcarboxamido)-7-N-mesitylenesulfonyl-12-isobutyl-cyclotridecane-11-(N-hydroxycarboxamide);

2S,11S,12R-1,7-Diaza-8,13-dioxo-2-(N-methylcarboxamido)-7-N-t-butyloxycarbonyl-12-isobutyl-cyclotridecane-11-(N-hydroxycarboxamide);

2S,11S,12R-1,7-Diaza-8,13-dioxo-2-(N-methylcarboxamido)-12-isobutylcyclotridecane-11-(N-hydroxycarboxamide) hydrogen chloride;

5S,8R,9S-6-Aza-2,7-dioxo-5-(N-methylcarboxamido)-1-oxa-8-isobutylcyclcdodecane-9-(N-hydroxycarboxamide);

2S,11S,12R-7-N-Benzenesulfonyl-1,7-Diaza-8,13-dioxo-2-(N-methylcarboxamido)-12-isobutylcyclotridecane-11-(N-hydroxycarboxamide);

2S,11S,12R-1,7-Diaza-8,13-dioxo-2-(N-methylcarboxamido)-7-(p-amino-N-benzenesulfonyl)-12-isobutylcyclotridecane-11-(N-hydroxycarboxamide);

2S,11S,12R-1,7-Diaza-8,13-dioxo-2-(N-methylcarboxamido)-7-N-trifluoromethanesulfonyl-12-isobutylcyclotridecane-11-(N-hydroxycarboxamide);

2S,11S,12R-1,7-Diaza-8,13-dioxo-2-(N-methylcarboxamido)-7-N-(N-methyl-imidazolesulfon-4-yl)-12-isobutylcyclotridecane-11-(N-hydroxycar- boxamide);

2S,11S,12R-1,7-Diaza-8,13-dioxo-12-isobutylcyclotridecane-2-(L-norleucine-a-N-methyl amide)-11-(N-hydroxycarboxamide);

2S,11S,12R-1,7-Diaza-8,13-dioxo-12-isobutylcyclotridecane-2-(L-serine-a-N-methyl amide)-11-(N-hydroxycarboxamide);

2S,11S,12R-1,7-Diaza-8,13-dioxo-12-isobutylcyclotridecane-2-(glycine N-dimethyl amide)-11-(N-hydroxycarboxamide);

2S,11S,12R-1,7-Diaza-8,13-dioxo-12(R)-isobutyl-cyclotridecane-2(S)-(glycine N-1,2-ethylenediamine-N',N'-dimethyl amide)-11(S)-(N-hydroxycarboxamide);

2S,11S,12R-1,7-Diaza-8,13-dioxo-12-isobutylcyclotridecane-2-(glycine N-morpholino amide)-11-(N-hydroxycarboxamide);

2S,11S,12R-1,7-Diaza-8,13-dioxo-12-isobutylcyclotridecane-2-(L-leucine-a-N-methyl amide)-11-(N-hydroxycarboxamide);

2S,11S,12R-1,7-Diaza-8,13-dioxo-12-isobutylcyclotridecane-2-(L-threonine-a-N-methyl amide)-11-(N-hydroxycarboxamide);

2S,13S,14R-1,7-diaza-8,15-dioxo-9-oxa-14-isobutyl-2 [glycine-n-pentyl ester]-cyclopentadecane-13-N-hydroxycarboxamide 2S,13S,14R-1,7-diaza-8,15-dioxo-9-oxa-14-isobutyl-2[N-4-phenyl-1-butylamide]-cyclopentadecane-13-N-hydroxycarboxamide 2S,13S,14R-1,7-diaza-8,15-dioxo-9-oxa-14-isobutyl-2[5-methoxytryptamine]-cyclopentadecane-13-N-hydroxycarboxamide 2S,13S,14R-1,7-diaza-8,15-dioxo-9-oxa-14-isobutyl-2[1-(2,5-dimethoxyphenyl)-2-glycine amidoethanol]-cyclopentadecane-13-N-hydroxycarboxamide 2S,13S,14R-1,7-diaza-8,15-dioxo-9-oxa-14-isobutyl-2 [glycine-t-butyl ester]-cyclopentadecane-13-N-hydroxycarboxamide 2S,13S,14R-1,7-diaza-8,15-dioxo-9-oxa-14-isobutyl-2[L-glutamic acid-a, g-di-t-butyl ester]-cyclopentadecane-13-N-hydroxycarboxamide 2S,13S,14R-1,7-diaza-8,15-dioxo-9-oxa-14-isobutyl-2 [glycine]-cyclopentadecane-13-N-hydroxycarboxamide 2S,13S,14R-1,7-diaza-8,15-dioxo-9-oxa-14-isobutyl-2[N-2-phenyl-1-butylamide]-cyclopentadecane-13-N-hydroxycarboxamide 2S,13S,14R-1,7-diaza-8,15-dioxo-9-oxa-14-isobutyl-2[2-(2-aminoethyl)-1-methylpyrrole]-cyclopentadecane-13-N-hydroxycarboxcamide 2S,13S,14R-1,7-diaza-8,15-dioxo-9-oxa-14-isobutyl-2[2-(2-aminoethyl)benzenesulphonamide]-cyclopentadecane-13-N-hydroxycarboxamide 2S,13S,14R-1,7-diaza-8,15-dioxo-9-oxa-14-isobutyl-2[L-glutamic acid-g-cyclohexyl ester-N-methyl amide]-cyclopentadecane-13-N-hydroxycarboxamide 2S,13S,14R-1,7-diaza-8,15-dioxo-9-oxa-14-isobutyl-2[L-phenylalanine-p-fluoro-N-methylamide]-cyclopentadecane-13-N-hydroxycarboxamide 2S,13S,14R-1,7-diaza-8,15-dioxo-9-oxa-14-isobutyl-2[L-phenylalanine-p-methoxy-N-(S)-a-methylbenzylamide]-cyclopentadecane-13-N-hydroxycarboxamide 2S,13S,14R-1,7-diaza-8,15-dioxo-9-oxa-14-isobutyl-2[N-cyclohehylmethyl amide]-cyclopentadecane-13-N-hydroxycarboxamide 2S,13S,14R-1,7-diaza-8,15-dioxo-9-oxa-14-isobutyl-2[N-3-phenyl-1-propyl amide]-cyclopentadecane-13-N-hydroxycarboxamide 2S,13S,14R-1,7-diaza-8,15-dioxo-9-oxa-14-isobutyl-2[N-3,3-diphenylpropyl amide]-cyclopentadecane-13-N-hydroxycarboxamide 2S,13S,14R-1,7-diaza-8,15-dioxo-9-oxa-14-isobutyl-2[N-(2-aminoethylamino)ethyl pyrrolidine]-cyclopentadecane-13-N-hydroxycarboxamide 2S,13S,14R-1,7-diaza-8,15-dioxo-9-oxa-14-isobutyl-2[L-3-(2'-naphthl)alanine-N-methyl amide]-cyclopentadecane-13-N-hydroxycarboxamide 2S,13S,14R-1,7-diaza-8,15-dioxo-9-oxa-14-isobutyl-2[ethyl-4-amino-1-piperidine carboxylate]-cyclopentadecane-13-N-hydroxycarboxamide 2S,13S,14R-1,7-diaza-8,15-dioxo-9-oxa-14-isobutyl-2[5-methyl tryptamine]-cyclopentadecane-13-N-hydroxycarboxamide 2S,13S,14R-1,7-diaza-8,15-dioxo-9-oxa-14-isobutyl-2[N-4-trifluoromethylbenzyl amide]-cyclopentadecane-13-N-hydroxycarboxamide 2S,13S,14R-1,7-diaza-8,15-dioxo-9-oxa-14-isobutyl-2[L-glutamic acid]-cyclopentadecane-13-N-hydroxycarboxamide 2S,13S,14R-1,7-diaza-8,15-dioxo-9-oxa-14-isobutyl-2[2-(diethylamino)ethyl-4-amino benzoate]-cyclopentadecane-13-N-hydroxycarboxamide 2S,13S,14R-1,7-diaza-8,15-dioxo-9-oxa-14-isobutyl-2[6-fluorotryptamine]-cyclopentadecane-13-N-hydroxycarboxamide 2S,13S,14R1,7-diaza-8,15-dioxo-9-oxa-14-isobutyl-2[6-methoxy tryptamine]-cyclopentadecane-13-N-hydroxycarboxamide 2S,13S,14R-1,7-diaza-8,15-dioxo-9-oxa-14-isobutyl-2[tryptamine]-cyclopentadecane-13-N-hydroxycarboxamide 2S,13S,14R-1,7-diaza-8,15-dioxo-9-oxa-14-isobutyl-2-[N-(glycine-N-4-methylpiperazinamide)carboxamide]cyclopentadecane-13-N-hydroxycarboxamide;

2S,13S,14R-1,7-diaza-8,15-dioxo-9-oxa-14-isobutyl-2-[N-(L-alanine-N-morpholinamide)carboxamide]cyclopentadecane-13-N-hydroxycarboxamide;

2S,13S,14R-1,7-diaza-8,15-dioxo-9-oxa-14-isobutyl-2-[N-(L-valine-N-mnorpholinamide)carboxamide]cyclopentadecane-13-N-hydroxycarboxamide;

2S,13S,14R-1,7-diaza-8,15-dioxo-9-oxa-14-isobutyl-2-[N-(L-tert-butylglycine-N-morpholinamide)carboxamide]cyclopentadecane-13-N-hydroxycarboxamide;

2S,13S,14R-1,7-diaza-8,15-dioxo-9-oxa-14-isobutyl-2-[N-(b-alanine-N-morpholinamide)carboxamide]cyclopentadecane-13-N-hydroxycarboxamide;

2S,13S,14R-1,7-diaza-8,15-dioxo-9-oxa-14-isobutyl-2-[N-(ethoxycarbonyl-N-morpholinamide)carboxamide]cyclopentadecane-13-N-hydroxycarboxamide;

2S,13S,14R-1,7-diaza-8,15-dioxo-9-oxa-14-isobutyl-2-[N-(2-hydroxy-2-phenylethyl)carboxamide]cyclopentadecane-13-N-hydroxycarboxamide;

2S,13S,14R-1,7-diaza-8,15-dioxo-9-oxa-14-isobutyl-2-[N-(glycine-N-4-benzylpiperazinamide)carboxamide]cyclopentadecane-13-N-hydroxycarboxamide;

2S,13S,14R-1,7-diaza-8,15-dioxo-9-oxa-14-isobutyl-2-[N-(glycine-N-4-phenylpiperazinamide)carboxamide]cyclopentadecane-13-N-hydroxycarboxamide;

2S,13S,14R-1,7-diaza-8,15-dioxo-9-oxa-14-isobutyl-2-[N-(glycine-N-4-(2-pyridyl)piperazinamide)carboxamide]cyclopentadecane-13-N-hydroxycarboxamide;

2S,13S,14R-1,7-diaza-8,15-dioxo-9-oxa-14-isobutyl-2-[N-(a-cyclopropaneethyloxycarboxamide-b-alanine)carboxamide]cyclopentadecane-13-N-hydroxycarboxamide;

2S,13S,14R-1,7-diaza-8,15-dioxo-9-oxa-14-isobutyl-2-{N-[glycine-N-4-(1-piperidinyl)piperidinamide]carboxamide}cyclopentadecane-13-N-hydroxycarboxamide;

2S,13S,14R-1,7-diaza-8,15-dioxo-9-oxa-14-isobutyl-2-[N-(R-isopropyloxycarbonyl-N-morpholinamide)carboxamide]cyclopentadecane-13-N-hydroxycarboxamide;

2S,13S,14R-1,7-diaza-8,15-dioxo-9-oxa-14-isobutyl-2-[N-(S-isopropyloxycarbonyl-N-morpholinamide)carboxamide]cyclopentadecane-13-N-hydroxycarboxamide;

2S,13S,14R-1,7-diaza-8,15-dioxo-9-oxa-14-isobutyl-2-[N-(2-thiazole-4-acetic acid)carboxamide]cyclopentadecane-13-N-hydroxycarboxamide;

2S,13S,14R-1,7-diaza-8,15-dioxo-9-oxa-14-isobutyl-2-[N-(a-cyclopropaneethyloxycarboxamide-b-alanine-N-dimethylamide)carboxamide]cyclopentadecane-13-N-hydroxycarbcxamide;

2S,13S,14R-1,7-diaza-8,15-dioxo-9-oxa-14-isobutyl-2-[N-(a-cyclopropaneethyloxycarboxamide-b-alanine-N-morpholinamide)carboxamide]cyclopentadecane-13-N-hydroxycarboxamide;

2S,13S,14R-1,7-diaza-8,15-dioxo-9-oxa-14-isobutyl-2-[N-(2-thiazole-4-acetyl-N-morpholinamide)carboxamide]cyclopentadecane-13-N-hydroxycarboxamide;

2S,13S,14R-1,7-diaza-8,15-dioxo-9-oxa-14-isobutyl-2-[N-(L-serine-N-morpholinamide)carboxamide]cyclopentadecane-13-N-hydroxycarboxamide;

2S,13S,14R-1,7-diaza-8,15-dioxo-9-oxa-14-isobutyl-2-[N-(glycine-N-piperidinamide-3-carboxylic acid)carboxamide]cyclopentadecane-13-N-hydroxycarboxamide;

2S,13S,14R-1,7-diaza-8,15-dioxo-9-oxa-14-isobutyl-2-[N-(glycine-N-2,6-dimethylmorpholinamide)carboxamide]cyclopentadecane-13-N-hydroxycarboxamide;

2S,13S,14R-1,7-diaza-8,15-dioxo-9-oxa-14-isobutyl-2-[N-(glycine-N-4-ethoxycarbonylpiperazinamide)carboxamide]cyclopentadecane-13-N-hydroxycarboxamide;

2S,13S,14R-1,7-diaza-8,15-dioxo-9-oxa-14-isobutyl-2-[N-(glycine-N-4-ethoxycarbonylpiperidinamide)carboxamide]cyclopentadecane-13-N-hydroxycarboxamide;

2S,13S,14R-1,7-diaza-8,15-dioxo-9-oxa-14-isobutyl-2-{N-[4-(1-morphoinyl)phenyl]carboxamide}cyclopentadecane-13-N-hydroxycarboxamide;

2S,13S,14R-1,7-diaza-8,15-dioxo-9-oxa-14-isobutyl-2-{N-[glycine-N-(4(1-morpholinyl)anilide)carboxamide]cyclopentadecane-13-N-hydroxycarboxamide;

2S,13S,14R-1,7-diaza-8,15-dioxo-9-oxa-14-isobutyl-2-[N-(glycine-N-piperidinamide-4-carboxylic acid)carboxamide]cyclopentadecane-13-N-hydroxycarboxamide;

2S,13S,14R-1,7-diaza-8,15-dioxo-9-oxa-14-isobutyl-2-[N-methylcarboxamide]-cyclopentadecane-13-N-hydroxycarboxamide 2S,13S,14R-1,7-diaza-8,15-dioxo-9-oxa-14-isobutyl-2-[alanine-N-methylamide]-cyclopentadecane-13-N-hydroxycarboxamide 2S,13S,14R-1,7-diaza-8,15-dioxo-9-oxa-14-isobutyl-2-[methylcarboxy]-cyclopentadecane-13-N-hydroxycarboxamide 2S,13S,14R-1,7-diaza-8,15-dioxo-9-oxa-14-isobutyl-2-[glycine-N-methylamide]-cyclopentadecane-13-N-hydroxycarboxamide 2S,13S,14R-1,7-diaza-8,15-dioxo-9-oxa-14-isobutyl-2-[2-N-morpholinoethylcarboxamide]-cyclopentadecane-13-N-hydroxycarboxamide 2S,13S,14R-1,7-diaza-8,15-dioxo-9-oxa-14-isobutyl-2-[3-N-morpholinopropylcarboxamide]-cyclopentadecane-13-N-hydroxycarboxamide 2S,13S,14R-1,7-diaza-8,15-dioxo-9-oxa-14-isobutyl-2-[pheylalanine-N-methylamide]-cyclopentadecane-13-N-hydroxycarboxamide 2S,13S,14R-1,7-diaza-8,15-dioxo-9-oxa-14-isobutyl-2-[leucine-N-methylamide]-cyclopentadecane-13-N-hydroxycarboxamide 2S,13S,14R-1,7-diaza-8,15-dioxo-9-oxa-14-isobutyl-2-[N-4-pyridylmethylcarboxamide]-cyclopentadecane-13-N-hydroxycarboxamide 2S,13S,14R-1,7-diaza-8,15-dioxo-9-oxa-14-isobutyl-2-[N-(R,S)-furfurylcarboxamide]-cyclopentadecane-13-N-hydroxycarboxamide 2S,13S,14R-1,7-diaza-8,15-dioxo-9-oxa-14-isobutyl-2-[N-phenylcarboxamide]-cyclopentadecane-13-N-hydroxycarboxamide 2S,13S,14R-1,7-diaza-8,15-dioxo-9-oxa-14-isobutyl-2-[t-butylglycine-N-methylamide]-cyclopentadecane-13-N-hydroxycarboxamide 2S,13S,14R-1,7-diaza-8,15-dioxo-9-oxa-14-isobutyl-2-[N-benzylcarboxamide]-cyclopentadecane-13-N-hydroxycarboxamide 2S,13S,14R-1,7-diaza-8,15-dioxo-9-oxa-14-isobutyl-2-[3-N-(2-oxo-pyrrolidino)propylcarboxamide]-cyclopentadecane-13-N-hydroxycarboxamide 2S,13S,14R-1,7-diaza-8,15-dioxo-9-oxa-14-isobutyl-2-[2-N-ethylpyrrolidinocarboxamide]-cyclopentadecane-13-N-hydroxycarboxamide 2S,13S,14R-1,7-diaza-8,15-dioxo-9-oxa-14-isobutyl-2-[N-3-pyridylmethylcarboxamide]-cyclopentadecane-13-N-hydroxycarboxamide 2S,13S,14R-1,7-diaza-8,15-dioxo-9-oxa-14-isobutyl-2-[N-2-(1,1,1-trifluoroethyl)carboxamide]-cyclopentadecane-13-N-hydroxycarboxamide 2S,13S,14R-1,7-diaza-8,15-dioxo-9-oxa-14-isobutyl-2-[N-2-(2-pyridyl)ethylcarboxamide]-cyclopentadecane-13-N-hydroxycarboxamide 2S,13S,14R-1,7-diaza-8,15-dioxo-9-oxa-14-isobutyl-2-[N-(R,S-1-methyl-3-pheylpropyl)carboxamide]-cyclopentadecane-13-N-hydroxycarboxamide 2S,13S,14R-1,7-diaza-8,15-dioxo-9-oxa-14-isobutyl-2-[3-N-imidazoylpropylcarboxamide]-cyclopentadecane-13-N-hydroxycarboxamide 2S,13S,14R-1,7-diaza-8,15-dioxo-9-oxa-14-isobutyl-2-[e-N-t-butyloxycarbonyllysine-N-methylamide]-cyclopentadecane-13-N-hydroxycarboxamide 2S,13S,14R-1,7-diaza-8,15-dioxo-9-oxa-14-isobutyl-2-[lysine-N-methylamide]-cyclopentadecane-13-N-hydroxycarboxamide 2S,13S,14R-1,7-diaza-8,15-dioxo-9-oxa-14-isobutyl-2-[N-2-pyridylmethylcarboxamide]-cyclopentadecane-13-N-hydroxycarboxamide 22S,13S,14R-1,7-diaza-8,15-dioxo-9-oxa-14-isobutyl-2-[N-N-morpholinosarboxyamide]-cyclopentadecane-13-N-hydroxycarboxamide 2S,13S,14R-1,7-diaza-8,15-dioxo-9-oxa-14-isobutyl-2-[N-(R)-furfurylcarboxamide]-cyclopentadecane-13-N-hydroxycarboxamide 2S,13S,14R-1,7-diaza-8,15-dioxo-9-oxa-14-isobutyl-2-[N-2(4-imidazoyl)ethylcarboxyamide]-cyclopentadecane-13-N-hydroxycarboxcamide 2S,13S,14R-1,7-diaza-8,15-dioxo-9-oxa-14-isobutyl-2-[N-R-(2-R-hydroyindane)carboxamide]-cyclopentadecane-13-N-hydroxycarboxamide 2S,13S,14R-1,7-diaza-8,15-dioxo-9-oxa-14-isobutyl-2-[N-S-(2-S-hydroxyindane)carboxamide]-cyclopentadecane-13-N-hydroxycarboxamide 2S,13S,14R-1,7-diaza-8,15-dioxo-9-oxa-14-isobutyl-2-[N-4-aminobenzylcarboxamide]-cyclopentadecane-13-N-hydroxycarboxamide 2S,13S,14R-1,7-diaza-8,15-dioxo-9-oxa-14-isobutyl-2-[2-N-piperazinoetylcarboxamide]-cyclopentadecane-13-N-hydroxycarboxamide 2S,13S,14R-1,7-diaza-8,15-dioxo-9-oxa-14-isobutyl-2-[N-4-methylpiperinocarboxamide]-cyclopentadecane-13-N-hydroxycarboxamide 2S,13S,14R-1,7-diaza-8,15-dioxo-9-oxa-14-isobutyl-2-[3-N-(2-R,S-methyl-piperidino)propylcarboxamide]-cyclopentadecane-13-N-hydroxycarboxamide 2S,13S,14R-1,7-diaza-8,15-dioxo-9-oxa-14-isobutyl-2-[N-(S)-furfurylcarboxamide]-cyclopentadecane-13-N-hydroxycarboxamide 2S,13S,14R-1,7-diaza-8,15-dioxo-9-oxa-14-isobutyl-2-[aspartate(O-t-butyl)-N-methylamide]-cyclopentadecane-13-N-hydroxycarboxamide 2S,13S,14R-1,7-diaza-8,15-dioxo-9-oxa-14-isobutyl-2-[aspartate-N-methylamide]-cyclopentadecane-13-N-hydroxycarboxcamide 2S,13S,14R-1,7-diaza-8,15-dioxo-9-oxa-14-isobutyl-2-[3-azaphenylalanine-N-methylamide]-cyclopentadecane-13-N-hydroxycarboxamide 2S,13S,14R-1,7-diaza-8,15-dioxo-9-oxa-14-isobutyl-2-[N-benzhydrylcarboxamide]-cyclopentadecane-13-N-hydroxycarboxamide In the present invention it has been discovered that the compounds above are useful as inhibitors of metalloproteinases, including aggrecanase and TNF-C, and are useful for the treatment of rheumatoid arthritis, osteoarthritis and related inflammatory disorders, as described previously. These compounds inhibit the production of TNF in animal models and are useful for the treatment of diseases mediated by TNF.

The present invention also provides methods for the treatment of osteo- and rheumatoid arthritis and related disorders as described previously, by administering to a host a pharmaceutically or therapeutically effective or acceptable amount of a compound of formulas (I to IV) as described above. By therapeutically effective amount, it is meant an amount of a compound of the present invention effective to inhibit the target enzyme or to treat the symptoms of osteo- or rheumatoid arthritis or related disorder, in a host.

The compounds of the present invention can also be administered in combination with one or more additional therapeutic agents. Administration of the compounds of Formulas I–IV of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

By "therapeutically effective amount" it is meant an amount of a compound of Formulas I–IV that when administered alone or in combination with an additional therapeutic agent to a cell or mammal is effective to inhibit the target enzyme so as to prevent or ameliorate the inflammatory disease condition or the progression of the disease.

By "administered in combination" or "combination therapy" it is meant that the compound of Formulas I–IV and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

By "stable compound" or "stable structure" is meant herein a compound that is sufficiently robust to survive isolation to a useful degree of purity from a reaction mixture, and formulation into an efficacious therapeutic agent.

When any variable occurs more than one time in any constituent or in Formulas I–IV (or any other formula herein), its definition on each occurrence is independent of its definition at every other occurrence. Thus, for example, if a group is shown to be substituted with 0–2 $R^5$, then said group may optionally be substituted with up to two $R^5$ and $R^5$ at each occurrence is selected independently from the defined list of possible $R^5$. Also, combinations of substituents and/or variables are permissible only if such combinations result in stable compounds.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention may contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When a bond to a substituent is shown to cross the bond connecting two atoms in a ring, then such substituent may be bonded to any atom on the ring.

When a substituent is listed without indicating the atom via which such substituent is bonded to the rest of the compound of Formulas I–IV then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_1$–$C_{10}$" denotes alkyl having 1 to 10 carbon atoms); in addition lower alkyl defines branched and/or unbranched alkyl chain of from 1 to 8 C atoms; "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or polycyclic ring systems, such as cyclopropyl, cyclobutyl, cyclopentyl, cyclohexyl, cycloheptyl, cyclooctyl, and adamantyl; and "bicycloalkyl" is intended to include saturated bicyclic ring groups such as [3.3.0]bicyclooctane, [4.3.0]bicyclononane, [4.4.0] bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

"Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

The terms "alkylene", "alkenylene", "phenylene", and the like, refer to alkyl, alkenyl, and phenyl groups, respectively, which are connected by two bonds to the rest of the structure of Formula I–III. Such "alkylene", "alkenylene", "phenylene", and the like, may alternatively and equivalently be denoted herein as "-(alkyl)-", "-(alkyenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "carbocycle" or "carbocyclic residue" or "carbocyclic ring system" is intended to mean any stable 3- to 7-membered monocyclic or bicyclic or 7- to 14-membered bicyclic or tricyclic or up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, "aryl" or "aromatic residue" is intended to include phenyl or naphthyl as well as commonly referred to "heterocycle" or "heteroaryl" or "heterocyclic" compounds; the term "arylalkyl" represents an aryl group attached through an alkyl bridge.

As used herein, the terms "heterocycle" or "heteroaryl" or "heterocyclic" is intended to mean a stable 5- to 7-membered monocyclic or bicyclic or 7- to 10-membered bicyclic ring which may be partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. A heterocyclic ring may be attached to its pendant group at any heteroatom or carbon atom which results in a stable structure. The aromatic rings described herein may be substituted on carbon or on a nitrogen atom if the resulting compound is stable. Examples of aryl groups include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl,4-piperidonyl, pyrrolidinyl,2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl,2H,6H-1,5,2-dithiazinyl, thiophenyl, thianthrenyl, pyranyl, isobenzofuranyl, chromenyl, xanthenyl, phenoxathiinyl,2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl,3H-indolyl, indolyl, 1H-indazolyl, purinyl,4H-quinolizinyl, isoquinolinyl, quinolinyl, phthalazinyl, naphthyridinyl, quinoxalinyl, quinazolinyl, cinnolinyl, pteridinyl,4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, hexahydropyridazinyl, indolinyl, isoindolinyl, quinuclidinyl, morpholinyl or oxazolidinyl. Also included are fused ring and spiro compounds containing, for example, the above heterocycles.

As used herein, the term "aryl" is intended to mean a stable 5- to 7-membered monocyclic or bicyclic or 7- to 10-membered bicyclic ring which may be partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. A heterocyclic ring may be attached to its pendant group at any heteroatom or carbon atom which results in a stable structure. The aromatic rings described herein may be substituted on carbon or on a nitrogen atom if the resulting compound is stable. Examples of aryl groups include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, hexahydropyridazinyl, indolinyl, isoindolinyl, quinuclidinyl, morpholinyl or oxazolidinyl. Also included are fused ring and spiro compounds containing, for example, the above heterocycles.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) *The Peptides,* 5: 342–429, the teaching of which is hereby incorporated by reference. Modified or unusual amino acids which can be used to practice the invention include, but are not limited to, D-amino acids, hydroxylysine,4-hydroxyproline, an N-Cbz-protected amino acid, ornithhne, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl) benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

"Prodrugs" are considered to be any covalently bonded carriers which release the active parent drug according to Formula I–III in vivo when such prodrug is administered to a mammalian subject. Prodrugs of the compounds of Formula I–III are prepared by modifying functional groups present in the compounds in such a way that the modifications are cleaved, either in routine manipulation or in vivo, to the parent compounds. Prodrugs include compounds of Formulas I–IV wherein hydroxyl, amino, sulfhydryl, or carboxyl groups are bonded to any group that, when administered to a mammalian subject, cleaves to form a free hydroxyl, amino, sulfhydryl, or carboxyl group respectively.

Examples of prodrugs include, but are not limited to, acetate, formate and benzoate derivatives of alcohol and amine functional groups in the compounds of Formulas I–IV, phosphate esters, dimethylglycine esters, aminoalkylbenzyl esters, aminoalkyl esters and carboxyalkyl esters of alcohol and phenol functional groups in the compounds of formula (I) and the like.

As used herein, "pharmaceutically acceptable salts" refer to derivatives of the disclosed compounds wherein the parent compound of Formulas I–IV is modified by making acid or base salts of the compound of Formulas I–IV. Examples of pharmaceutically acceptable salts include, but are not limited to, mineral or organic acid salts of basic residues such as amines; alkali or organic salts of acidic residues such as carboxylic acids and the like.

The pharmaceutically acceptable salts of the compounds of Formulas I–IV include the conventional non-toxic salts or the quaternary ammonium salts of the compounds of Formulas I–IV formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonlic, methanesulfonic, ethane disulfonic, oxalic, isethionic, and the like.

The pharmaceutically acceptable salts of the present invention can be synthesized from the compounds of Formula I–III which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formulas I–IV with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylainmonium hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A series of compounds of formula 21 are prepared by the methods outlined in Schemes 1–5. A diprotected 2,3-diaminopropionic acid, 2,4-diaminobutyric acid, ornithine or lysine (compound 1, Scheme 1) is converted to its corresponding amide 2 using a coupling agent such as BOP. Coupling of 1 with a diaminobenzene followed by reaction in acetic acid at 60° C. produces a benzimidazole analog 3. 1 can also be converted to an aldehyde 4 which is reacted with ammonia and glyoxal trimer to give an imidazole analog 5. Deprotection of the $N^{\alpha}$-Boc group of 2, 3 and 5 using an acid such as 4 N HCl in dioxane gave compound 6. Removal of the side chain protecting group of 2, 3 and 5 using hydrogenation afforded compound 7.

Scheme 1

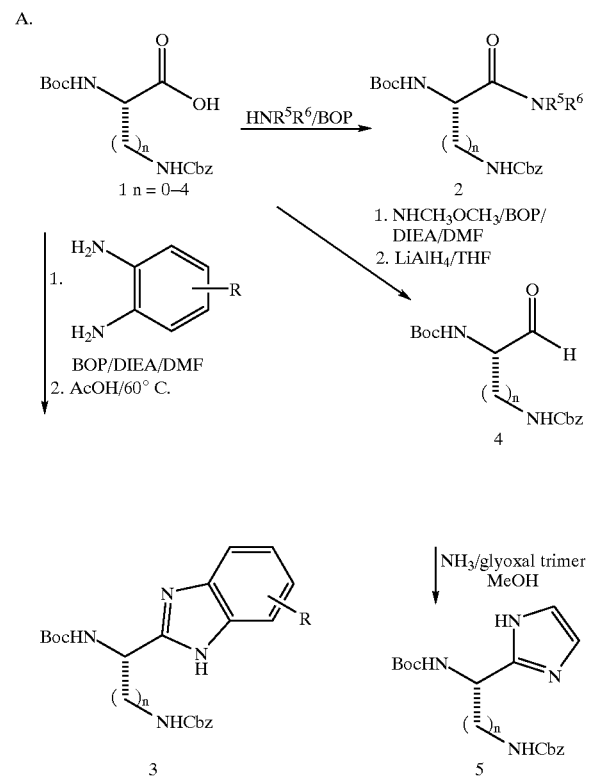

B.

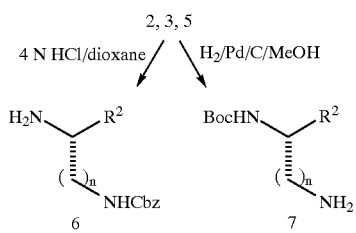

The synthesis of the 2,3-disubstituted succinic acid portion is described in Scheme 2 below. An acid halide (e.g. X=Cl) is converted to its oxazolidinone derivative 8 using n-butyl lithium. An Evan's aldol reaction with a glyoxylate (JACS, 1982, 104, 1737) converts 8 to an intermediate 9. The oxazolidinone group is removed using $H_2O_2$/LiOH and the resulting carboxylic acid is converted to a benzyl ester 11. Alkylation of 11 with t-butyl bromoacetate gives compound 12. The benzyl ester of 12 is removed by hydrogenation to give 13. Removal of the t-butyl group of 12 affords 14.

Scheme 2

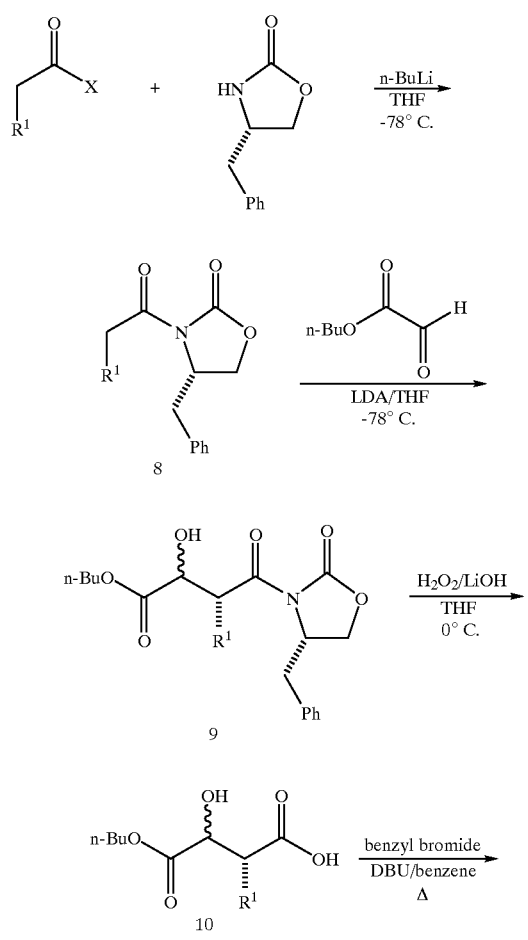

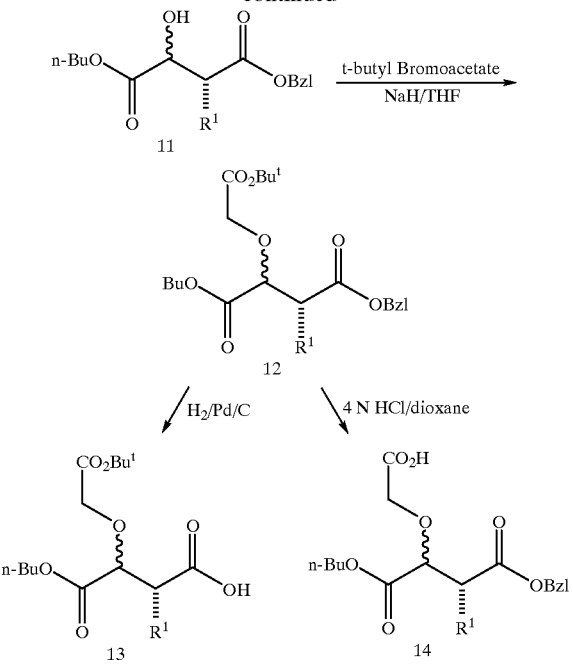

The formation of the macrocyclic ring of this series of compounds can be accomplished via two routes as described in schemes 3 and 4 below. Coupling of the intermediates 6 and 13 produces the intermediate 15. Hydrogenation followed by acid deprotection gives compound 16. Cyclization of 16 using a coupling agent such as BOP affords the macrocyclic intermediate 17. Alternatively, compound 17 can be synthesized by coupling 7 and 14 followed by deprotection and cyclization as described in Scheme 4. Saponification of 17 followed by reversed phase HPLC separation gives two isomers 20a and 20b. The final two products 21a and 21b were obtained by coupling 20a or 20b with O-benzylhydroxlamine hydrochloride followed by hydrogenation.

Scheme 3

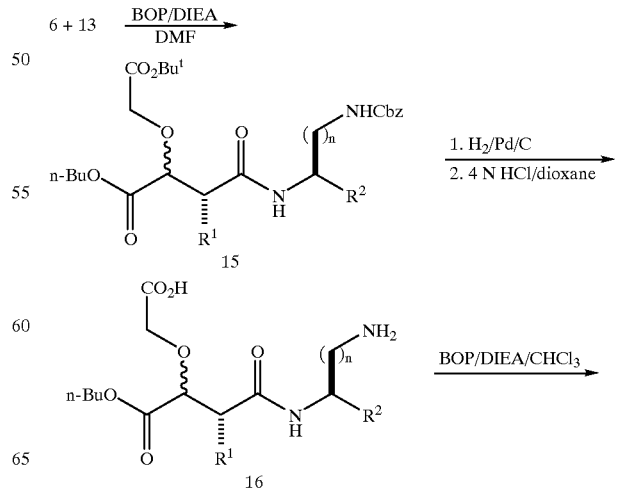

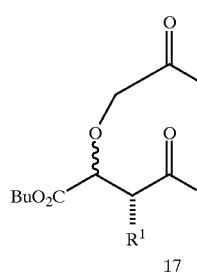
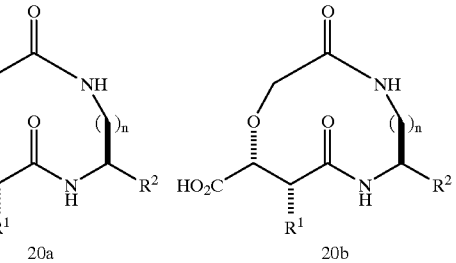

Scheme 4

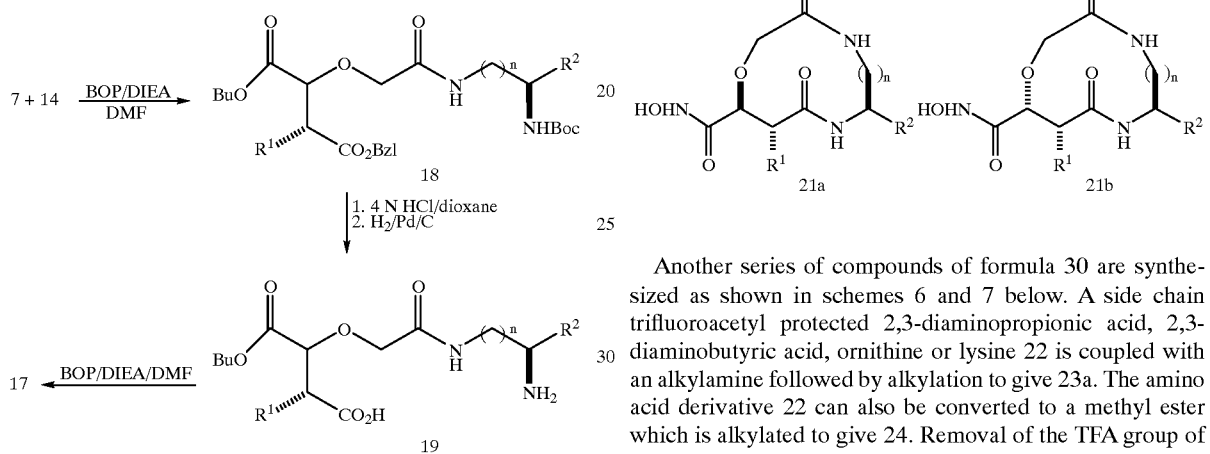

Another series of compounds of formula 30 are synthesized as shown in schemes 6 and 7 below. A side chain trifluoroacetyl protected 2,3-diaminopropionic acid, 2,3-diaminobutyric acid, ornithine or lysine 22 is coupled with an alkylamine followed by alkylation to give 23a. The amino acid derivative 22 can also be converted to a methyl ester which is alkylated to give 24. Removal of the TFA group of 24 followed by protection of the resulting amine using benzyl chloroformate affords compound 25. 25 can be converted to a benzimidazole derivative 23b or an imidazole derivative 23c. Removal of the TFA group of 23a using LiOH or of the Cbz group of 23b and 23c using hydrogenation produces the intermediate 26. The target compound 30 is obtained using the procedures described in Scheme 7 which are similar to those used for the synthesis of the first series of compounds 21 (Schemes 4–5 above).

Scheme 5

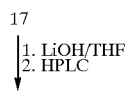

Scheme 6

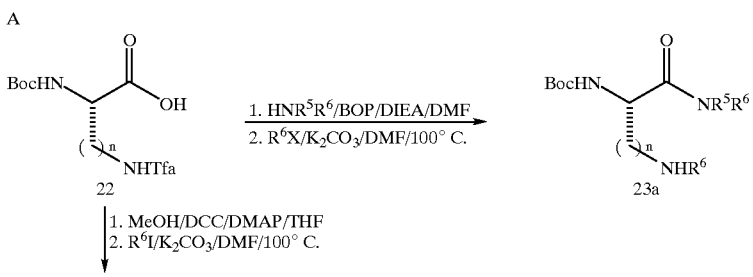

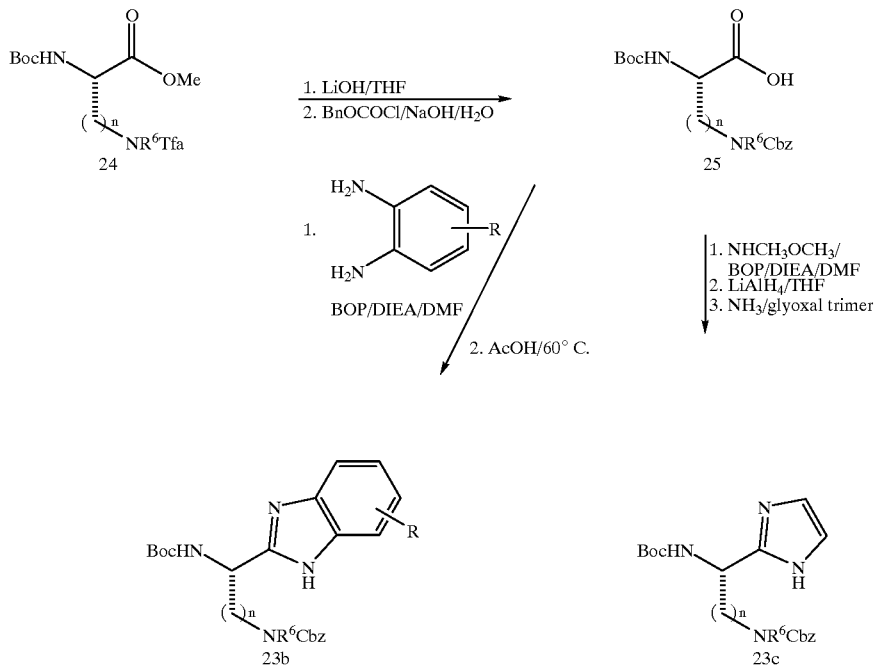

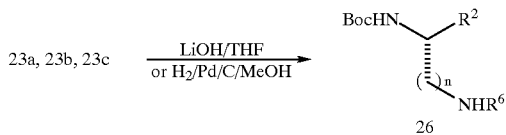

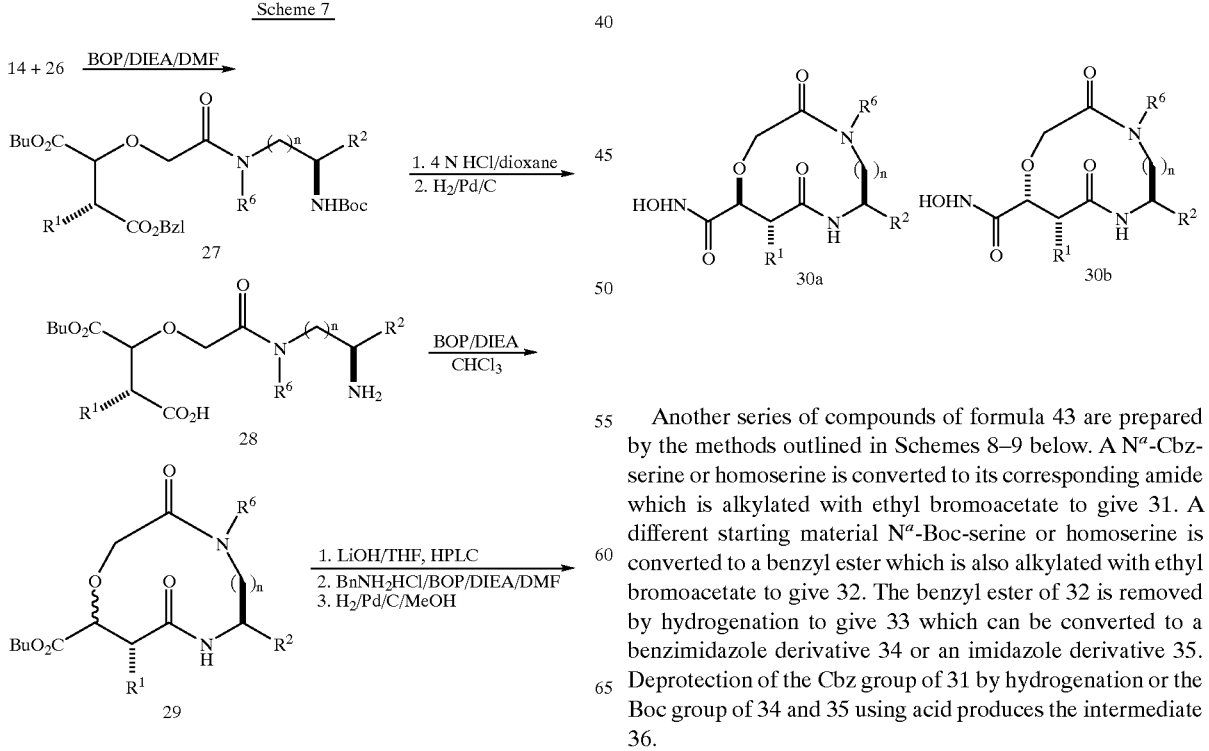

Another series of compounds of formula 43 are prepared by the methods outlined in Schemes 8–9 below. A $N^\alpha$-Cbz-serine or homoserine is converted to its corresponding amide which is alkylated with ethyl bromoacetate to give 31. A different starting material $N^\alpha$-Boc-serine or homoserine is converted to a benzyl ester which is also alkylated with ethyl bromoacetate to give 32. The benzyl ester of 32 is removed by hydrogenation to give 33 which can be converted to a benzimidazole derivative 34 or an imidazole derivative 35. Deprotection of the Cbz group of 31 by hydrogenation or the Boc group of 34 and 35 using acid produces the intermediate 36.

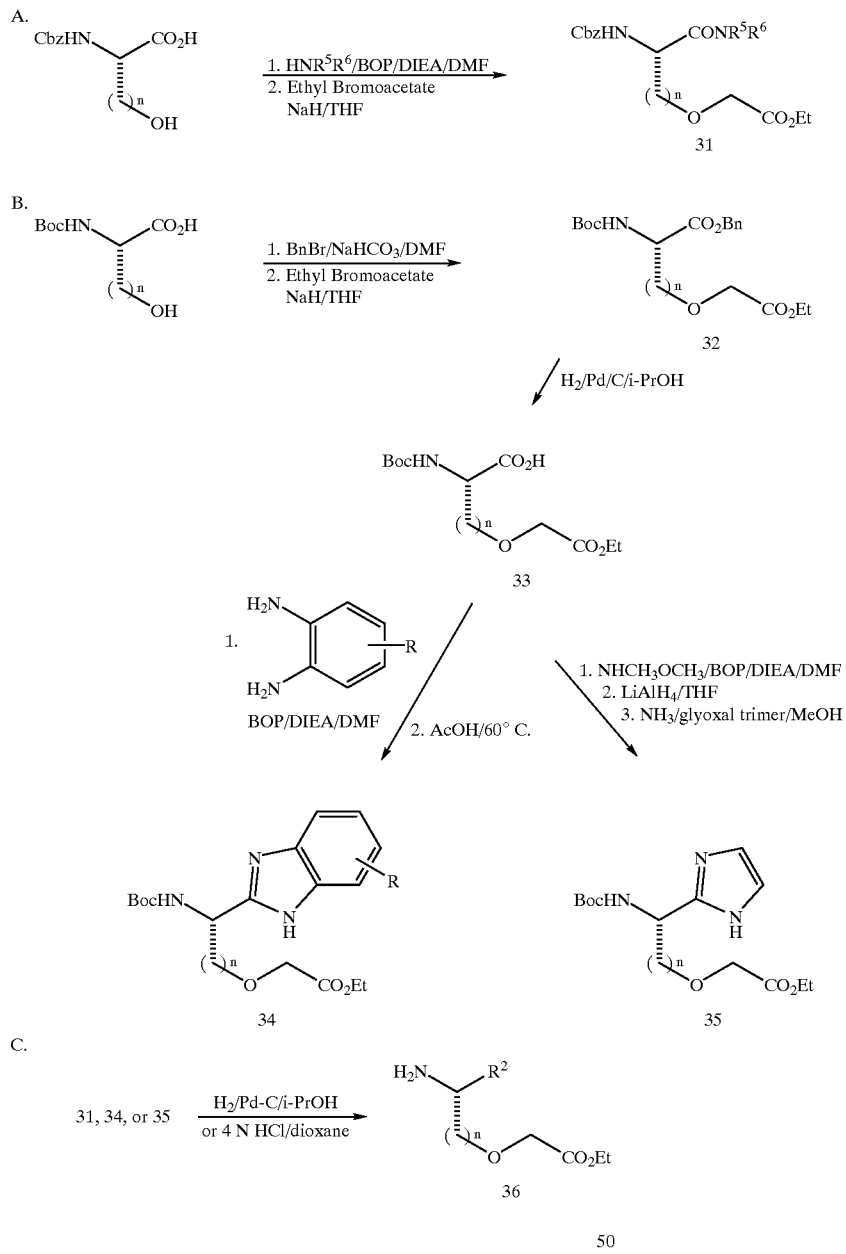
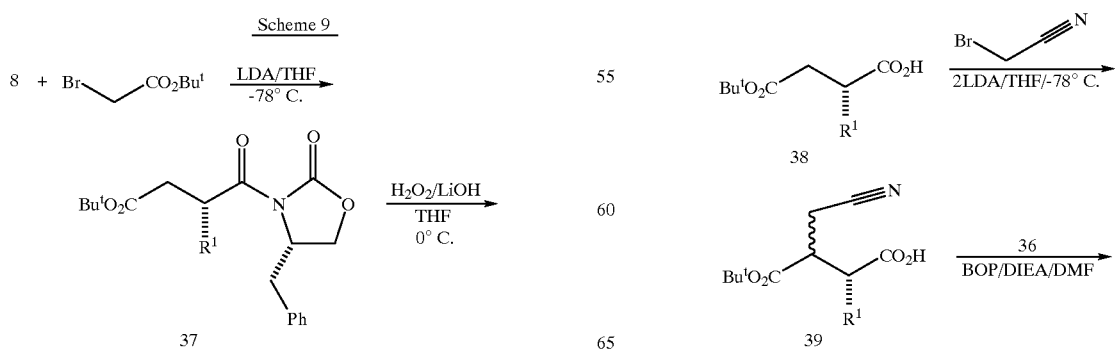

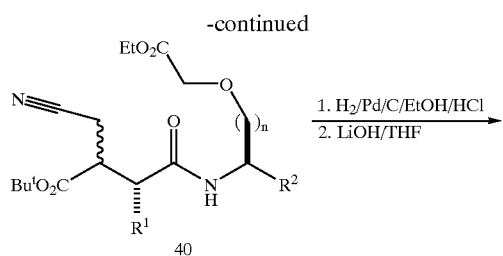

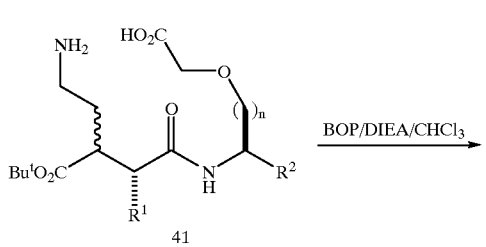

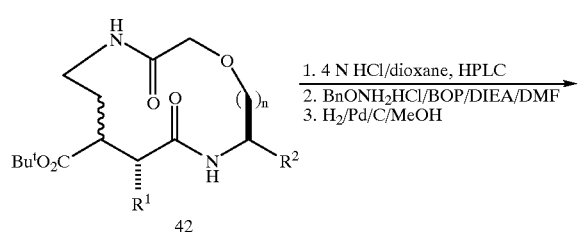

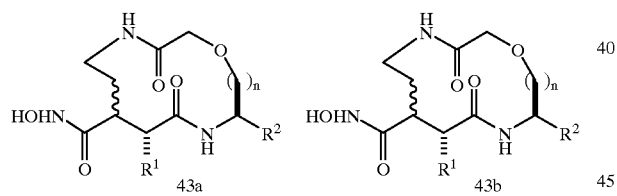

The synthesis of disubstituted succinic acid derivative 39 is described in Scheme 9 above. Alkylation of 8 with t-butyl bromoacetate produces the intermediate 37. The auxiliary group of 37 is removed and alkylation of the resultant acid 38 with bromoacetonitrile gives a mixture of two isomers 39. Coupling of 39 with 36 followed by hydrogenation and saponification yields 41. Cyclization is carried out using BOP to give the cyclic compound 42. The t-butyl group is removed using acid and the two isomers are separated using reversed phase HPLC. The carboxylic acid of each isomer is converted to its corresponding O-benzylhydroxamide and subsequent hydrogenation affords the target products 43a and 43b.

Another series of compounds of formula 51 are prepared as depicted in Schemes 10–11 below. Reaction of a cysteine or homocysteine with a halo-nitrobenzene followed by treatment of the resulting intermediate with di-t-butyl dicarbonate yields $N^{\alpha}$-Boc-S-2-nitrophenyl-cysteine or -homocysteine 44. 44 is converted to an amide 46 or a benzimidazole derivative 45. Deprotection of 45 and 46 using an acid produces the intermediate 47.

Coupling of 47 with the acid component 8 gives the intermediate 48. The nitro group is reduced using zinc in acetic acid/water and the t-butyl group is removed using 4 N HCl in dioxane. Macrocyclization of 49 using BOP yields two isomers 50a and 50b which are separated on a silica gel column. Saponification of each isomer followed by coupling with hydroxylamine produces the target products 51a and 51b.

Scheme 10

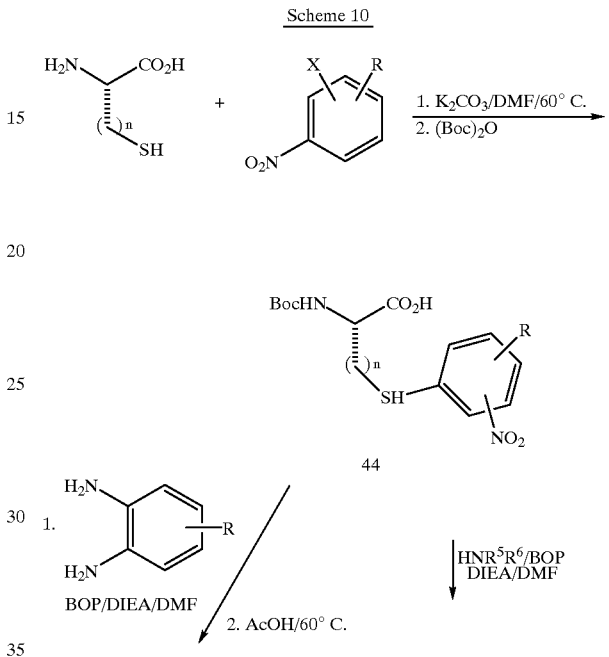

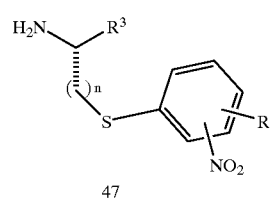

Scheme 11

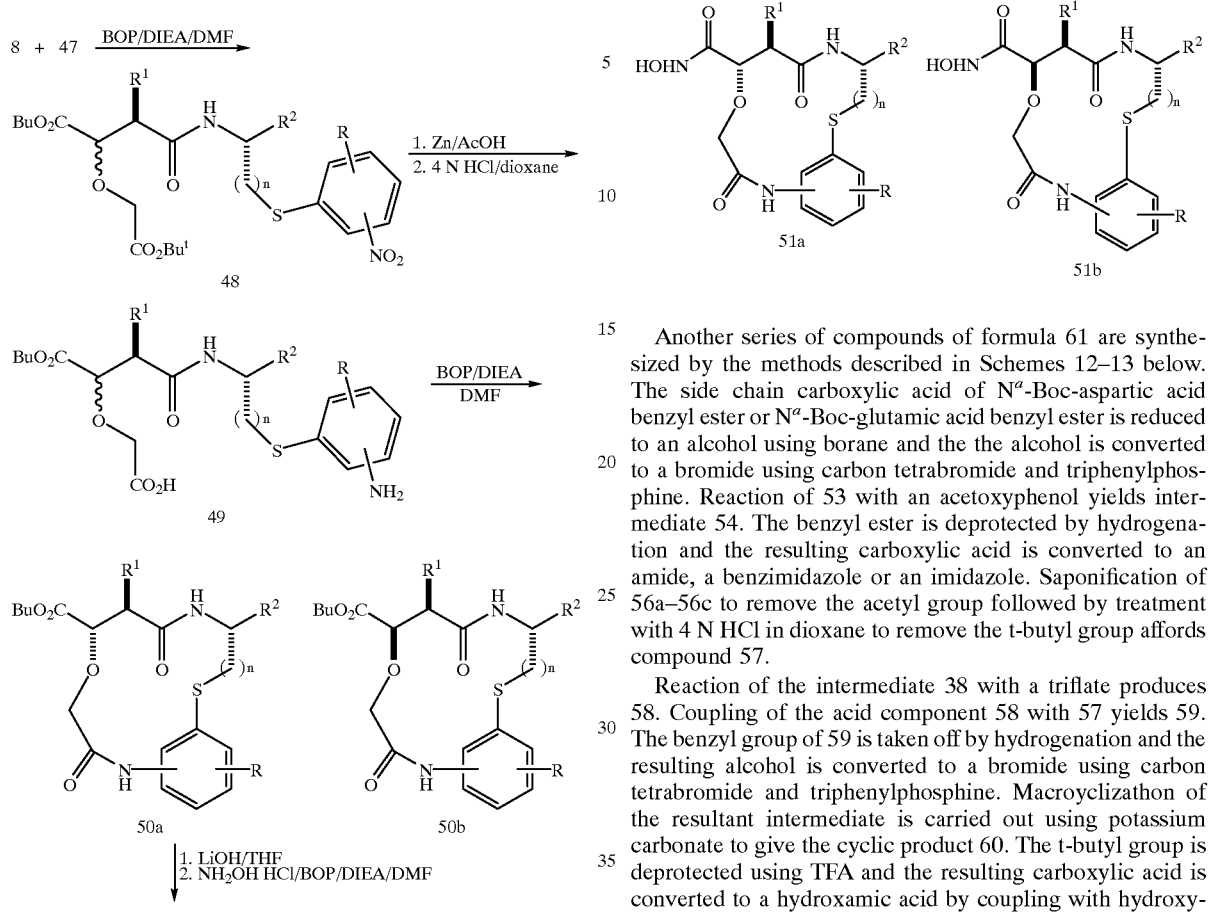

Another series of compounds of formula 61 are synthesized by the methods described in Schemes 12–13 below. The side chain carboxylic acid of $N^{\alpha}$-Boc-aspartic acid benzyl ester or $N^{\alpha}$-Boc-glutamic acid benzyl ester is reduced to an alcohol using borane and the the alcohol is converted to a bromide using carbon tetrabromide and triphenylphosphine. Reaction of 53 with an acetoxyphenol yields intermediate 54. The benzyl ester is deprotected by hydrogenation and the resulting carboxylic acid is converted to an amide, a benzimidazole or an imidazole. Saponification of 56a–56c to remove the acetyl group followed by treatment with 4 N HCl in dioxane to remove the t-butyl group affords compound 57.

Reaction of the intermediate 38 with a triflate produces 58. Coupling of the acid component 58 with 57 yields 59. The benzyl group of 59 is taken off by hydrogenation and the resulting alcohol is converted to a bromide using carbon tetrabromide and triphenylphosphine. Macroyclizathon of the resultant intermediate is carried out using potassium carbonate to give the cyclic product 60. The t-butyl group is deprotected using TFA and the resulting carboxylic acid is converted to a hydroxamic acid by coupling with hydroxylamine to afforded the target product 61.

Scheme 12

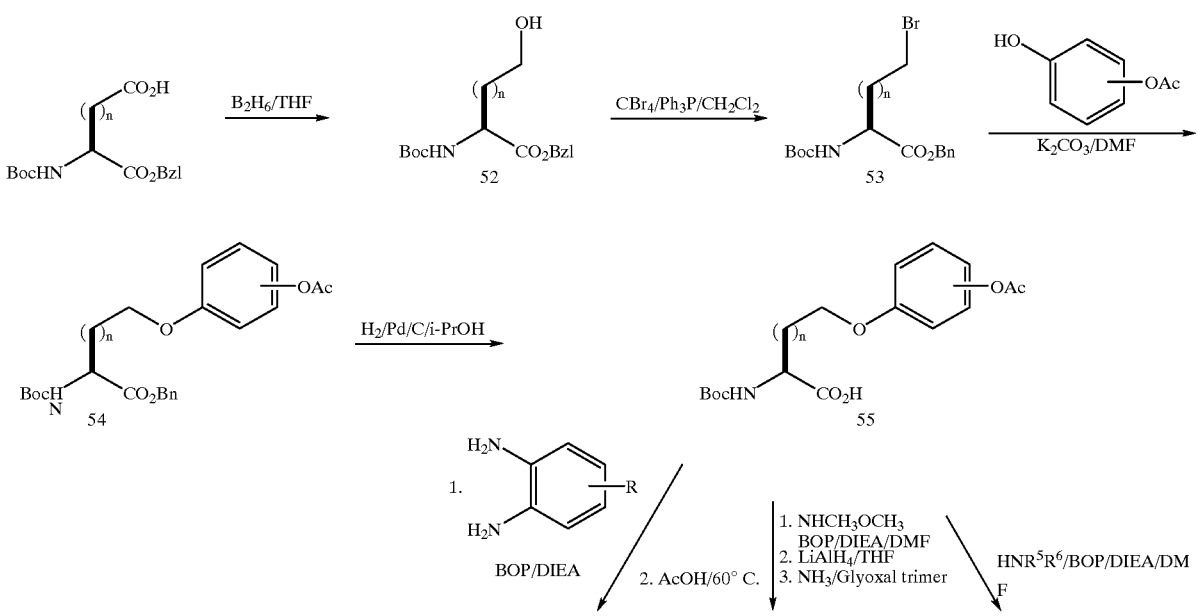

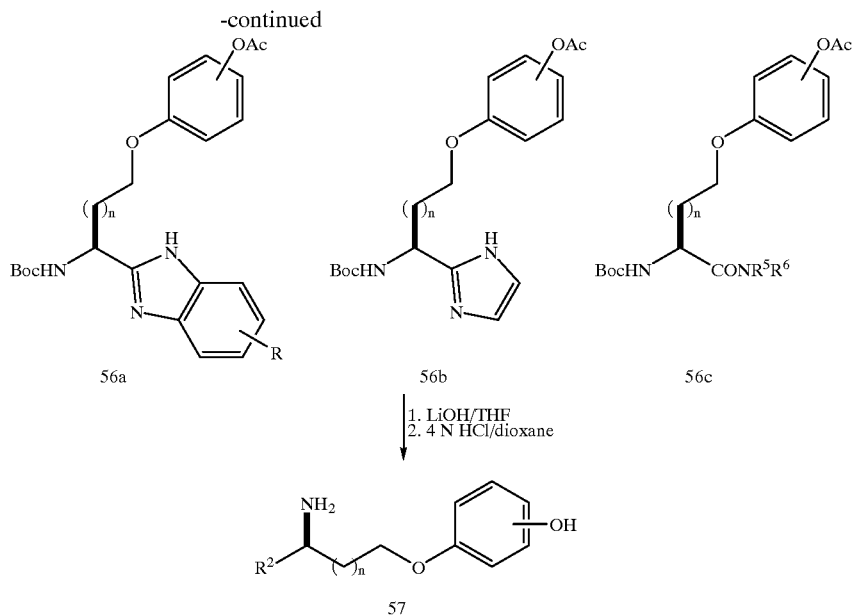

Scheme 13

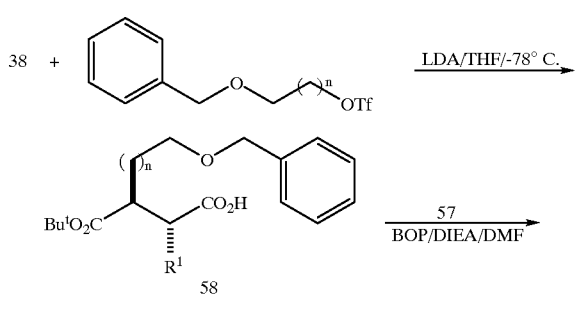

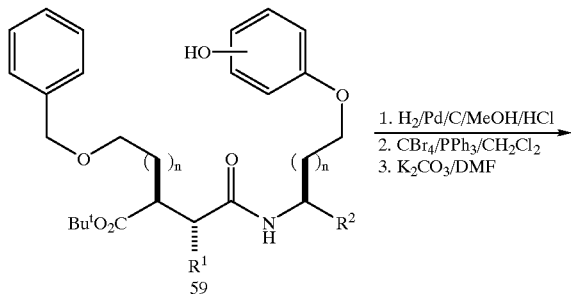

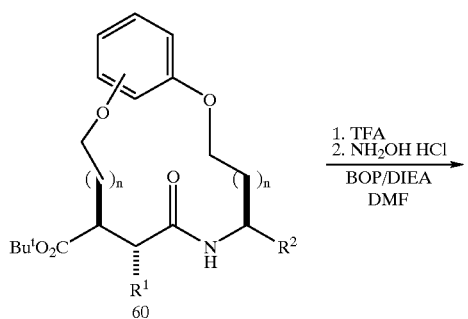

Another series of compounds of formula 67b are prepared as shown in scheme 14 below. The side chain of an aspartic acid or a glutamic acid derivative is reduced to an alcohol which is converted to a bromide 62. Reaction of 62 with sodium acetylide yields 63 which is converted to an amide, a benzimidazole or an imidazole derivative 64 as described above.

Alkylation of 11 with a bromoacetal followed by acid treatment and reaction with hydroxylamine produces the intermediate 65. Reaction of 65 with 64 using bleach affords an isoxazole derivative 66. Deprotection of the Boc group using acid and the Bn group by hydrogenation followed by cyclization using BOP yields the cyclic compound 67a. Saponification followed by coupling with hydroxylamine produces the target compound 67b.

Scheme 14

A.

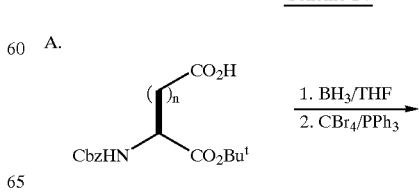

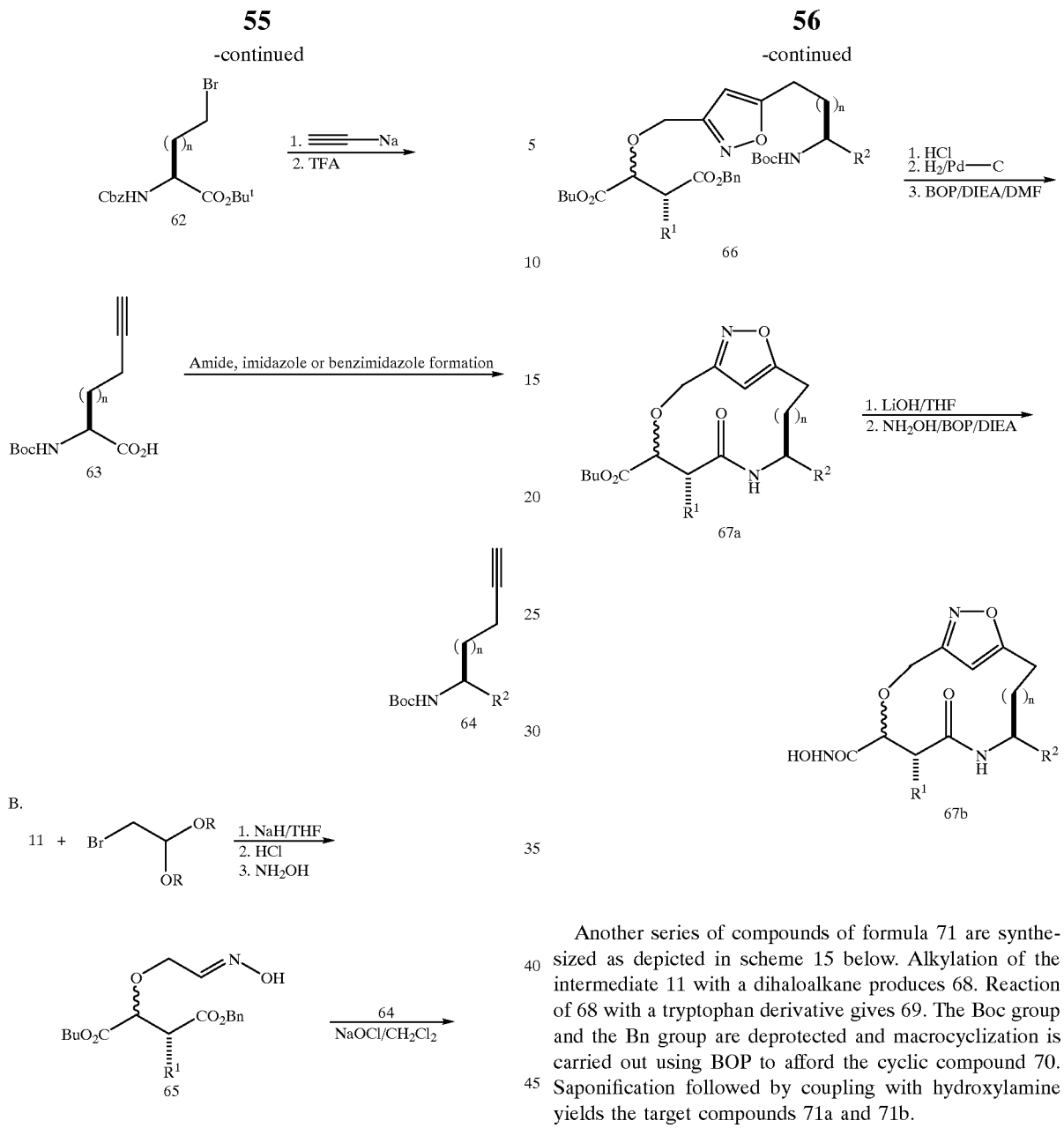

Another series of compounds of formula 71 are synthesized as depicted in scheme 15 below. Alkylation of the intermediate 11 with a dihaloalkane produces 68. Reaction of 68 with a tryptophan derivative gives 69. The Boc group and the Bn group are deprotected and macrocyclization is carried out using BOP to afford the cyclic compound 70. Saponification followed by coupling with hydroxylamine yields the target compounds 71a and 71b.

Scheme 15

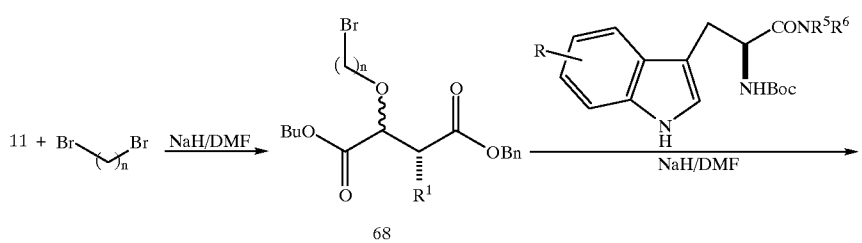

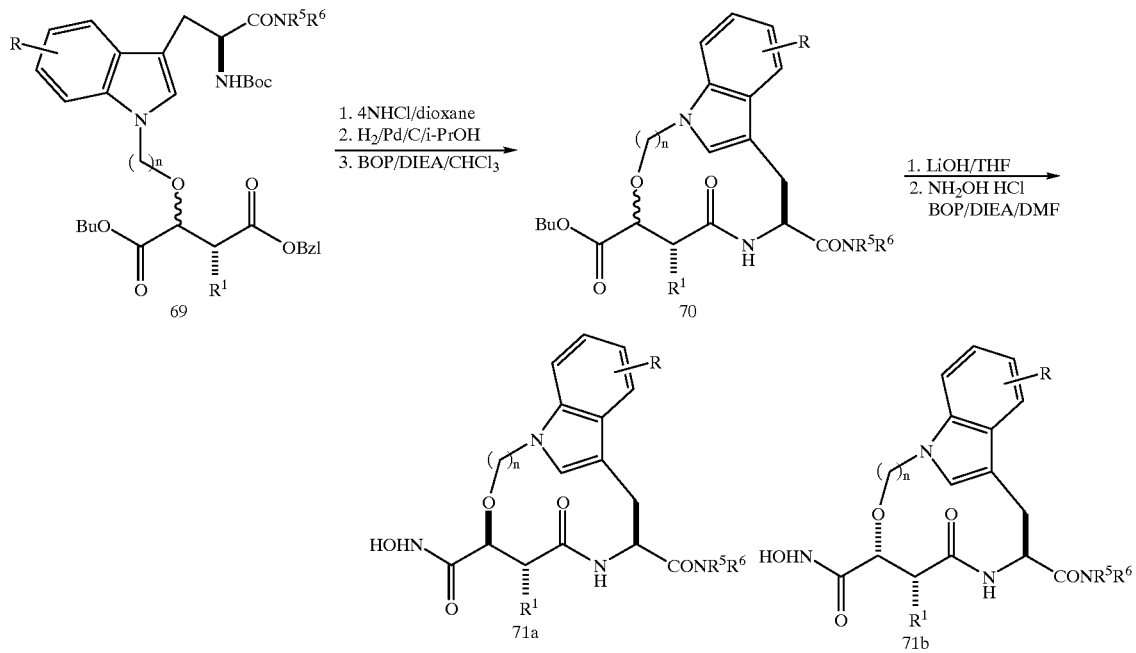

Compounds of formula 75, could be prepared by the route shown in scheme 16 below. The succinate 61 could be coupled with a tyrosine derivative using the BOP reagent to afford the amide 72. Deprotection of the benzyl ether under hydrogenation conditions gave an alcohol, which could be converted to the bromide 73. Macrocylization provides compound 74. The tert-butyl ester is deprotected to the acid, which is converted to the benzyl protected hydroxamic acid. The desired compound 75 is obtained after deprotection by hydrogenation.

Scheme 16

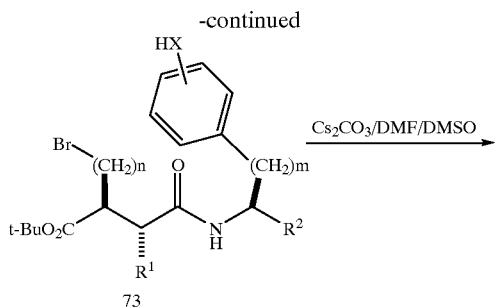

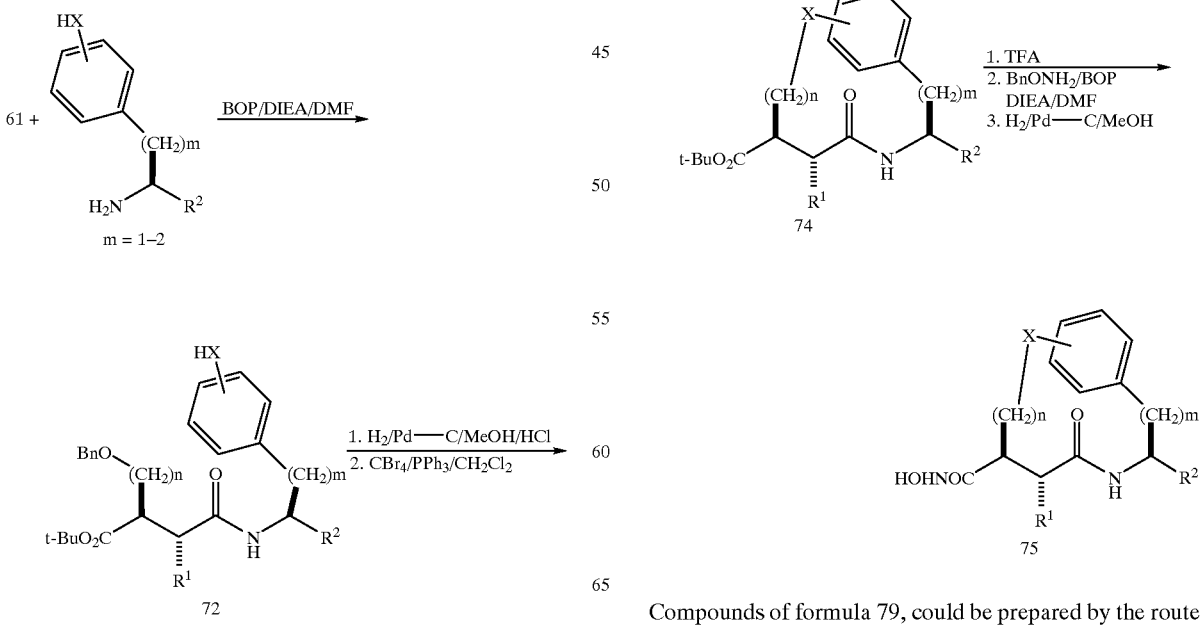

Compounds of formula 79, could be prepared by the route shown in scheme 17 below. The succinate 61 could be coupled with a histidine derivative using the BOP reagent to afford the amide 76. Deprotection of the benzyl carbamate and the benzyl ether under hydrogenation conditions would give an alcohol, which could be converted to the bromide 77. Macrocylization would provide compound 78. The tert-butyl ester is deprotected to the acid, which is converted to the benzyl protected hydroxamic acid. The desired compound 79 is obtained after deprotection by hydrogenation.

Scheme 17

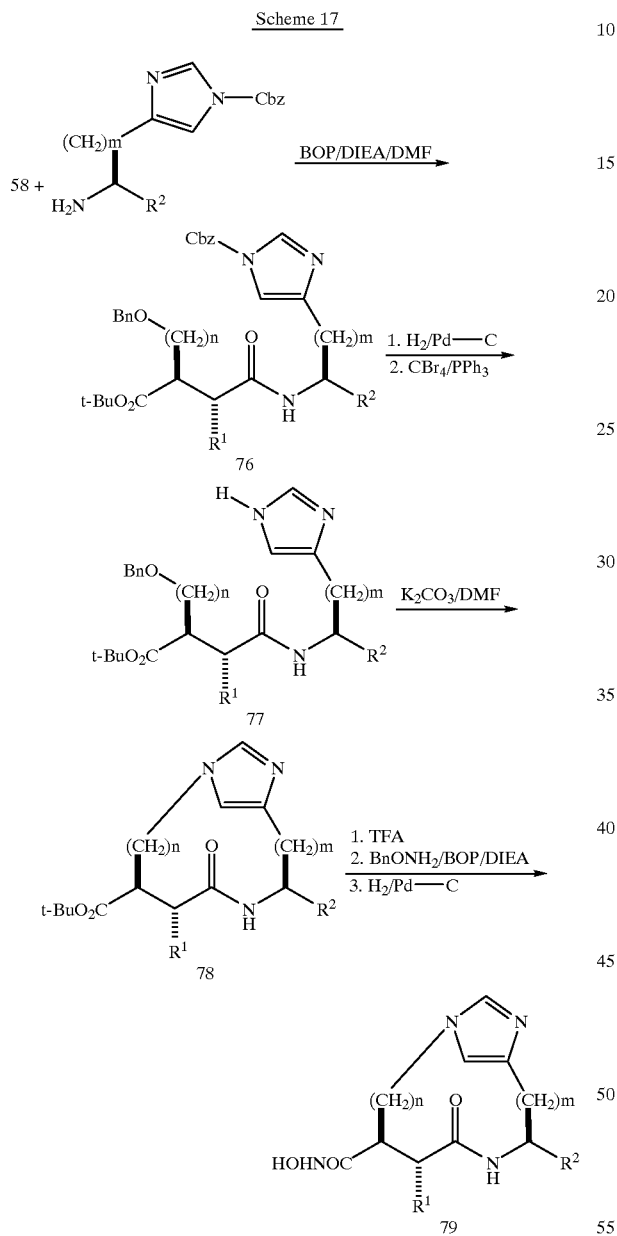

Compounds of formula 84, could be prepared by the route shown in scheme 18 below. The succinate 38 could be converted to the enolate with LDA and alkylated with a triflate to provide 80. This material is coupled with a phenylalanine derivative using the BOP reagent to afford the amide 81. Deprotection of the benzyl groups under hydrogenation conditions gives the amino acid 82. Macrocyliza-tion would provide compound 83. The tert-butyl ester is deprotected to the acid, which is converted to the benzyl protected hydroxamic acid. The desired compound 84 is obtained after deprotection by hydrogenation.

Scheme 18

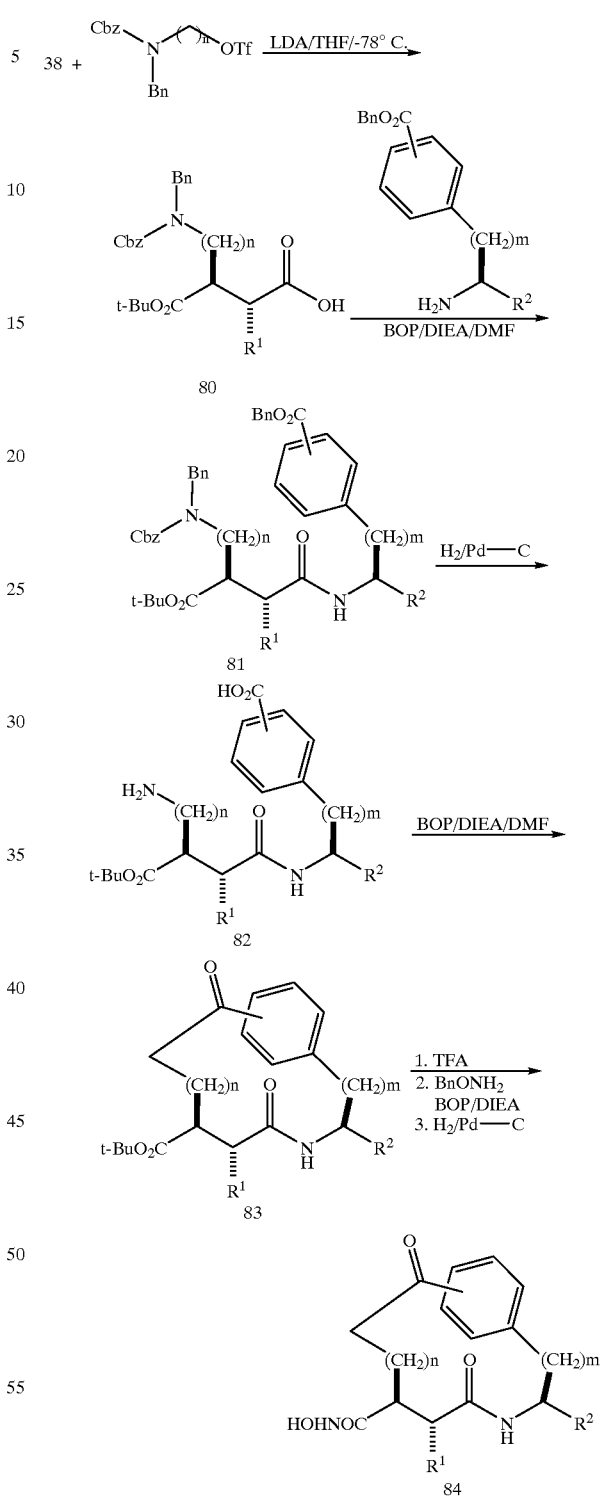

Compounds of formula 98, could be prepared by the route shown in scheme 21 below. The succinate 38 could be converted to the enolate with LDA and alkylated with a triflate to provide 95. This material is coupled with a lysine derivative using the BOP reagent to afford the amide 96. Deprotection of the benzyl carbamate under hydrogenation conditions and saponification of the ethyl ester gives the amino acid. Macrocylization provides compound 96. The tert-butyl ester is deprotected to the acid, which is converted to the benzyl protected hydroxamic acid. The desired compound 98 is obtained after deprotection by hydrogenation.

Scheme 21

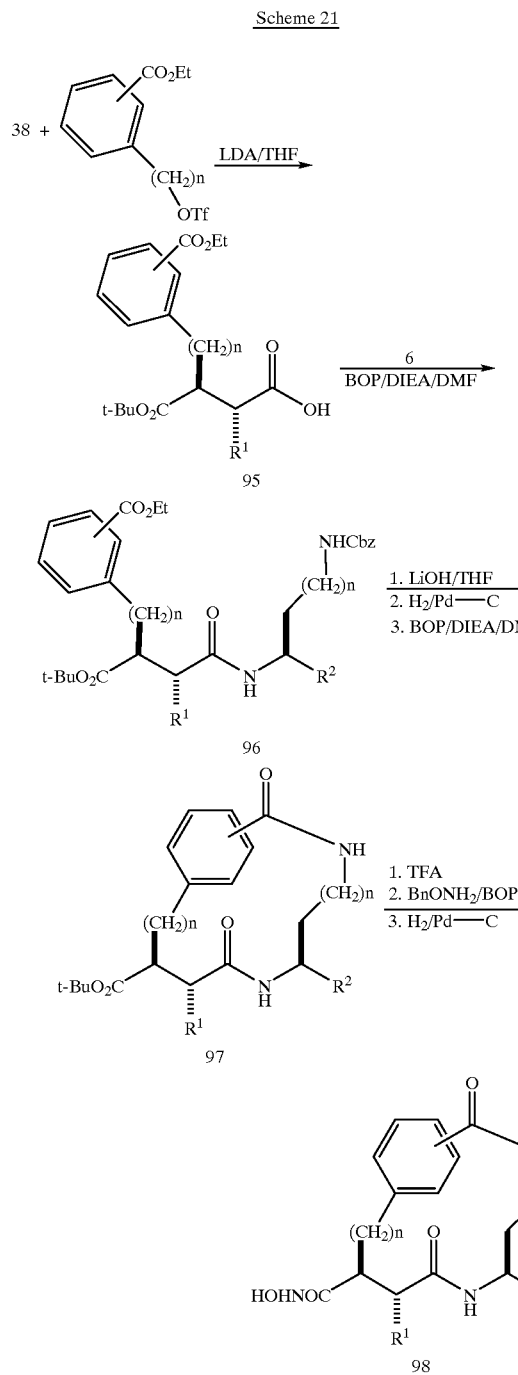

Scheme 22

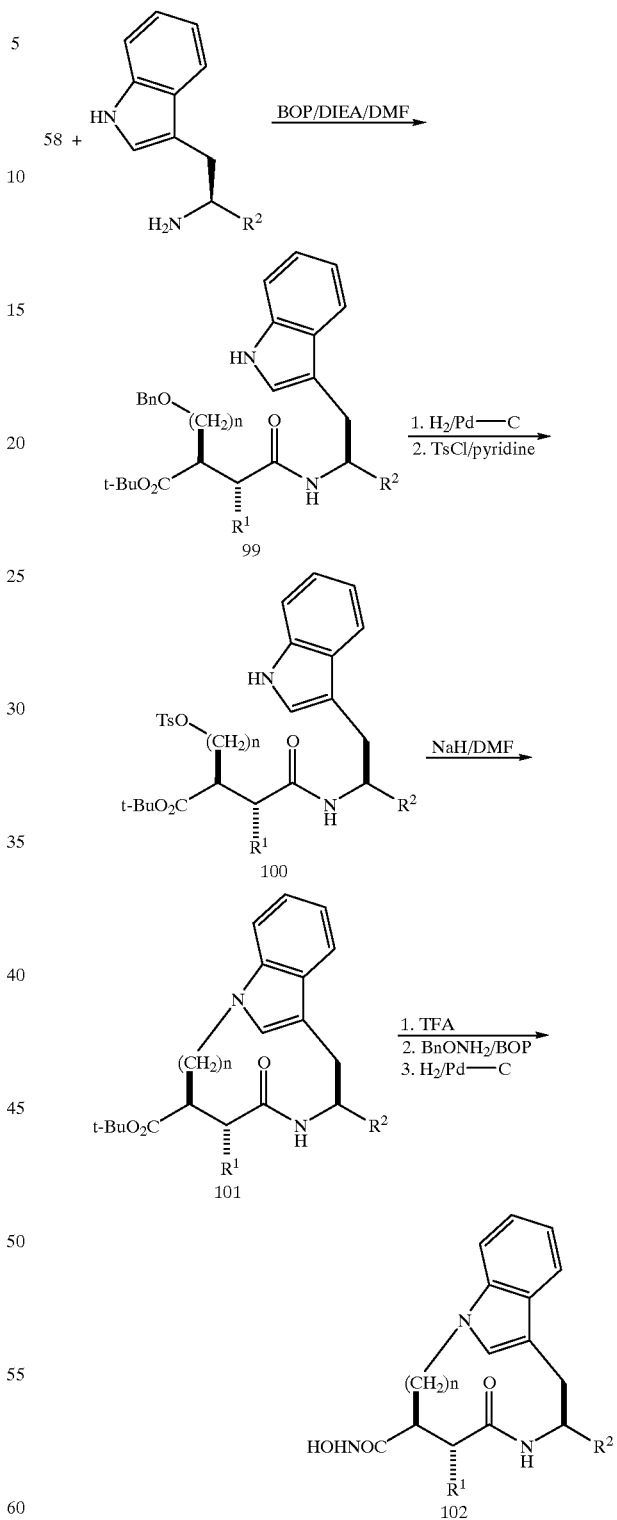

Compounds of formula 102, could be prepared by the route shown in scheme 22 below. The succinate 58 could be coupled with a tryptophan derivative using the BOP reagent to afford the amid 99. Deprotection of the benzyl group and conversion to the tosylate gives 100. Macrocylization would provide compound 101. The tert-butyl ester is deprotected to the acid, which is converted to the benzyl protected hydroxamic acid. The desired compound 102 is obtained after deprotection by hydrogenation.

Compounds of formula 108, could be prepared by the route shown in scheme 23 below. The imide 8 can be converted to the enolate with LDA and alkylated with a triflate to provide 103. The chiral auxiliary is then saponified to the acid 104. As above, this material can be converted to the enolate with LDA and alkylated with a triflate. The resulting 105 can be coupled with a tyrosine derivative using the BOP reagent to afford the amide 106. Deprotection of the benzyl ether under hydrogenation conditions gives an alcohol, which could be converted to the bromide. Macrocylization provides compound 107. The tert-butyl ester is then deprotected to give the desired acid 108.

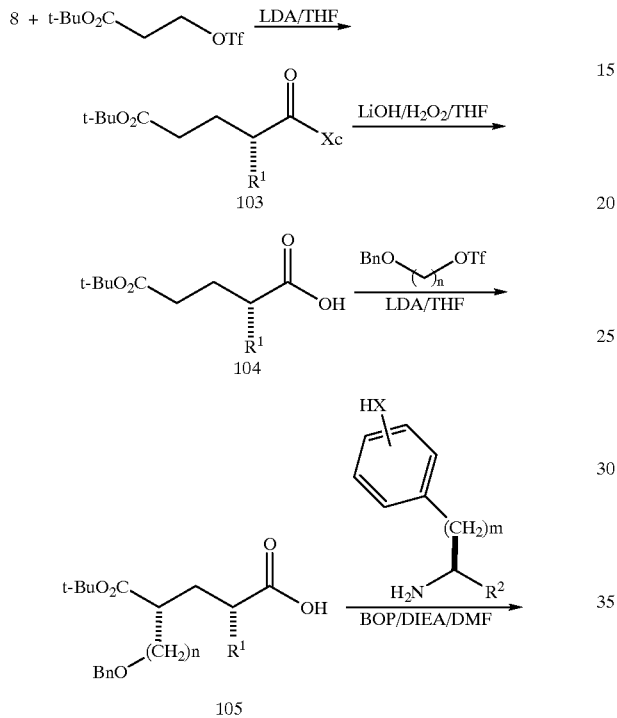

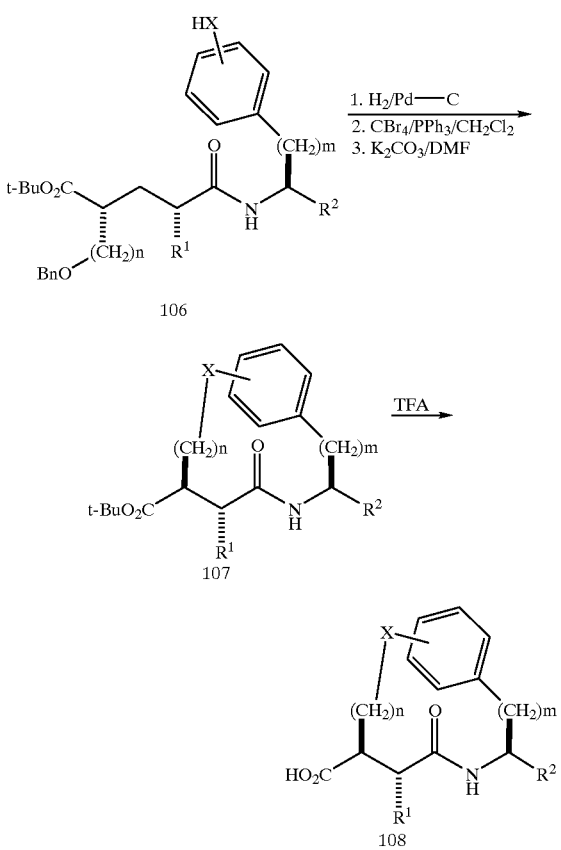

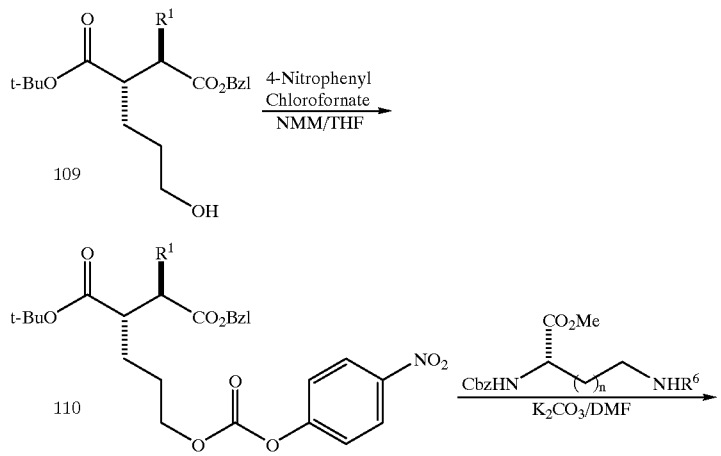

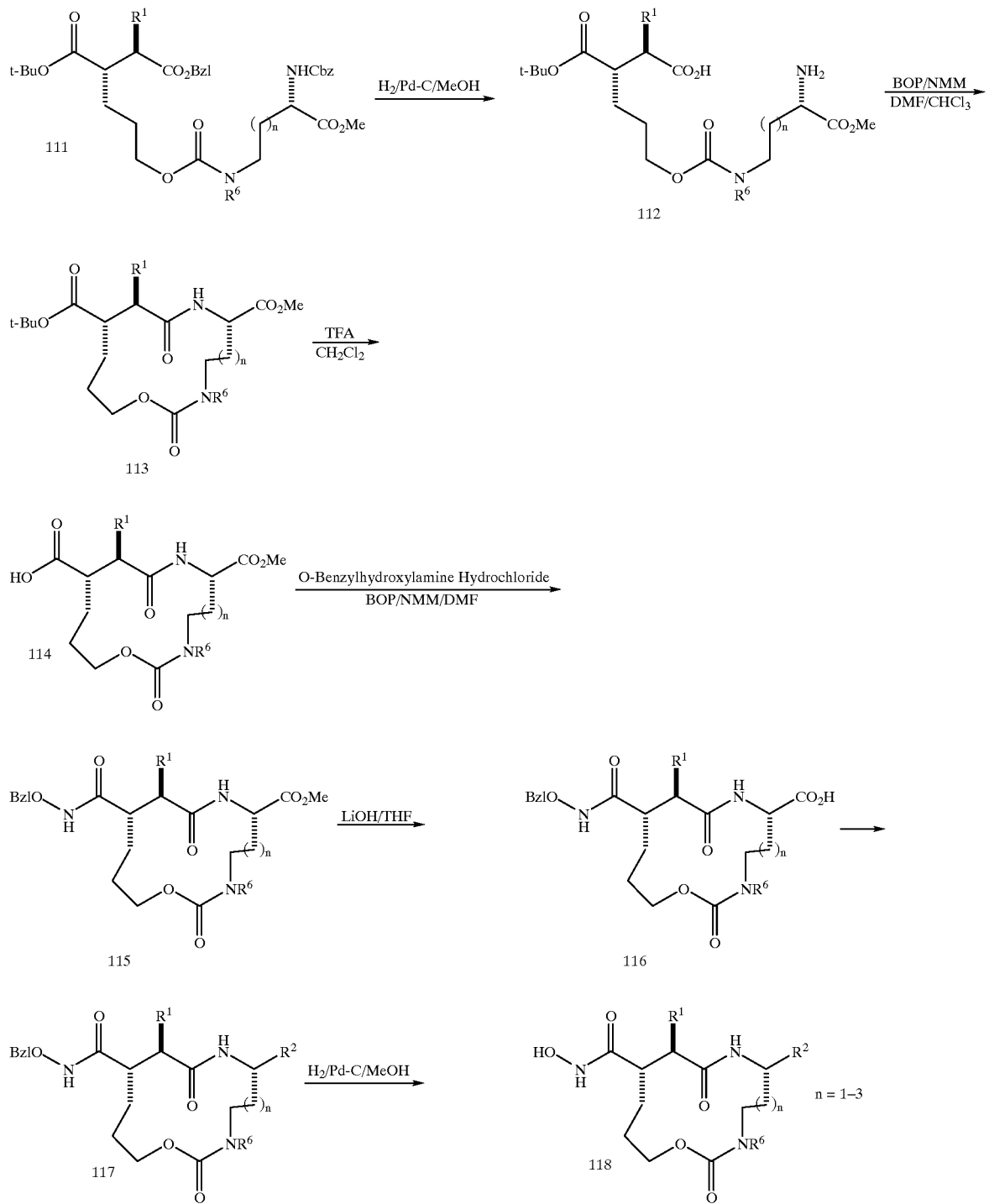

Another series of compounds of formula 131 are prepared by the method outlined in Schemes 25–27 below. Methyl 3S-4-benzyloxy-3-hydroxybutyrate (119) is prepared according to a published procedure (Abood, N. A. *Synth. Communu.* 1993, 23, 811). Stereoselective allylation of 119 with allyl bromide 120 gives compound 121. Following ester hydrolysis, the resultant acid 122 is coupled with appropriately functionalized lysine (123, n=2), ornithine (123, n=1) or 1,4-diaminobutyric acid (123, n=0). Reaction of 124 with E-1,4-dibromo-2-butene yields bromide 125.

Following removal of BOC group, the macrocyclization is achieved with a mild base, such as diisopropylethylamine. The resultant cyclic amine is protected with di-t-butyl dicarbonate in one pot. Treatment of 127 with $Pd(OH)_2$ under hydrogen leads to reduction of both olefinic bonds as well as cleavage of benzyl ether. Oxidation of alcohol 128 followed by coupling with O-benzyl hydroxyamine yields 130. At this point, the $R_4$ group is introduced by acid hydrolysis of BOC group and reaction with $R_4$—Cl. Finally, hydrogenolysis gives 131.

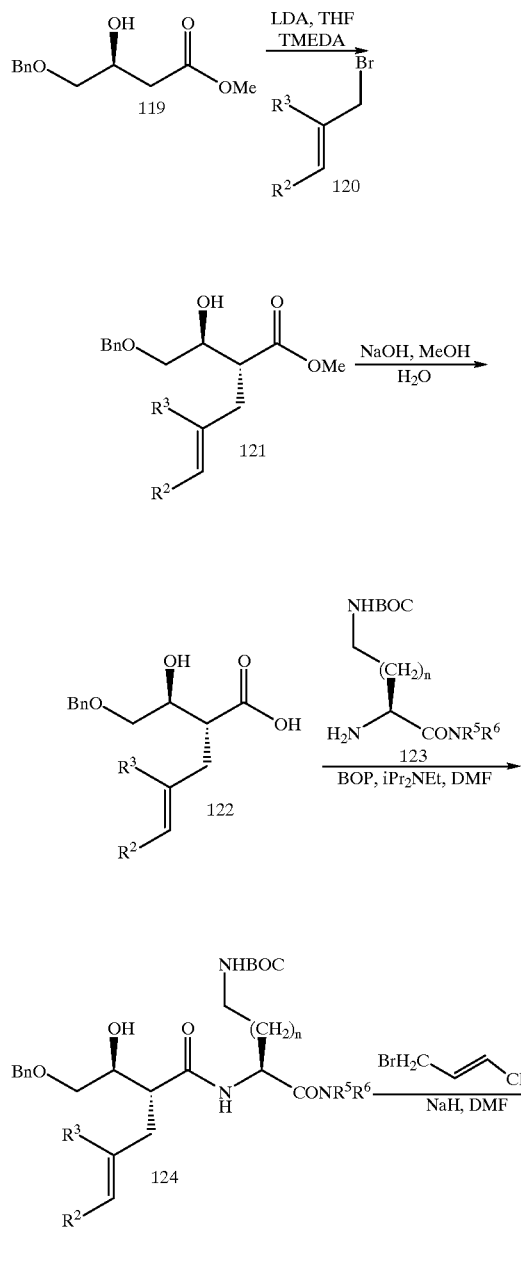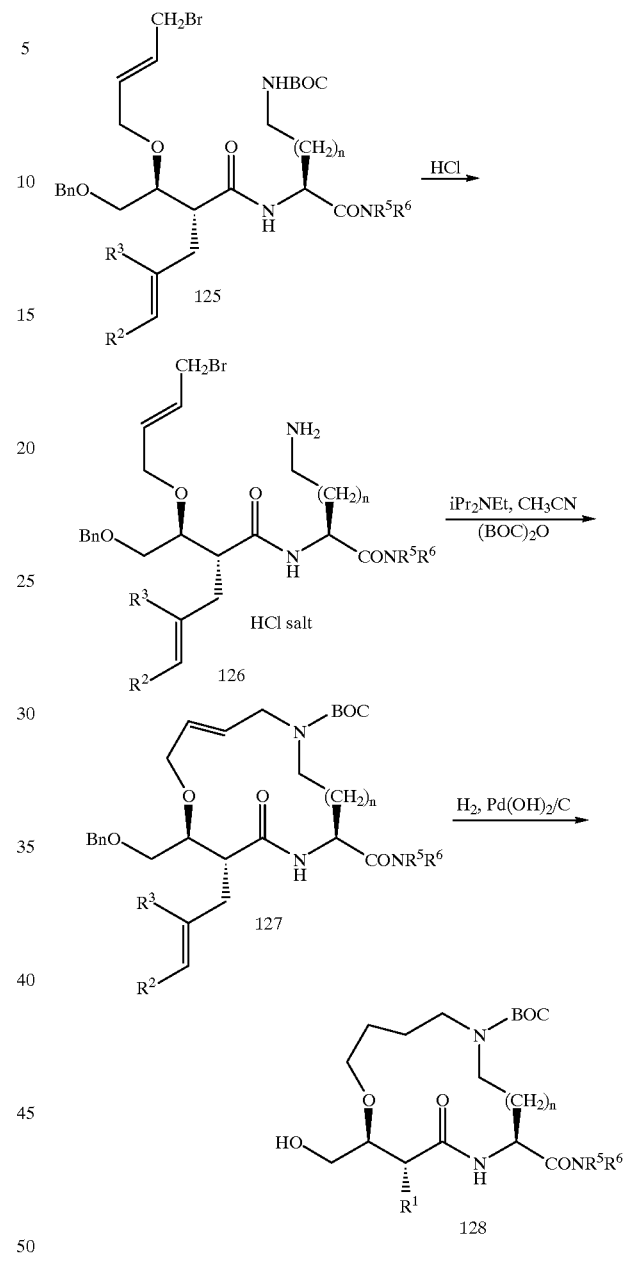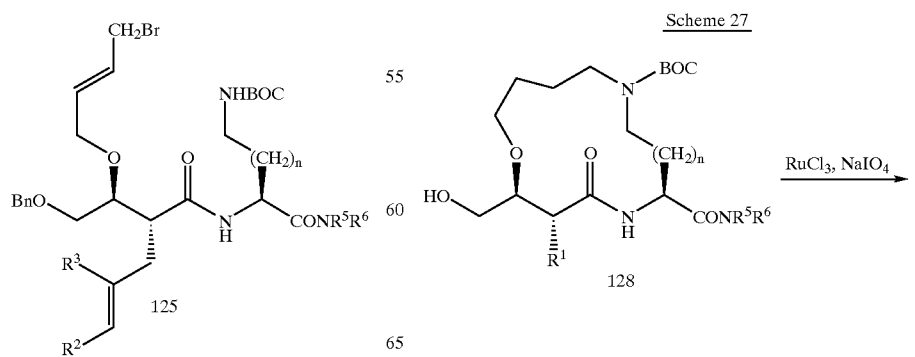

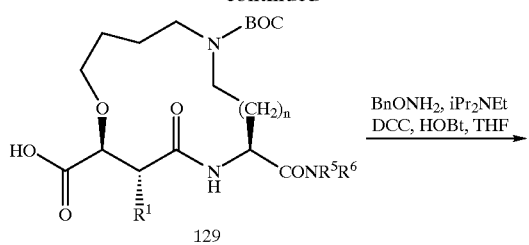

129

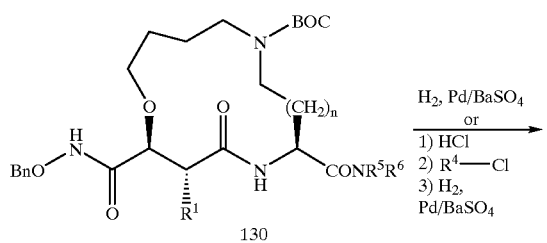

130

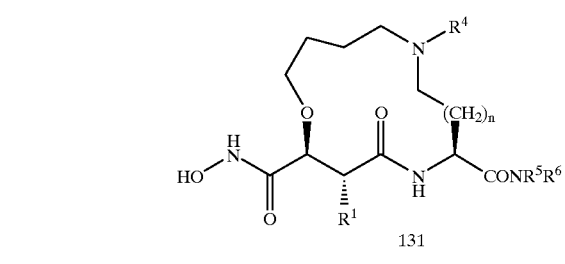

131

Another series of compounds of formula 133 are prepared by he method outlined in Schemes 28 below. Reaction of alcohol 124 with sodium hydride and 3-bromo-2-bromomethyl-1-propene provides 132. 132 is converted to 133 following sequence analogous to that outlined in Schemes 26 and 27.

Scheme 28

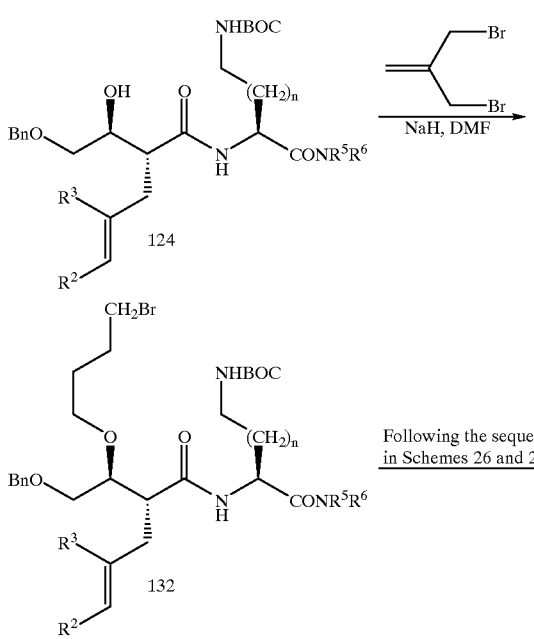

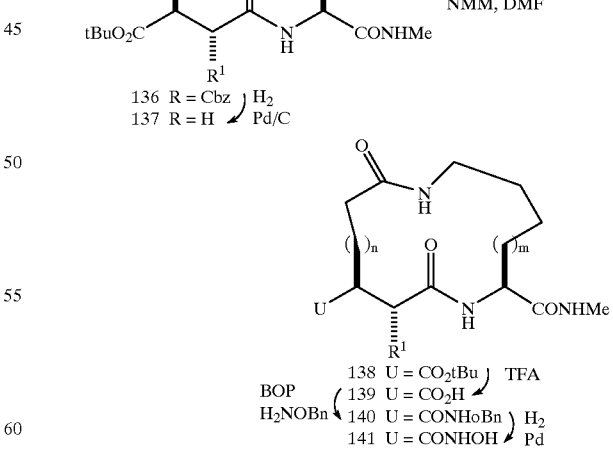

133

This invention also includes cyclic hydroxamates as described in scheme 29. In the first step, succinate 134 is coupled with L-lysine($N^e$-Cbz)—NHMe to yield the amide 135. The primary alcohol of 135 is oxidized to the acid 136 with $RuCl_3 \cdot H_2O$. After removal of the carbamate group, a macrocyclization affords the lactam 138. The t-butyl ester of 138 is then converted to the acid 139. This acid is coupled with $BnONH_2$ to give the protected hydroxamate 140. Hydrogenation of 140 provides the target hydroxamate 141.

Scheme 29

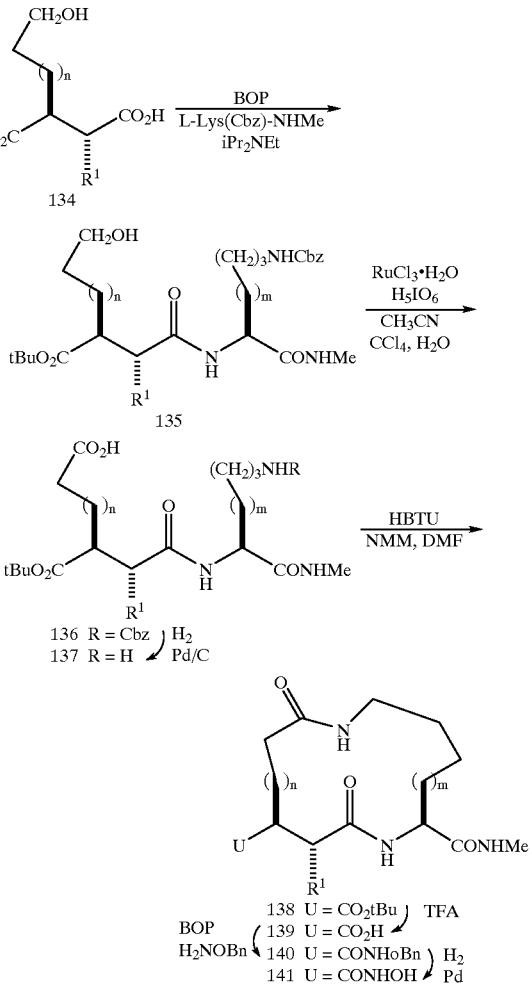

This invention also includes compounds available by the methods described in Scheme 30 which allows for the simple variation of $R^3$ from the common intermediate 145a. In the first step, succinate 134 is coupled with L-lysine($N^e$-Cbz)—$CO_2Me$ to yield the amide 142. The primary alcohol of 142 is oxidized to the acid 143 with $RuCl_3 \cdot H_2O$. After removal of the carbamate group, a macrocyclization affords the lactam 144. The t-butyl ester of 144 is converted to the protected hydroxamate 145 under our standard protocol. The methyl ester of 145 is hydrolyzed with LiOH. The resulting acid 145a is manipulated to give a desired $R^3$. Hydrogenation of 146 gives the target hydroxamate 147.

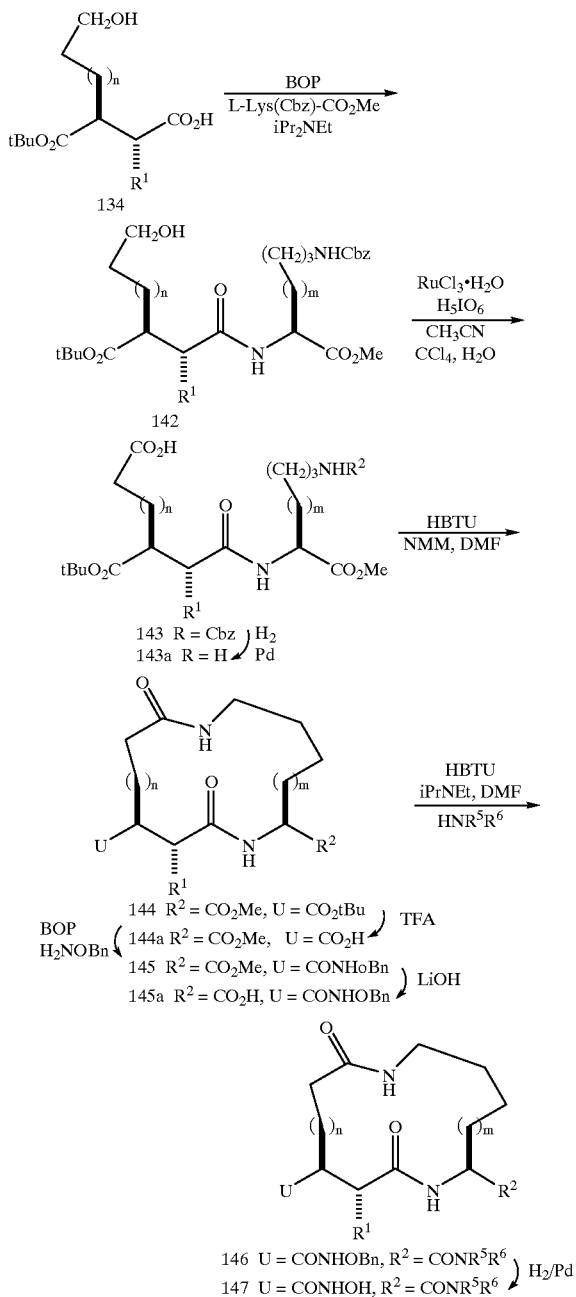

Scheme 30

This invention also includes cyclic amino carboxylates of formula II, where $U=\!\!-\!CO_2H$, R4=H, X=$-$NH, R1=alkylaryl, Y=$-$C(O)NH$-$, R2=H, R3=$-$C(O)NHMe, C=alkyl, B=$-$C(O)NH, A=alkyl. Scheme 31 depicts how a compound of this type is available from D-glutamic-N-Fmoc t-butyl ester or D-aspartic-N-Fmoc t-butyl ester through standard peptide chemistry. Standard BOP coupling of this material with 7 gives the amide 148. The Fmoc group can be deprotected to the primary amine 149 followed by alkylation with a triflate to yield the secondary amine 150 (Kogan, T. P.; Somers, T. C.; Venuti, M. C. *Tetrahedron* 1990, 46, 6623).

Dual deprotection via hydrogenation affords the amino acid 151, which can be cyclized to give the macrolactam 152. Simple deprotection with TFA provides the desired, cyclic amino carboxylate 153.

Scheme 31

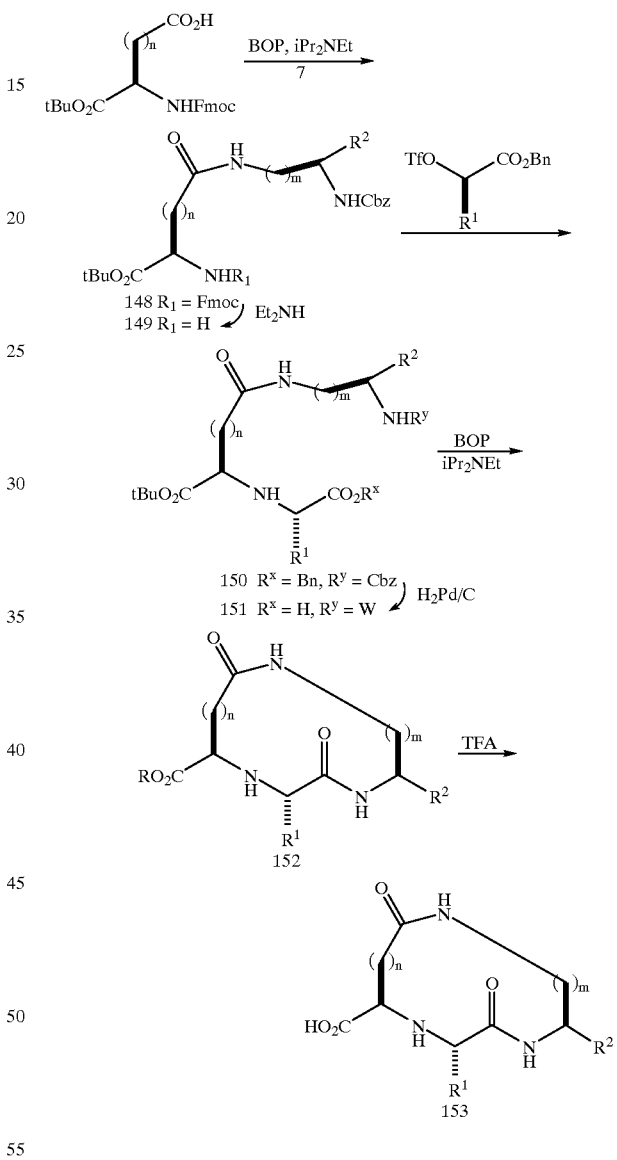

This invention also includes cyclic amino carboxylates of formula II, where $U=\!\!-\!CO_2H$, R4=H, X=$-$NH, R1=alkylaryl, Y=$-$NHC(O)$-$, R2=H, R3=$-$C(O)NHMe, C=alkyl, B=$-$C(O)NH, A=alkyl. Scheme 32 depicts how a compound of this type is available from D-lysine-N-Fmoc t-butyl ester or D-ornithine-N-Fmoc t-butyl ester through standard peptide chemhstry. Standard BOP coupling of this material with L-glutarmic-$N^\alpha$-Cbz methyl ester or L-aspartic-$N^\alpha$ gives the amide 154. Deprotection of the Fmoc group leads to the primary amine 155. The primary amine can be alkylated as above with a triflate to give the secondary amine 156. Dual deprotect via hydrogenation gives the amino acid 157. Macrocycization can be performed using BOP to give lactam 158. Saponification of 158 followed by standard coupling with BOP and methylamine gives the amide 159. Simple deprotection with TFA affords the cyclic amino carboxylate 160.

Scheme 32

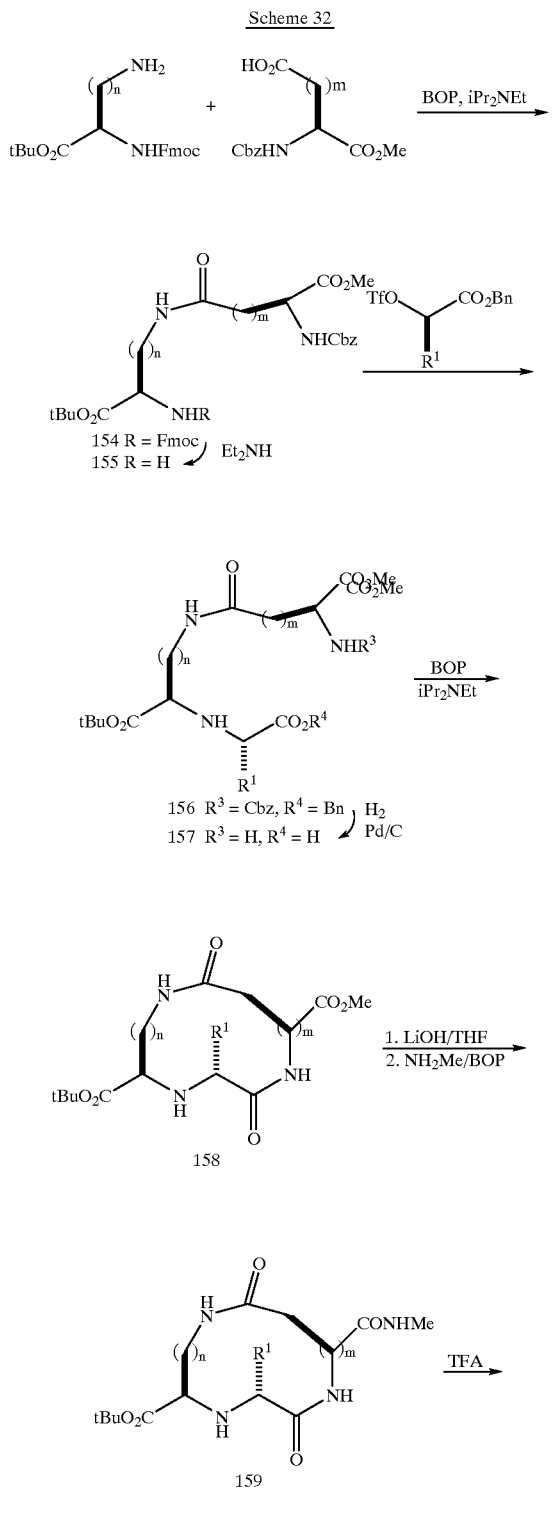

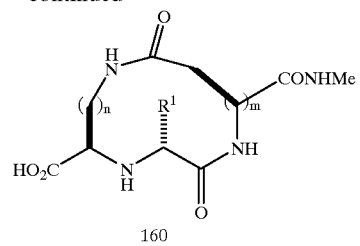

This intention also includes cyclic amino carboxylates of formula II, where U=—$CO_2H$, R4=H, X=—NH, R1=alkylaryl, Y=—C(O)NH—, R2=H, R3=—C(O)NHMe, C=alkyl, B=—$C_6H_4CO_2$—, A=alkyl. Scheme 33 depicts how a compound of this type is available from D-Aspartic-N-Boc-(a)-t-butyl ester or D-glutamic-N-Boc-(a)-t-butyl ester through standard peptide chemistry. The b-acid is converted into an aldehyde 161 using Weinreb chemistry (Wernic, D.; DiMaio, J.; Adams, J. *J. Org. Chem.* 1989, 54, 4224).

This material can be converted into the olefin 162 via a Wittig[2] reaction with 4-carbomethoxybenzyl triphenylphosphonium bromide (Lancaster). A serine amide is coupled with 163 to make the ester 164. The Boc protected amine of 164 is deprotected with HCl to provide the primary amine 165. The primary amine can be alkylated as above with a triflate to give the secondary amine 166. Dual deprotect via hydrogenation gives the amino acid 167. Macrocycization can be performed to give lactam 168. Simple deprotection with TFA affords the cyclic amino carboxylate 169.

Scheme 33

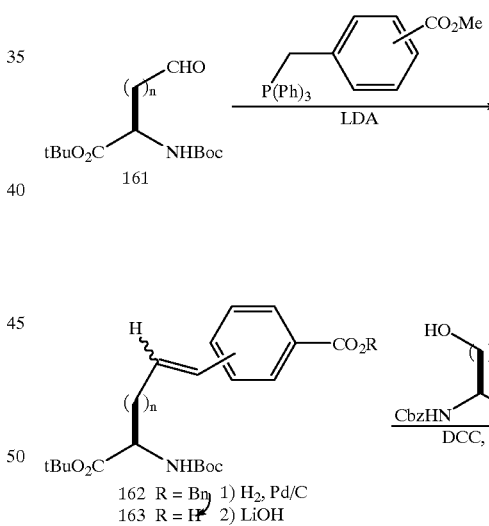

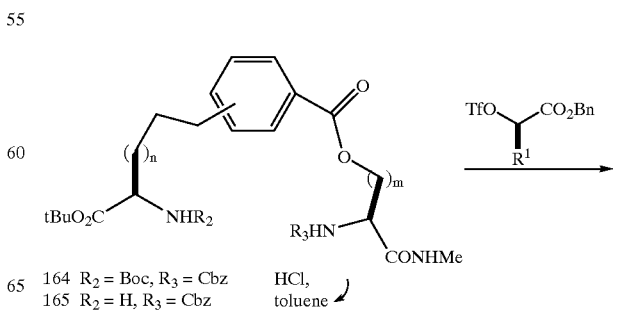

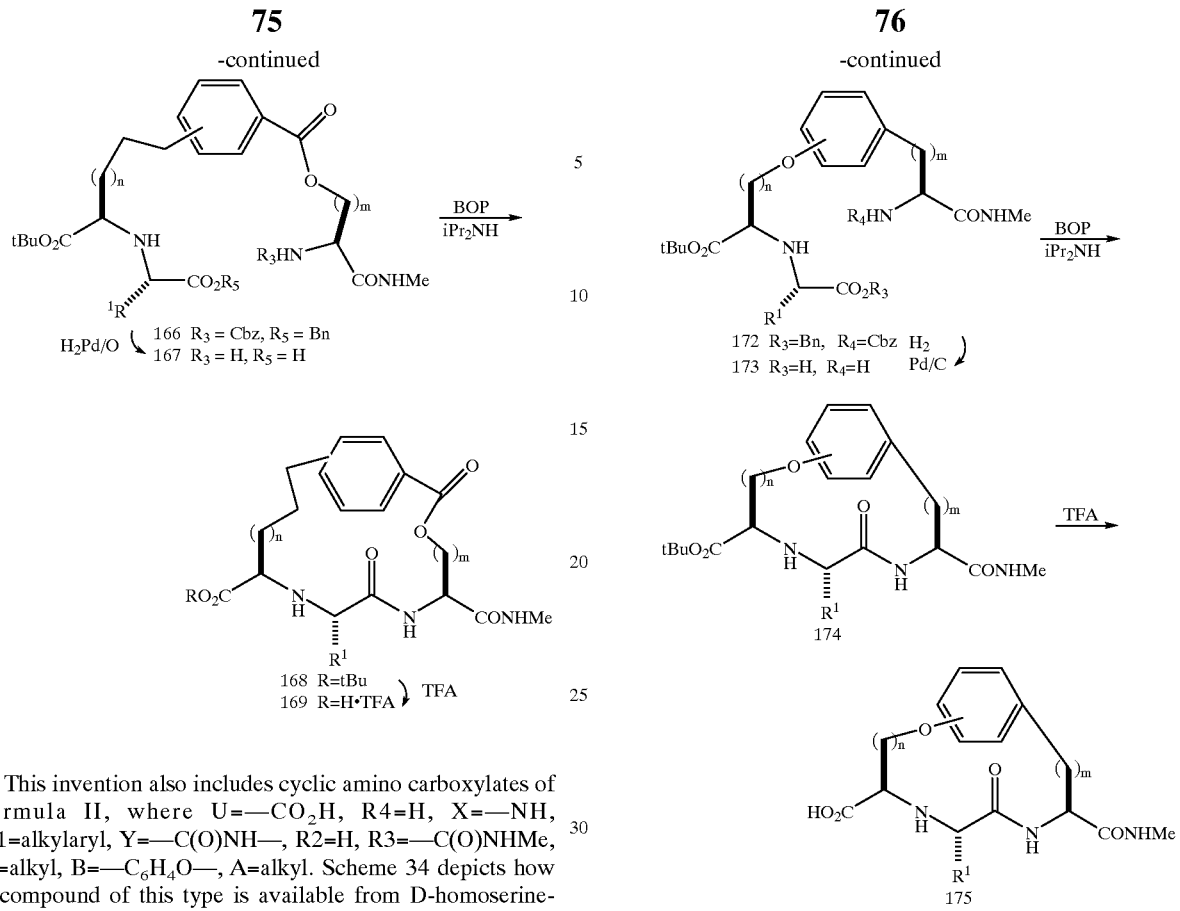

This invention also includes cyclic amino carboxylates of formula II, where U=—CO$_2$H, R4=H, X=—NH, R1=alkylaryl, Y=—C(O)NH—, R2=H, R3=—C(O)NHMe, C=alkyl, B=—C$_6$H$_4$O—, A=alkyl. Scheme 34 depicts how a compound of this type is available from D-homoserine-N-Fmoc-(a)-t-butyl ester through standard peptide chemistry. The primary alcohol of the serine derivative can be coupled to the phenol of a tyrosine derivative via a Mitsunobu reaction to give 170 (Hughes, D. 1. *Org. React.* 1992, 42, 335). The Fmoc is deprotected with Et$_2$NH to give the primary amine 171. As above, this primary amine is alkylated with the a triflate to give the secondary amine 172. Dual deprotection gives the amino acid 173. Macrocyclization of 173 with BOP affords the lactam 174. Simple deprotection with TFA gives the desired amino carboxylate 175.

Scheme 34

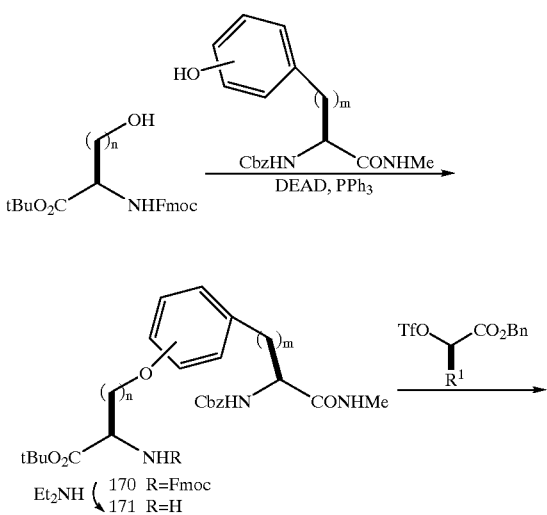

This invention also includes cyclic amino carboxylates of formula II, where U=—CO$_2$H, R4=H, X=—NH, R1=alkylaryl, Y=—C(O)NH—, R2=H, R3=—C(O)NHMe, C=-alkylCO$_2$—, B=—C(O)NH—, A=alkyl. Scheme 35 depicts how a compound of this type is available from L-glutamic-N-Cbz-(a)-methyl ester or L-aspartic-N-Cbz-(a)-methyl ester through standard peptide chemistry. This material can be coupled to 2-N-Boc-aminoethanol with DCC and DMAP to yield the ester 176. Functional group manipulation leads to the acid followed by the amide 177 by standard chemistry. The Boc group of 177 is then removed with TFA to give 178. This material can be coupled to D-glutamic-N-Fmoc-(a)-t-butyl ester or D-aspartic-N-Fmoc-(a)-t-butyl ester to give the amide 179. The Fmoc is removed with diethylamine to reveal the primary amine 180. As above, this primary amine can be alkylated with a triflate to give 181. Hydrogenation and macrocyclization of this amino acid with BOP affords the lactam 182. Simple deprotection with TFA gives the desired amino carboxylate 183.

Scheme 35

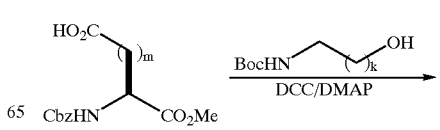

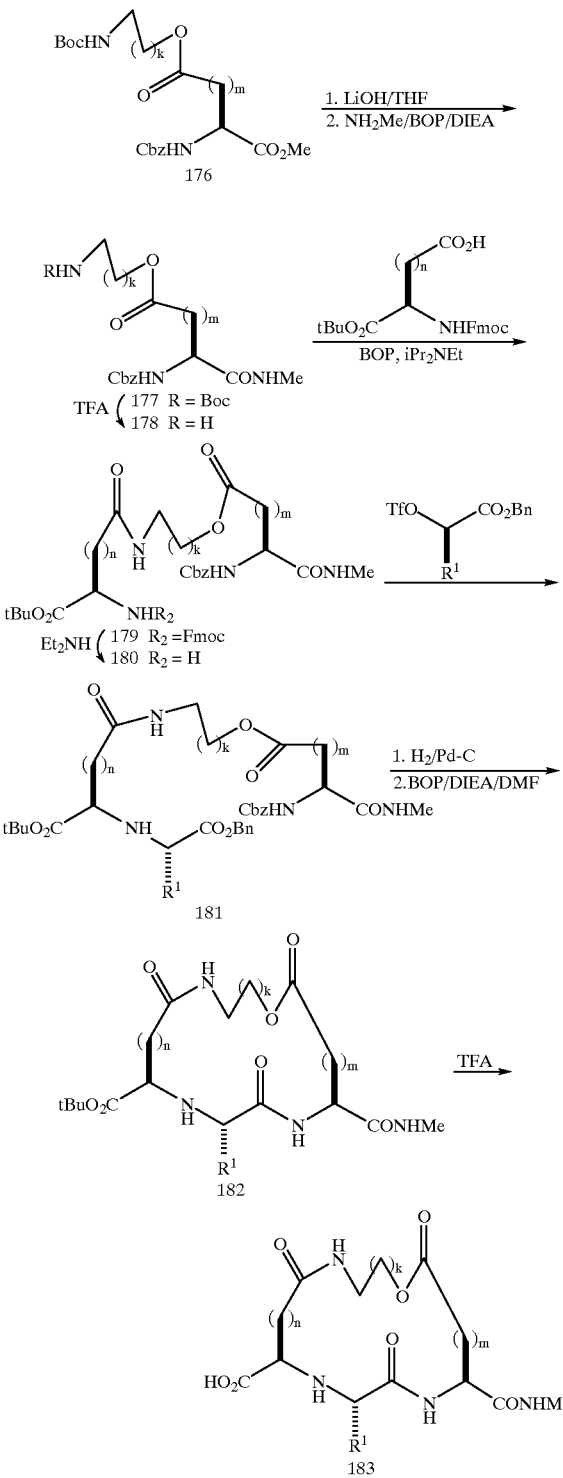

with a lysine derivative to produce the amine 185. After protection with (Boc)₂O, the Fmoc is removed with diethylamine to give primary amime 185. As above, the primary amine 185 can be alkylated with a trifate to provide the secondary amine 188. Dual deprotection of the material via hydrogenation yields the amino acid 189. Macrocyclization of this amino acid with BOP affords the lactam 188. Simple deprotection with TFA gives the desired amino carboxylate 189.

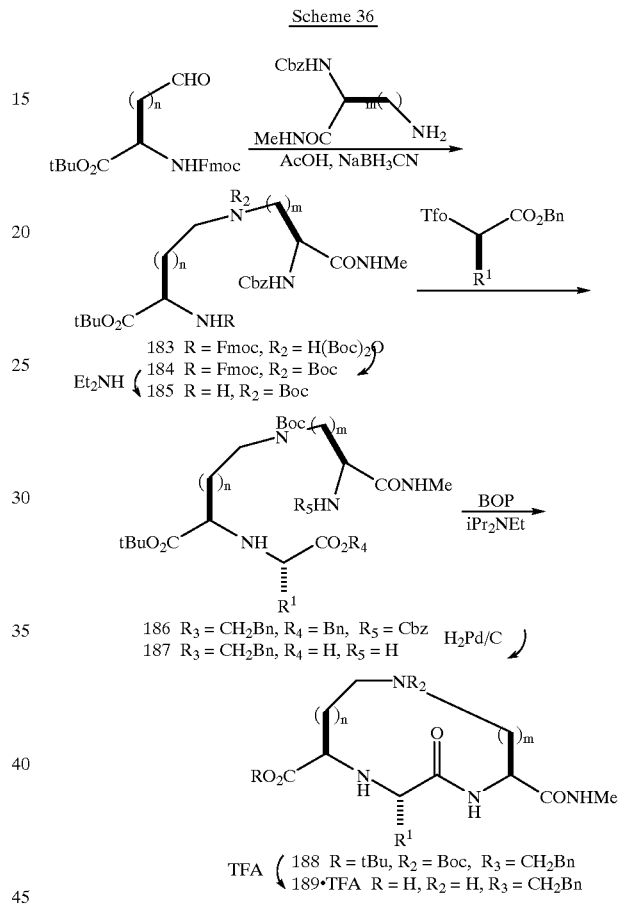

Another series of compounds are synthesized as shown in Scheme 37. The succinate 134 is coupled with L-lysine($N^e$-Mts)—NHMe to afford the amide 190. This material is cyclized under Mitsunobu conditions to give the macrocycle 191. The t-butyl ester of 191 is converted to the acid 192. This acid is coupled to H₂NOBn with BOP to give the protected hydroxamate 21193. Hydrogenation of the benzyl group gives the target hydroxamate 194.

Scheme 37

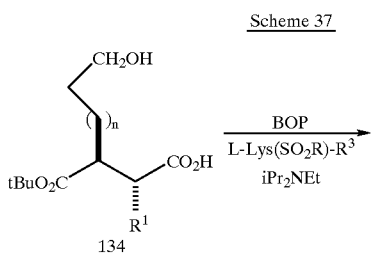

This invention also includes cyclic amino carboxylates of formula II, where U=—CO₂H, R4=H, X=—NH, R1=alkylaryl, Y=—C(O)NH—, R2=H, R3=—C(O)NHMe, C=-alkyl, B=—NR—, A=alkyl. Scheme 36 depicts how a compound of this type is available from L-aspartic-N-Fmoc-(a)-t-butyl ester or L-glutamic-N-Fmoc-(a)-t-butyl ester through standard peptide chemistry. As above, the acid can be converted[2] into the aldehyde 184 using Weinreb chemistry. This aldehyde can participate in a reductive amination

Scheme 39

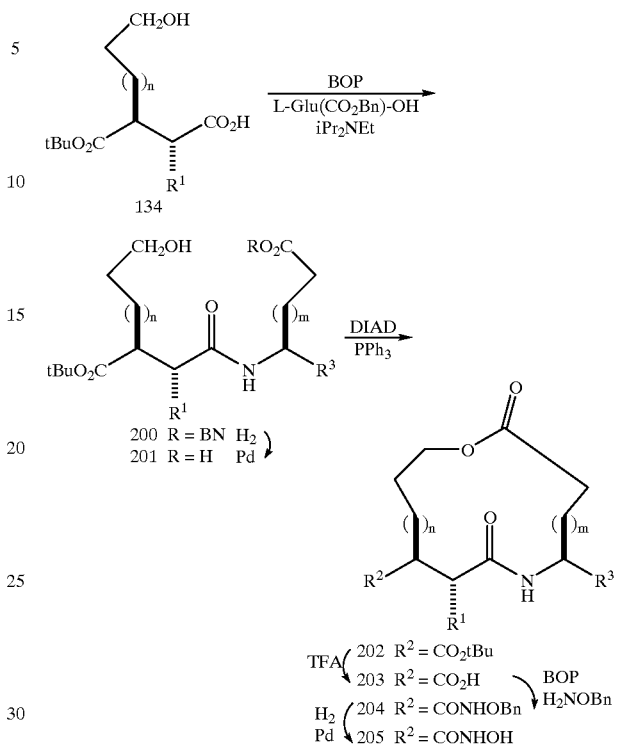

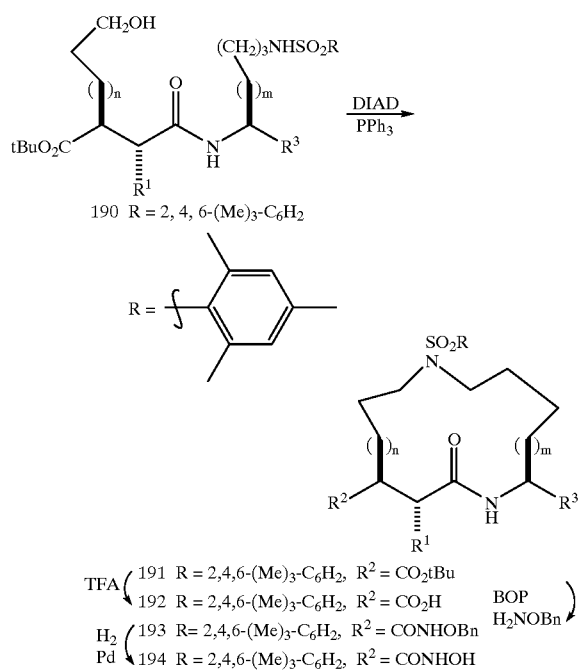

Another series of compounds are synthesized as shown in Scheme 38. The mesitylenesulfonamide 191, from Scheme 37, is converted to the amine 195 with HBr. The amine 195 is reacted with Boc$_2$O to afford the carbamate 196. The acid of 196 is coupled to H$_2$NOBn with BOP to give the protected hydroxamate 197. This material is hydrogenated he hydroxamate 198. The carbamate is then the amine 199 with HCl.

Compounds of formula 3004, where Z is a N-alkyl amide, an imidazole or benzimidazole could be prepared by the route shown in scheme 40 below. Deprotonation of 8 with a strong base (e.g. LDA) followed by treatment with an

Scheme 38

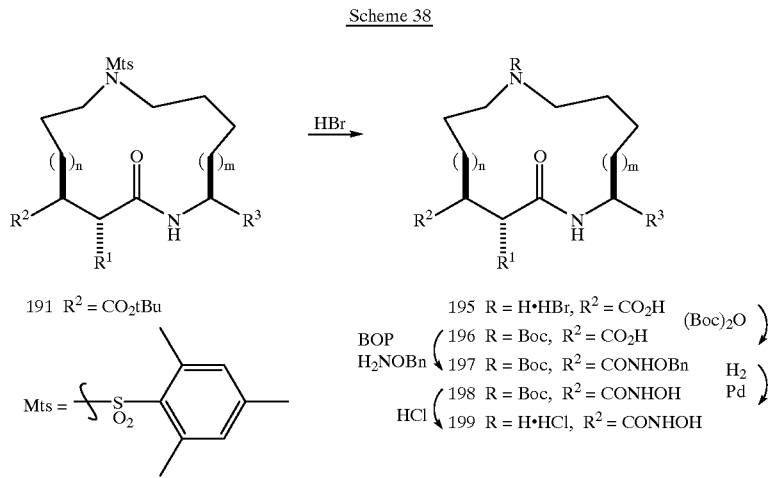

Another series of compounds of formula 205 are synthesized as shown in Scheme 39. The succinate 134 is coupled with L-glutamate(g-CO$_2$Bn) N-methyl amide to afford the amide 200. After benzyl removal, the compound is cyclized under the Mitsunobu conditions to yield 202. The t-butyl ester of 202 is converted to the acid 203. This acid is coupled with BnONH$_2$ to give the protected hydroxamate 204. Hydrogenation of 204 provides the target hydroxamate 205.

a-ketoester produces intermediate 3000. Coupling of 3000 with the intermediate 7 using standard peptide chemistry affords 3001. Removal of the chiral auxiliary, followed by the deprotection of the amino group affords amino acid of the formula 3002. Macrocyclization provides compound 3003. Hydrolysis of the ester, followed by the formation of O-benzyl protected hydroxylamine and final hydrogenation gives the desired compound 3004.

Scheme 40

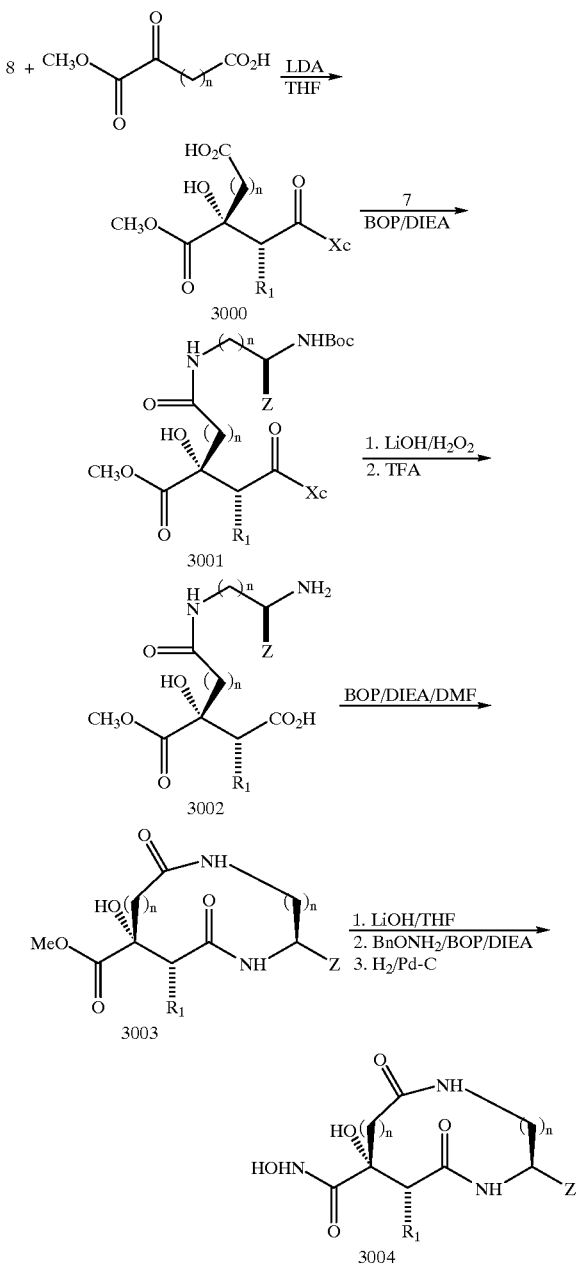

Scheme 41

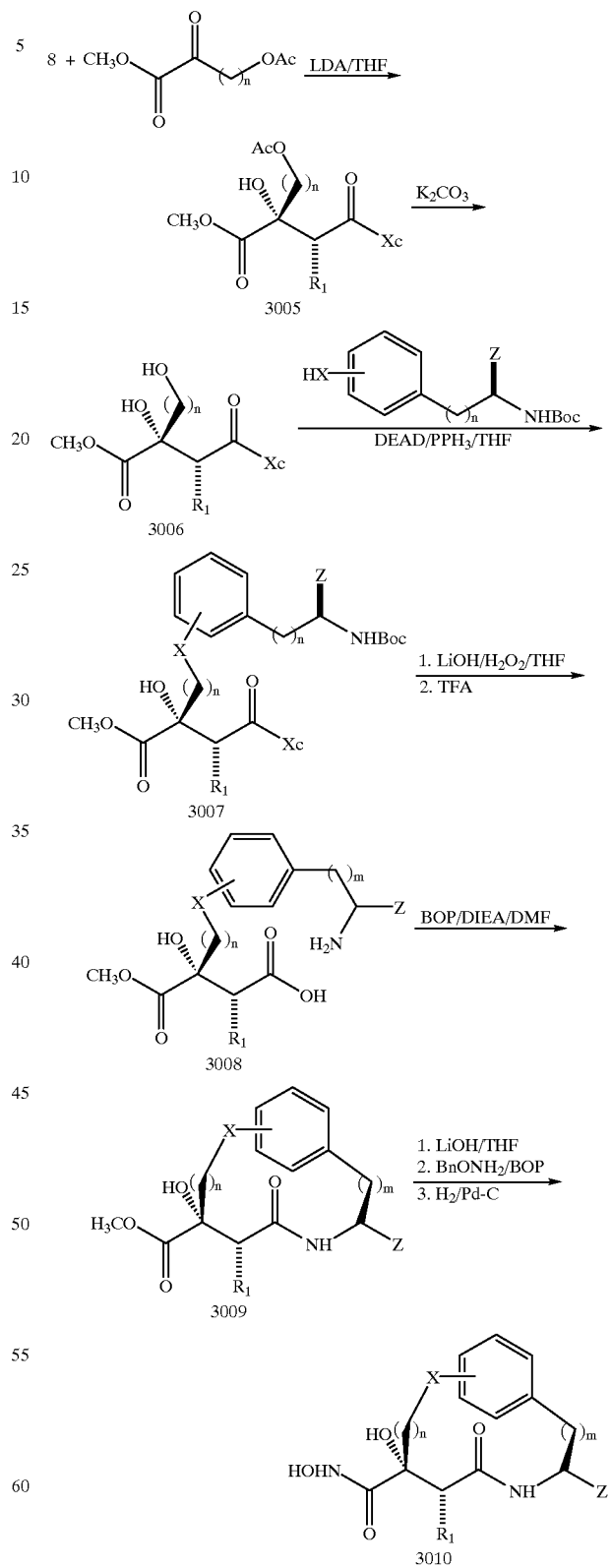

Compounds of formula 3010, where Z is a N-alkyl amide, an imidazole or a benzimidazole could be prepared by the route shown in scheme 41 below. An intermediate 3005 prepared in the same manner as depicted in scheme 40 is treated with a mild base to give the alcohol 3006. A Mitsunobu reaction with an appropriately substituted tyrosine derivative affords compound 3007. Removal of the chiral auxiliary and deprotection of the amino group affords amino acid 3008. Macrocyclization provides compound of formula 3009. Conversion to the desired final product 3010 is done in a manner analogous to that depicted in scheme 40 above.

Compounds of formula 3014, where Z is a N-alkyl amide, an imidazole or a benzimidazole could be prepared as shown in scheme 42 below. Coupling of 7 with 3006 using CDI produces the carbamate 120. Hydrolysis of the chiral auxiliary and deprotection of the amino group affords the amino acid 3012 that undergoes macrocyclization to produce compound 3013. The desired compound of formula 3014 is then obtained in a manner analogous to that depicted in scheme 40.

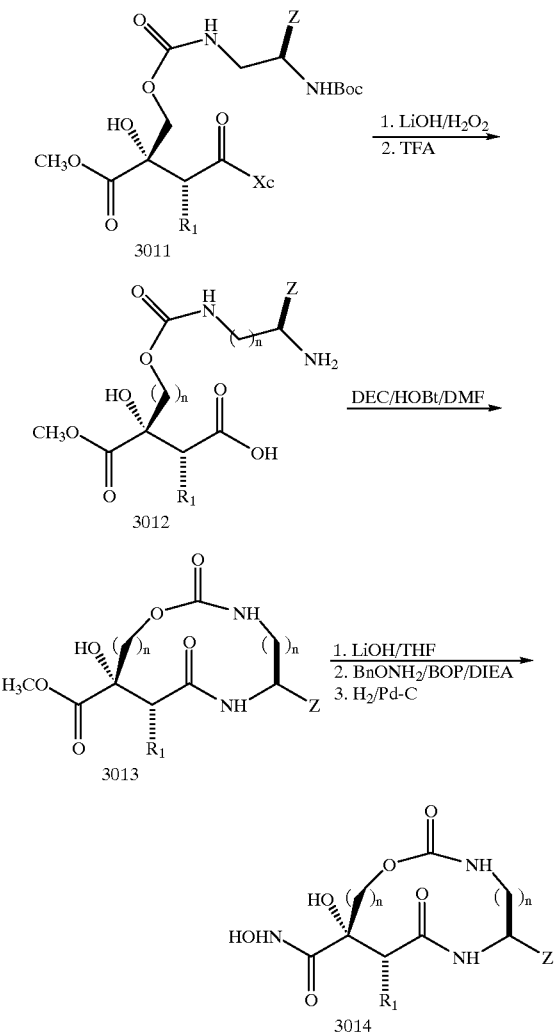

Cyclic ureas of formula 3019, where Z is a N-alkyl amide, an imidazole or a benzimidazole could be prepared as shown in scheme 43 below. An intermediate 3015 is obtained by reaction of 8 with a a-keto-aminocarboxylic ester. Removal of the chiral auxiliary is followed by the standard peptide coupling with a lysine or ornithine derivative 6 to afford 3017. Hydrogenolysis of the protecting groups and treatment with CDI yields cyclic urea 3018. Conversion to the final compound 3019 is done in a manner analogous to that described in scheme 40.

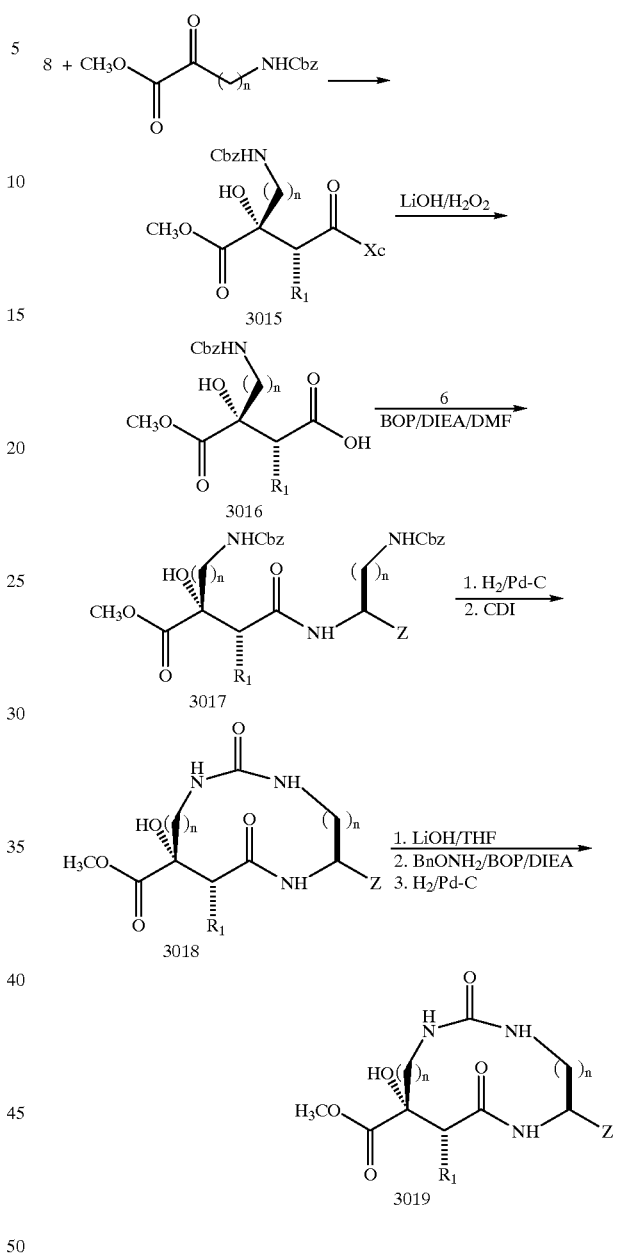

Cyclic lactams of formula 3023, where Z is a N-alkyl amide, an imidazole or a benzimidazole could be prepared as depicted in scheme 44. The intermediate 3015 is hydrogenated to give the amine 3019. Coupling of 3019 with an aspartic acid or a glutamic acid derivative under standard peptide coupling conditions affords 3020. Removal of chiral auxiliary and hydrogenolysis afford amino acid 3021. Macrocyclization produces cyclic lactam 3022, which is converted to the desired compound 3023 using conditions described in scheme 40.

Scheme 44

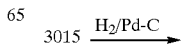

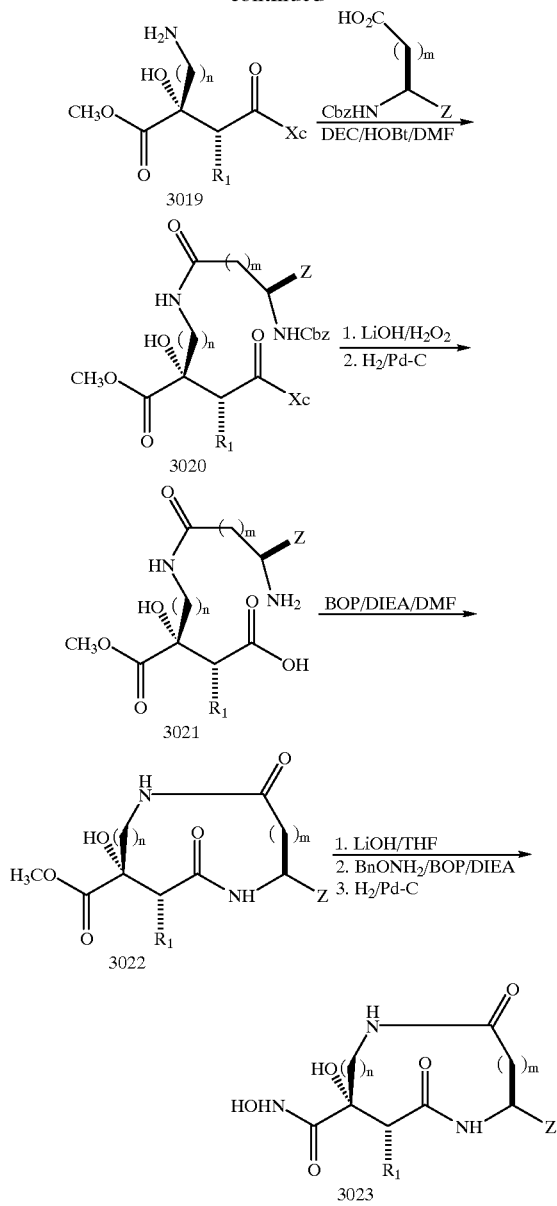

Preparation of the compounds of formula 141, where Z is a N-alkyl amide, an imidazole or a benzimidazole could be achieved as desribed in scheme 29 below. Dibal reduction of an appropriately substituted ester of an amino acid to an aldehyde is followed by the formation of a cyanohydrin which is hydrolyzed to afford an acid 134. The acid is converted to a benzyl ester 135 that undergoes Mitsunobu reaction to afford 136. Deprotection of the t-butyl ester followed by peptide coupling with a lysine or an ornithine derivative affords 138. Base hydrolysis affords an amino acid that undergoes macrocyclization to give 139. Hydrogenolysis of 139 produces the carboxylic acid 140. Coupling of 140 with O-benzylhydroxylamine followed by hydrogenation affords the final compound 141.

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Not all compounds of Formula I falling into a given class may be compatible with some of the reaction conditions required in some of the methods described. Such restrictions to the substituents which are compatible with the reaction conditions will be readily apparent to one skilled in the art and alternate methods must then be used.

EXAMPLES

Abbreviations used in the Examples are defined as follows: "1×" for once, "2×" for twice, "3×" for thrice, "bs" for broad singlet, "° C." for degrees Celsius, "Cbz" for benzyloxycarbonyl, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "$^1$H" for proton, "hr" for hour or hours, "m" for multiplet, "M" for molar, "min" for minute or minutes, "mp" for melting point range, "MHz" for megahertz, "MS" for mass spectroscopy, "nmr" or "NMR" for nuclear magnetic resonance spectroscopy, "t" for triplet, "tlc" for thin layer chromatography, "v/v" for volume to volume ratio. "a", "b", "R" and "S" are stereochemical designations familiar to those skilled in the art.

1(a) 3R-Allyl-3-t-Butoxycarbonyl-2(R)-isobutyl propanoic acid

To a stirred cooled(−78° C.) solution of 20 grams (87 mmol) of 3-t-Butoxycarbonyl-2(R)-isobutylpropanoic acid (1.15 g, 5 mnol) (previously aziotroped with toluene) in 400 mL of anhydrous THF, was added 180 mmol of LDA via cannula over 30 minutes. After stirring for 1 hour, 8.3 mL (96 mmol) of allyl bromide was added dropwise. The reaction was allowed to slowly warm to room temperature while stirring overnight. The reaction was quenched with 10% aqueous citric acid followed by removal of the volatiles under reduced pressure. The remaining material was taken into ethyl acetate and washed with H$_2$O. The aqueous phase was then extracted 3 times with ethyl acetate and the combined organic fractions were washed with 10% citric acid, saturated NaHCO$_3$ (2×), H$_2$O (2×), and brine then dried over MgSO$_4$. The solvent was removed under reduced pressure obtaining 23.3 grams (99% yield) which was carried on without purification. MS (M+Na)$^+$=293

1(b) 3S-Allyl-3-t-butoxycarbonyl-2(R)-isobutyl propanoic acid

To a stirred, cooled (−78° C.) solution of 2 grams of acid 1(a) (previously aziotroped 2 times with benzene) in 25 ml of anhydrous THF, was added 16.3 mmol of LDA via cannule over 15 minutes. The reaction was stirred 15 minutes at −78° C. and then for 15 minutes in a room temperature (24° C.) water bath. The reaction was then cooled to −78° C. for 15 minutes, followed by the addition of 15.6 ml of 1 M diethylalluminum chloride (hexane). The reaction was stirred 10 minutes at −78° C., 15 minutes in a room temperature water bath, then for 15 minutes at −78° C. again, followed by quench with the rapid addition of methanol. The reaction mixture was concentrated to ~1/4 its origional volume under reduced pressure and the resulting material was dissolved in 200 ml of ethyl acetate and washed with a mixture of 70 mL of 1N HCl and 100 grams of ice. The aqueous was extracted 2 times with ethyl acetate. The combined organic fractions were washed with a solution of 3.5 grams of KF dissolved in 100 mL of water and 15 mL of 1 N HCl (pH 3–4). The organic phase was washed with brine, dried with $MgSO_4$, filtered and the solvent was removed under reduced pressure affording a 92% mass recovery. $^1$H NMR in acetone d-6 indicated an ~8:1 anti syn ratio. MS (M+Na)$^+$=293

1(c) Benzyl 3S-Allyl-3-t-butoxycarbonyl-2(R)-isobutylpropanoate

To a stirred cooled (0° C.) solution of 20.6 grams(76 mmol) of crude equilibrated acid 1(b) (8:1 mixture) in 75 mL of benzene, was added 11.4 mL (76 mmol) of DBU followed by 9.98 mL (84 mmol) of benzyl bromide. After 10 minutes the reaction was refluxed for 4 hours. The reaction was then diluted to 3 times origional volume with ethyl acetate and washed 3 times with 10% aqueous citric acid. The combined aqueous was extracted 3 times with ethyl acetate. The combined organic fractions were then washed with brine, dried over $MqSO_4$ and the volatiles were removed under reduced pressure. The resulting material was chromatographed over silica gel eluting with 2.2% ethyl acetate/hexanes affording 16.9 grams of benzyl ester (62% yield). MS (M+NH$_4$)$^+$=378

1(d) Benzyl 3S-(3-hydroxypropyl)-3-t-butoxycarbonyl-2(R)-isobutylpropanoate

To a stirred, cooled (0° C.) solution of 5.2 grams of olefin 1(c) in 100 mL of anhydrous THF, was added 72.2 mL of 0.5M 9-BBN in THF over 1 hour. The reaction was allowed to warm to room temperature while stirring 12 h. The reaction was cooled to 0° C. followed by the addition of 2.9 mL of H$_2$O added (caution foaming) dropwise over 5 minutes. After stirring for an additional 20 minutes, 8 mL of H$_2$O containing 3.21 grams of NaOAc was added simultaneously with 8 mL of 30% H$_2$O$_2$ over 5 minutes. The mixture was stirred 20 additional minutes followed by removal of the volatiles under reduced pressure. The remaining material was dissolved in ethyl acetate and washed with brine. The aqueous phase was extracted 2 times with ethyl acetate. The combined organic fractions were washed with water, brine, dried MgSO$_4$ followed by removal of the volatiles under reduced pressure. The resulting material was chromatographed on silica gel with an eluting gradient from 1:20 to 1:10 to 1:5 ethyl acetate/hexanes affording 3.5 grams (64% yield). MS (M+H)$^+$379

1(e) Benzyl 3S-(3-bromopropyl)-3-t-butoxycarbonyl-2(R)-isobutylpropanoate

To a stirred, cooled (0° C.) solution of 8.32 grams of triphenylphosphine, 2.15 grams of imidazole and 10.54 grams of carbon tetrabromide in 60 mL of anhydrous CH$_2$Cl$_2$, was added a solution of 8.0 grams of alcohol 1(d) dissolved in 60 mL of anhydrous CH$_2$Cl$_2$ dropwise over 15 minutes. The reaction was stirred at 0° C. for 30 minutes and then an additional 1/2 equivalent of triphenylphosphine, imidazole and carbon tetrabromide in 30 mL of CH$_2$Cl$_2$ was added at one time. The reaction was stirred an additional 2.5 hours at 0° C., 20 minutes at room temperature (24° C.) then diluted with 320 mL of hexanes and filtered through a short silica gel plug rinsing with 25% ethyl acetate/hexanes. The volatiles were removed under reduced pressure and the resulting material was chromatographed on silica gel eluting with a 1–10% ethyl acetate/hexanes gradient affording 6.1 grams (65% yield) of the bromide. M+H=442.

1(f) 3S-(3-bromopropyl)-3-t-butoxycarbonyl-2(R)-isobutylpropanoic acid

To 10.5 grams of benzyl ester 1(e) in 250 mL of methanol, was added 1 g of 10% Pd—C. The mixture was stirred under H$_2$ (balloon) for 3 hours. The catalyst was removed by filtration and the solvent was removed under reduced pressure affording 8.3 grams of material. M+H=352.

1(g) 3S-(3-bromopropyl)-3-t-butoxycarbonyl-2R-isobutylpropanoyl-[tyrosine-methylester]

To 8.4 g of acid in 200 mL of DMF was added 5.5 g of tyrosine methylester hydrochloride and 9.1 mL of NMM. To this mixture was added 9.52 g of TBTU dissolved in 120 mL of DMF over 30 minutes. The reaction was stirred 2 hours at room temperature followed by removal of the volatiles under reduced pressure. The resulting mass was dissolved in ethyl acetate and washed with cold 1N HCl. The aqueous phase was extracted 3 times with ethyl acetate. The combined organic fraction was washed sequentially with H$_2$O, saturated NaHCO$_3$, H$_2$O, brine, and dried over MgSO$_4$. The solvent was removed under reduced pressure and the resulting material was chromatographed on silica gel eluting with 25 to 33% ethyl acetate/hexanes affording 9.5 grams (75% yield) of coupled material and 2.35 grams of HOBt addition product. The HOBT adduct was dissolved in 25 mL of DMF, and to this was added 0.57 mL of NMM and 1.2 grams of tyrosine methylester hydrochloride. The reaction was heated at 60° C. for 30 minutes at which time 1.4 ml of NMM and 2.4 grams of ester were added followed by an additional 30 minutes at 60° C. This was worked up in a mannor analogous to the initial reaction affording 2.6 grams of additional product. M+H=329.

1(h) 2S,5R,6S-3-aza-4-oxo-10-oxa-5-isobutyl-2-(carboxymethyl)-[10]paracyclophane-6-t-butoxycarbonyl To a stirred, heated (60° C.) suspension of 5.2 g of Cs$_2$CO$_3$ in 130 mL of anhydrous DMF and 32.5 mL of anhydrous DMSO, was added a solution of 3.25 g of bromide 1(g) dissolved in 25 mL, of DMF over 15 minutes. The reaction was then heated at 80° C. for an additional 30 minutes. It was then cooled in an ice bath and quenched with 10% aqueous citric acid. The volatiles were removed under reduced pressure and the resulting material was partitioned in ethyl acetate/H$_2$O. The aqueous was extracted 4 times with ethyl acetate and the combined 5 extracts were washed 4 times with H$_2$O, once with brine, dried over MgSO$_4$ followed by removal of the volatiles under reduced pressure. The resulting material was chromatographed on silica gel eluting with 1.5% MeOH/CH$_2$Cl$_2$ affording 2.0 grams(74% yield) of the macrocycle. M+H=448.

1(i) 2S,5R,6S-3-aza-4-oxo-10-oxa-5-isobutyl-2-(carboxymethyl)-[10]paracyclophane-6-carboxylic acid To 0.77 g of t-butyl ester 1(h), was added 25 ml of TFA. The reaction was stirred for 1 h at room temperature. The TFA was removed under reduced pressure affording 0.67 grams of acid. M+H=392.

1(j) 2S,5R,6S-3-aza-4-oxo-10-oxa-5-isobutyl-2-(carboxymethyl)-[10]paracyclophane-6-[N-(O-benzyl)carboxamide]

To 1.8 g of acid in 150 mL of $CH_2Cl_2$ was added 0.75 g of HOBt, 2 mL of NMM, 0.81 g of O-benzylhydroxylamine hydrochloride, and 1.06 g of EDC. The reaction was stirred for 3 h at room temperature. TLC in 10% $MeOH/CHCl_3$ indicated presence of starting acid so 50 mg of TBTU was added and the reaction was stirred 30 additional minutes. When TLC indicated consumption of acid, the solvent was removed under reduced pressure and to the remaining material was added 50 mL of DMF and 4.3 g of the free base of O-benzylhydroxylamine. The reaction was heated to 80° C. for one hour. The volatiles were removed under reduced pressure and the resulting material was dissolved in ethyl acetate and washed with 1N HCl, $H_2O$, saturated aqueous $NaHCO_3$, $H_2O$, brine and dried over $MgSO_4$. The volatiles were then removed under reduced pressure affording material slightly comtaminated with HOBT adduct as determined by $^1H$ NMR. The slightly yellow solid was triterated in boiling $Et_2O$ followed by filtration to afford 2.18 g (95%) of white solid, or alternatively the above coupling can be carried out using HATU;

To a solution of 2.4 g of acid in 75 mL of anhydrous DMF was added 3.37 mL of NMM, 5.24 g of HATU and 3.77 grams of O-benzylhydroxylamine. After stirring overnight at room temperature, the reaction mixture was heated to 60° C. for 30 minutes. After cooling, the volatiles were removed under reduced pressure and the resulting material was dissolved in ethyl acetate and washed with 10% aqueous citric acid. The organic layer was extracted three times with ethyl acetate. The 4 combined organic extracts were washed three times with $H_2O$, one with brine, dried over $MgSO_4$ and the volatiles were removed under reduced pressure. The resulting material was triterated 4 times with a mixture of 1:1:2 ethyl acetate:hexane:ether to afford 1.4 g of product. The mothor liquor was concentrated and the resulting material was chromatographed on silica ge:L eluting with a gradient of 25–90% ethyl acetate/hexane affording another 1.05 grams of product for a combined yield of 81%.

1(k) 2S,5R,6S-3-aza-4-oxo-10-oxa-5-isobutyl-2-(carboxy)-[10]paracyclophane-6-[N-(O-benzyl)carboxamide]

To 0.7 g of methylester 1(j) in 65 mL of THF and 15 mL of $H_2O$ was added 2.23 mL of saturated aqueous LiOH. The reaction was stirred 2 hours at room temperature and quenched with 10 mL of 1N HCl. The majority of solvent was removed under reduced pressure, diluted with ethyl acetate and washed with $H_2O$ and 20 mL of 1N HCl. The aqueous was extracted 4 times with ethyl acetate. The combined ethyl acetate fractions were washed with $H_2O$, brine, dried over $MgSO_4$ and the solvent was removed under reduced pressure affording 0.67 g (99% yield) of white solid. M+H=483.

Example 15

2S,5R,6S-3-aza-4-oxo-10-oxa-5-isobutyl-2-(hydroxymethyl)-[10]paracyclophane-6-N-hydroxycarboxamide To a stirred, cooled (0° C.) solution of 0.031 grams (0.064 mmols) of acid in 2 mL of anhydrous THF was added 0.19 mL of 1M $B_2H_6$ in THF followed in 2 hours by the addition of an additional 0.19 mL of 1M $B_2H_6$. The reaction was allowed to slowly warm to room temperature while stirring overnight. Excess borane was quenched with the dropwise addition of $H_2O$. The material was partitioned in EtOAc and $H_2O$, separated then the aqueous was extracted an additional 3 times with EtoAc. All 4 extracts were combined and washed with $H_2O$, brine, dried over $MgSO_4$ and the volatiles were removed under reduced pressure. The resulting material was purified by prep-plate chromatography in a mannor analogous to previously described, affording 19 mg of material.

To 18 mg of alcohol in 10 mL of MeOH was added 25 mg of 5% $Pd/BaSO_4$. Shaken under 50 psi $H_2$ for 4 hours, filtered and volatiles removed under reduced pressure affording 15 mg of hydroxamic acid. M+H=379.

Example 20

2S,5R,6S-3-aza-4-oxo-10-oxa-5-isobutyl-2-[(3-imidazolyl)propylcarboxamido]-[10]paracyclophane-6-N-hydroxycarboxamide A solution of 0.035 grams of acid in 2 mL of DMF was added 0.024 mL of NMM, 17 mL of aminopropylimidazole and 0.030 grams of TBTU was stirred at room temperature overnight then heated at 80° C. for 30 minutes. The volatiles were removed under reduced pressure and the resulting material was purified by prep-plate chromatography (1 mm with 0.25 mm concentration zone) eluting two times with 5% $MeOH/CHCl_3$ affording 0.042 grams of the product.

LRMS found (M+H$^+$=590

HPLC reverse phase 70–5% H2O/CH3CN (0.1% TFA) 30 minute ramp: Rt=4.96 minutes

To 0.040 grams in 10 mL of MeOH was added 0.065 grams of 5% Pd/BaSO4. The reaction was shaken at 50 psi for 6 hours, filtered and the resulting material was purified by reverse phase HPLC (90% to 30% $H_2O/CH_3CN$ with 0.1 TFA over 45 minutes) affording 0.025 grams of the hydroxamic acid. LRMS found (M+H)$^+$=500

Example 23

2S,5R,6S-3-aza-4-oxo-10-oxa-5-isobutyl-2-(2-pyridyl-2-ethylcarboxamido)-[10]paracyclophane-6-N-hydroxycarboxamide To a stirred mixture of 0.037 grams of acid in 2 mL of $CH_2Cl_2$ was added 0.020 mL of NMM, 10 mL of aminoethyl pyridine and 0.032 grams of TBTU. The reaction was run in a mannor analogous to the above affording 20 mg after purification.

To 20 mg in 10 mL of MeOH was added 35 mg of 5% $Pd/BaSO_4$. Shaken under 50 psi $H_2$ for 4 hours, filtered and volatiles removed under reduced pressure affording material purified by reverse phase HPLC (90% to 30% $H_2O/CH_3CN$ with 0.1 TFA over 30 minutes) affording 15 mg of the hydroxamic acid as the TFA salt. M+H=497.

Example 27

2S,5R,6S-3-aza-4-oxo-10-oxa-5-isobutyl-2-(4-methylpiperazinylcarboxamido)-[10]paracyclophane-6-N-hydroxycarboxamide To 0.030 grams of acid in 2 mL of $CH_2Cl_2$ was added 0.016 mL of NMM and 14 mL of N-methylpiperazine. The reaction was run in a mannor analogous to the above affording 25 mg after purification.

To 25 mg in 10 mL of MeOH was added 45 mg of 5% Pd/BaSO$_4$. Shaken under 50 psi H$_2$ for 4 hours, filtered and volatiles removed under reduced pressure affording 15 mg of the hydroxamic acid. M+H=475.

Example 41

2S,5R,6S-3-aza-4-oxo-10-oxa-5-isobutyl-2-(2-imidazolyl)-[10]paracyclophane-6-N-hydroxycarboxamide A solution of 0.061 grams of acid in 4 mL of DMF was added 0.096 mL of NMM, 0.033 grams of 2-aminoimidazole and 0.053 grams of TBTU was stirred at room temperature overnight then heated at 80° C. for 30 minutes. The volatiles were removed under reduced pressure and the resulting material was purified by prep-plate chromatography (1 mm with 0.25 mm concentration zone) eluting two times with 5% MeOH/CHCl$_3$ affording 0.018 grams of the coupled product.

To 0.015 grams in 5 mL of MeOH was added 0.020 grams of 5% Pd/BaSO4. The reaction was shaken at 50 psi for 6 hours, filtered and the resulting material was purified by reverse phase HPLC (90% to 30% H$_2$O/CH$_3$CN with 0.1 TFA over 30 minutes) affording 0.007 grams of the hydroxamic acid as the TFA salt. M+H=457.

Example 50

2S,5R,6S-3-aza-4-oxo-10-oxa-5-isobutyl-2-(N-methyl carboxamido)-[10]paracyclophane-6-N-hydroxycarboxamide The N-methyl amide of 1(k) was prepared as described previously to give 50(a).

To 0.130 grams of 50(a) in 14 mL of MeOH was added 0.19 grams of 5% Pd/BaSO$_4$. The mixture was shaken under 45 psi H$_2$ in a Parr bottle for 2 hours. The mixture was then filtered through a 0.45 mM PTFE membrane filter and the volatiles were removed under reduced pressure affording 0.12 grams of a white solid. MP 350–152° C. decomp. M+H=406.

Example 55

2S,5R,6S-3-aza-4-oxo-10-oxa-5-isobutyl-2-(2-benzimidazolyl)-[10]paracyclophane-6-N-hydroxycarboxamide A solution of 0.050 grams of acid in 3 mL of CH$_2$Cl$_2$ was added 0.028 mL of NMM, 0.022 grams of phenylamine diamine and 0.043 grams of TBTU was stirred at room temperature overnight. The volatiles were removed under reduced pressure and the resulting material was purified by prep-plate chromatography (1 mm with 0.25 mm concentration zone) eluting two times with 5% MeOH/CHCl$_3$ affording 0.025 grams of the product.

To a solution of 0.022 grams of the above in 3 mL of THF was added 3 mL of HOAc. The reaction was refluxed 1 hour then the volatiles were removed under reduced pressure affording 0.021 grams of benzamidizole product.

To 0.020 grams in 10 mL of MeOH was added 0.035 grams of 5% Pd/BaSO$_4$. The reaction was shaken at 50 psi for 4 hours, filtered and the volatiles were removed under reduced pressure affording 0.012 grams product. M+H=465.

Example 61

2S,5R,6S-3-aza-4-oxo-10-oxa-5-isobutyl-2-(glycine-N-methylamide)-[10]paracyclophane-6-N-hydroxycarboxamide A solution of 0.030 grams of acid in 2 mL of DMF was added 0.030 mL of NMM, 0.015 grams of glycine-N-methylamide hydrochloride, and 0.026 grams of TBTU was stirred at room temperature for 18 h then heated at 80° C. for 15 minutes. The volatiles were removed under reduced pressure and the resulting material was purified by prep-TLC (1 mm with 0.25 mm concentration zone) eluting two times with 5% MeOH/CHCl$_3$ affording 0.030 grams of the product.

To 0.025 grams in 10 mL of MeOH was added 0.035 grams of 5% Pd/BaSO4. The reaction was shaken at 50 psi for 6 hours, filtered and the volatiles were removed under reduced pressure affording 0.020 grams product. M+H=463.

Example 63

2S,5R,6S-3-aza-4-oxo-10-oxa-5-isobutyl-2-(L-alanine-N-methylamide)-[10]paracyclophane-6-N-hydroxycarboxamide To a stirred solution of 0.030 grams (0.062 mmol) of acid in 2 mL of CH$_2$Cl$_2$ was added 0.034 mL of NMM and 17 mg of L-alanine methylamide hydrochloride and 26 mg of TBTU. The reaction was stirred overnight at room temperature. It was poured into 10% aqueous citric acid and extracted 3 times with CHCl$_3$. All CHCl$_3$ were combined and washed with H$_2$O, saturated aqueous NaHCO3, H2O, brine and dried over MgSO$_4$. The volatiles were removed under reduced pressure and the resulting material was purified by prep-plate chromatography (1 mm with 0.25 mm concentration zone) eluting two times with 5% MeOH/CHCl$_3$. The main band was removed, pulverized and rinsed with 150 mL of 10% MeOH/CHCl$_3$ affording 20 mg of the desired product.

To a solution of 20 mg of the above in 10 mL of MeOH was added 30 mg of 5% Pd/BaSO$_4$. This was shaken at 50 psi for 4 hours, filtered and the volatiles were removed under reduced pressure affording 15 mg of the desired hydroxamic acid. M+H=477.

Example 65

2S,5R,6S-3-aza-4-oxo-10-oxa-5-isobutyl-2-(D-alanine-N-methylamido)-[10]paracyclophane-6-N-hydroxycarboxamide A solution of 0.036 grams of acid in 2 mL of DMF was added 0.037 mL of NMM, 0.021 grams of D-alanine N-methylamide and 0.031 grams of TBTU was stirred at room temperature overnight then heated at 80° C. for 15 minutes. The volatiles were removed under reduced pressure and the resulting material was purified by prep-plate chromatography (1 mm with 0.25 mm concentration zone) eluting two times with 5% MeOH/CHCl$_3$ affording 0.050 grams of coupled product.

To 0.040 grams in 10 mL of MeOH was added 0.050 grams of 5% Pd/BaSO$_4$. The reaction was shaken at 50 psi for 4 hours, filtered and the volatiles were removed under reduced pressure affording 0.029 grams product. M+H=477.

Example 67

2S,5R,6S-3-aza-4-oxo-10-oxa-5-isobutyl-2-(L-valine-N-metylcarboxamido)-[10]paracyclophane-6-N-hydroxycarboxamide A solution of 0.035 grams of acid in 2 mL of DMF was added 0.039 mL of NMM, 0.022 grams of L-valine-N-methylamide and 0.030 grams of TBTU was stirred at room temperature overnight then heated at 80° C. for 30 minutes. The volatiles were removed under reduced pressure and the resulting material was purified by prep-plate chromatography (1 mm with 0.25 mm concentration zone) eluting two times with 5% MeOH/CHCl₃ affording 0.038 grams of the coupled product.

To 0.035 grams in 10 mL of MeOH was added 0.050 grams of 5% Pd/BaSO₄. The reaction was shaken at 50 psi for 6 hours, filtered and the volatiles were removed under reduced pressure affording 0.030 grams product. M+H=505.

Example 70

2S,5R,6S-3-aza-4-oxo-10-oxa-5-isobutyl-2-(L-(O-methyl)tyrosine-N-methylamido)-[10]paracyclophane-6-N-hydroxycarboxamide To 0.030 grams (0.062 mmols) acid in 3 mL of DMF was added 0.030 mL of NMM and 0.029 grams of O-methyltyrosine N-methylamide and 0.026 grams of TBTU. The reaction was heated to 80° C. for 20 minutes. The DMF was removed under reduced pressure and the resulting material was taken into EtOAc and washed with 10% aqueous citric acid. The water was extracted 3 times with EtOAc, combined and washed with H₂O, saturated aqueous NaHCO₃, H₂O, brine, dried over MgSO₄ and the solvent was removed under reduced pressure affording 0.033 grams of product which was carried on with out purification.

To 0.030 grams of the above in 10 mL of MeOH was added 0.040 grams of 5% Pd/BaSO4. The reaction was shaken at 50 psi for 6 hours, filtered and the resulting material was purified by reverse phase HPLC (90% to 30% H₂O/CH₃CN with 0.1 TFA over 30 minutes) affording 19 mg of the hydroxamic acid. M+H=583.

Example 71

2S,5R,6S-3-aza-4-oxo-10-oxa-5-isobutyl-2-(L-serine-N-methylamido)-[10]paracyclophane-6-N-hydroxycarboxamide To 0.025 grams of the above t-butylether 75 was added 3 mL of TFA. The reaction was stirred at room temperature for 2 hours. The volatiles were removed under reduced pressure affording 0.020 grams of product. M+H=493.

Example 72

2S,5R,6S-3-aza-4-oxo-10-oxa-5-isobutyl-2-(beta-alanine-N-methylcarboxamido)-[10]paracyclophane-6-N-hydroxycarboxamide A solution of 0.035 grams of acid in 2 mL of DMF was added 0.039 mL of NMM, 0.020 grams of b-alanine-N-methylamide and 0.030 grams of TBTU was stirred at room temperature overnight then heated at 80° C. for 15 minutes. The volatiles were removed under reduced pressure and the resulting material was purified by prep-plate chromatography (1 mm with 0.25 mm concentration zone) eluting two times with 5% MeOH/CHCl₃ affording 0.043 grams of coupled product.

To 0.040 grams of the above in 10 mL of MeOH was added 0.050 grams of 5% Pd/BaSO₄. The reaction was shaken at 50 psi for 6 hours, filtered and the volatiles were removed under reduced pressure affording 0.030 grams product. M+H=499.

Example 73

2S,5R,6S-3-aza-4-oxo-10-oxa-5-isobutyl-2-(D-serine-N-methylamide)-[10]paracyclophane-6-N-hydroxycarboxamide To 0.020 grams of ether was added 3 mL of TFA. The reaction was stirred at room temperature for 2 hours. The volatiles were removed under reduced pressure affording 0.015 grams of product.

LRMS found (M+H)⁺=493, (M+Na)⁺=515.

HPLC reverse phase 90–20% H2O/CH3CN (0.1% TFA) 30 minute ramp: RT=11.67 minutes

Example 75

2S,5R,6S-3-aza-4-oxo-10-oxa-5-isobutyl-2-(L-O-tertbutyl)serine-N-methylamide)-[10]paracyclophane-6-N-hydroxycarboxamide A solution of 0.062 grams of acid in 3 mL of DMF was added 0.035 mL of NMM, 0.045 grams of O-t-Butyl serene-N-methylamide, and 0.054 grams of TBTU was stirred at room temperature overnight then heated at 80° C. for 15 minutes. The volatiles were removed under reduced pressure and the resulting material was purified by prep-plate chromatography (1 mm with 0.25 mm concentration zone) eluting two times with 5% MeOH/CHCl₃ affording 0.080 grams of the product.

To 0.075 grams of the above in 10 mL of MeOH was added 0.100 grams of 5% Pd/BaSO₄. The reaction was shaken at 50 psi for 4 hours, filtered and the volatiles were removed under reduced pressure affording 0.050 grams product. M+H=549.

Example 77

2!S,5R,6S-3-aza-4-oxo-10-oxa-5-isobutyl-2-[D-(O-tert-butyl)serine-N-methylamide]-[10]paracyclophane-6-N-hydroxycarboxamide A solution of 0.035 grams of acid in 2 mL of DMF was added 0.024 mL of NMM, 0.033 grams of O-t-butyl-D-serine-N-methylamide arid 0.030 grams of TBTU was stirred at room temperature overnight then heated at 80° C. for 30 minutes. The volatiles were removed under reduced pressure and the resulting material was purified by prep-plate chromatography (1 mm with 0.25 mm concentration zone) eluting two times with 3% MeOH/CHCl₃ affording 0.040 grams of the product.

To 0.031grams in 10 mL of MeOH was added 0.050 grams of 5% Pd/BaSO₄. The reaction was shaken at 50 psi for 6 hours, filtered and the volatiles were removed under reduced pressure affording 0.030 grams product. LRMS found (M+H)⁺=549.

Example 90

2S,5R,6S-3-aza-4-oxo-10-oxa-5-isobutyl-2-(L-lysine-N-methlylamide)-[10]paracyclophane-6-N-hydroxycarboxamide A solution of 0.035 grams of acid in 2 mL of DMF was added 0.024 mL of NMM, 0.035 grams of L-lysine-N-methylamide and 0.030 grams of TBTU was stirred at room temperature overnight then heated at 80° C. for 30 minutes. The volatiles were removed under reduced pressure and the resulting material was purified by prep-plate chromatography (1 mm with 0.25 mm concentration zone) eluting two times with 5% MeOH/CHCl₃ and one elution with 10% MeOH/CHCl₃ affording 0.035 grams of the coupled product.

LRMS found (M+H)⁺=744, (M+Na)⁺=766.

To 0.030 grams in 10 mL of MeOH was added 0.040 grams of 5% Pd/BaSO₄. The reaction was shaken at 50 psi for 6 hours, filtered and the volatiles were removed under reduced pressure affording 0.026 grams product.

LRMS found (M+H)$^+$=520

Example 95

2S,5R,6S-3-aza-4-oxo-10-oxa-5-isobutyl-2-(N-benzyl carboxamido)-[10]paracyclophane-6-N-hydroxycarboxamide

To a slurry of 0.030 grams (0.06 mmol) of acid in 2 mL of CH$_2$Cl$_2$ was added 0.015 mL of NMM and 24 mg of TBTU. The reaction was stirred 30 minutes at which time 10 mL of benzyl amine was added and the reaction was stirred for 1 hour. The mixture was diluted with CHCl$_3$ and washed once with 1N HCl and once with H$_2$O. Both aqueous were combined and extracted 3 times with CHCl$_3$. All 4 CHCl$_3$ were combined and and washed with H$_2$O, saturated aqueous NaHCO$_3$, water, brine, and dried over MgSO$_4$. The solvent was removed under reduced pressure affording 30 mg (85% yield) of the benzyl amide. M+H=572; M+Na=594.

To 25 mg of the above in 10 mL of MeOH was added 35 mg of 5% Pd/BaSO$_4$. The mixture was shaken under 50 psi H2 for 5 hours. The reaction was filtered through a 0.45 mM PTFE membrane filter and the volatiles were removed under reduced pressure affording 15 mg. of the hydroxamic acid. M+H=482.

Example 106

2S,5R,6S-3-aza-4-oxo-10-oxa-5-isobutyl-2-[2-(4-aminosulfonylphenyl)ethylcarboxamido]-[10]paracyclophane-6-N-hydroxycarboxamide

A solution of 0.035 grams of acid in 2 mL of DMF was added 0.024 mL of NMM, 0.029 grams of (4-aminosulfonylphenyl)ethylamine and 0.030 grams of TBTU was stirred at room temperature overnight then heated at 80° C. for 30 minutes. The volatiles were removed under reduced pressure and the resulting material was purified by prep-plate chromatography (1 mm with 0.25 mm concentration zone) eluting two times with 5% MeOH/CHCl$_3$ and one elution with 10% MeOH/CHCl$_3$ affording 0.040 grams of the coupled product.

LRMS found (M+H)$^+$=665, (M+Na)$^+$=687

HPLC reverse phase 70–5% H$_2$O/CH$_3$CN (0.1% TFA) 30 minute ramp: RT=11.39 minutes To 0.035 grams in 10 mL of MeOH was added 0.050 grams of 5% Pd/BaSO$_4$. The reaction was shaken at 50 psi for 6 hours, filtered and the volatiles were removed under reduced pressure affording 0.030 grams product.

LRMS found (M+H)$^+$=575, (M+Na)$^+$=597

Example 107

2S,5R,6S-3-aza-4-oxo-10-oxa-5-isobutyl-2-[(2-benzimidazol)methylcarboxamido]-[10]paracyclophane-6-N-hydroxycarboxamide

A solution of 0.035 grams of acid in 2 mL of DMF was added 0.024 mL of NMM, 0.021 grams of aminomethylbenzamidizole and 0.030 grams of TBTU was stirred at room temperature overnight then heated at 80° C. for 30 minutes. The volatiles were removed under reduced pressure and the resulting material was purified by prep-plate chromatography (1 mm with 0.25 mm concentration zone) eluting two times with 3% MeOH/CHCl$_3$ affording 0.030 grams of the product.

LRMS found (M+H)$^+$=612.

HPLC reverse phase 90–20% H$_2$O/CH3CN (0.1% TFA) 30 minute ramp: RT=13.01 minutes To 0.025 grams in 10 mL of MeOH was added 0.035 grams of 5% Pd/BaSO4. The reaction was shaken at 50 psi for 6 hours, filtered and the resulting material was purified by reverse phase HPLC (90% to 30% H$_2$O/CH$_3$CN with 0.1 TFA over 45 minutes) affording 0.020 grams of the hydroxamic acid.

LRMS found (M+H)$^+$=522.

Example 108

2S,5R,6S-3-aza-4-oxo-10-oxa-5-isobutyl-2-(2-benzimidazolecarboxamido)-[10]paracyclophane-6-N-hydroxycarboxamide

A solution of 0.035 grams of acid in 2 mL of DMF was added 24 mL of NMM, 0.019 grams of aminobenzamidazole and 0.030 grams of TBTU was stirred at room temperature overnight then heated at 80° C. for 30 minutes. The volatiles were removed under reduced pressure and the resulting material was purified by prep-plate chromatography (1 mm with 0.25 mm concentration zone) eluting two times with 3% MeOH/CHCl$_3$ affording 0.036 grams of the coupled product.

To 0.030 grams in 10 mL of MeOH was added 0.045 grams of 5% Pd/BaSO4. The reaction was shaken at 50 psi for 6 hours, filtered and the resulting material was purified by reverse phase HPLC (90% to 30% H$_2$O/CH$_3$CN with 0.1 TFA over 45 minutes) affording 0.020 grams of the hydroxamic acid. M+H=508.

120(a): 2S,5R,6S-3-aza-4-oxo-10-oxa-5-hexyl-2-(carboxymethyl)-[10]paracyclophane-6-N-benzyloxycarboxamide

Following the synthetic sequence used previously 120(a) was prepared as a white solid. ESI-MS (M+H)$^+$: calcd 525.3, found 525.6.

Example 120

2S,5R,6S-3-aza-4-oxo-10-oxa-5-hexyl-2-(carboxymethyl)-[10]paracyclophane-6-N-hydroxycarboxamide

Following a procedure analogous to that used previously, hydrogenolysis of 120(a) (122.1 mg, 0.233 mmol) gave the hydroxamate (102 mg, 100%). ESI-MS (M+H)$^+$: calcd 435.3, found 435.3.

Example 126

2S,5R,6S-3-aza-4-oxo-10-oxa-5-hexyl-2-((2-methoxylethyloxy)carboxyl)-[10]paracyclophane-6-N-hydroxycarboxamide

Following a procedure analogous to that used previously, hydrogenolysis of 126(a) (50.6 mg, 0.0890 mmol) gave hydroxairate 126 (42.6 mg, 100%). ESI-MS (M+H)$^+$: calcd 479.3, found 479.4.

126(a): 2S,5R,6S-3-aza-4-oxo-10-oxa-5-hexyl-2-((2-methoxylethyloxy)carboxyl)-[10]paracyclophane-6-N-benzyloxycarboxamide

A 1.0 N dichloromethane solution of N,N'-dicyclohexylcarbodiimde (0.2 mL, 1 equiv.) was added to a solution of 212(a) (100.6 mg, 0.197 mmol), 2-methoxyethanol (0.020 mL, 1.3 equiv.), 1-hydroxybenzotriazole hydrate (0.0266 g, 1 equiv.) in tetrahydrofuran (6 mL) at room temperature. After 20 h at room temperature and 4 h at reflux, the reaction mixture was quenched with saturated ammonium chloride and extracted with ethyl acetate. The combined extracts were washed with brine, dried (MgSO4) and concentrated. Silica gel chromatography (methanol-dichloromethane, 2:98 then 4:96 then 6:94) gave 126(a) (51.2 mg, 46%) as a white solid. ESI-MS (M+H)$^+$: calcd 569.4, found 569.5.

Example 128

2S,5R,6S-3-aza-4-oxo-10-oxa-5-hexyl-2-((2-phenylethyoxy)carboxy)-[10]paracyclophane-6-N-hydroxycarboxamide Following a procedure analogous to that used previously, 212(a) (32.3 mg, 0.063 mmol) was reacted with 2-phenylethanol (9.3 mg, 1.2 equiv.) to give the desired coupling product (34.6 mg, 89%). Hydrogenolysis of the coupling product (34.6 mg, 0.0563 mmol) then gave the hydroxamate (26.0 mg, 88%). ESI-MS (M+H)$^+$: calcd 525.3, found 525.4.

Example 129

2S,5R,6S-3-aza-4-oxo-10-oxa-5-hexyl-2-(dimethylcarboxamido)-[10]paracyclophane-6-N-hydroxycarboxamide Following a procedure analogous to that used previously, 212(a) (40.8 mg, 0.0800 mmol) was reacted with dimethylamine hydrochloride (16 mg, 2.45 equiv.) to give the desired coupling product (36.0 mg, 84%). Hydrogenolysis of the coupling product (31.7 mg, 0.0590 mmol) then gave the hydroxamate (26.2 mg, 99%). ESI-MS (M+H)$^+$: calcd 448.3, found 448.5.

Example 132

2S,5R,6S-3-aza-4-oxo-10-oxa-5-hexyl-2-(1-(n-methylcarboximido)methylcarboxyl)-[10] paracyclophane-6-N-hydroxycarboxamide Following a procedure analogous to that used previously, 212(a) (32.9 mg, 0.0644 mmol) was reacted with 2-hydroxy-N-methylacetamide (8.6 mg, 1.5 equiv.) to give the desired coupling product (25.3 mg, 68%). Hydrogenolysis of the coupling product (25.1 mg, 0.0431 mmol) then gave the hydroxamate (21.1 mg, 99%). ESI-MS (M+H)$^+$: calcd 429.3, found 429.4.

Example 139

2S,5R,6S-3-aza-4-oxo-10-oxa-5-hexyl-2-(3-(1-imidazolyl)proylcarboxamido)-[10]paracyclophane-6-N-hydroxycarboxamide Following a procedure analogous to that used previously, 212(a) (97.2 mg, 0.190 mmol) was reacted with 1-(3-aminopropyl)imidazole (0.0273 mL, 1.2 equiv.) to give the desired coupling product (96.0 mg, 82%). Hydrogenolysis of the coupling product (92.9 mg, 0.150 mmol) then gave the hydroxamate (76.0 mg, 96%). ESI-MS (M+H)$^+$: calcd 528.3, found 528.5.

Example 139.TFA 2S,5R,6S-3-aza-4-oxo-10-oxa-5-hexyl-2-(3-(1-imidazolyl)proylcarboxamido)-[10]paracyclophane-6-N-hydroxycarboxamide trifluoroacetate Trifluoroacetic acid (1 drop) was added to a suspension of 139 (38.5 mg, 0.0730 mmol) in dichloromethane (6 mL). After stirring for several minutes at room temperature, the homogeneous solution was concentrated to give 34 (48 mg, 100%) as a white solid. ESI-MS (M+H)$^+$: calcd 528.3, found 528.6.

Example 142

2S,5R,6S-3-aza-4-oxo-10-oxa-5-hexyl-2-(2-(2-pyridyl)ethylcarboxamido)-[10]paracyclophane-6-N-hydroxycarboxamide Following a procedure analogous to that used previously, 212(a) (35.2 mg, 0.0689 mmol) was reacted with 2-(2-aminoethyl)pyridine (10.9 mg, 1.3 equiv.) to give the desired coupling product (36.1 mg, 85%). Hydrogenolysis of the coupling product (35.8 mg, 0.0582 mmol) then gave the hydroxamate (31.3 mg, 100%). ESI-MS (M+H)$^+$: calcd 525.4, found 525.5.

Example 146

2S,5R,6S-3-aza-4-oxo-10-oxa-5-hexyl-2-(4-methylpiperazin-1-yl)-[10]paracyclophane-6-N-hydroxycarboxamide Following a procedure analogous to that used previously, 212(a) (43.5 mg, 0.0852 mmol) was reacted with 1-methylpiperazine (0.0142 mL, 1.5 equiv.) to give the desired coupling product (43.5 mg, 86%). Hydrogenolysis of the coupling product (43.5 mg, 0.0734 mmol) then gave the hydroxamate (38.2 mg, 99%). ESI-MS (M+H)$^+$: calcd 503.3, found 503.6.

Example 156

2S,5R,6S-3-aza-4-oxo-10-oxa-5-hexyl-2-(2-(N-methylaminoslfonyl)ethylcarboxamido)-[10] paracyclophane-6-N-hydroxycarboxamide Following a procedure analogous to that used previously, 212(a) (34.9 mg, 0.0683 mmol) was reacted with ethylenediamine (0.050 mL, 11 equiv.) and then methanesulfonyl chloride (0.145 mL, 27.5 equiv.) to give the desired coupling product (35.6 mg, 83%). Hydrogenolysis of the coupling product (46.9 mg, 0.0743 mmol) gave the hydroxamate (40.3 mg, 100%). ESI-MS (M+H)$^+$: calcd 541.3, found 541.5.

Example 157

2S,5R,6S-3-aza-4-oxo-10-oxa-5-hexyl-2-(4-(N-methylaminosulfonyl)butylcarboxamido)-[10] paracyclophane-6-N-hydroxycarboxamide Following a procedure analogous to that used previously, 212(a) (35.2 mg, 0.0689 mmol) was reacted with 1,4-diaminobutane (84.6 mg, 14 equiv.) and then methanesulfonyl chloride (0.186 mL, 35 equiv.) to give the desired coupling product (24.2 mg, 53%). Hydrogenolysis of the coupling product (24.0 mg, 0.0364 mmol) gave the hydroxamate (20.0 mg, 97%). ESI-MS (M+H)$^+$: calcd 569.3, found 569.5.

Example 158

2S,5R,6S-3-aza-4-oxo-10-oxa-5-hexyl-2-(cyclohexylcarboxamido)-[10]paracyclophane-6-N-hydroxycarboxamide Following a procedure analogous to that used previously, 212(a) (40.8 mg, 0.0689 mmol) was reacted with cyclohexylamine (0.012 mL, 1.3 equiv.) to give the desired coupling product (41.7 mg, 88%). Hydrogenolysis of the coupling product (35.4 mg, 0.0598 mmol) then gave the hydroxamate (30.5 mg, 100%). ESI-MS (M+H)$^+$: calcd 502.4, found 502.5.

Example 159

2S,5R,6S-3-aza-4-oxo-10-oxa-5-hexyl-2-(2-(N-methylaminosulfonyl)hexyllcarboxamido)-[10]paracyclophane-6-N-hydroxycarboxamide Following a procedure analogous to that used previously, 212(a) (35.2 mg, 0.0689 mmol) was reacted with 1,6-diaminohexane (89.6 mg, 11 equiv.) and then methanesulfonyl chloride (0.150 mL, 28 equiv.) to give the desired coupling product (28.1 mg, 59%). Hydrogenolysis of the coupling product (28.1 mg, 0.0409 mmol) gave the hydroxamate (25.0 mg, 100%). ESI-MS (M+H)$^+$: calcd 597.3, found 597.6.

Example 165

2S,5R,6S-3-aza-4-oxo-10-oxa-5-hexyl-2-(L-ornithine-N-methylamide)-[10]paracyclophane-6-N-hydroxycarboxamide hydrochloride Hydroxamate 205 (25 mg, 0.0386 mmol) was treated with 4 N dioxane solution of hydrogen chloride (1 mL) for 40 min and then concentrated to give the desired product (18.2 mg, 81%) as a white solid. ESI-MS (M+H)$^+$: calcd 548.4, found 548.5.

Example 169

2S,5R,6S-3-aza-4-oxo-10-oxa-5-hexyl-2-(methylcarboxamido)-[10]paracyclophane-6-N-hydroxycarboxamide Following a sequence analogous to that used in the preparation of 50, 169 was synthesized as a white solid. ESI-MS (M+H)$^+$: calcd 434.3, found 434.4.

Example 180

2S,5R,6S-3-aza-4-oxo-10-oxa-5-hexyl-2-(glycine-N-methylamide)-[10]paracyclophane-6-N-hydroxycarboxamide Following a procedure analogous to that used previously, 212(a) (40.8 mg, 0.080 mmol) was reacted with glycine-N-methylamide hydrochloride (15.0 mg, 1.5 equiv.) to give the desired coupling product (42.2 mg, 91%). Hydrogenolysis:Ls of the coupling product (33.1 mg, 0.057 mmol) then gave the hydroxamate (27.1 mg, 97%). ESI-MS (M+H)$^+$: calcd 491.3, found 491.5.

Example 182

2S,5R,6S-3-aza-4-oxo-10-oxa-5-hexyl-2-(L-alanine-N-methylamide)-[10]paracyclophane-6-N-hydroxycarboxamide Following a procedure analogous to that used previously, 212(a) (40.8 mg, 0.080 mmol) was reacted with L-alanine-N-methylamide (12.2 mg, 1.5 equiv.) to give the desired coupling product (40.9 mg, 86%). Hydrogenolysis of the coupling product (33.0 mg, 0.0555 mmol) then gave the hydroxamate (28.0 mg, 100%). ESI-MS (M+H)$^+$: calcd 505.4, found 505.6.

Example 184

2S,5R,6S-3-aza-4-oxo-10-oxa-5-hexyl-2-(D-alanine-N-methylamide)-[10]paracyclophane-6-N-hydroxycarboxamide Following a procedure analogous to that used previously, 212(a) (40.8 mg, 0.080 mmol) was reacted with D-alanine-N-methylamide (12.2 mg, 1.5 equiv.) to give the desired coupling product (39.0 mg, 82%). Hydrogenolysis of the coupling product (32.0 mg, 0.054 mmol) then gave the hydroxamate (27.9 mg, 100%). ESI-MS (M+H)$^+$: calcd 505.4, found 505.5.

Example 194

2S,5R,6S-3-aza-4-oxo-10-oxa-5-hexyl-2-(L-serine (O-tert-butyl)-N-methylamide)-[10]paracyclophane-6-N-hydroxycarboxamide Following a procedure analogous to that used previously, 212(a) (81.6 mg, 0.160 mmol) was reacted with O-tert-butyl--L-serine-N-methylamide (41.8 mg, 1.5 equiv.) to give the desired coupling product (82.8 mg, 77.6%). Hydrogenolysis of the coupling product (76.0 mg, 0.114 mmol) then gave the hydroxamate (66.7 mg, 100%). ESI-MS (M+H)$^+$: calcd 577.4, found 577.6.

Example 199

2S,5R,6S-3-aza-4-oxo-10-oxa-5-hexyl-2-(2-(carbomethoxy)ethylcarboxamido)-[10]paracyclophane-6-N-hydroxycarboxamide Following a procedure analogous to that used previously, :212(a) (35.2 mg, 0.0689 mmol) was reacted with methyl 3-aminopropionate hydrochloride (12.4 mg, 1.3 equiv.) to give the desired coupling product (36.9 mg, 90%). Hydrogenolysis of the coupling product (36.9 mg, 0.0620 mmol) then gave the hydroxamate (31.0 mg, 100%). ESI-MS (M+H)$^+$: calcd 506.3, found 506.4.

Example 201

2S,5R,6S-3-aza-4-oxo-10-oxa-5-hexyl-2-(2-(hydroxycarbonyl)ethylcarboxamido)-[10]paracyclophane-6-N-hydroxycarboxamide Following a procedure analogous to that used previously, 212(a) (35.2 mg, 0.0689 mmol) was reacted with benzyl 3-aminopropionate (31.5 mg, 1.3 equiv.) to give the desired coupling product (40.6 mg, 90%). Hydrogenolysis of the coupling product (40.6 mg, 0.0617 mmol) then gave the hydroxamate (30.5 mg, 100%) as a white solid. ESI-MS (M+H)$^+$: calcd 492.3, found 492.3.

Example 203

2S,5R,6S-3-aza-4-oxo-10-oxa-5-hexyl-2-(L-ornithine(4-t-butoxycarbonyl)carboxymethyl)-[10]paracyclophane-6-N-hydroxycarboxamide Following a procedure analogous to that used previously, 212(a) (50.2 mg, 0.0983 mmol) was reacted with Nd-BOC-ornithine methyl ester hydrochloride (36.2 mg, 1.3 equiv.) to give the desired coupling product (58.2 mg, 80%). Hydrogenolysis of the coupling product (28.0 mg, 0.0379 mmol) then gave the hydroxamate (24.6 mg, 100%). ESI-MS (M+H)$^+$: calcd 649.4, found 649.5.

Example 205

2S,5R,6S-3-aza-4-oxo-10-oxa-5-hexyl-2-(L-ornithine(4-t-butoxycarbonyl)-N-methylamide)-[10]paracyclophane-6-N-hydroxycarboxamide Following a procedure analogous to that used previously, 212(a) (60 mg, 0.118 mmol) was reacted with Nd-BOCornithine N-methylamide hydrochloride (42.9 mg, 1.3 equiv.) to give the desired coupling product (52.2 mg, 60%). Hydrogenolysis of the coupling product (21.0 mg, 0.0285 mmol) then gave the hydroxamate (18.6 mg, 100%). ESI-MS (M+H)$^+$F: calcd 648.4, found 648.6.

Example 207

2S,5R,6S-3-aza-4-oxo-10-oxa-5-hexyl-2-(L-ornithinecarboxymethyl)-[10]paracyclophane-6-N-hydroxycarboxamide hydrochloride The amide coupling product (31.1 mg, 0.0421 mmol) for the preparation of 203 was treated with 4 N dioxane solution of hydrogen chloride (1 mL) for 1 h to remove the BOC group. Hydrogenolysis of the crude material then gave the hydroxamate (24.8 mg, 100%). ESI-MS (M+H)$^+$: calcd 549.4, found 549.5.

Example 209

2S,5R,6S-3-aza-4-oxo-10-oxa-5-hexyl-2-(L-lysinecarboxamide)-[10]paracyclophane-6-N-hydroxycarboxamide Following a procedure analogous to that used previously, 212(a) (105.6 mg, 0.207 mmol) was reacted with N$^e$-Cbz-L-lysine amide hydrochloride (85.0 mg, 1.3 equiv.) to give the desired coupling product (130 mg, 82%). Hydrogenolysis of the coupling product (113.2 mg, 0.147 mmol) then gave the hydroxamate (74.5 mg, 93%). ESI-MS (M+H)$^+$: calcd. 548.4, found 548.5.

Example 211

2S,5R,6S-3-aza-4-oxo-10-oxa-5-hexyl-2-(phenylethylcarboxamido)-[10]paracyclophane-6-N-hydroxycarboxamide Following a procedure analogous to that used previously, 212(a) (44.6 mg, 0.0873 mmol) was reacted with phenethylamine (0.0219 mL, 2 equiv.) to give the desired coupling product (46.5 mg, 87%). Hydrogenolysis of the coupling product (46.5 mg, 0.0758 mmol) then gave the hydroxamate l:39.2 mg, 99%). ESI-MS (M+H)$^+$: calcd 524.4, found 524.5.

Example 212

2S,5R,6S-3-aza-4-oxo-10-oxa-5-hexyl-2-(hydroxycarboxyl)-[10]paracyclophane-6-N-hydroxycarboxamide Following a procedure analogous to that used previously, hydrogenolysis of 212(a) (205 mg, 0.401 mmol) gave the hydroxamate (168 mg, 99%). ESI-MS (M+H)$^+$: calcd 421.3, found 421.4.

212(a). 2S,5R,6S-3-aza-4-oxo-10-oxa-5-hexyl-2-(hydroxycarboxyl)-[10]paracyclophane-6-N-benzyloxycarboxamide A 1 N aqueous solution of lithium hydroxide (7.5 mL, 4.23 equiv.) was added to a solution of 120(a) (930 mg, 1.77 mmol) in tetrahydrofuran (20 mL) at 0 ° C. After 25 min at room temperature, the mixture was neutralized with 1 N hydrochloric acid and extracted with ethyl acetate (3×40 mL). The combined extracts were washed with brine, dried (MgSO4) and concentrated to give 212(a) (840 mg, 93%) as a white solid. ESI-MS (M+H)$^+$: calcd 511.3, found 511.4.

Example 213

2S,5R,6S-3-aza-4-oxo-10-oxa-5-hexyl-2-(2-(3,4-dimethoxyphenyl)ethylcarboxamido)-[10]paracyclophane-6-N-hydroxycarboxamide Following a procedure analogous to that used previously, 212(a) (29.2 mg, 0.0572 mmol) was reacted with 2-(3,4-dimethoxyphenyl)ethylamine (14.7 mg, 1.2 equiv.) to give the desired coupling product (31.8 mg, 83%). Hydrogenolysis of the coupling product (31.6 mg, 0.0469 mmol) then gave the hydroxamate (24.6 mg, 90%). ESI-MS (M+H)$^+$: calcd 584.4, found 584.6.

Example 214

2S,5R,6S-3-aza-4-oxo-10-oxa-5-hexyl-2-(benzylcarboxamido)-[10]paracyclophane-6-N-hydroxycarboxamide Following a procedure analogous to that used previously, 212(a) (40.8 mg, 0.080 mmol) was reacted with benzylamine (0.0114 mL, 1.3 equiv.) to give the desired coupling product (43.0 mg, 90%). Hydrogenolysis of the coupling product (33.0 mg, 0.055 mmol) then gave the hydroxamate (28.2 mg, 100%). ESI-MS (M+H)$^+$: calcd 510.3, found 510.5.

Example 215

2S,5R,6S-3-aza-4-oxo-10-oxa-5-hexyl-2-(2-(4-morpholino)ethylcarboxamido)-[10]paracyclophane-6-N-hydroxycarboxamide Following a procedure analogous to that used previously, 212(a) (41.2 mg, 0.0807 mmol) was reacted with 4-(2-aminoethyl)morpholine (0.015 mL, 1.4 equiv.) to give the desired coupling product (40.0 mg, 80%). Hydrogenolysis of the coupling product (39 mg, 0.0626 mmol) then gave the hydroxamate (30.4 mg, 91%). ESI-MS (M+H)$^+$: calcd 533.4, found 533.5.

Example 217

2S,5R,6S-3-aza-4-oxo-10-oxa-5-hexyl-2-(3-(4-morpholino)propylcarboxamido)-[10]paracyclophane-6-N-hydroxycarboxamide hydrochloride Following a procedure analogous to that used previously, 212(a) (44.4 mg, 0.0870 mmol) was reacted with 4-(3-aminopropyl)pyridine (0.0254 mL, 2 equiv.) to give the desired coupling product (40.0 mg, 72%). Hydrogenolysis of the coupling product (40.0 mg, 0.0628 mmol) in the presence of hydrogen chloride (1 equiv.) then gave the hydroxamate (34.2 mg, 93%). ESI-MS (M+H)$^+$: calcd 547.4, found 547.5.

Example 224

2S,5R,6S-3-aza-4-oxo-10-oxa-5-hexyl-2-(diphenylethylcarboxamido)-[10]paracyclophane-6-N-hydroxycarboxamide Following a procedure analogous to that used previously, 212(a) (29.8 mg, 0.0584 mmol) was reacted with 2,2-diphenylethylamine (11.5 mg, 1.2 equiv.) to give the desired coupling product (32.2 mg, 80%). Hydrogenolysis of the coupling product (32.0 mg, 0.0464 mmol) then gave the hydroxamate (27.6 mg, 100%). ESI-MS (M+H)$^+$: calcd 600.4, found 600.6.

Example 225

2S,5R,6S-3-aza-4-oxo-10-oxa-5-hexyl-2-(2-(4-sulfonylaminophenyl)ethylcarboxamido)-[10]paracyclophane-6-N-hydroxycarboxamide Following a procedure analogous to that used previously, 212(a) (70.0 mg, 0.137 mmol) was reacted with 4-(2-aminoethyl)benzenesulfonamide (33.0 mg, 1.2 equiv.) to give the desired coupling product (80.7 mg, 85%). Hydrogenolysis of the coupling product (76.6 mg, 0.111 mmol) then gave the hydroxamate (65.4 mg, 98%). ESI-MS $(M+H)^+$: calcd 603.3, found 603.6.

Example 710

4S,7R,8S-5-aza-6-oxo-12-oxa-7-isobutyl-2-(carboxymethyl)-[12]paracyclophane-8-N-hydroxycarboxamide Synthesis of Homo-homo Tyrosine 710(a) To a stirred, cooled (0° C.) solution of 5.0 grams of the 3-(4-benzyloxyphenyl)propanol in 100 mL of anhydrous $CH_2Cl_2$ was added 4.3 mL of triethylamine followed in 10 minutes by 1.76 mL of methanesulfonyl chloride. The reaction was stirred for one hour then poured into saturated aqueous $NaHCO_3$. The aqueous was extracted 2 times with $C_2Cl_2$. All three $CH_2Cl_2$ were combined, washed with $H_2O$, 10% aqueous citric acid, $H_2O$, brine, dried over $MgSO_4$ and the solvent was removed under reduced pressure affording a quantitative yield of the mesylate as a white solid.

LRMS M+H=338.

710(b) To the mesylate above in 100 mL of acetone was added 3.9 grams of NaI. After stirring overnight at room temperature then an additional 3.9 grams of NaI was added and the reaction was refluxed 1 hour. The reaction mixture was filtered and the volatiles were removed under reduced pressure. The solid, which immediately turned yellow, was dissolved in hexane and washed with $H_2O$, two times with 5% aqueous sodium thiosulfate, $H_2O$, brine, dried over MgSO4 and the solvent was removed under reduce pressure affording 6.79 grams of the iodide as a white solid.

LRMS M+H=370

710(c) To a stirred, cooled (−78° C.) slurry of 1.15 grams of LiCl (flame dried in flask under vacuum) and 0.99 grams Meyers reagent(Meyers et al. JACS,1995, 117, 8488), in 30 mL of anhydrous THF was added 8.7 mL of 1M LDA in THF/hexanes over 10 minutes. The mixture was stirred for 20 minutes at −78° C. and 30 minutes at 0° C. then 1.57 grams of the iodide in 10 mL of anhydrous THF was added dropwise over 10 minutes. The reaction was allowed to slowly warm to room temperature while stirring overnight. It was quenched with 10% aqueous citric acid and the volatiles were removed under reduced pressure. The remaining material was dissolved in EtOAc, washed with $H_2O$, 5% aqueous sodium thiosulfate, $H_2O$, saturated aqueous $NaHCO_3$, $H_2O$, brine, dried over $MgSO_4$ and the solvent was removed under reduced pressure. The resulting material was chromatographed on silica gel eluting with 4:100 MeOH/$CHCl_3$ affording 0.9 grams of the product 710(c)
LRMS M+H=447.

Hydrolysis of Pseudoephedrine Amide

710(d) To 3.5 grams of the alkylation product 710(c) in 40 mL of $H_2O$ and 25 mL of MeOH was added 15.7 mL of 1N aqueous NaOH. The reaction was refluxed 1 hour at which time 25 mL more MeOH was added. The reaction was refluxed an additional 3 hours then the volatiles were removed under reduced pressure. The solid was tricherated with $CH_2Cl_2$ and filtered affording 5.5 grams of sodium hydroxide and the sodium salt of the product. The $CH_2Cl_2$ in the filtrate was removed under reduced pressure and the remaining solid was tricherated with $Et_2O$ affording an additional 1.1 grams of product 710(d).

LRMS sM+H=298

Formation of Methylester

710(e) To the NaOH and sodium salt above in 150 nL of MeOH was added 3 mL of concentrated HCl. The reaction was refluxed overnight at which time the volatiles were removed under reduced pressure and the resulting material was taken up in EtOAc and washed with saturated aqueous $NaHCO_3$, brine, and dried over $MgSO_4$. The volatiles were removed under reduced pressure affording 2.4 grams of the methylester.

LRMS found $(M+H)^+$=314

Coupling of Homo-homo Tyrosine to the Succinate Fragment

710(f) To a stirred, cooled (0° C.) solution of 0.90 grams of acid in 20 mL of anhydrous DMF was added 0.79 grams of amino acid methyl ester 710(e), 1.14 mL of NMM and 0.884 grams of TBTU. The reaction was stirred 20 minutes at 0° C. and 2 hours at room temperature. The reaction was duluted with 300 mL of EtoAc and washed 5 times with 10% aqueous citric acid. All aqueous washes were combined and extracted 5 times with EtoAc. All 6 organics were combined and washed 5 times with saturated aqueous $NaHCO_3$, once with brine and dried over $MgSO_4$. The volatiles were removed under reduced pressure and the resulting material was chromatographed on silica gel eluting with a gradient of 15–20% EtOAc in hexanes affording 1.2 grams of the coupled material.

LRMS M+H=674

710(g) To a stirred solution of 1.2 grams of benzylether in 50 mL of MeOH was added 5 mL of acetic acid and 0.15 grams of palladium black as an IPA slurry. The mixture was stirred under 1 ATM of H2 for 3 hours. The catalyst was removed by filtration and the volatiles were removed under reduced pressure affording 0.76 grams of the deprotected product.

LRMS M+H=494

710(h) To a stirred solution of 0.40 grams of the alcohol 710(i) in 20 mL of anhydrous $CH_2Cl_2$ was added 0.89 grams of carbon tetrabromide and 0.70 g of triphenyl phosphine. The reaction was stirred 1 hour then poured into 10% aqueous citric acid, separated and the aqueous was extracted 3 times with $CH_2Cl_2$. All 4 $CH_2Cl_2$ were combined and washed with $H_2O$, brine and dried over $MgSO_4$. The solvent was removed under reduced pressure and the resulting material was chromatographed on silica gel eluting with a gradient of 25–50% EtOAc in hexanes affording 0.32 grams of the bromide 710(h).

LRMS found $(M+H)^+$=558

710(j) To a stirred, cooled (0° C.) solution of 0.29 grams of bromide in 60 mL of anhydrous DMF was added 0.21 grams of $Cs_2CO_3$ in one portion. After stirring for 2 hours the mixture was poured into EtoAc and washed two times with 10% aqueous citric acid and 3 times with $H_2O$. All aqueous were combined and extracted 5 times with EtOAc. All six EtOAc were combined, washed with $H_2O$, two times with brine and dried over $MgSO_4$. The solvent was removed under reduced pressure and the resulting material was chromatographed on silica gel eluting with 20% EtOAc/hexanes affording 0.08 g (32% yield) of the macrocycle.

LRMS found $(M+H)^+$=476; $(M+Na)^+$=498

710(k) To 0.150 grams of 710(j) was added 5 mL of TFA. After stirring for 2 hours the volatiles were removed under reduced pressure affording 0.125 grams of the acid.

LRMS (M+H)$^+$=420

710(l) To a stirred solution of 0.073 grams of 710(k) in 8 mL of a anhydrous $CH_2Cl_2$ was added 0.024 grams of HOBT, 0.077 mL of NMM, 0.033 grams of O-benzylhydroxylamine hydrochloride and 0.043 grams of DEC. The reaction was stirred 2 hours then the volatiles were removed under reduced pressure. To the remaining material was added 3 mL of anhydrous DMF and 0.16 grams of O-benzylhydroxylamine. The reaction was heated at 80° C. for 45 minutes then poured into EtOAc and washed 5 times with 10% aqueous citric acid. The combined aqueous was extracted 5 times with EtoAc, and the 6 combined extracts were washed 2 times with $H_2O$, two times with brine and dried over $MgSO_4$. The resulting material was chromatographed on silica gel eluting with 3% MeOH/ $CHCl_3$ affording 0.079 grams of the O-benzylhydroxamate.

Example 710

4S,7R,8S-5-aza-6-oxo-12-oxa-7-isobutyl-2-(carboxymethyl)-[12]paracyclophane-8-N-hydroxycarboxamide To 10 mg in 5 mL of MeOH was added 25 mg of 5% Pd/$BaSO_4$. Shaken under 50 psi $H_2$ for 2 hours, filtered and volatiles removed under reduced pressure affording 7 mg of hydroxamic acid.

LRMS found (M+H)$^+$=435

759(a) To 0.035 grams of methylester 710(l) in 3 mL of THF and 1 mL of $H_2O$ was added 0.13 mL of saturated aqueous LiOH. The reaction was stirred 4 hours at room temperature and quenched with 2 mL of IN HCl. The mixture was diluted with EtOAc and acidified with 1N HCl and extracted three times with EtOAc. All 3 EtOAc were combined and washed with $H_2O$, brine, dried $MgSO_4$ and solvent was removed under reduced pressure affording 0.025 grams of the acid.

LRMS found (M+H)$^+$=511; (M+Na)$^+$=533

Example 759

4S,7R,8S-5-aza-6-oxo-12-oxa-7-isobutyl-2-(N-methylcarboxamido)-[12]paracyclophane-8-N-hydroxycarboxamide A solution of 0.023 grams of acid 759(a) in 1 mL of DMF was added 15 mL of NMM, and 0.016 grams of TBTU. After stirring 5 minutes 16 mL of 40% aqueous MMA was added and the reaction was stirred at room temperature for 15 minutes diluted with EtoAc and washed 4 times with 10% aqueous citric acid. All 5 EtoAc were combined and washed with $H_2O$, brine, and dried over $MgSO_4$. The volatiles were removed under reduced pressure and the resulting material was purified by prep-plate chromatography (1 mm with 0.25 mm concentration zone) eluting once with 3% MeOH/ $CHCl_3$ affording 0.011 grams of the product.

LRMS found (M+H)$^+$=524; (M+Na)$^+$=546

To 11 mg in 10 mL of MeOH was added 30 mg of 5% Pd/$BaSO_4$. Shaken under 45 psi $H_2$ for 3 hours, filtered and volatiles removed under reduced pressure affording 7 mg of hydroxamic acid Example 759.

LRMS found (A+H)$^+$=434

Example 869

2S,13S,14R-1,7-diaza-8,15-dioxo-9-oxa-14-isobutyl-7-methyl-2-(N-methylcarboxamido)-cyclopentadecane-13-N-hydroxycarboxamide 869(a). To a solution of the alcohol intermediate 1(d) (11.4 g, 33.1 mmol) and 4-nitrophenyl chloroformate (10.0 g, 50 mmol) in 50 mL $CH_2Cl_2$ cooled in an ice bath was slowly added N-methylmorpholine (4.4 mL, 40 mmol) and the mixture was stirred at room temperature overnight. The solvent was removed in vacuo and the residue was taken up in 200 mL EtOAc.The solution was washed with brine 3 times, dried ($MgSO_4$) and concentrated. Purification on a silica gel column using 10% EtOAc/hexane gave the desired product (15.0 g, 91%) as a pale yellow solid. DCI-MS: calcd (M+$NH_4$)$^+$=561; found 561.

869(b). To a solution of 869(a) (15.20 g, 27.28 mmol) and N$^a$-Cbz-N$^d$-methyl-L-lysine methyl ester HCl salt (11.22 g, 32.78 mmol) was added potassium carbonate (15 g, 109 mmol) and the mixture was heated at 50° C. for 1 hour. Insoluble material was filtered off and EtOAc was added. The solution was washed with 10% citric acid, brine, $NaHCO_3$ and brine, dried ($MgSO_4$) and concentrated. Purification on a silica gel column using 15% EtOAc/hexane gave an oily product (17.0 g, 91%). ESI-MS: calcd M+1=713.5; found 713.7.

869(c). 869(b) (10.0 g, 14.02 mmol) was dissolved in 30 mL MeOH and the solution was hydrogenated for 1 hour under atmospheric pressure using 10% Pd-C (1.0 g) as catalyst. The catalyst was filtered off and the solution was concentrated to give an oily product (6.8 g, 100%). ESI-MS: calcd M+1=489.4; found 489.6.

869(d). To a solution of BOP (9.2 g, 20.8 mmol) and diisopropylethylamine (12 mL, 70 mmol) in 600 mL $CHCl_3$ cooled in an ice bath was dropwise added a solution of 869(c) (6.8 g, 13.9 mmol) in 50 mL $CHCl_3$ over 2 hours and the mixture was stirred at room temperature overnight. $CHCl_3$ was removed in vacua and EtOAc was added. The solution was washed with 5% citric acid, brine, $NaHCO_3$ and brine, dried ($MgSO_4$) and concentrated. Purification on a silica gel column using 4% MeOH/$CH_2Cl_2$ gave the cyclic product (3.4 g, 46%) as a powder. ESI-MS: calcd M+1=471.4; found 471.5.

869(e). 869(c) (2.6 g, 5.5 mmol) was treated with 20 mL 50% TFA in $CH_2Cl_2$ for 1 hour and the solution was concentrated to give an oily product (2.3 g, 100%). ESI-MS: calcd. M+1=415.3; found 415.4.

869(f). To a solution of 869(e) (2.2 g, 5.3 mmol) and O-benzylhydroxylamine hydrochloride (0.96 g, 6.15 mmol) in 10 mL DMF cooled in an ice bath was added Diisopropylethylamine (4.3 mL, 24.6 mmol) followed by BOP (2.72 g, 6.15 mmol) and the solution was allowed to stir overnight. Et:OAc was added and the solution was washed with 5% citric acid, brine, NaHCO3 and brine, dried ($MgSO_4$) and concentrated to give a crude product which was washed with ether to give the desired product as a pure solid (2.9 g, 90%). ESI-MS: calcd. M+1=520.5; found 520.5.

869(g). 869(f) (0.5 g, 0.96 mmol) was treated with 5 mL THF and 4 mL 1 N LiOH for 1 hour and the solution was acidified with TFA and concentrated. EtOAc was added and the solution was washed with brine, dried ($MgSO_4$) and concentrated to give the acid as a solid (0.3 g, 63%). ESI-MS: calcd M+1=506.5; found 506.5.

869(h) To a solution of 869(g) (0.2 g, 0.396 mmol) and methylamine hydrochloride (0.11 g, 1.58 mmol) in 2 mL DMF cooled in an ice bath was added BOP (0.18 g, 0.4 mmol) followed by diisopropylethylamine (0.52 mL, 3 mmol). The mixture was allowed to stir at room temperature for 2 hours. EtOAc was added and the product precipitated out.

The precipitate was filtered and washed with EtOAc and water to give the title compound as a solid (0.15 g, 73%). ESI-MS: calcd M+1=519.4; found 519.5.

Example 869

869(h) (120 mg, 0.23 mmol) in 5 mL MeOH was hydrogenated for 30 min at atmospheric pressure using 10% Pd—C (40 mg) as catalyst. The catalyst was filtered off and the solution was concentrated. Purification on reversed phase HPLC afforded the final product as a powder (81 mg, 82%). ESI-MS: calcd M+1=429.3; found 429.4.

Example 871

2S,13S,14R-1,7-diaza-8,15-dioxo-9-oxa-14-isobutyl-7-methyl-2-(glycine-N,N-dimethylamide)-cyclopentadecane-13-N-hydroxycarboxamide This compound was prepared using the procedures analogous to those for Example 869. ESI-MS: calcd. M+1=500.5; found 500.5.

Example 880

2S,13S,14R-1,7-diaza-8,15-dioxo-9-oxa-14-isobutyl-7-methyl-2-(glycine-N-methylamide)-cyclopentadecane-13-N-hydroxycarboxamide This compound was prepared using the procedures analogous to those for Example 869. ESI-MS: calcd. M+1=486.3; found 486.5.

Example 904

2S,13S,14R-1,7-diaza-8,15-dioxo-9-oxa-14-isobutyl-7-methyl-2-[glycine-(4-methyl)N-piperazinylamide]-cyclopentadecane-13-N-hydroxycarboxamide trifluoroacetate This compound was prepared using the procedures analogous to those for Example 869. ESI-MS: calcd. M+1=555.6; found 555.5.

Example 908

2S,13S,14R-1,7-diaza-8,15-dioxo-9-oxa-14-isobutyl-7-methyl-2-[glycine-N-morpholinoamide]-cyclopentadecane-13-N-hydroxycarboxamide This compound was prepared using the procedures analogous to those for Example 869. ESI-MS: calcd. M+1=542.4; found 542.5.

Example 910

2S,13S,14R-1,7-diaza-8,15-dioxo-9-oxa-14-isobutyl-7-methyl-2-[(2-pyridyl)carboxamido]-cyclopentadecane-13-N-hydroxycarboxamide This compound was prepared using the procedures analogous to Example 869. ESI-MS: found 555.7

Example 916

2S,13S,14R-1,7-diaza-8,15-dioxo-9-oxa-14-isobutyl-7-methyl-2-[(2-pyridyl)carboxamido]-cyclopentadecane-13-N-hydroxycarboxamide This compound was prepared using the procedures analogous to those for Example 869. ESI-MS: calcd. M+1=492.5; found 496.5.

Example 919

2S,13S,14R-1,7-diaza-8,15-dioxo-9-oxa-14-isobutyl-7-methyl-2-(glycine-2-pyridylamide)-cyclopentadecane-13-N-hydroxycarboxamide This compound was prepared using the procedures analogous to those for Example 869. ESI-MS: calcd. M+1=549.4; found 549.5.

Example 926

2S,13S,14R-1,7-diaza-8,15-dioxo-9-oxa-14-isobutyl-7-methyl-2-[2-(5-methylthiazolyl)carboxamido]-cyclopentadecane-13-N-hydroxycarboxamide This compound was prepared using the procedures analogous to those for Example 869. ESI-MS: calcd. M+1=512.3; found 512.4.

Example 927

2S,13S,14R-1,7-diaza-8,15-dioxo-9-oxa-14-isobutyl-7-methyl-2-[glycine-2-(3.4.5,6-tetrahydropyridyl)amide]-cyclopentadecane-13-N-hydroxycarboxamide This compound was prepared using the procedures analogous to those for Example 869. ESI-MS: calcd. M+1=553.6; found 553.6.

Example 928

2S,13S,14R-1,7-diaza-8,15-dioxo-9-oxa-14-isobutyl-7-methyl-2-[glycine-2-(5-methyl)thiazolylamide]-cyclopentadecane-13-N-hydroxycarboxamide trifluoroacetate This compound was prepared using the procedures analogous to those for Example 869. ESI-MS: calcd. M+1=569.3; found 569.3

Example 929

2S,13S,14R-1,7-diaza-8,15-dioxo-9-oxa-14-isobutyl-7-methyl-2-[N-(2-pyridyl)methylcarboxamido]-cyclopentadecane-13-N-hydroxycarboxamide trifluoroacetate This compound was prepared using the procedures analogous to those for Example 869. ESI-MS: calcd. M+1=506.3; found 506.5.

Example 1175

2S,13S,14R-1,7-diaza-8,15-dioxo-9-oxa-14-(3-phenyl propyl))-7-methyl-2-(N-morpholinecarboxamido)-cyclopenta-decane-13-N-hydroxycarboxamide This compound was prepared using the procedures analogous to those above. ESI-MS: calcd. M+1=547.4; found 547.4.

Example 1176

2S,13S,14R-1,7-diaza-8,15-dioxo-9-oxa-14-(3-phenyl propyl)-7-methyl-2-((4-methyl)N-piperazinylamide)-cyclopenta-decane-13-N-hydroxycarboxamide trifluoroacetate This compound was prepared using the procedures analogous to those above. ESI-MS: calcd. M+1=560.4; found 560.6.

Example 1228

2S,13S,14R-1,7-diaza-8,15-dioxo-9-oxa-14-(3-phenyl propyl)-7-methyl-2-(N-methylcarboxamido)-cyclopenta-decane-13-N-hydroxycarboxamide This compound was prepared using the procedures analogous to those above. ESI-MS: calcd. M+1=491.3; found 491.5.

Example 1442

2S,11S,12R-1,7-Diaza-8,13-dioxo-12-isobutylcyclcotridecane-2-(glycine N-methyl amide)-11-(N-hydroxycarboxamide)

1442(a): To a solution of the succinate 1(c) (2.7 g, 9.4 mmol) and $N^e$-benzyloxycarbonyl-L-lysine methyl ester (4.6 g, 14.0 mmol) in DMF (10 mL) was added diisopropylethylamine (4.1 mL, 23.4 mmol) and BOP (4.9 g, 11.2 mmol). After stirring overnight, ethyl acetate was added and the solution was washed with 10% citric acid, saturated $NaHCO_3$ solution, and brine. The ethyl acetate was dried ($MgSO_4$) and concentrated. The resulting residue was purified by silica gel chromatography to yield the amide (4.1 g. 77%) as a white foam: ES-MS $(M+H)^+565.5$.

1442(b): Compound 1442(a) (2.0 g, 3.5 mmol) was dissolved in a mixture of $CH_3CN$ (8.3 mL), $CCl_4$ (8.3 mL), and $H_2O$ (12.3 mL). At room temperature, $H_5IO_6$ (3.7 g, 16.2 mmol) and $RuCl_3.H_2O$ (16.4 mg, 0.08 mmol) were added. After 1.5 h, 10% citric acid was added and the layers were separated. The organic layer was dried and concentrated. The resulting residue was purified by silica gel chromatography to yield the acid (1.1 g, 56%) as a white foam: ES-MS $(M+H)^+579.5$.

1442(c): Compound Example 1442(b) (500 mg, 0.8 mmol) was hydrogenated in MeOH (10 mL) with 5% Pd/C-Degussa (58 mg) under a hydrogen atmosphere (40 psi). After stirring overnight, the catalyst was filtered off and the solution was concentrated to yield the amino acid (370 mg, 97%) as a white foam: ES-MS $(M+H)^+445.5$.

1442(d): To a solution of HBTU (375 mg, 1.0 mmol) and NMM (0.07 mL, 0.7 mmol) in DMF (5 mL) at 60° C. was added compound 1442(c) (100.0 mg, 0.2 mmol) in DMF (5 mL). After the addition was complete, the mixture was stirred an additional 30 min. The solution was concentrated and silica gel chromatography afforded the lactam (60 mg, 63%) as white solid: ES-MS $(M+H)^+427.5$.

1442(e): Compound Example 1442(d) (250 mg, 0.6 mmol) was dissolved in $CH_2Cl_2$ (2 mL) and TFA (2 mL). After stirring overnight, the solution was concentrated to afford the crude acid (220 mg), which was dissolved in DMF. To the DMF was added O-benzylhydroxylamine (157 mg, 1.3 mmol), diisopropylethylamine (0.2 mL, 1.1 mmol), and BOP (334 mg, 0.7 mmol). After stirring overnight, the solid product was filtered from the solution to give the O-benzyl hydroxamate (165 mg, 60%): ES-MS $(M+H)^+$ 476.4.

1442(f): Compound Example 1442(e) (50 mg, 0.1 mmol) was dissolved in 1:1 THF/MeOH (8 mL) and 1M LiOH (0.5 mL, 0.5 mmol) was added. After 2 h, more 1M LiOH (0.5 mL, 0.5 mmol) was added. The reation was stirred an addition 1.5 h before the solvent was removed. The remaining $H_2O$ was acidified with 1N HCl and was extracted with $CHCl_3$. The $CHCl_3$ was dried ($MgSO_4$) and concentrated to give the acid (52 mg, 86%) as a white foam: ES-MS $(M+H)^+371.4$.

1442(g): To a solution of Compound 1442(f) (70 mg, 0.15 mmol) and glycine N-methyl amide (29 mg, 0.25 mmol) in DMF was added diisopropylethylamine (0.06 mL, 0.37 mmol) and HBTU (85 mg, 0.25 mmol). After stirring overnight, the solid product was filtered from the solution to give the coupled glycine (60 mg, 75%) as a white solid: ES-MS $(M+H)^+532.4$.

Example 1442

Compound Example 1442(g) (60 mg, 0.1 mmol) was hydrogenated in a MeOH-$CHCl_3$ mixture (3:1, 15 mL) with 5% $Pd/BaSO_4$ (120 mg) under a hydrogen atmosphere (40 psi). After stirring 3.5 h, the catalyst was filtered off and the solution was concentrated to yield the title hydroxamate (20 mg, 41%) as a white solid: ES-MS $(M+H)^+442.4$.

Example 1443

2S,11S,12R-1,7-Diaza-8,13-dioxo-12-isobutylcyclotridecane-2-(L-alanine-a-N-methyl amide)-11-(N-hydroxycarboxamide)

1443(a): To a solution of Compound Example 1442(f) (80 mg, 0.17 mmol) and L-alanine N-methyl amide (23 mg, 0.22 mmol) in DMF was added NMM (0.06 mL, 0.52 mmol) and HBTU (256 mg, 0.69 mmol). After stirring overnight, the solid product was filtered from the solution to give the coupled material (66 mg), which was dissolved in a MeOH-$CHCl_3$ mixture (3:1, 30 mL). This was hydrogenated with 5% $Pd/BaSO_4$ (150 mg) under a hydrogen atmosphere (50 psi). After stirring 3 h, the catalyst was filtered off and the solution was concentrated to yield the title hydroxamate (27 mg, 45%) as a yellowish solid: ES-MS $(M+H)^+456.4$.

Example 1447

2S,11S,12R-1,7-Diaza-8,13-dioxo-12-isobutylcyclotridecane-2-(L-serine-a-N-methyl amide)-11-(N-hydroxycarboxamide)

1447(a): To ia solution of Compound Example 1442(f) (700 mg, 1.5 mmol) and L-serine N-methyl amide (234 mg, 1.9 mmol) in DMF was added NMM (0.5 mL, 5.4 mmol) and HBTU (2.2 mg, 5.9 mmol). After stirring overnight, the solid product was filtered fromr the solution to give the coupled material (640 mg), which was dissolved in a MeOH—$CHCl_3$ mixture (3:1, 300 mL). This was hydrogenated with 5% $Pd/BaSO_4$ (1.6 g) under a hydrcgen atmosphere (50 psi). After stirring 3 h, the catalyst was filtered off and the solution was concentrated to yield the title hydroxamate (250 mg, 47%) as a yellowish solid: ES-MS $(M+H)^+$ 472.4.

Example 1462

2S,11S,12R-1,7-Diaza-8,13-dioxo-2-(N-methylcarboxamido)-12-isobutylcyclotridecane-11-(N-hydroxycarboxamide)

1462(a): To ea solution of the succinate 1(c) (170 mg, 0.6 mmol) and $N^e$-benzyloxycarbonyl-L-lysine N-methyl amide (224.6 mg, 0.8 mmol) in DMF (6 mL) was added diisopropylethylamine (0.26 mL, 1.5 mmol) and BOP (286.9 mg, 0.6 mmol). After stirring overnight, ethyl acetate was added and the solution was washed with 10% citric acid, saturated $NaHCO_3$ solution, and brine. The ethyl acetate was dried ($MqSO_4$) and concentrated. The resulting residue was purified by silica gel chromatography to yield the amide (255 mg, 77%) as a white foam: ES-MS $(M+H)^+564.4$.

1462(b): Compound Example 1462(a) (813 mg, 1.4 mmol) was dissolved in a mixture of $CH_3CN$ (3 mL), $CCl_4$ (3 mL), and $H_2O$ (4.5 mL). At room temperature, $H_5IO_6$ (1.3 g, 5.9 mmol) and $RuCl_3.H_2O$ (6 mg, 0.03 mmol) were added. After 1.5 h, 10% citric acid was added and the layers were separated. The organic Layer was dried and concentrated. The resulting residue was purified by silica gel chromatography to yield the acid (504 mg, 60%) as a white foam: ES-MS $(M+H)^+578.5$.

1462(c): Compound Example 1462(b) (45 mg, 0.08 mmol) was hydrogenated in MeOH (5 mL) with 5% Pd/C-

Degussa (15 mg) under a hydrogen atmosphere (50 psi). After stirring overnight, the catalyst was filtered off and the solution was concentrated to yield the amino acid (32 mg, 90%) as a white foam: ES-MS (M+H)$^+$444.4.

1462(d): To a solution of HBTU (769 mg, 2.0 mmol) and NMM (0.15 mL, 6.0 mmol) in DMF (10 mL) at 60° C. was added compound 1462(c) (200.0 mg, 0.4 mmol) in DMF (10 mL) dropwise. After the addition was complete, the mixture was stirred an additional 30 min. The solution was concentrated and silica gel chromatography afforded the lactam (135 mg, 70%) as light yellow solid: ES-MS (M+H)$^+$426.3.

1462(e): Compound Example 1462(d) (85 mg, 0.2 mmol) was dissolved in $CH_2Cl_2$ (2 mL) and TFA (2 mL). After stirring overnight, the solution was concentrated to afford the acid (80 mg, quant.) as a white foam: ES-MS (M+H)$^+$ 370.3.

1462(f): To a solution of compound Example 1462(e) (75.0 mg, 0.2 mmol) and O-benzylhydroxylamine (78.8 mg, 0.6 mmol) in DMF (1.5 mL) was added diisopropylethylamine (0.07 mL, 0.4 mmol) and BOP (97.3 mg, 0.2 mmol). After stirring overnight, the solid product was filtered from the solution to give the O-benzyl hydroxamate (58 mg, 61%): ES-MS (M+H)$^+$475.3.

1462: Compound Example 1462(f) (50 mg, 0.1 mmol) was hydrogenated in a MeOH-CHCl$_3$ mixture (3:1, 40 mL) with 10% Pd/C (20 mg) under a hydrogen atmosphere (balloon). After stirring 6 h, the catalyst was filtered off and the solution was concentrated to yield the title hydroxamate (38 mg, 93%) as a white foam: ES-MS (M+H)$^+$385.4.

Example 1473

2S,11S,12R-1,7-Diaza-8,13-dioxo-12-isobutylcyclotridecane-2-(b-alanine N-methyl amide)-11-(N-hydroxycarboxamide)

1473(a): To a solution of Compound Example 1442(f) (100 mg, 0.22 mmol) and b-glycine N-methyl amide (29 mg, 0.28 mmol) in DMF was added NMM (0.07 mL, 0.66 mmol) and HBTU (320 mg, 0.84 mmol). After stirring overnight, the solid product was filtered from the solution to give the coupled material (80 mg), which was dissolved, in a MeOH—CHCl$_3$ mixture (1:1, 30 mL). This was hydrogenated with 5% Pd/BaSO$_4$ (180 mg) under a hydrogen atmosphere (balloon). After stirring 3 h, the catalyst was filtered off and the solution was concentrated to yield the title hydroxamate (70 mg, quant.) as a white solid: ES-MS (M+H)$^+$456.4.

Example 1491

2S,11S,12R-1,7-Diaza-8,13-dioxo-12-isobutylcyclotridecane-2-(N$^e$—H-L-lycine-a-N—H-amide trifluoroacet,ate)-11-(N-hydroxycarboxamide)

1491(a): To a solution of Compound Example 1442(f) (50 mg, 0.11 mmol) and N$^e$-benzyloxycarbonyl-L-lycine amide (41 mg, 0.13 mmol) in DMF was added diisopropylethylamine (0.05 mL, 0.27 mmol) and BOP (57 mg, 0.13 mmol). After stirring overnight, the solid product was filtered from the solution to give the coupled lycine (58 mg, 72%) as a white solid: ES-MS (M+H)$^+$723.4.

1491: Compound Example 1491(a) (60 mg, 0.1 mmol) was hydrogenated in a MeOH—CHCl$_3$ mixture (3:1, 15 mL) with TFA (1 mL) including 5% Pd/BaSO$_4$ (150 mg) under a hydrogen atmosphere (40 psi). After stirring 5 h, the catalyst was filtered off and the solution was concentrated to yield the title hydroxamate (21 mg, 45%) as a white solid: ES-MS (M+H)$^+$499.5.

Example 1930

2S,11S,12R-1,7-Diaza-8,13-dioxo-2-(N-methylcarboxamido)-12-isobutylcyclotridecane-11-(N-hydroxycarboxamide) hydrogen chloride 1930(a): Compound Example 7(c) (56 mg, 0.12 mmol) was dissolved in 4 M HCl/dioxane (2 mL) at room temperature. After 3 h, the solvent was removed to yield the amine salt (45 mg, quant.) as a pale yellow solid: ES-MS (M+H)$^+$471.4.

Example 2038

2S,11S,12R-7-N-Benzenesulfonyl-1,7-Diaza-8,13-dioxo-2-(N-methylcarboxamido)-12-isobutylcyclctridecane-11-(N-hydroxycarboxamide)

2038(a): To e. solution of the succinate 1(c) (460.0 mg, 1.6 mmol), N$^e$-benzenesulfonyl-L-lysine N-methyl amide (696.5 mg, 2.1 mmol), and diisopropylethylamine (0.84 mL, 4.8 mmol) in DMF was added BOP (849.6 mg, 1.9 mmol). After stirring overnight, ethyl acetate was added and the solution was washed with 10% citric acid, saturated NaHCO$_3$ solution, and brine. The ethyl acetate was dried (MgSO$_4$) and concentrated. The resulting residue was purified by silica gel chromatography to yield the amide (833 mg, 90%) as a white foam: ES-MS (M+H)$^+$570.3.

2038(b): Compound Example 2038(a) (875.0 mg, 1.5 mmol) and PPh$_3$ (1.21 g, 4.6 mmol) were dissolved in THF (137 mL). DIAD (0.88 g, 4.5 mmol) in THF (27 mL) was added dropwise to the mixture. After stirring overnight, the solution was concentrated and the residue was purified by silica gel chromatography to yield the cyclic material (470 mg, 55%) as a white solid: ES-MS (M+H)$^+$552.3

2038(c): Compound Example 2038(b) (473.0 mg, 0.86 mmol) was dissolved in $CH_2Cl_2$ (6 mL) and TFA (5 mL). After stirring overnight, the solution was concentrated to afford the acid (500 mg, quant.) as a white solid: ES-MS (M+H)$^+$496.3.

2038(d): To a solution of compound Example 2038(c) (260.0 mg, 0.52 mmol), O-benzylhydroxylamine (192.0 mg, 1.6 mmol), and diisopropyl-ethylamine (0.18 mL, 1.0 mmol) in DMF was added BOP (278.0 mg, 0.63 mmol). After stirring overnight, the solid product was filtered from the solution to give the O-benzyl hydroxamate (172 mg, 57%): CIMS-NH$_3$ (M+H)$^+$601.2.

2038: Compound Example 2038(d) (150.0 mg, 0.25 mmol) was hydrogenated in a MeOH-CHCl$_3$ mixture (3:1, 50 mL) with 5% Pd/BaSO$_4$ (300 mg) under a hydrogen atmosphere (50 psi). After stirring 3 h, the catalyst was filtered off and the solution was concentrated to yield the title hydroxamate (52 mg, 41%) as a white solid: ES-MS (M+H)$^+$511.3.

Example 2135

2S,11S,12R-1,7-Diaza-8,13-dioxo-2-(N-methylcarboxamido)-7-N-trifluoromethanesulfonyl-12-isobutylcyclotridecane-11-(N-hydroxycarboxamide)

2135(a): To a solution of the succinate 1(c) (608.0 mg, 2.1 mmol), N$^e$-trifluoromethanesulfonyl-L-lysine N-methyl amide (900.0 mg, 2.7 mmol), and diisopropylethylamine (1.09 mL, 6.3 mmol) in DMF (8 mL) was added BOP (1.12 g, 2.5 mmol). After stirring overnight, the DMF was removed and $CH_2Cl_2$ was added. The $CH_2Cl_2$ was washed with 10% citric acid, saturated NaHCO$_3$ solution, and brine. The CH$_2$Cl$_2$ was dried (MgSO$_4$) and concentrated. The resulting residue was purified by silica gel chromatography to yield the crude amide (1.30 g), which was dissolved in THF (100 mL). PPh$_3$ (1.84 g, 7.0 mmol) was added followed by DIAD (1.33 mL, 6.8 mmol) in THF (35 mL). After stirring overnight, the solution was concentrated and the residue was purified by silica gel chromatography to yield the cyclic material (600 mg, 52%) as a white solid: ES-MS (M+H)$^+$544.3

2135(b): Compound Example 2135(a) (300.0 mg, 0.55 mmol) was dissolved in CH$_2$Cl$_2$ (4 mL) and TFA (4 mL). After stirring overnight, the solution was concentrated to the acid, which was dissolved in DMF (6 mL). To this solution was added O-benzylhydroxylamine (146.0 mg, 1.18 mmol) and diisopropyl-ethylamine (0.19 mL, 1.0 mmol) followed by BOP (270.0 mg, 0.61 mmol). After stirring overnight, the DMF was removed to give the O-benzyl hydroxamate (190 mg, 58%): ES-MS (M+H)$^+$593.4.

2135: Compound Example 2135(b) (180.0 mg, 0.3 mmol) was hydrogenated in MeOH (35 mL) with 5% Pd/BaSO$_4$ (210 mg) under a hydrogen atmosphere (50 psi). After stirring 2.5 h, the catalyst was filtered off and the solution was concentrated to yield the title hydroxamate (150 mg, 98%) as a solid: ES-MS (M+H)$^+$503.3.

Example 2227

2S,11S,12R-1,7-Diaza-8,13-dioxo-2-(N-methylcarboxamido)-7-(p-amino-N-benzenesulfonyl)-12-isobutylcyclotridecane-11-(N-hydroxycarboxamide)

2227(a): To EL solution of the succinate 1(c) (850.0 mg, 2.95 mmol), N$^e$-p-nitro-benzenesulfonyl-L-lysine N-methyl amide (1.45 g, 3.80 mmol), and diisopropylethylamine (1.54 mL, 8.80 mmol) in DMF was added BOP (1.56 g, 3.50 mmol). After stirring overnight, ethyl acetate was added and the solution was washed with 10% citric acid, saturated NaHCO$_3$ solution, and brine. The ethyl acetate was dried (MgSO$_4$) and concentrated. The resulting residue was purified by silica gel chromatography to yield the amide (1.37 g, 75%) as a white foam: ES-MS (M+H)$^+$**570.3.

2227(b): Compound Example 2227(a) (547.0 mg, 0.89 mmol) and PPh$_3$ (700.1 g, 2.67 mmol) were dissolved in THF (30 mL). DIAD (0.50 mL, 2.5 mmol) in THF (6 mL) was added dropwise to the mixture. After stirring overnight, the solution was concentrated and the residue was purified by silica gel chromatography to yield the cyclic material (0.14 g, 26%) as a white foam: ES-MS (M+H)$^+$597.4.

2227(c): Compound Example 2227(b) (24.0 mg, 0.04 mmol) was hydrogenated in a MeOH—CHCl$_3$ mixture (1:1, 2 mL) with 10% Pd/C (12 mg) under a hydrogen atmosphere (30 psi). After stirring overnight, the catalyst was filtered off and the solution was concentrated to yield the amino compound (20 mg, 90%) as a white foam: ES-MS (M+H)$^+$567.4.

2227(d): Compound Example 2227(c) (226.0 mg, 0.40 mmol) was dissolved in CH$_2$Cl$_2$ (2 mL) and TFA (2 mL). After stirring overnight, the solution was concentrated to the crude acid, which was dissolved in DMF (4 mL). To this DMF solution was added O-benzylhydroxylamine (108.0 mg, 0.88 mmol), diisopropyl-ethylamine (0.2 mL, 1.2 mmol), and BOP (230.0 mg, 0.52 mmol). After stirring overnight, the solvent was removed to give the O-benzyl hydroxamate (170 mg, 69%): ES-MS (M+H)$^+$616.4.

2227: Compound Example 2227(d) (150.0 mg, 0.24 mmol) was hydrogenated in a MeOH—CHCl$_3$ mixture (1.7:1, 19 mL) with 5% Pd/BaSO$_4$ (200 mg) under a hydrogen atmosphere (50 psi). After stirring 4 h, the catalyst was filtered off and the solution was concentrated to yield the title hydroxamate (107 mg, 84%; as a white solid: ES-MS (M+H)$^+$526.3.

Example 2323

2S,11S,12R-1,7-Diaza-8,13-dioxo-2-(N-methylcarboxamido)-7-N-mesitylenesulfonyl-12-isobutylcyclotridecane-11-(N-hydroxycarboxamide)

2323(a): To a solution of succinate 1(c) (990 mg, 3.4 mmol) and N$^e$-mesitylenesulfonyl-L-lycine N-methyl amide hydrogen chloride (1.7 g, 4.5 mmol) in DMF was added diisopropylethylamine (1.8 mL, 10.2 mmol) and BOP (1.8 mg, 4.1 mmol). After stirring overnight, the DMF was removed and CH$_2$Cl$_2$ was added. The solution was washed with 10% citric acid, saturated NaHCO$_3$ solution, and brine. The CH$_2$Cl$_2$ was dried (MgSO$_4$) and concentrated. The resulting residue was purified by silica gel chromatography to yield the crude amide (2 g), which was dissolved in THF (158 mL). To the THF was added PPh$_3$ (2.8 mg, 10.6 mmol) followed by DIAD (2 mL, 10.1 mmol) in THF. After stirring overnight, the solution was concentrated and the residue was purified by silica gel chromatography to yield the cyclic material (680 mg, 30%) as a yellowish solid: ES-MS (M+H)$^+$594.5.

2323(b): Compound Example 2323(a) (280 mg, 0.47 mmol) was dissolved in CH$_2$Cl$_2$ (3.5 mL) and TFA (3.5 mL). After stirring overnight, the solution was concentrated to afford the crude acid, which was dissolved in DMF. To this DMF solution was added O-benzylhydroxylamine (118 mg, 0.9 mmol), diisopropyl-ethylamine (0.15 mL, 0.8 mmol), and BOP (218 mg, 0.5 mmol). After stirring overnight, the solvent was removed to give the O-benzyl hydroxamate (70 mg, 25%): ES-MS (M+H)$^+$643.5.

2323: Compound Example 2323(b) (120 mg, 0.19 mmol) was hydrogenated in a MeOH—CHCl$_3$ mixture (3:1, 28 mL) with 5% Pd/BaSO$_4$ (180 mg) under a hydrogen atmosphere (50 psi). After stirring 4 h, the catalyst was filtered off and the solution was concentrated to yield the title hydroxamate (100 mg, 96%) as a white foam: ES-MS (M+H)$^+$ 553.5.

Example 2413

5S,8R,9S-6-Aza-2,7-dioxo-5-(N-methylcarboxamido)-1-oxa-8-isobutylcyclododecane-9-(N-hydroxycarboxamide)

2413(a): To a solution of the succinate 1(c) (200 mg, 0.69 mmol) and (L)-g-benzyl ester Glutamate-a-N-methyl amide (200 mg, 0.70 mmol) in DMF (6 mL) was added diisopropylethylamine (0.25 mL, 1.5 mmol) and BOP (305 mg, 0.69 mmol). After stirring overnight, the DMF was removed. The resulting residue was purified by silica gel chromatography to yield the amide (255 mg, 70%) as an oil: ES-MS (M+H)$^+$521.3.

2413(b): Compound Example 2413(a) (240.0 mg, 0.46 mmol) was hydrogenated in MeOH (5 mL) with 10% Pd/C (25 mg) under a hydrogen atmosphere (balloon). After stirring overnight, the catalyst was filtered off and the solution was concentrated to yield the acid, which was dissolved in THF (40 mL). To the THF was added PPh$_3$ (364.0 mg, 1.4 mmol) followed by DIAD (0.27 mL, 1.4 mmol) in THF (9 mL). After stirring, the solution was concentrated and the residue was purified by silica gel chromatography to yield the cyclic material (45 mg, 24%) as a white solid: ES-MS (M+H)+413.3.

2413(c): Compound Example 2413(b) (200 mg, 0.49 mmol) was dissolved in CH$_2$Cl$_2$ (5 mL) and TFA (5 mL). After stirring overnight, the solution was concentrated to afford the acid, which was dissolved in DMF (50 mL). To this solution was added O-benzylhydroxylamine (122.0 mg, 0.93 mmol) and diisopropyl-ethylamine (0.16 mL, 0.92 mmol) followed by BOP (226.0 mg, 0.5 mmol). After stirring overnight, the solid product was filtered from the solution to give the O-benzyl hydroxamate (110 mg, 48%): CIMS-NH$_3$ (M+H)+462.

2413: Compound Example 2413(c) (105 mg, 0.23 mmol) was hydrogenated in a MeOH—CHCl$_3$ mixture (3:1, 40 mL) with 5% Pd/BaSO$_4$ (150 mg) under a hydrogen atmosphere (50 psi). After stirring 2.5 h, the catalyst was filtered off and the solution was concentrated to yield the title hydroxamate (100 mg) as a white solid: ES-MS (M+H)+ 372.3.

2518(a). N$^a$-t-Butyloxycarbonyl-N$^e$-benzyloxycarbonyl-L-Lysine N-methyl amide To a solution of N$^a$-t-Butyloxycarbonyl-N$^e$-benzyloxycarbonyl-L-Lysine (12.39 g, 32 mmol) and methylamine hydrochloride (4.4 g, 65 mol) in 30 mL DMF cooled in an ice bath was added BOP (14.16 g, 32 mmol) followed by diisopropylethylamine (25 mL, 128 mmol). The solution was allowed to stir at room temperature overnight. Ethyl acetate (150 mL) was added and the solution was washed with 10% citric acid, brine, saturated NaHCO$_3$ and brine, dried (MgSO$_4$), and concentrated. Purification on a silica gel column using 80% EtOAc/hexane gave 12.92 g (95%) product. ES-MS (M+H)+: calcd 394.3; found 394.4.

2518(b). N$^e$-benzyloxycarbonyl-L-Lysine N-methyl amide hydrochloride

Compound Example 2518(a) (6 g, 15.26 mmol) was dissolved in 25 mL of 4 N HCl in dioxane. After stirring at room temperature for 1 hour, the solution was concentrated. The residue was triturated with ether to give 5.2 g (100%) product. ES-MS (M+H)+: Calcd 294.2; found 294.3.

2518(c). 4-Methylpentanoic acid 4(S)-phenylmethyl-2-oxazolidinonamide

To a Solution of 4(S)-phenylmethyl-2-oxazolidinone (48.3 g, 272 mmol) in 500 mL THF cooled to −78° C. was added 131 mL of 2.5 M n-butyllithium (327 mmol) in hexane over 20 min and the solution was stirred at −78° C. for 45 min. To it was added 4-methylpentanoy chloride (44 g, 327 mmol) and the solution was stirred at room temperature for 2.5 hours and quenched with ethyl acetate. The solvents were removed by concentration to a small amount and 500 mL ethyl acetate was added. The solution was washed with 10% citric acid, water, NaHCO$_3$ and brine, dried (MgSO$_4$), and concentrated. Purification on a silica gel column using 10% ethyl acetate in hexane as eluent gave 68.53 g (91.5%) oily product. ES-MS (M+H)+: calcd 276.2; found 276.3.

2518(d). 3-n-Butoxycarbonyl-3(R,S)-hydroxy-2(R)-isobutylpropionic acid 4(S)-phenylmethyl-2-oxazolidinonamide To a solution of diisopropylethylamine (3.25 mL, 23.25 mmol) in 20 mL THF cooled to −78° C. was added 9.3 mL of 2.5 M n-butyllithium (23.25 mmol) in hexane and the solution was warmed to 0° C. for 30 min and then cooled to −78° C. The resulting solution was added to a solution of Example 2518(c) (5.82 g, 21.13 mmol) in 50 mL dry THF cooled to −78° C. over 20 min and the mixture was stirred at −78° C. for 1 hour. To it was added a solution of n-butyl glyoxalate (4.12 g, 31.69 mmol) in 10 mL dry THF cooled to −78° C. over 20 min and the mixture was stirred at −78° C. for 3 hours. The reaction was quenched with ice water. Ethyl acetate was added followed by 10% citric acid. The organic layer was separated, washed with water, NaHCO$_3$ and brine, dried (MgSO$_4$), and concentrated. Purification on a silica gel column using 5% ethyl acetate, 10% ethyl acetate and 20% ethyl acetate in hexane gradually as eluent gave 3.1 g (36%) oily product. ES-MS (M+H)+: calcd 406.3; found 406.2.

2518(e). 3-n-Butoxycarbonyl-3(R,S)-hydroxy-2(R)-isobutylpropionic acid

To a solution of the compound Example 2518(d) (5.1 g, 12.57 mmol) in 250 mL THF/H$_2$O (4:1) cooled in an ice bath was added hydrogen peroxide (7.84 mL, 50.3 mmol) followed by a solution of LiOH (791 mg, 18.85 mmol) in 8 mL water. After 1 hour, the reaction was qenched with a solution of Na$_2$SO$_3$ (6.33 g, 50.28 mmol). THF was removed by concentration under reduced pressure and the solution was extracted with with ethyl acetate twice. The water layer was acidified with cold concentrated HCl to pH 3 and extracted 3x with CH$_2$Cl$_2$. The organic solution was washed with water and brine, dried (MgSO$_4$) and concentrated. Purification on a silica gel column using CHCl3, 5% MeOH/CHCl3 and then 10% MeOH/CHCl$_3$ as eluents gave 2.29 g (74%) oily product. CI-MS (M+NH$_4$)+: calcd 264.1; found 264.0.

2518(f). Benzyl 3-n-butoxycarbonyl-3(R,S)-hydroxy-2(R)-isobutylpropionate

A solution of Example 2518(e) (8.33 g, 33.82 mmol), benzyl bromide (7.0 g, 37.2 mmol) and DBU (6.07 mL, 40.58 mmol) in 100 mL benzene was heated at 50° C. for 3 hours and concentrated. Ethyl acetate was added and the solution was washed with brine 3x, dried (MgSO$_4$), and concentrated. Purification on a silica gel column using 10% ethyl acetate/hexane as eluent gave 9 g (79%) oily product. ES-MS (M+H)+: calcd 337.3; found 337.3.

2518(g). Benzyl 3-n-butoxycarbonyl-3(R,S)-t-butoxycarbonylmethoxy-2(R)-isobutylpropionate A solution of Example 2518(f) (8.95 g, 26.64 mmol) and t-butyl bromoacetate (4.33 mL, 29.3 mmol) in 50 mL THF was cooled to 0° C. and to it was added NaH (1.5 g,60% oil dispersion, 32 mmol). The mixture was stirred at 0° C. for 30 min and at room temperature for 2 hours. THF was removed by concentration. Ethyl acetate was added and the solution was washed with 10% citric acid and brine, dried (MgSO$_4$), and concentrated. Purification on a silica gel column gave 8.6 g (71%) product. ES-MS (M+H)+: calcd 451.3; found 451.4.

2518(h). 3-n-Butoxycarbonyl-3(R,S)-t-butoxycarbonylmethoxy-2(R)-isobutylroionic acid Compound Example 2518(g) (5 g, 11.11 mmol) was hydrogenated in 25 mL isopropanol in the presence of 1.4 mL 4 N HCl/dioxane using 10% Pd/C as catalyst at atmospheric pressure for 3 hours. The catalyst was filtered off and the solution was concentrated to give 3.96 g (99%) product. ES-MS (M+H)+: calcd 361.3; found 361.4.

2518(i). 3-n-Butoxycarbonyl-3(R,S)-t-butoxycarbonylmethoxy-2(R)-isobutylpropionic-$N^e$-benzyloxycarbonyl-L-lysine N-methyl amide Compound Example 2518(h) (1.76 g, 4.88 mmol) and compound Example 1(b) (1.61 g, 4.88 mmol) were dissolved in 10 mL DMF and the solution was cooled in an ice bath. To it was added BOP (2.16 g, 4.88 mmol) followed by diisopropylethylamine (3.42 mL, 10.58 mmol). After stirring at room temperature for 4 hours, ethyl acetate was added and the solution was washed with 10% citric acid, brine, NaHCO3 and brine, dried (MgSO$_4$), and concentrated. Purification on a silica gel column using 10% MeOH/CHCl$_3$ as eluent gave 2.32 g (75%) product. ES-MS (M+H)$^+$: calcd 636.4; found 636.6.

2518(j). 3-n-Butoxycarbonyl-3(R,S)-carboxymethoxy-2(R)-isobutylpropionoyl-L-lysine N-methyl amide Compound Example 2518(i) (2.21 g, 3.47 mmol) was hydrogenated in 15 mL isopropanol in the presence of 4 N HCl/dioxane (1 mL) for 2 hours using 10% Pd/C (0.35 g) as catalyst. The catalyst was filtered off and the solution was concentrated. The residue was taken up in 4 N HCl/dioxane (30 mL). The solution was stirred for 2 hours and concentrated to give 1.78 g (99%) product. ES-MS (M+H)$^+$: calcd 446.3; found 446.4.

2518(k) BOP (1.64 g, 3.7 mmol) was dissolved in 30 mL CHCl$_3$ and the solution was cooled in an ice bath. To it were added compound Example 2518(j) (1.78 g, 3.7 mmol) and diisopropylethylamine (2.6 mL, 14.6 mmol) in 50 mL CHCl$_3$ over 2 hours, The solution was allowed to stir at room temperature overnight and concentrated. The residue was taken up in ethyl acetate and the solution was washed with 10% citric acid, brine, NaHCO$_3$ and brine, dried (MgSO$_4$), and concentrated. Purification on a silica gel column using 15% MeOH/CH$_2$Cl$_2$ as eluent gave 0.8 g (50%) product. ES-MS (M+H)$^+$: calcd 428.3; found 428.3.

2518(l) Compound Example 2518(k) (0.77 g, 1.8 mmol) was treated with 4 mL 1 N LiOH in 20 mL THF for 2 hours and the solution was acidified with 4 N HCl/dioxane to pH 3. t-Butanol was added and the solution was washed with brine 3×, dried (MgSO4) and concentrated to give 0.49 g (73%) product. ES-MS (M+H)$^+$: calcd 372.3; found 372.2.

2518(m) To a solution of compound Example 2518(l) (0.47 g, 1.27 mmol) and O-benzylhydroxylamine hydrochloride (0.2 g, 1.27 mmol) in 5 mL DMF cooled in an ice bath was added BOP (0.56 g, 1.27 mmol) followed by diisopropylethylamine (1.0 mL, 5.2 mmol). The solution was allowed to stir at room temperature overnight. Ethyl acetate was added and the solution was washed with 10% citric acid, brine, NaHCO$_3$ and brine, dried (MgSO$_4$) and concentrated. Purification on a silica gel column using 5% MeOH/CH$_2$Cl$_2$ gave 0.13 g (21%) of the first isomer and 80 mg (14%) of the second isomer. ES-MS (M+H)$^+$: calcd 477.3; found 477.3 (both isomers).

Example 2518

Compound Example 2518(m), isomer 1 (100 mg, 0.21 mmol) was hydrogenated in 5 mL MeOH for 2 hours at atmospheric pressure using 10% Pd/C (15 mg) as catalyst. The catalyst was filtered and the solution was concentrated to give 50 mg (62%) product. ES-MS (M+H)$^+$: calcd 387.3; found 387.3.

Compound Example 2518(m), isomer 2 (50 mg, 0.105 mmol) was hydrogenated in a similar manner to give 20 mg (50%) product. ES-MS (M+H)$^+$: calcd 387.3; found 387.3.

Example 2519

This compound was synthesized in a manner analogous to that described in above. ES-MS (M+H)$^+$: calcd 449.3; found 449.3.

Example 2708

2708(a). $N^a$-t-Butyloxycarbonyl-$N^e$-trifluoro-L-Lysine N-methyl amide

To a solution of $N^a$-t-Butyloxycarbonyl-$N^e$-trifluoro-L-Lysine (10.27 g, 30 mmol) and methylamine hydrochloride (4.05 g, 60 mmol) in 30 mL DMF cooled in an ice bath was added BOP (13.27 g, 30 mmol) followed by diisopropylethylamine (23.5 mL, 135 mmol) and the mixture was stirred at room temperature overnight. Ethyl acetate was added and the solution was washed with citric acid, brine, NaHCO$_3$ and brine, dried (MgSO$_4$), and concentrated. Crystallization from ethyl acetate-ether gave 10.1 g (94.8%) product. m.p. 95–98° C. ES-MS (M+H)$^+$: calcd 356.2; found 356.3.

2708(b). $N^a$-t-Butyloxycarbonyl-$N^e$-methyl-$N^e$-trifluoro-L-Lysine N-methyl amide A mixture of compound 2708(a), iodomethane (14 mL, 223 mmol) and potassium carbonate (7.7 g, 56 mmol) in 50 mL DMF was stirred at 100° C. overnight and insoluble material was filtered off. Ethyl acetate was added and the solution was washed with citric acid, brine, NaHCO$_3$ and brine, dried (MgSO$_4$), and concentrated. Purification on a silica gel column gave 4.45 g (43%) product. ES-MS (M+H)$^+$: calcd 370.2; found 370.3.

2708(c). $N^a$-t-Butyloxycarbonyl-$N^e$-methyl-L-Lysine N-methyl amide

Compound 2708(b) (4.35 g, 11.78 mmol) was treated with 14.5 mL 1 N NaOH in 20 mL MeOH for 30 min and the solution was concentrated. The residue was taken up in chloroform and insoluble material was filtered off. The filtrate was concentrated to give 3.65 g (100%) product. ES-MS (M+H)$^+$: calcd 274.3; found 274.5.

2708(d). $N^a$-t-Butyloxycarbonyl-$N^e$-methyl-$N^e${[(1(R,S)-n-butoxycarbonyl-2(R)-benzyloxycarbonyl-3-methyl)pentyloxy]acetyl}-L-Lysine N-methyl amide Compound 2518(g) (3.5 g, 7.77 mmol) was treated with 25 mL 4 N HCl in dioxane for 2 hours and the solution was concentrated. The residue was taken up in 15 mL DMF and the solution was cooled in an ice bath. To it was added compound 4(c) (2.4 g, 7.77 mmol) followed by BOP (3.44 g, 7.77 mmol) and diisopropylethylamine (4.74 mL, 27 mmol). The mixture was stirred at room temperature overnight. EtOAc was added and the solution was washed with citric acid, brine, NaHCO$_3$ and brine, dried (MgSO$_4$), and concentrated. Purification on a silica gel column gave 4.46 g (93%) product. ES-MS (M+H)$^+$: calcd 650.7; found 650.7.

2708(e). $N^e$-Methyl-$N^e$-{[(1(R,S)-n-butoxycarbonyl-2(R)-carboxy-3-methyl)pentyloxy]acetyl}-L-Lysine N-methyl amide Compound 2708(d) (4.31 g, 6.98 mmol) was treated with 50 mL 4 N HCl in dioxane for 1 hour and the solution was concentrated. The residue was taken up in 60 mL isopropanol and the solution was hydrogenated at atmospheric pressure for 2 hours using 10% Pd—C (0.5 g) as catalyst.

The catalyst was filtered off and the solution was concentrated to give 3.15 g (91%) product. ES-MS (M+H)$^+$: calcd 460.4; found 460.5.

2708(f). To a solution of BOP (2.68 g, 6.05 mmol) in 20 mL chloroform cooled in an ice bath were slowly added compound 2708(e) (3 g, 6.05 mmol) in 20 mL chloroform and diisopropylethylamine (3.69 mL, 21.2 mmol) in 20 mL chloroform simultaneously over 1 hour. The mixture was stirred at room temperature overnight and concentrated. The residue was taken up in EtOAc and the solution was washed with citric acid, brine, NaHCO$_3$ and brine, dried (MgSO$_4$), and concentrated. Purification on a silica gel column gave 2 g (75%) product. ES-MS (M+H)$^+$: calcd 442.3; found 442.5.

2708(g). Compound 2708(f) (1.8 g, 4 mmol) was treated with 4.9 mL 1 N LiOH in 10 mL THF for 1 hour and the solution was concentrated. Purification on HPLC gave 390 mg (25%) product. ES-MS (M+H)$^+$: calcd 386.3; found 386.3.

Example 2708

To a solution of compound 4(g) (0.17 g, 0.48 mmol) and Obenzylhydroxylamine hydrochloride (91 mg, 0.576 mmol) in 2 mL DMSO cooled in an ice bath was added BOP (254 mg, 0.576 mmol) followed by diisopropylethylamine (0.33 mL, 1.92 mmol) and the solution was stirred at room temperature for 1 hour. Purification on reversed phase HPLC gave 30 mg isomer 1 and 140 mg isomer 2. ES-MS (M+H)$^+$: calcd 491.5; found 491.6 (both isomers).

Example 2708

Compounds 2708(h), isomer 1 and isomer 2 were hydrogenated in a manner analogous to that described in 1(n). ES-MS (M+H)$^+$: calcd 401.5; found 401.6.

Example 2809

2809(a). Na-Boc-S-(2-nitrophenyl)-L-cysteine

2-Chloro-nitrobenzene (7.88 g, 50 mmol), L-cysteine (6.66 g, 55 mmol) and potassium carbonate (7.6 g, 55 mmol) were suspended in 30 mL DMF and the solution was stirred at 80° C. for 4 hours and cooled to room temperature. Water (20 mL) was added and the solution was cooled in an ice bath. To it was added di-t-butyl dicarbonate (10.9 g, 50 mmol). After stirring for 2 hours, water was added and the solution was extracted with ether 3×. The water layer was acidified with HCl at 0° C. and the solution was extracted with ethyl acetate 3×. The combined extracts were washed with brine, dried (MgSO$_4$) and concentrated to give 8.21 g (48%) product. ES-MS (M+H)$^+$: calcd 343.3; found 343.2.

2809(b). Na-Boc-S-(2-nitrophenyl)-L-cysteine N-methyl amide

To a solution of compound 2518(a) (8.1 g, 23.66 mmol) and methylamine hydrochloride (2.03 g, 30 mmol) cooled in an ice bath was added diisopropylethylamine (16.5 mL, 95 mmol) followed by BOP (10.47 g, 23.66 mmol). After stirring for 2 hours at room temperature, ethyl acetate was added and the solution was washed with citric acid, brine, NaHCO$_3$ and brine, dried (MgSO$_4$) and concentrated. Purification on a silica gel column using 5% methanol in methylene chloride as eluent gave 6.24 g (82%) product. ES-MS (M+H)$^+$: calcd 356.2; found 356.3.

2809(c). S-2-Nitrophenyl-L-cysteine N-methyl amide

Compound 2518(b) (6.0 g, 17 mmol) was treated with 4 N HCl in dioxane for 1 hour and the solution was concentrated. The residue was triturated with ether to 3.88 g (71%) product. ES-MS (M+H)$^+$: calcd 256.1; found 256.1.

2809(d). 3-n-Butoxycarbonyl-3(R,S)-t-butoxycarbonylmethoxy-2(R)-isobutylpropionoyl-S-(2-nitrophenyl)-L-cysteine N-methyl amide To a solution of compound 2518(h) (2.36 g, 6.5 mmol) and compound 3(c) (1.91 g, 6.5 mmol) in 15 mL chloroform cooled in an ice bath was added diisopropylethylamine (4.53 mL, 26 mmol) followed by BOP (2.88 g, 6.5 mmol) and the solution was stirred at room temperature overnight and concentrated. The residue was taken up in ethyl acetate and the solution was washed with citric acid, brine, NaHCO$_3$ and brine, dried (MgSO$_4$), and concentrated. Purification on a silica gel column using 3% MeOH-25% EtOAc-72% CH$_2$Cl$_2$ as eluent gave 3.21 g (83%) product. ES-MS (M+H)$^+$: calcd 598.3; found 598.6.

2809(e). 3-n-Butoxycarbonyl-3(R,S)-carboxymethoxy-2(R)-isobutylpropionoyl-S-(2-aminophenyl)-L-cysteine N-methyl amide Compound 2809(d) (3.05 g, 5.1 mmol) was treated with 3 g zinc in 15 mL, acetic acid and 0.5 mL water for 30 min. 30 mL methanol was added and the solid was filtered off. The filtrate was concentrated and the residue was taken up in ethyl acetate. The solution was washed with NaHCO$_3$ 3×, dried (MgSO$_4$), and concentrated. The residue was treated with 30 mL 4 N HCl in dioxane and 0.5 mL water for 1 hour and the solution was concentrated to give 2.2 g (84%) product. ES-MS (M+H)$^+$: calcd 512.5; found 512.5.

2809(f). BOP (1.36 g, 3.06 mmol) was dissolved in 10 mL DMF and the solution was cooled in an ice bath. To it were added compound 2809(e) (1.4 g, 2.55 mmol) and diisopropylethylamine (1.78 mL, 10.2 mmol) slowly over 2 hours. The solution was allowed to stir at room temperature overnight. Ethyl acetate was added and the solution was washed with citric acid, brine, NaHCO$_3$ and brine, dried (MgSO$_4$) and concentrated. The crude product was purified on a reversed phase HPLC to give 250 mg isomer 1 and 620 mg isomer 2 (69%). ES-MS (M+H)$^+$: calcd 494.3; found 494.3 (both isomers).

2809(g). Compound 2809(f), isomer 1 (0.2 g, 0.4 mmol) or isomer 2 (0.55 g, 1.11 mmol) was treated with 1.1 equivalent LiOH in THF for 1 hour and both products were purified on HPLC. Yield: isomer 1 0.15 g; isomer 2 0.41 g. ES-MS (M+Na)$^+$: calcd 460.2; found 460.3 (both isomers).

2809. To a solution of compound 2809(g), isomer 1 (100 mg, 0.228 mmol) and hydroxylamine hydrochloride (20 mg, 0.274 mmol) in 3 mL DMF cooled in an ice bath was added diisopropylethylamine (0.15 mL, 1 mmol) and BOP (0.12 g, 0.274 mmol) and the solution was stirred at room temperature for 2 hours. Purification on HPLC gave 85 mg (82%) product. ES-MS (M+H)$^+$: calcd 453.2; found 453.3. Compound 2809(g), isomer 2 was converted to the same product in the same manner. ES-MS (M+Na)$^+$: calcd 475.2; found 475.3.

Example 2880

2S,11S,12R-1,7-Diaza-8,13-dioxo-2-(N-methylcarboxamido)-7-N-t-butyloxycarbonyl-12-isobutylcyclotridecane-11-(N-hydroxycarboxamide)

2880(a): Compound Example 2323(a) (300 mg, 0.5 mmol) was dissolved in 33% HBr/AcOH (6.8 mL) containing phenol (63 mg, 0.67 mmol). After stirring for 5 h, the solution was concentrated and the solid was filtered off with $CH_2Cl_2/Et_2O$. This provided the crude amino acid salt (500 mg, quant.): ES-MS (M+H)$^+$ 356.4.

2880(b). Compound Example 2880(a) (140 mg, 0.32 mmol) was dissolved in THF (4 mL)/H$_2$O (0.6 mL) and Et$_3$N (0.38 mL, 2.6 mmol) was added. Next, (Boc)$_2$O (452 mg, 206 mmol) was added at room temperature. After stirring overnight, the solvent was removed and CH$_2$Cl$_2$ was added. The CH$_2$Cl$_2$ was washed with 10% HCl, dried (MgSO$_4$), and concentrated. The resulting residue was purified by silica gel chromatography to yield the crude carbamate, which was dissolved in DMF (5 mL). To this solution was added O-benzylhydroxylamine (108 mg, 0.87 mmol), diisopropylethylamine (0.15 mL, 0.82 mmol) and BOP (214 mg, 0.48 mmol). After stirring overnight, the solid product was filtered from solution with CH$_2$Cl$_2$ to give the O-benzyl hydroxamate (120 mg, 67%): ES-MS (M+H)$^+$ 561.5.

2880: Compound Example 2880(b) (160 mg, 0.29 mmol) was hydrogenated in MeOH (40 mL) with 5% Pd/BaSO$_4$ (240 mg) under a hydrogen atmosphere (50 psi). After stirring 3 h, the catalyst was filtered off and the solution was concentrated to yield the title hydroxamate (140 mg, quant.) as a pale yellow solid: ES-MS (M+H)$^+$ 471.5.

Example 2890

2S,11S,12R-1,7-Diaza-8,13-dioxo-2-(N-methylcarboxamido)-7-N-(N-methyl-imidazolesulfon-4-yl)-12-isobutylcyclotridecane-11-(N-hydroxycarboxamide)

2890(a): To a solution of the succinate 1(c) (1.27 g, 4.39 mmol), N$^e$-4-(N-methyl)imidazolesulfonyl-L-lysine N-methyl amide (1.73 g, 5.70 mmol), and diisopropylethylamine (3.19 mL, 17.6 mmol) in DMF was added BOP (2.34 g, 5.27 mmol). After stirring overnight, the DMF was removed and CH$_2$Cl$_2$ was added. The CH$_2$Cl$_2$ was washed with saturated NaHCO$_3$ solution and brine. The CH$_2$Cl$_2$ was dried (MgSO$_4$) and concentrated. The resulting residue was purified by silica gel chromatography to yield the amide (1.73 g, 69%) as a white foam: ES-MS (M+H)$^+$ 574.5.

2890(b). Compound Example 2890(a) (200.0 mg, 0.35 mmol) and PPh$_3$ (274.0 g, 1.05 mmol) were dissolved in THF (15.5 mL). DIAD (0.20 ml, 1.05 mmol) in THF (5 mL) was added dropwise to the mixture. After stirring overnight, the solution was concentrated and the residue was purified by silica gel chromatography to yield the cyclic material (100 mg, 52%) as a white foam: ES-MS (M+H)$^+$ 556.5.

2890(c): Compound Example 2890(b) (400.0 mg, 0.72 mmol) was dissolved in CH$_2$Cl$_2$ (5.5 mL) and TFA (5.5 mL). After stirring overnight, the solution was concentrated to the acid, which was dissolved in DMF (6.4 mL). To this solution was added O-benzylhydroxylamine (172.0 mg, 1.40 mmol) and diisopropyl-ethylamine (0.24 mL, 1.38 mmol) followed by BOP (341.0 mg, 0.77 mmol). After stirring overnight, the DMF was removed and silica gel chromatography gave the O-benzyl hydroxamate (140 mg, 33%): ES-MS (M+H)$^+$ 605.5.

2890: Compound Example 2890(c) (135.0 mg, 0.22 mmol) was hydrogenated in MeOH (25 mL) with 5% Pd/BaSO$_4$ (202 mg) under a hydrogen atmosphere (50 psi). After stirring 3 h, the catalyst was filtered off and the solution was concentrated to yield the title hydroxamate (98 mg, 85%) as a solid: ES-MS (M+H)$^+$ 515.4.

Example 2900

2900(a). 2R,3S-Methyl 4-benzyloxy-3-hydroxy-2-(2E-3-phenyl-2-propen-1-yl)butyrate A 1.6 M hexane solution of n-butyllithium (140.4 mL, 2.1 equiv.) was added over 15 min to a solution of diisopropylamine (29.48 mL, 2.1 equiv.) in tetrahydrofuran (650 mL) at 0° C. The mixture was stirred at 0° C. for 15 min and cooled to −78 ° C. Methyl 4-benzyloxy-3S-hydroxybutyrate (24.00 g, 107 mmol) in tetrahydrofuran (40 mL) was added over 20 min via a cannula and the residue was rinsed with tetrahydrofuran (2×20 mL). The resultant mixture was stirred at −45° C. for 1 h, −20° C. for 0.5 h and cooled to −78° C. A tetrahydrofuran (90 mL) solution of cinnamyl bromide (31.69 mL, 2.0 equiv.) and neat N,N,N',N'-tetramethylethylenediamine (32.33 mL, 2.0 equiv.) were added sequentially. After 15 min at −40° C. and 4 h at −20° C., saturated ammonium chloride (500 mL) and hexane (400 mL) were added. Following extraction of the aqueous phase with ether (3×800 mL), the combined organic extracts were washed with water (50 mL), brine (50 mL), dried (MgSO4) and concentrated. Silica gel chromatography (ethyl acetate-hexane, 20:80, then 30:70, then 50:50) gave product (28.78 g, 73%, d.s.=8:1) as a yellow oil. ESI-MS (M+H)$^+$: calcd 341.2, found 341.2.

2900(b). 2R,3S-4-Benzyloxy-3-hydroxy-2-(2E-3-phenyl-2-propen-1-yl)butyric acid

A 1.0 M aqueous solution of sodium hydroxide (450 mL) was added to a solution of 2900(a) (28.08 g, 82.6 mmol) in methanol (450 mL) at 0° C. and the resultant mixture was stirred at room temperature for 2 h. Following removal of methanol in vacuo, the aqueous residue was adjusted to pH 5 with 1 N sulfuric acid, and extracted with ethyl acetate. The combined extracts were washed with brine, dried (MgSO$_4$) and concentrated to give the product (27.06 g, 100%) as a solid. DCI-MS (M+NH$_4$)$^+$: calcd 344.2, found 340.

2900(c). 2R,3S-4-Benzyloxy-3-hydroxy-2-(2E-3-phenyl-2-propen-1-yl)butyryl-N$^d$-t-butoxycarbonyl-L-ornithine N-methyl amide Diisopropylethylamine (12.18 mL, 4 equiv.) was added to a solution of 2900(b) (5.70 g, 17.48 mmol), N$^d$-t-butoxycarbonyl-L-ornithine N-methyl amide (7.49 g, 1.5 equiv., HCl salt) and benzotriazol-1-yloxy-tris(dimethylamino)phosphonium hexafluorophosphate (7.97 g, 1.03 equiv.) in N,N-dimethylformamide (20 mL) at 0° C. After 2 h at 0° C., ethyl acetate (200 mL) was added. The mixture was washed with 10% citric acid (2×25 mL), brine (25 mL), saturated sodium bicarbonate (2×25 mL), brine (25 mL), dried (MgSO4) and concentrated. Silica gel chromatography (methanol-dichloromethane, 5:95 then 8:92) gave product (7.16 g, 74%) as a solid. ESI-MS (M+H)$^+$: calcd 554.4, found 554.4.

2900(d). 2R,3S-4-Benzyloxy-3-(2E-4-bromo-2-buten-1-yl)-2-(2E-3-phenyl-2-propen-1-yl)butyryl-N$^d$-t-butoxycarbonyl-L-ornithine N-methyl amide Sodium hydride (0.28 g, 1.8 equiv., 60% dispersion in mineral oil) was added to a solution of 2900(c) (2.13 g, 3.85 mmol) and 2E-1,4-dibromo-2-butene (8.00 g, 9.7 equiv.) in N,N-dimethylformamide (100 mL) at 0° C. Additional portions of 2E-1,4-dibromo-2-butene (4 g each) and sodium hydride (0.23 g each) were added every 20 min and the disappearance of starting material was monitored by TLC analysis. After a total of 1.5 h, reaction seems complete. Following addition of saturated ammonium chloride (40 mL) and ethyl acetate (120 mL), the aqueous phase was separated and extracted with ethyl acetate (6×60 mL). The combined extracts were dried (MgSO4), and concentrated. Silica gel chromatography (methanol-chloroform, 3:97 then 4:96) provided the desired product (1.86 g, 70%). ESI-MS (M+H)+: calcd 688.3, found 688.2.

2900(e). 2S,3R,6S,11E-2-Benzyloxymethyl-10-t-butoxycarbonyl-5,10-diaza-6-(N-methylcarboxamido)-1-oxa-4-oxo-3-(2E-3-phenyl-2-propen-1-yl)cyclotetradecene A 4 N dioxane solution of hydrogen chloride (20 mL) was added to 2900(e) (1.86 g, 2.707 mmol). After 1.5 h at room temperature, the solvent was removed in vacuo. The solid residue was washed with small amount ether, pumped to dryness to give the product (1.64 g). Diisopropylethylamine (2.33 mL, 5 equiv.) was added to a solution of this crude material in acetonitrile (1.3 L) at 0° C. The resultant mixture was stirred at room temperature for 3 h. Di-t-butyl dicarbonate (2.33 g, 4 equiv.) was added. After 20 min at room temperature, the mixture was then quenched with saturated ammonium chloride and extracted with ethyl acetate. The combined organic extracts were dried (MgSO4), and concentrated. Silica gel chromatography twice (isopropanol-chloroform, 3:97 then 4:96 then 6:94 the first time, 5:95 the second time) provided the product (0.73 g, 45% for two steps). ESI-MS (M+H)+: calcd 606.4, found 606.4.

2900(f). 2S,3R,6S-10-t-Butoxycarbonyl-5,10-diaza-2-hydroxymethyl-6-(N-methylcarboxamido)-1-oxa-4-oxo-3-(3-phenylprop-1-yl)cyclotetradecane A suspension of 2900(e) (0.73 g, 1.205 mmol) and Pearlman's catalyst (0.35 g) in methanol (200 mL) was stirred under balloon pressure hydrogen for 1 h 20 min. The catalyst was removed by filtration. The filtrate was concentrated and purified by silica gel chromatography (methanol-chloroform, 3:97 then 5:95) to give the product (0.35 g, 56%). ESI-MS (M+H)+: calcd 520.4, found 520.3.

2900(g). 2S,3R,6S-10-t-Butoxycarbonyl-5,10-diaza-2-hydroxycarbonyl-6-(N-methylcarboxamido)-1-oxa-4-oxo-3-(3-phenylprop-1-yl)cyclotetradecane Ruthenium(III) chloride (7.2 mg, 0.04 equiv.) and sodium periodate (0.74 g, 4 equiv.) were added sequentially to a mixture of 2900(f) (0.45 g, 0.866 mmol), acetonitrile (8 mL), carbon tetrachloride (8 mL) and water (12 mL). After 2 h at room temperature, chloroform (60 mL) was added. The aqueous layer was separated and extracted with chloroform (5×30 mL). The combined organic phase was dried (MgSO4) and filtered through a pad of celite to give the desired carboxylic acid (0.43 g, 93%). ESI-MS (M+H)+: calcd 534.4, found 534.3.

2900(h). 2S,3R,6S-2-(N-Benzyloxycarboxamido)-10-t-butoxycarbonyl-5,10-diaza-6-(N-methylcarboxamido)-1-oxa-4-oxo-3-(3-phenylprop-1-yl)cyclotetradecane A 1.0 M dichloromethane solution of dicyclohexylcarbodiimide (0.038 mL, 1 eq.) was added to a solution of 2900(g) (20.1 mg, 0.0377 mmol), O-benzylhydroxyamine hydrochloride (7.2 mg, 1.2 eq), 1-hydroxybenzotriazole hydrate (5.1 mg, 1.0 eq.) and diisopropylethylamine (0.0079 mL, 1.2 eq) in tetrahydrofuran (2 mL). The mixture was stirred until starting material disappeared as monitored by TLC then quenched with saturated ammonium chloride. Following extraction with ethyl acetate, the combined extracts were washed with brine, dried (MgSO4) and concentrated. Preparative thin layer chromatography (methanol-chloroform, 5:95) yielded the desired product (12.8 mg, 53%) as a white solid. ESI-MS (M+H)+: calcd 639.4, found 639.3.

2900: 2S,3R,6S-10-t-Butoxycarbonyl-5,10-diaza-2-(N-hydroxycarboxamido)-6-(N-methylcarboxamido)-1-oxa-4-oxo-3-(3-phenylprop-1-yl)cyclotetradecane A mixture of 2900(h) (34.0 mg, 0.0532 mmol) and 5% Pd on BaSO4 (56.7 mg) in ethanol (4 mL) was stirred under balloon-pressure hydrogen at room temperature. Additional Pd on BaSO4 (115.3 mg) was added 1 h later. After a total of 2 h, the catalyst was removed by filtration. The filtrate was concentrated to give the desired hydroxamate (26.7 mg, 91%) as a white solid. ESI-MS (M+H)+: calcd 549.3, found 549.3.

Example 2910

2910(a). 2S,3R,6S-2-(N-Benzyloxycarboxamido)-5,10-diaza-6-(N-methylcarboxamido)-1-oxa-4-oxo-3-(3-phenylprop-1-yl)cyclotetradecane hydrochloride A mixture of 2900 (36.1 mg, 0.0565 mmol) and 4 N dioxane solution of HCl (1.0 mL) was stirred at room temperature for 30 min. Removal of solvent in vacuo gave the desired product as a white solid. The crude material was taken to the next step without purification. ESI-MS (M+H)+: calcd 539.3, found 539.3.

2910(b). 2S,3R,6S-5,10-Diaza-2-(N-hydroxycarboxamido)-6-(N-methylcarboxamino)-1-oxa-4-oxo-3-(3-phenylprop-1-yl)cyclotetradecane hydrochloride Following a procedure analogous to the conversion of 2900(h) to 2900(i), 2900(a) converted to the desired product (26.3 mg, (95%, for two steps). ESI-MS (M+H)+: calcd 449.3, found 449.4.

Example 2920

2920(a). 2S,3R,6S-10-Acetyl-2-(N-Benzyloxycarboxamido)-5,10-diaza-6-(N-methylcarboxamido)-1-oxa-4-oxo-3-(3-phenylprop-1-yl)cyclotetradecane A crude material of 2910(a) derived from 2900(h) (45.4 mg, 0.071 mmol) was treated with acetic anhydride (1.5 mL) and diisopropylethylamine (0.040 mL, 3.2 equiv.). 10 min later, the reaction mixture was quenched with saturated ammonium chloride and extracted with ethyl acetate. The combined extracts were washed with saturated sodium bicarbonate, brine dried (MgSO4) and concentrated. Silica gel chromatography (methanol-chloroform, 5:95 then 7.5:92.5) furnished the desired product (32.9 mg, 80% for two steps). ESI-MS (M+H)+: calcd 581.4, found 581.5.

2920: 2S,3R,6S-10-Acetyl-5,10-diaza-2-(N-hydroxycarboxamido)-6-(N-methylcarboxamido)-1-oxa-4-oxo-3-(3-phenylprop-1-yl)cyclotetradecane Following a procedure analogous to the conversion of 2900(h) to 2900(i), 2920(a) (31.8 mg, 0.0548 mmol) was converted to the desired product (24.0 mg, 89%). ESI-MS (M+H)+: calcd 491.3, found 491.4.

Example 2930

2S,13S,14R-1,7-diaza-8,15-dioxo-9-oxa-14-isobutyl-2-[glycine-N-morpholino]-cyclopentadecane-13-N-hydroxycarboxamide This compound was prepared using the procedures analogous to those above. ESI-MS: found 527.6.

Example 2931

2S,13S,14R-1,7-diaza-8,15-dioxo-9-oxa-14-isobutyl-2-[glycine-N-(4-hydroxypiperidine)]-cyclopentadecane-13-N-hydroxycarboxamide This compound was prepared using the procedures analogous to those above. ESI-MS: found 541.7.

Example 2934

2S,13S,14R-1,7-diaza-8,15-dioxo-9-oxa-14-isobutyl-2-[N-(glycine-N-4-methylpiperazinamide)carboxamide]cyclopentadecane-13-N-hydroxycarboxamide This compound was prepared using the procedures analogous to those above. ESI-MS: 541.3

Example 2935

2S,13S,14R-1,7-diaza-8,15-dioxo-9-oxa-14-isobutyl-2-[N-(L-alanine-N-morpholinamide)carboxamide]cyclopentadecane-13-N-hydroxycarboxamide This compound was prepared using the procedures analogous to those above. ESI-MS: 564.3 (M+Na)

Example 2936

2S,13S,14R-1,7-diaza-8,15-dioxo-9-oxa-14-isobutyl-2-[N-(L-valine-N-morpholinamide)carboxamide]cyclopentadecane-13-N-hydroxycarboxamide This compound was prepared using the procedures analogous to those above. ESI-MS: 592.2 (M+Na)

Example 2937

2S,13S,14R-1,7-diaza-8,15-dioxo-9-oxa-14-isobutyl-2-[N-(L-tert-butylglycine-N-morpholinamide)carboxamide]cyclopentadecane-13-N-hydroxycarboxamide This compound was prepared using the procedures analogous to those above. ESI-MS: 606.4 (M+Na)

Example 2938

2S,13S,14R-1,7-diaza-8,15-dioxo-9-oxa-14-isobutyl-2-[N-(b-alanine-N-morpholinamide)carboxamide]cyclopentadecane-13-N-hydroxycarboxamide This compound was prepared using the procedures analogous to those above. ESI-MS: 564.3 (M+Na)

Example 2939

2S,13S,14R-1,7-diaza-8,15-dioxo-9-oxa-14-isobutyl-2-[N-(ethoxycarbonyl-N-morpholinamide)carboxamide]cyclopentadecane-13-N-hydroxycarboxamide This compound was prepared using the procedures analogous to those above. ESI-MS: 580.3 (M+Na)

Example 2940

2S,13S,14R-1,7-diaza-8,15-dioxo-9-oxa-14-isobutyl-2-[N-(2-hydroxy-2-phenylethyl)carboxamide]cyclopentadecane-13-N-hydroxycarboxamide This compound was prepared using the procedures analogous to those above. ESI-MS: 543.3 (M+Na)

Example 2941

2S,13S,14R-1,7-diaza-8,15-dioxo-9-oxa-14-isobutyl-2-[N-(glycine-N-4-benzylpiperazinamide)carboxamide]cyclopentadecane-13-N-hydroxycarboxamide This compound was prepared using the procedures analogous to those above. ESI-MS: 617.3 (M+1)

Example 2942

2S,13S,14R-1,7-diaza-8,15-dioxo-9-oxa-14-isobutyl-2-[N-(glycine-N-4-phenylpiperazinamide)carboxamide]cyclopentadecane-13-N-hydroxycarboxamide This compound was prepared using the procedures analogous to those above. ESI-MS: 616.7 (M+1)

Example 2943

2S,13S,14R-1,7-diaza-8,15-dioxo-9-oxa-14-isobutyl-2-[N-(glycine-N-4-(2-pyridyl)piperazinamide)carboxamide]cyclopentadecane-13-N-hydroxycarboxamide This compound was prepared using the procedures analogous to those above. ESI-MS: 604.4(M+1)

Example 2944

2S,13S,14R-1,7-diaza-8,15-dioxo-9-oxa-14-isobutyl-2-[N-(α-cyclopropanethyloxycarboxamide-β-alanine)carboxamide]cyclopentadecane-13-N-hydroxycarboxamide This compound was prepared using the procedures analogous to those above. ESI-MS: 600.3(M+1)

Example 2945

2S,13S,14R-1,7-diaza-8,15-dioxo-9-oxa-14-isobutyl-2-{N-[glycine-N-4-(1-piperidinyl)piperidinamide]carboxamide}cyclopentadecane-13-N-hydroxycarboxamide This compound was prepared using the procedures analogous to those above. ESI-MS: 609.4(M+1)

Example 2946

2S,13S,14R-1,7-diaza-8,15-dioxo-9-oxa-14-isobutyl-2-[N-(R-isopropyloxycarbonyl-N-morpholinamide)carboxamide]cyclopentadecane-13-N-hydroxycarboxamide This compound was prepared using the procedures analogous to those above. ESI-MS: 572.3(M+1)

Example 2947

2S,13S,14R-1,7-diaza-8,15-dioxo-9-oxa-14-isobutyl-2-[N-(S-isopropyloxycarbonyl-N-morpholinamide)carboxamide]cyclopentadecane-13-N-hydroxycarboxamide This compound was prepared using the procedures analogous to those above. ESI-MS: 572.3(M+1)

Example 2948

2S,13S,14R-1,7-diaza-8,15-dioxo-9-oxa-14-isobutyl-2-[N-(2-thiazole-4-acetic acid)carboxamide]cyclopentadecane-13-N-hydroxycarboxamide This compound was prepared using the procedures analogous to those above. ESI-MS: 564.2(M+Na)

Example 2949

2S,13S,14R-1,7-diaza-8,15-dioxo-9-oxa-14-isobutyl-2-[N-(a-cyclopropaneethyloxycarboxamide-b-alanine-N-dimethylamide)carboxamide]cyclopentadecane-13-N-hydroxycarbocamide This compound was prepared using the procedures analogous to those above. ESI-MS: 627.3(M+1)

Example 2950

2S,13S,14R-1,7-diaza-8,15-dioxo-9-oxa-14-isobutyl-2-[N-(α-cyclopropaneethyloxycarboxamide-β-alanine-N-morpholinamide)carboxamide]cyclopentadecane-13-N-hydroxycarboxamide This compound was prepared using the procedures analogous to those above. ESI-MS: 627.3(M+1)

Example 2951

2S,13S,14R-1,7-diaza-8,15-dioxo-9-oxa-14-isobutyl-2-[N-(2-thiazole-4-acetyl-N-morpholinamide)carboxamide]cyclopentadecane-13-N-hydroxycarboxamide This compound was prepared using the procedures analogous to those above. ESI-MS: 611.2(M+1)

Example 2952

2S,13S,14R-1,7-diaza-8,15-dioxo-9-oxa-14-isobutyl-2-[N-(L-serine-N-morpholinamide)carboxamide]cyclopentadecane-13-N-hydroxycarboxamide This compound was prepared using the procedures analogous to those above. ESI-MS: 558.2(M+1)

Example 2953

2S,13S,14R-1,7-diaza-8,15-dioxo-9-oxa-14-isobutyl-2-[N-(glycine-N-piperidinamide-3-carboxylic acid)carboxamide]cyclopentadecane-13-N-hydroxycarboxamide This compound was prepared using the procedures analogous to those above. ESI-MS: 592.2(M+Na)

Example 2954

2S,13S,14R-1,7-diaza-8,15-dioxo-9-oxa-14-isobutyl-2-[N-(glycine-N-2,6-dimethylmorpholinamide)carboxamide]cyclopentadecane-13-N-hydroxycarboxamide This compound was prepared using the procedures analogous to those above. ESI-MS: 556.4(M+1)

Example 2955

2S,13S,14R-1,7-diaza-8,15-dioxo-9-oxa-14-isobutyl-2-[N-(glycine-N-4-ethoxycarbonylpiperazinamide)carboxamide]cyclopentadecane-13-N-hydroxycarboxamide This compound was prepared using the procedures analogous to those above. ESI-MS: 599.4(M+1)

Example 2956

2S,13S,14R-1,7-diaza-8,15-dioxo-9-oxa-14-isobutyl-2-[N-(glycine-N-4-ethoxycarbonylpiperidinamide)carboxamide]cyclopentadecane-13-N-hydroxycarboxamide This compound was prepared using the procedures analogous to those above. ESI-MS: 598.4(M+1)

Example 2957

2S,13S,14R-1,7-diaza-8,15-dioxo-9-oxa-14-isobutyl-2-{N-[4-(1-morpholinyl)phenyl]carboxamide}cyclopentadecane-13-N-hydroxycarboxamide This compound was prepared using the procedures analogous to those above. ESI-MS: 562.3(M+1)

Example 2958

2S,13S,14R-1,7-diaza-8,15-dioxo-9-oxa-14-isobutyl-2-{N[-glycine-N-(4-(1-morpholinyl)anilide)carboxamide]cyclopentadecane-13-N-hydroxycarboxamide This compound was prepared using the procedures analogous to those above. ESI-MS: 619.4(M+1)

Example 2959

2S,13S,14R-1,7-diaza-8,15-dioxo-9-oxa-14-isobutyl-2-[N-(glycine-N-piperidinamide-4-carboxylic acid)carboxamide]cyclopentadecane-13-N-hydroxycarboxamide This compound was prepared using the procedures analogous to those above. ESI-MS: 592.3(M+Na)

Example 2960

2S,13S,14R-1,7-diaza-8,15-dioxo-9-oxa-14-isobutyl-2-[N-methylcarboxamide]-cyclopentadecane-13-N-hydroxycarboxamide This compound was prepared using the procedures analogous to those above. ESI-MS: 437(M+Na)

Example 2961

2S,13S,14R-1,7-diaza-8,15-dioxo-9-oxa-14-isobutyl-2-[alanine-N-methylamide]-cyclopentadecane-13-N-hydroxycarboxamide This compound was prepared using the procedures analogous to those above. ESI-MS: 508(M+Na)

Example 2962

2S,13S,14R-1,7-diaza-8,15-dioxo-9-oxa-14-isobutyl-2-[methylcarboxy]-cyclopentadecane-13-N-hydroxycarboxamide This compound was prepared using the procedures analogous to those above. ESI-MS: 438(M+Na)

Example 2963

2S,13S,14R-1,7-diaza-8,15-dioxo-9-oxa-14-isobutyl-2-[glycine-N-methylamide]-cyclopentadecane-13-N-hydroxycarboxamide This compound was prepared using the procedures analogous to those above. ESI-MS: 494(M+Na)

Example 2964

2S,13S,14R-1,7-diaza-8,15-dioxo-9-oxa-14-isobutyl-2-[2-N-morpholinoethylcarboxamide]-cyclopentadecane-13-N-hydroxycarboxamide This compound was prepared using the procedures analogous to those above. ESI-MS: 514(M+H)

Example 2965

2S,13S,14R-1,7-diaza-8,15-dioxo-9-oxa-14-isobutyl-2-[3-N-morpholinopropylcarboxamide]-cyclopentadecane-13-N-hydroxycarboxamide This compound was prepared using the procedures analogous to those above. ESI-MS: 528(M+H)

Example 2966

2S,13S,14R-1,7-diaza-8,15-dioxo-9-oxa-14-isobutyl-2-[pheylalanine-N-methylamide]-cyclopentadecane-13-N-hydroxycarboxamide This compound was prepared using the procedures analogous to those above. ESI-MS: 584(M+Na)

Example 2967

2S,13S,14R-1,7-diaza-8,15-dioxo-9-oxa-14-isobutyl-2-[leucine-N-methylamide]-cyclopentadecane-13-N-hydroxycarboxamide This compound was prepared using the procedures analogous to those above. ESI-MS: 550(M+Na)

Example 2968

2S,13S,14R-1,7-diaza-8,15-dioxo-9-oxa-14-isobutyl-2-[N-4-pyridylmethylcarboxamide]-cyclopentadecane-13-N-hydroxycarboxamide This compound was prepared using the procedures analogous to those above. ESI-MS: 492(M+H)

Example 2969

2S,13S,14R-1,7-diaza-8,15-dioxo-9-oxa-14-isobutyl-2-[N-(R,S)-furfurylcarboxamide]-cyclopentadecane-13-N-hydroxycarboxamide This compound was prepared using the procedures analogous to those above. ESI-MS: 507(M+Na)

Example 2970

2S,13S,14R-1,7-diaza-8,15-dioxo-9-oxa-14-isobutyl-2-[N-phenylcarboxamide]-cyclopentadecane-13-N-hydroxycarboxamide This compound was prepared using the procedures analogous to those above. ESI-MS: 499(M+Na)

Example 2971

2S,13S,14R-1,7-diaza-8,15-dioxo-9-oxa-14-isobutyl-2-[t-butylglycine-N-methylamide]-cyclopentadecane-13-N-hydroxycarboxamide This compound was prepared using the procedures analogous to those above. ESI-MS: 550(M+Na)

Example 2972

2S,13S,14R-1,7-diaza-8,15-dioxo-9-oxa-14-isobutyl-2-[N-benzylcarboxamide]-cyclopentadecane-13-N-hydroxycarboxamide This compound was prepared using the procedures analogous to those above. ESI-MS: 513(M+Na)

Example 2973

2S,13S,14R-1,7-diaza-8,15-dioxo-9-oxa-14-isobutyl-2-[-N-(2-oxo-pyrrolidino)propylcarboxamide]-cyclopentadecane-13-N-hydroxycarboxamide This compound was prepared using the procedures analogous to those above. ESI-MS: 548(M+Na)

Example 2974

2S,13S,14R-1,7-diaza-8,15-dioxo-9-oxa-14-isobutyl-2-[2-N-ethylpyrrolidinocarboxamide]-cyclopentadecane-13-N-hydroxycarboxamide This compound was prepared using the procedures analogous to those above. ESI-MS: 498(M+H)

Example 2975

2S,13S,14R-1,7-diaza-8,15-dioxo-9-oxa-14-isobutyl-2-[N-3-pyridylmethylcarboxamide]-cyclopentadecane-13-N-hydroxycarboxamide This compound was prepared using the procedures analogous to those above. ESI-MS: 492(M+H)

Example 2976

2S,13S,14R-1,7-diaza-8,15-dioxo-9-oxa-14-isobutyl-2-[N-2-(1,1,1-trifluoroethyl)carboxamide]-cyclopentadecane-13-N-hydroxycarboxamide This compound was prepared using the procedures analogous to those above. ESI-MS: 505(M+Na)

Example 2977

2S,13S,14R-1,7-diaza-8,15-dioxo-9-oxa-14-isobutyl-2-[N-2-(2-pyridyl)ethylcarboxamide]-cyclopentadecane-13-N-hydroxycarboxamide This compound was prepared using the procedures analogous to those above. ESI-MS: 506(M+H)

Example 2978

2S,13S,14R-1,7-diaza-8,15-dioxo-9-oxa-14-isobutyl-2-[N-(R,S-1-methyl-3-pheylpropyl)carboxamide]-cyclopentadecane-13-N-hydroxycarboxamide This compound was prepared using the procedures analogous to those above. ESI-MS: 555(M+Na)

Example 2979

2S,13S,14R-1,7-diaza-8,15-dioxo-9-oxa-14-isobutyl-2-[3-N-imidazoylpropylcarboxamide]-cyclopentadecane-13-N-hydroxycarboxamide This compound was prepared using the procedures analogous to those above. ESI-MS: 509(M+H)

Example 2980

2S,13S,14R-1,7-diaza-8,15-dioxo-9-oxa-14-isobutyl-2-[e-N-t-butyloxycarbonyllysine-N-methylamide]-cyclopentadecane-13-N-hydroxycarboxamide This compound was prepared using the procedures analogous to those above. ESI-MS: 665(M+H)

Example 2981

2S,13S,14R-1,7-diaza-8,15-dioxo-9-oxa-14-isobutyl-2-[lysine-N-methylamide]-cyclopentadecane-13-N-hydroxycarboxamide This compound was prepared using the procedures analogous to those above. ESI-MS: 543(M+H)

Example 2982

2S,13S,14R-1,7-diaza-8,15-dioxo-9-oxa-14-isobutyl-2-[N-2-pyridylmethylcarboxamide]-cyclopentadecane-13-N-hydroxycarboxamide This compound was prepared using the procedures analogous to those above. ESI-MS: 492(M+H)

Example 2983

22S,13S,14R-1,7-diaza-8,15-dioxo-9-oxa-14-isobutyl-2-[N-N-morpholinocarboxyamide]-cyclopentadecane-13-N-hydroxycarboxamide This compound was prepared using the procedures analogous to those above. ESI-MS: 508(M+Na)

Example 2984

2S,13S,14R-1,7-diaza-8,15-dioxo-9-oxa-14-isobutyl-2-[N-(R)-furfurylcarboxamide]-cyclopentadecane-13-N-hydroxycarboxamide This compound was prepared using the procedures analogous to those above. ESI-MS: 507(M+Na)

Example 2985

2S,13S,14R-1,7-diaza-8,15-dioxo-9-oxa-14-isobutyl-2-[N-2(4-imidazoyl)ethylcarboxyamide]-cyclopentadecane-13-N-hydroxycarboxamide This compound was prepared using the procedures analogous to those above. ESI-MS: 495(M+H)

Example 2986

2S,13S,14R-1,7-diaza-8,15-dioxo-9-oxa-14-isobutyl-2-[N-R-(2-R-hydroxyindane)carboxamide]-cyclopentadecane-13-N-hydroxycarboxamide This compound was prepared using the procedures analogous to those above. ESI-MS: 555(M+Na)

Example 2987

2S,13S,14R-1,7-diaza-8,15-dioxo-9-oxa-14-isobutyl-2-[N-S-(2-S-hydroxyindane)carboxamide]-cyclopentadecane-13-N-hydroxycarboxamide This compound was prepared using the procedures analogous to those above. ESI-MS: 555(M+Na)

Example 2988

2S,13S,14R-1,7-diaza-8,15-dioxo-9-oxa-14-isobutyl-2-[N-4-aminobenzylcarboxamide]-cyclopentadecane-13-N-hydroxycarboxamide This compound was prepared using the procedures analogous to those above. ESI-MS: 504(M–H)

Example 2989

2S,13S,14R-1,7-diaza-8,15-dioxo-9-oxa-14-isobutyl-2-[2-N-piperazinoethylcarboxamide]-cyclopentadecane-13-N-hydroxycarboxamide This compound was prepared using the procedures analogous to those above. ESI-MS: 513(M+H)

Example 2990

2S,13S,14R-1,7-diaza-8,15-dioxo-9-oxa-14-isobutyl-2-[N-4-methylpiperinocarboxamide]-cyclopentadecane-13-N-hydroxycarboxamide This compound was prepared using the procedures analogous to those above. ESI-MS: 498(M+H)

Example 2991

2S,13S,14R-1,7-diaza-8,15-dioxo-9-oxa-14-isobutyl-2-[3-N-(2-R,S-methyl-piperidino)propylcarboxamide]-cyclopentadecane-13-N-hydroxycarboxamide This compound was prepared using the procedures analogous to those above. ESI-MS: 540(M+H)

Example 2992

2S,13S,14R-1,7-diaza-8,15-dioxo-9-oxa-14-isobutyl-2-[N-(S)-furfurylcarboxamide]-cyclopentadecane-13-N-hydroxycarboxamide This compound was prepared using the procedures analogous to those above. ESI-MS: 507(M+Na)

Example 2993

2S,13S,14R-1,7-diaza-8,15-dioxo-9-oxa-14-isobutyl-2-[aspartate(O-t-butyl)-N-methylamide]-cyclopentadecane-13-N-hydroxycarboxamide This compound was prepared using the procedures analogous to those above ESI-MS: 608(M+Na)

Example 2994

2S,13S,14R-1,7-diaza-8,15-dioxo-9-oxa-14-isobutyl-2-[aspartate-N-methylamide]-cyclopentadecane-13-N-hydroxycarboxamide This compound was prepared using the procedures analogous to those above. ESI-MS: 552(M+Na)

Example 2995

2S,13S,14R-1,7-diaza-8,15-dioxo-9-oxa-14-isobutyl-2-[3-azaphenylalanine-N-methylamide]-cyclopentadecane-13-N-hydroxycarboxamide This compound was prepared using the procedures analogous to those above. ESI-MS: 563(M+H)

Example 2996

2S,13S,14R-1,7-diaza-8,15-dioxo-9-oxa-14-isobutyl-2-[N-benzhydrylcarboxamide]-cyclopentadecane-13-N-hydroxycarboxamide This compound was prepared using the procedures analogous to those above. ESI-MS: 589(M+Na)

Example 2997

2S,13S,14R-1,7-diaza-8,15-dioxo-9-oxa-14-isobutyl-2[glycine-n-pentyl ester]-cyclopentadecane-13-N-hydroxycarboxamide This compound was prepared using the procedures analogous to those above. ESI-MS: 528.6

Example 2998

2S,13S,14R-1,7-diaza-8,15-dioxo-9-oxa-14-isobutyl-2[N-4-phenyl-1-butylamide]-cyclopentadecane-13-N-hydroxycarboxamide This compound was prepared using the procedures analogous to those above. ESI-MS: 532.7

Example 2999

2S,13S,14R-1,7-diaza-8,15-dioxo-9-oxa-14-isobutyl-2[5-methoxytrytramine]-cyclopentadecane-13-N-hydroxycarboxamide This compound was prepared using the procedures analogous to those above. ESI-MS: 573.7

Example 3000

2S,13S,14R-1,7-diaza-8,15-dioxo-9-oxa-14-isobutyl-2[1-(2,5-dimethoxyphenyl)-2-glycine amidoethanol]-cyclopentadecane-13-N-hydroxycarboxamide This compound was prepared using the procedures analogous to those above. ESI-MS: 637.7

Example 3001

2S,13S,14R-1,7-diaza-8,15-dioxo-9-oxa-14-isobutyl-2[glycine-t-butyl ester]-cyclopentadecane-13-N-hydroxycarboxamide This compound was prepared using the procedures analogous to those above. ESI-MS: 514.6

Example 3002

2S,13S,14R-1,7-diaza-8,15-dioxo-9-oxa-14-isobutyl-2[L-glutamic acid-a,g-di-t-butyl ester]-cyclopentadecane-13-N-hydroxycarboxamide This compound was prepared using the procedures analogous to those above. ESI-MS: 658.8

Example 3003

2S,13S,14R-1,7-diaza-8,15-dioxo-9-oxa-14-isobutyl-2[glycine]-cyclopentadecane-13-N-hydroxycarboxamide This compound was prepared using the procedures analogous to those above. ESI-MS: 458.5

Example 3004

2S,13S,14R-1,7-diaza-8,15-dioxo-9-oxa-14-isobutyl-2[N-2-phenyl-1-butylamide]-cyclopentadecane-13-N-hydroxycarboxamide This compound was prepared using the procedures analogous to those above. ESI-MS: 519.7

Example 3005

2S,13S,14R-1,7-diaza-8,15-dioxo-9-oxa-14-isobutyl-2[2-(2-aminoethyl)-1-methylpyrrole]-cyclopentadecane-13-N-hydroxycarboxamide This compound was prepared using the procedures analogous to those above. ESI-MS: 507.6

Example 3006

2S,13S,14R-1,7-diaza-8,15-dioxo-9-oxa-14-isobutyl-2[2-(2-aminoethyl)benzenesulfonamide]-cyclopentadecane-13-N-hydroxycarboxamide This compound was prepared using the procedures analogous to those above. ESI-MS: 583.7

Example 3007

2S,13S,14R-1,7-diaza-8,15-dioxo-9-oxa-14-isobutyl-2[L-glutamic acid-g-cyclohexyl ester-N-methyl amide]-cyclopentadecane-13-N-hydroxycarboxamide This compound was prepared using the procedures analogous to those above. ESI-MS: 611.7

Example 3008

2S,13S,14R-1,7-diaza-8,15-dioxo-9-oxa-14-isobutyl-2[L-phenylalanine-p-fluoro-N-methylamide]-cyclopentadecane-13-N-hydroxycarboxamide This compound was prepared using the procedures analogous to those above. ESI-MS: 579.7

Example 3009

2S,13S,14R-1,7-diaza-8,15-dioxo-9-oxa-14isobutyl-2[L--phenylalanine-p-methoxy-N-(S)-a-methylbenzylamide]-cyclopentadecane-13-N-hydroxycarboxamide This compound was prepared using the procedures analogous to those above. ESI-MS: 681.8

Example 3010

2S,13S,14R-1,7-diaza-8,15-dioxo-9-oxa-14-isobutyl-2[N-cyclohehylmethyl amide]-cyclopentadecane-13-N-hydroxycarboxamide This compound was prepared using the procedures analogous to those above. ESI-MS: 496.7

Example 3011

2S,13S,14R-1,7-diaza-8,15-dioxo-9-oxa-14-isobutyl-2[N-3-phenyl-1-propyl amide]-cyclopentadecane-13-N-hydroxycarboxamide This compound was prepared using the procedures analogous to those above. ESI-MS: 518.7

Example 3012

2S,13S,14R-1,7-diaza-8,15-dioxo-9-oxa-14-isobutyl-2[N-3,3-diphenylpropyl amide]-cyclopentadecane-13-N-hydroxycarboxamide This compound was prepared using the procedures analogous to those above. ESI-MS: 594.8

Example 3013

2S,13S,14R-1,7-diaza-8,15-dioxo-9-oxa-14-isobutyl-2[N-(2-aminoethylamino)ethyl pyrrolidine]-cyclopentadecane-13-N-hydroxycarboxamide This compound was prepared using the procedures analogous to those above. ESI-MS: 654.7

Example 3014

2S,13S,14R-1,7-diaza-8,15-dioxo-9-oxa-14-isobutyl-2[L-3(2'-naphthyl)alanine-N-methyl amide]-cyclopentadecane-13-N-hydroxycarboxamide This compound was prepared using the procedures analogous to those above ESI-MS: 611.7

Example 3015

2S,13S,14R-1,7-diaza-8,15-dioxo-9-oxa-14-isobutyl-2[ethyl-4-amino-1-pipieridine carboxylate]-cyclopentadecane-13-N-hydroxycarboxamide This compound was prepared using the procedures analogous to those above. ESI-MS: 555.7

Example 3016

2S,13S,14R-1,7-diaza-8,15-dioxo-9-oxa-14-isobutyl-2[5-methyl tryptamine]-cyclopentadecane-13-N-hydroxycarboxamide This compound was prepared using the procedures analogous to those above. ESI-MS: 557.7

Example 3017

2S,13S,14R-1,7-diaza-8,15-dioxo-9-oxa-14-isobutyl-2[N-4-trifluoromethylbenzyl amide]-cyclopentadecane-13-N-hydroxycarboxamide This compound was prepared using the procedures analogous to those above. ESI-MS: 558.6

Example 3018

2S,13S,14R-1,7-diaza-8,15-dioxo-9-oxa-14-isobutyl-2[L-glutamic acid]-cyclopentadecane-13-N-hydroxycarboxamide This compound was prepared using the procedures analogous to those above. ESI-MS: 546.6

Example 3019

2S,13S,14R-1,7-diaza-8,15-dioxo-9-oxa-14-isobutyl-2[2-(diethylamino)ethyl-4-amino benzoate]-cyclopentadecane-13-N-hydroxycarboxamide This compound was prepared using the procedures analogous to those above. ESI-MS: 733.8

Example 3020

2S,13S,14R-1,7-diaza-8,15-dioxo-9-oxa-14-isobutyl-2[6-fluorotryptamine]-cyclopentadecane-13-N-hydroxycarboxamide This compound was prepared using the procedures analogous to those above. ESI-MS: 561.7

Example 3021

2S,13S,14R-1,7-diaza-8,15-dioxo-9-oxa-14-isobutyl-2[6-methoxy tryptamine]-cyclopentadecane-13-N-hydroxycarboxamide This compound was prepared using the procedures analogous to those above. ESI-MS: 573.7

Example 3022

2S,13S,14R-1,7-diaza-8,15-dioxo-9-oxa-14-isobutyl-2[tryptamine]-cyclopentadecane-13-N-hydroxycarboxamide This compound was prepared using the procedures analogous to those above. ESI-MS: 543.7

Example 3122

3122(a). 2S,3R,6S-2-(N-Benzyloxycarboxamido)-10-benzenesulfonyl-5,10-diaza-6-(N-methylcarboxamido)-1-oxa-4-oxo-3-(3-phenylprop-1-yl)cyclotetradecane Benzenesulfonyl chloride (0.13 mL, 25 equiv.) was added to 2910(a) (23.2 mg, 0.0403 mmol), and 4-(N,N-dimethylamino)pyridine (0.5 mg, 0.1 equiv.) in pyridine (1 mL). After 30 min at room temperature, saturated ammonium chloride (2 mL) was added and the mixture was extracted with ethyl acetate. The combined extracts were washed with water, brine, dried (MgSO4) and concentrated. Preparative thin layer chromatography (methanol-methylene chloride, 10:90) yielded the desired product (11.1 mg, 41%). ESI-MS (M+H)$^+$: calcd 679.4, found 679.3.

Example 3122

2S,3R,6S-10-Benzenesulfonyl-5,10-diaza-2-(N-hydroxycarboxamido)-6-(N-methylcarboxamido)-1-oxa-4-oxo-3-(3-phenylprop-1-yl)cyclotetradecane Following a procedure analogous to the conversion of 2900(h) to 2900(i), 3122(a) (14 mg, 0.021 mmol) was converted to the desired product (12.7 mg, 100%) as a white solid. ESI-MS (M+H)$^+$: calcd 589.3, found 589.4.

Example 3172

3172(a). 2R,3S-4-Benzyloxy-3-(2-bromomethyl-2-propen-1-yl)-2-(2E-3-phenyl-2-propen-1-yl)butyryl-N$^d$-t-butoxycarbonyl-L-ornithine N-methyl amide Following a procedure analogous to the conversion of 2900(c) to 2900(d), 2900(c) (1.12 g, 2.03 mmol) was reacted with 3-bromo-2-bromomethylpropene to give the desired bromide (0.93 g, 67%) as a white solid. ESI-MS (M+H)$^+$: calcd 688.3, found 68.2.

3172(b). 2R,3S-4-Benzyloxy-3-(2-bromomethyl-2-propen-1-yl)-2-(2E-3-phenyl-2-propen-1-yl)butyryl-L-ornithine N-methyl amide hydrochloride Following a procedure analogous to the synthesis of 2900(e), 3172(a) (0.33 g, 0.48 mmol) was deprotected to give the desired product. The crude white solid was used in the next step without purification. ESI-MS (M+H)$^+$: calcd 588.3, found 588.1.

3172(c). 2S,3R,6S-10-Acetyl-2-Benzyloxymethyl-5,10-diaza-6-(N-methylcarboxamido)-12-methylene-1-oxa-4-oxo-3-(2E-3-phenyl-2-propen-1-yl)cyclotridecane Following a procedure analogous to the conversion of 2900(d) to 2900(e), crude 2950(b) was cyclized and reacted with acetic anhydride to give the desired product (0.202 g, 76% for two steps) as a white solid. ESI-MS (M+H)$^+$: calcd 548.3, found 548.4.

3172(d). 2S,3R,6S,12(R,S)-10-Acetyl-5,10-diaza-2-hydroxymethyl-6-(N-methylcarboxamido)-12-methyl-1-oxa-4-oxo-3-(3-phenylprop-1-yl)cyclotridecane Following a procedure analogous to the conversion of 2900(e) to 2900(f), 3172(c) (0.20 g, 0.365 mmol) was reduced with hydrogen to give the desired product (0.14 g, 83%) was an inseparable 1:1 mixture of two diastereomers. ESI-MS (M+H)$^+$: calcd 462.3, found 462.4.

3172(e). 2S,3R,6S,12(R,S)-10-Acetyl-5,10-diaza-2-hydroxycarbonyl-6-(N-methylcarboxamido)-12-methyl-1-oxa-4-oxo-3-(3-phenylprop-1-yl)cyclotridecane Following a procedure analogous to the conversion of 2900(f) to 2900(g), 3172(d) (0.14 g, 0.303 mmol) was oxidized to the desired acid (0.113 g, 78%). ESI-MS (M+H)$^+$: calcd 476.3, found 476.3.

3172(f). 2S,3S,6S,12(R,S)-10-Acetyl-2-(N-benzyloxycarboxamido)-5,10-diaza-6-(N-methylcarboxamido)-12-methyl-1-oxa-4-oxo-3-(3-phenylprop-1-yl)cyclotridecane Following a procedure analogous to the conversion of 2900(g) to 2900(h), 3172(e) (0.113 g, 0.237 mmol) was converted to the desired product (46 mg, 33%) as a white solid. ESI-MS (M+H)$^+$: calcd 581.3, found 581.2.

3172(g). 2S,3R,6S,12(R,S)-10-Acetyl-5,10-diaza-2-(N-hydroxycarboxamido)-6-(N-methylcarboxamido)-12-methyl-1-oxa-4-oxo-3-(3-phenylprop-1-yl)cyclotridecane Following a procedure analogous to the conversion of 2900(h) to 2900(i), 3172(f) (51 mg, 0.088 mmol) was converted to the desired product (33 mg, 76%). ESI-MS (M+H)$^+$: calcd 491.3, found 491.2.

Example 3220

2S,5S,12R-12-carboxy-3,10-dioxo-5-N-methylcarboxamido-2-phenethyl-1,4,9-triaza-cyclotridecane trifluoroacetate 3220. 2S,5S,12R-12-carboxy-3,10-dioxo-5-N-methylcarboxamido-2-phenethyl-1,4,9-triaza-cyclotridecane trifluoroacetate The compound 3220(d) (100 mg, 0.2 mmol) was dissolved in methylene chloride prior to the addition of TFA (1.7 ml). The reaction was stirred 4 hrs at RT. The solution was concentrated to give the title compound (80 mg, 75%). MS (CI) m/e 419 (M+1)$^+$.

3220(a). N-(9-Fluorenylmethoxycarbonyl)-D-(β)-aspartic-t-butyl ester N$_\alpha$-(benzyloxycarbonyl)-L-(ε)-lysine N-methylamide N-(9-Fluorenylmethoxycarbonyl)-D-Aspartic-α-t-butyl ester (5 g, 2.1 mmol) was dissolved in methylene chloride and cooled to 0° C. In succession, HOBt (1.8 g, 13.3 mmol), 4-methylmorpholine (4.4 ml, 39.9 mmol), N$_\alpha$-(benzyloxycarbonyl)-L-Lysine N-methylamide (4.8 g, 14.5 mmol), and EDC (3.0 g, 15.7 mmol) were added. The reaction was warmed to RT and stirred 15 hrs. The solution was washed with aqueous sodium bicarbonate, 10% aqueous citric acid, and brine solution. The organic layer was dried and concentrated. The resulting material was purified by chromatography to yield the desired amide (3.1 g, 47%). MS(CI) m/e 687 (M+1)$^+$.

3220(b). D-(β) -aspartic-t-butyl ester N$_\alpha$-(benzyloxycarbonyl)-L-(ε)-lysine N-methylaimide The compound of 2960(a) (3.1 g, 4.6 mmol) was dissolved in DMF prior to the addition of diethylamine (7 ml). The reaction was stirred for 20 min. The solution was concentrated and purified by chromatography to afford the desired amine (1.9 g, 86%). MS (CI) m/e 465 (M+1)$^+$.

3220(c). N-2'-(benzyl 4'-phenylbutanoate)-D-(β)-aspartic-t-butyl ester N$_\alpha$-(benzyloxycarbonyl)-L-(ε)-lysine N-methylamide The compound of 3220(b) (220 mg, 0.5 mmol) was dissolved in methylene chloride prior to the addition of Hunig's base (0.09 ml, 0.5 mmol) and (R)-benzyl 2-(trifluoromethyl)sulfonyloxy-4-phenylbutanoate (190 mg, 0.5 mmol) (Bennion, C.; Brown, R. C.; Cook, A. R.; Manners, C. N.; Payling, D. W.; Robinson, D. H. *J. Med. Chem.* 1991, 34, 439). After 15 hrs, the solution was concentrated and purified by chromatography to give the desired secondary amine (290 mg, 86%). MS (CI) m/e 717 (M+1)$^+$.

3220(d). 2S,5S,12R-12-t-butylcarboxy-3,10-dioxo-5-N-methylcarboxamido-2-phenethyl-1,4,9-triaza-cyclotridecane The compound 3220(c) (270 mg, 0.4 mmol) was placed under a hydrogen atmosphere in methanol with 10% Pd/C (60 mg). After 5 hrs, the solution was filtered and concentrated. The resulting material was dissolved in DMF and added to a solution of BOP (150 mg, 0.4 mmol) and Hunig's base (0.1 ml, 0.8 mmol) in DMF. This mixture was stirred 24 hrs. The solution was concentrated and purified by chromatography to give the desired triamide (55 mg, 30%). MS (CI) m/e 475 (M+1)$^+$.

Example 3221

2S,5S,13R-13-carboxy-3,10-dioxo-5-N-methylcarboxamido-2-phenethyl-1,4,9-triaza-cyclotetradecane trifluoroacetate 3221. 2S,5S,13R-13-carboxy-3,10-dioxo-5-N-methylcarboxamido-2-phenethyl-1,4,9-triaza-cyclotetradecane trifluoroacetate The compound 3221(d) (60 mg, 0.1 mmol) was dissolved in methylene chloride prior to the addition of TFA (1 ml). The reaction was stirred 4 hrs at RT. The solution was concentrated to give the title compound (50 mg, 74%). MS (CI) m/e 433 M+1)$^+$.

3221(a). N-(9-Fluorenylmethoxycarbonyl)-D-(β)-glutamic-t-butyl ester N$_\alpha$-(benzyloxycarbonyl)-L-(ε) lysine N-methylamide N-Fmoc-D-Glutamic-α-t-butyl ester (5 g, 11.8 mmol) was dissolved in DMF and cooled to 0° C. In succession, HOBt (1.8 g, 13.3 mmol), 4-methylmorpholine (4.0 ml, 36.6 mmol), N$_\alpha$-Cbz-L-Lysine-N-methylcarboxamido.HCl (5 g, 12.9 mmol), and BOP (6.8 g, 15.3 mmol) were added. The reaction was warmed to RT and stirred 15 hrs. The solution was diluted with ethyl acetate and washed with aqueous sodium bicarbonate, 10% aqueous citric acid, and brine solution. The organic layer was dried and concentrated. The resulting material was purified by chromatography to yield the desired amide (8 g, quant). MS(CI) m/e 701 (M+1)$^+$.

3221(b). D-(β)-glutamic-t-butyl ester N$_\alpha$-(benzyloxycarbonyl)-L-(ε)-lysine N-methylamide The compound 3221(a) (8 g, 11.8 mmol) was dissolved in DMF prior to the addition of diethylamine (36 ml). The reaction was stirred for 45 min. The solution was concentrated and purified by chromatography to afford the desired amine (2.9 g, 49%). MS (CI) m/e 479 (M+1)$^+$.

3221(c). N-2'-(benzyl 4'-phenylbutanoate)-D-(β)-glutamic-t-butyl ester N$_\alpha$-(benzyloxycarbonyl)-L-(ε)-lysine N-methylamide The compound 3221(b) (1 g, 2.1 mmol) was dissolved in methylene chloride prior to the addition of Hunig's base (0.4 ml, 2.1 mmol) and (R)-benzyl 2-(trifluoromethyl) sulfonyloxy-4-phenylbutanoate (0.6 mg, 2.1 mmol) (Bennion, C.; Brown, R. C.; Cook, A. R.; Manners, C. N.; Payling, D. W.; Robinson, D. H. *J. Med. Chem.* 1991, 34, 439). After 15 hrs, the solution was concentrated and purified by chromatography to give the desired secondary amine (2.3 g, 78%). MS (CI) m/e 731 (M+1)$^+$.

3221(d). 2S,5S,13R-13-t-butylcarboxy-3,10-dioxo-5-N-methylcarboxamido-2-phenethyl-1,4,9-triaza-cyclotetradecane The compound 3221(c) (2.1 g, 2.9 mmol) was placed under a hydrogen atmosphere in methanol with 10% Pd/C (430 mg). After 4.5 hrs, the solution was filtered and concentrated. A portion of the resulting material (400 mg, 0.8 mmol) was dissolved in DMF and added to a solution of BOP (454 mg, 1 mmol) and Hunig's base (0.3 ml, 1.6 mmol) in DMF. This mixture was stirred 24 hrs. The solution was concentrated and purified by chromatography to give the desired triamide (60 mg, 16%). MS (CI) m/e 489 (M+1)$^+$.

TABLE 1

For the cyclophane:

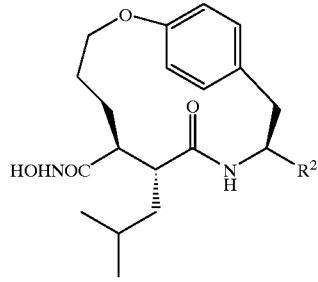

| Ex | R$^2$ (CI-MS) | ms |
|---|---|---|
| 1 | CO$_2$Me | 406 |
| 2 | CONH-cyclopentyl | |
| 3 | CO$_2$Et | |
| 4 | CONH$_2$ | |
| 5 | CO$_2$iPr | |
| 6 | CONHiPr | |
| 7 | CO$_2$(CH$_2$)$_2$OMe | |
| 8 | CONH-tert-butyl | |
| 9 | CO$_2$(CH$_2$)$_2$Ph | |
| 10 | CONMe$_2$ | |
| 11 | CO$_2$-tBu | |
| 12 | CONEt$_2$ | |
| 13 | CO$_2$CH$_2$CONHMe | |
| 14 | CONH-3-indazolyl | |
| 15 | CH$_2$OH | 379 |
| 16 | CONH-adamantyl | |
| 17 | CH$_2$OCH$_2$CH$_3$ | |
| 18 | CONHCH$_2$(p-SO$_2$NH$_2$-Ph) | |
| 19 | CH$_2$OCH$_2$CH$_2$CO$_2$CH$_3$ | |
| 20 | CONH(CH$_2$)$_3$-1-imidazolyl | 500 |
| 21 | CHOBn | |
| 22 | CONHSO$_2$NH$_2$ | |
| 23 | CONH(CH$_2$)$_2$-2-pyridyl | 497 |
| 24 | CONHSO$_2$CH$_3$ | |
| 25 | CO(N-morpholinyl) | |
| 26 | CONHSO$_2$Ph | |
| 27 | CO(N-Me-N-piperazinyl) | 475 |
| 28 | CONHSO$_2$Bn | |
| 29 | CONH(CH$_2$)$_2$-(N-Me-N-piperazinyl) | |
| 30 | CONHSO$_2$-N-Me-imidazolyl | |
| 31 | CONH-cyclopropyl | |
| 32 | CONHSO$_2$-p-NH$_2$Ph | |
| 33 | CONH-cyclobutyl | |
| 34 | CONHSO$_2$-p-MeOPh | |
| 35 | CONHSO$_2$-p-F-Ph | |
| 36 | CONH-S-CH[CH$_2$CH(CH$_3$)$_2$]CONHMe | |
| 37 | CONH(CH$_2$)$_2$NHSO$_2$Me | |
| 38 | CONH(CH$_2$)$_4$NHSO$_2$Me | |
| 39 | CONH-cyclohexyl | |
| 40 | CONH(CH$_2$)$_6$NHSO$_2$Me | |
| 41 | CONH-2-imidazolyl | 457 |
| 42 | CONH-R-CH[CH$_2$CH(CH$_3$)$_2$]CONHMe | |
| 43 | CH$_2$SO$_2$NHCH$_3$ | |
| 44 | CONH-S-CH[(CH$_2$)$_4$NH$_2$]CONHMe | |
| 45 | CH$_2$SO$_2$NHPh | |
| 46 | CONH-S-CH[(CH$_2$)$_3$NH$_2$]CONHMe | |
| 47 | CH$_2$SO$_2$NH-[4-NH$_2$Ph] | |
| 48 | CONH-S-CH[(CH$_2$)$_2$NH$_2$]CONHMe | |
| 49 | 2-imidazolyl | |
| 50 | CONHMe | 406 |
| 51 | 2-oxazoly | |
| 52 | CONHCH$_2$CONMe$_2$ | |
| 53 | 2-thiazolyl | |
| 54 | CONHCH$_2$CONHEt | |
| 55 | 2-benzimidazolyl | 465 |
| 56 | CONHCH$_2$CONEt$_2$ | |
| 57 | CONH-R-CH(CH$_3$)Ph | |
| 58 | CONHCH$_2$CONH-cyclopropyl | |

TABLE 1-continued

For the cyclophane:

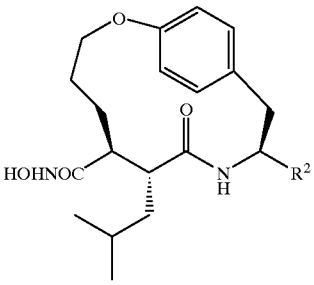

| Ex | R$^2$ (CI-MS) | ms |
|---|---|---|
| 59 | CONH-S-CH(CH$_3$)Ph | |
| 60 | CONHCH$_2$CONH-cyclobutyl | |
| 61 | CONHCH$_2$CONHMe | 463 |
| 62 | CONHCH$_2$CONH-cyclopentyl | |
| 63 | CONH-S-CH(CH$_3$)CONHMe | 477 |
| 64 | CONHCH$_2$CONH-cyclohexyl | |
| 65 | CONH-R-CH(CH$_3$)CONHMe | 477 |
| 66 | CONHCH$_2$CONH-tert-butyl | |
| 67 | CONH-S-CH(2-propyl)CONHMe | 505 |
| 68 | CONH-S-CH(CH$_2$Ph)CONHMe | |
| 69 | CONH-S-CH(CH$_2$SH)CONHMe | |
| 70 | CONH-S-CH(CH$_2$-p-MeOPh)CONHMe | 583 |
| 71 | CONH-S-CH(CH$_2$OH)CONHMe | 493 |
| 72 | CONHCH$_2$CH$_2$CONHMe | 499 |
| 73 | CONH-R-CH(CH$_2$OH)CONHMe | 493 |
| 74 | CONHCH$_2$CH$_2$CH$_2$CONHMe | |
| 75 | CONH-S-CH(CH$_2$O-t-Bu)CONHMe | 549 |
| 76 | CONH-S-CH(CH$_2$OH)CONHMe | |
| 77 | CONH-R-CH(CH$_2$O-t-Bu)CONHMe | 549 |
| 78 | CONH-S-(CH(CH$_2$)$_3$CH$_3$)CONHMe | |
| 79 | CONH-CH(Ph)$_2$ | |
| 80 | CONH(CH$_2$)$_2$CO$_2$Me | |
| 81 | CO-L-proline-NHMe | |
| 82 | CONH(CH$_2$)$_2$CO$_2$H | |
| 83 | CONHCH$_2$CO(N-piperazinyl) | |
| 84 | CONH-S-CH[(CH$_2$)$_3$NHBOC]CO$_2$Me | |
| 85 | CONHCH$_2$Co(N-methyl-N-piperazinyl) | |
| 86 | CONH-S-CH[(CH$_2$)$_3$NHBOC]CONHMe | |
| 87 | CONHCH$_2$Co(N-acetyl-N-piperazinyl) | |
| 88 | CONH-S-CH-[(CH$_2$)$_3$NH$_2$]CO$_2$Me | |
| 89 | CONHCH$_2$CO-N-morpholino | |
| 90 | CONH-S-CH[(CH$_2$)$_4$NH$_2$]CONH$_2$ | 520 |
| 91 | CONHCH$_2$CO-[N-(4-hydroxypiperidinyl)] | |
| 92 | CONH(CH$_2$)$_2$Ph | |
| 93 | CO$_2$H | |
| 94 | CONH(CH$_2$)$_2$-(3,4,-dimethoxyphenyl) | |
| 95 | CONHBn | 482 |
| 96 | CONH(CH$_2$)$_2$-(N-morpholinyl) | |
| 97 | CONH-2-Pyridyl | |
| 98 | CONH(CH$_2$)$_3$-(N-morpholino) | |
| 99 | CONH-Ph | |
| 100 | CONHCH$_2$CONH-(2-pyridyl) | |
| 101 | CONH-3-Pyridyl | |
| 102 | CONHCH$_2$CONH-(3-pyridyl) | |
| 103 | CONH-4-Pyridyl | |
| 104 | CONHCH$_2$CONH-(4-pyridyl) | |
| 105 | CONH-CH$_2$CH(Ph)$_2$ | 600.6 |
| 106 | CONH(CH$_2$)$_2$(P-SO$_2$NH$_2$-Ph) | 575 |
| 107 | CONHCH$_2$-2-benzimidazole | 522 |
| 108 | CONH-2-benzimidazole | 508 |

TABLE 2

For the cyclophane:

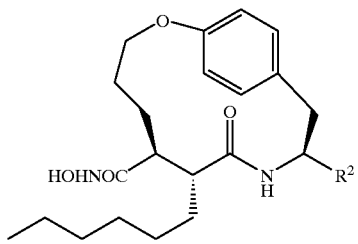

| Ex | R² (CI-MS) | ms |
|---|---|---|
| 120 | CO₂Me | 435.3 |
| 121 | CONH-cyclopentyl | |
| 122 | CO₂Et | |
| 123 | CONH₂ | |
| 124 | CO₂iPr | |
| 125 | CONHiPr | |
| 126 | CO₂(CH₂)₂OMe | 479.4 |
| 127 | CONH-tert-butyl | |
| 128 | CO₂(CH₂)₂Ph | 525.4 |
| 129 | CONMe₂ | 448.5 |
| 130 | CO₂-tBu | |
| 131 | CONEt₂ | |
| 132 | CO₂CH₂CONHMe | 429.4 |
| 133 | CONH-3-indazolyl | |
| 134 | CH₂OH | |
| 135 | CONH-adamantyl | |
| 136 | CH₂OCH₂CH₃ | |
| 137 | CONHCH₂(p-SO₂NH₂-Ph) | |
| 138 | CH₂OCH₂CH₂CO₂CH₃ | |
| 139 | CONH(CH₂)₃-1-imidazolyl | 528.5 |
| 140 | CHOBn | |
| 141 | CONHSO₂NH₂ | |
| 142 | CONH(CH₂)₂-2-pyridyl | 525.5 |
| 143 | CONHSO₂CH₃ | |
| 144 | CO(N-morpholinyl) | |
| 145 | CONHSO₂Ph | |
| 146 | CO(N-Me-N-piperazinyl) | 503.6 |
| 147 | CONHSO₂Bn | |
| 148 | CONH(CH₂)₂-(N-Me-N-piperazinyl) | |
| 149 | CONHSO₂-N-Me-imidazolyl | |
| 151 | CONHSO₂-p-NH₂Ph | |
| 150 | CONH-cyclopropyl | |
| 152 | CONH-cyclobutyl | |
| 153 | CONHSO₂-P-MeOPh | |
| 154 | CONHSO₂-p-F-Ph | |
| 155 | CONH-S-CH[CH₂CH(CH₃)₂]CONHMe | |
| 156 | CONH(CH₂)₂NHSO₂Me | 541.5 |
| 157 | CONH(CH₂)₄NHSO₂Me | 569.5 |
| 158 | CONH-cyclohexyl | 502.5 |
| 159 | CONH(CH₂)₆NHSO₂Me | 597.6 |
| 160 | CONH-2-imidozolyl | |
| 161 | CONH-R-CH[CH₂CH(CH₃)₂]CONHMe | |
| 162 | CH₂SO₂NHCH₃ | |
| 163 | CONH-S-CH[(CH₂)₄NH₂]CONHMe | |
| 164 | CH₂SO₂NHPh | |
| 165 | CONH-S-CH[(CH₂)₃NH₂]CONHMe | 548.5 |
| 166 | CH₂SO₂NH-[4-NH₂Ph] | |
| 167 | CONH-S-CH[(CH₂)₂NH₂]CONHMe | |
| 168 | 2-imidazolyl | |
| 169 | CONHMe | 434.4 |
| 170 | 2-oxazoly | |
| 171 | CONHCH₂CONMe₂ | |
| 172 | 2-thiazolyl | |
| 173 | CONHCH₂CONHEt | |
| 174 | 2-benzimidazoiyl | |
| 175 | CONHCH₂CONEt₂ | |
| 176 | CONH-R-CH(CH₃)Ph | |
| 177 | CONHCH₂CONH-cyclopropyl | |
| 178 | CONH-S-CH(CH₃)Ph | |
| 179 | CONHCH₂CONH-cyclobutyl | |
| 180 | CONHCH₂CONHMe | 491.5 |
| 181 | CONHCH₂CONH-cyclopentyl | |
| 182 | CONH-S-CH(CH₃)CONHMe | 505.6 |

TABLE 2-continued

For the cyclophane:

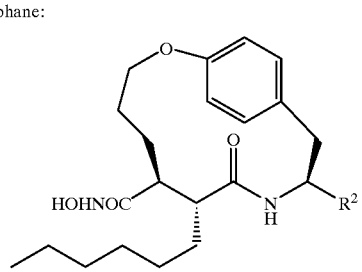

| Ex | R² (CI-MS) | ms |
|---|---|---|
| 183 | CONHCH₂CONH-cyclohexyl | |
| 184 | CONH-R-CH(CH₃)CONHMe | 505.5 |
| 185 | CONHCH₂CONH-tert-butyl | |
| 186 | CONH-S-CH(2-propyl)CONHMe | |
| 187 | CONH-S-CH(CH₂Ph)CONHMe | |
| 188 | CONH-S-CH(CH₂SH)CONHMe | |
| 189 | CONH-S-CH(CH₂-p-MeOPh)CONHMe | |
| 190 | CONH-S-CH(CH₂OH)CONHMe | |
| 191 | CONHCH₂CH₂CONHMe | |
| 192 | CONH-R-CH(CH₂OH)CONHMe | |
| 193 | CONHCH₂CH₂CH₂CONHMe | |
| 194 | CONH-S-CH(CH₂O-t-Bu)CONHMe | 577.6 |
| 195 | CONH-S-CH(CH₂CH₂OH)CONHMe | |
| 196 | CONH-R-CH(CH₂O-t-Bu)CONHMe | |
| 197 | CONH-S-(CH(CH₂)₃CH₃)CONHMe | |
| 198 | CONH-CH(Ph)₂ | |
| 199 | CONH(CH₂)₂CO₂Me | 506.4 |
| 200 | CO-L-proline-NHMe | |
| 201 | CONH(CH₂)₂CO₂H | 492.3 |
| 202 | CONHCH₂CO(N-piperazinyl) | |
| 203 | CONH-S-CH[(CH₂)₃NHBOC]CO₂Me | 649.5 |
| 204 | CONHCH₂CO(N-methyl-N-piperazinyl) | |
| 205 | CONH-S-CH[(CH₂)₃NHBOC]CONHMe | 648.6 |
| 206 | CONHCH₂CO(N-acetyl-N-piperazinyl) | |
| 207 | CONH-S-CH-[(CH₂)₃NH₂]CO₂Me | 549.5 |
| 208 | CONHCH₂CO-N-morpholinol | |
| 209 | CONH-S-CH[(CH₂)₄NH₂]CONH₂ | 548.5 |
| 210 | CONHCH₂CO-[N-(4-hydroxypiperidinyl)] | |
| 211 | CONH(CH₂)₂Ph | 524.5 |
| 212 | CO₂H | 421.4 |
| 213 | CONH(CH₂)₂-(3,4,-dimethoxyphenyl) | 584.6 |
| 214 | CONHBn | 510.5 |
| 215 | CONH(CH₂)₂-(N-morpholino) | 533.5 |
| 216 | CONH-2-pyridyl | |
| 217 | CONH(CH₂)₃-(N-morpholino) | 547.5 |
| 218 | CONH-Ph | |
| 219 | CONHCH₂CONH-(2-pyridyl) | |
| 220 | CONH-3-pyridyl | |
| 221 | CONHCH₂CONH-(3-pyridyl) | |
| 222 | CONH-4-pyridyl | |
| 223 | CONHCH₂CONH-(4-pyridyl) | |
| 224 | CONH-CH₂CH(Ph)₂ | 600.6 |
| 225 | CONH(CH₂)₂(P-SO₂NH₂-Ph) | 603.6 |

TABLE 3

For the cyclophane:

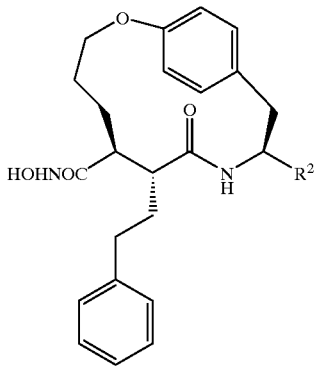

| Ex | R² (CI-MS) | ms |
|---|---|---|
| 240 | CO₂Me | |
| 241 | CONH-cyclopentyl | |
| 242 | CO₂Et | |
| 243 | CONH₂ | |
| 244 | CO₂iPr | |
| 245 | CONHiPr | |
| 246 | CO₂(CH₂)₂OMe | |
| 247 | CONH-tert-butyl | |
| 248 | CO₂(CH₂)₂Ph | |
| 249 | CONMe₂ | |
| 250 | CO₂-tBu | |
| 251 | CONEt₂ | |
| 252 | CO₂CH₂CONHMe | |
| 253 | CONH-3-indazolyl | |
| 254 | CH₂OH | |
| 255 | CONH-adamantyl | |
| 256 | CH₂OCH₂CH₃ | |
| 257 | CONHCH₂(p-SO₂NH₂-Ph) | |
| 258 | CH₂OCH₂CH₂CO₂CH₃ | |
| 259 | CONH(CH₂)₃-1-imidazolyl | |
| 260 | CHOBn | |
| 261 | CONHSO₂NH₂ | |
| 262 | CONH(CH₂)₂-2-pyridyl | |
| 263 | CONHSO₂CH₃ | |
| 264 | CO(N-morpholinyl) | |
| 265 | CONHSO₂Ph | |
| 266 | CO(N-Me-N-piperazinyl) | |
| 267 | CONHSO₂Bn | |
| 268 | CONH(CH₂)₂-(N-Me-N-piperazinyl) | |
| 269 | CONHSO₂-N-Me-imidazolyl | |
| 270 | CONH-cyclopropyl | |
| 271 | CONHSO₂-p-NH₂Ph | |
| 272 | CONH-cyclobutyl | |
| 273 | CONHSO₂-p-MeOPh | |
| 274 | CONHSO₂-p-F-Ph | |
| 275 | CONH-S-CH[CH₂CH(CH₃)₂]CONHMe | |
| 276 | CONH(CH₂)₂NHSO₂Me | |
| 277 | CONH(CH₂)₄NHSO₂Me | |
| 278 | CONH-cyclohexyl | |
| 279 | CONH(CH₂)₆NHSO₂Me | |
| 280 | CONH-2-imidozolyl | |
| 281 | CONH-R-CH[CH₂CH(CH₃)₂]CONHMe | |
| 282 | CH₂SO₂NHCH₃ | |
| 283 | CONH-S-CH[(CH₂)₄NH₂]CONHMe | |
| 284 | CH₂SO₂NHPh | |
| 285 | CONH-S-CH[(CH₂)₃NH₂]CONHMe | |
| 286 | CH₂SO₂NH-[4-NH₂Ph] | |
| 287 | CONH-S-CH[(CH₂)₂NH₂]CONHMe | |
| 288 | 2-imidazolyl | |
| 289 | CONHMe | |
| 290 | 2-oxazoly | |
| 291 | CONHCH₂CONMe₂ | |
| 292 | 2-thiazolyl | |
| 293 | CONHCH₂CONHEt | |
| 294 | 2-benzimidazolyl | |
| 295 | CONHCH₂CONEt₂ | |
| 296 | CONH-R-CH(CH₃)Ph | |

TABLE 3-continued

For the cyclophane:

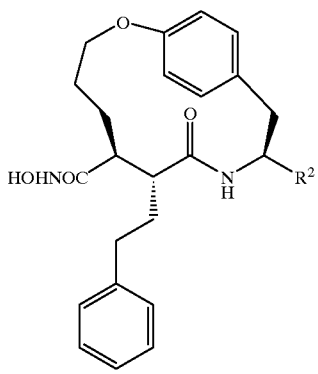

| Ex | R² (CI-MS) | ms |
|---|---|---|
| 297 | CONHCH₂CONH-cyclopropyl | |
| 298 | CONH-S-CH(CH₃)Ph | |
| 299 | CONHCH₂CONH-cyclobutyl | |
| 300 | CONHCH₂CONHMe | |
| 301 | CONHCH₂CONH-cyclopentyl | |
| 302 | CONH-S-CH(CH₃)CONHMe | |
| 303 | CONHCH₂CONH-cyclohexyl | |
| 304 | CONH-R-CH(CH₃)CONHMe | |
| 305 | CONHCH₂CONH-tert-butyl | |
| 306 | CONH-S-CH(2-propyl)CONHMe | |
| 307 | CONH-S-CH(CH₂Ph)CONHMe | |
| 308 | CONH-S-CH(CH₂SH)CONHMe | |
| 309 | CONH-S-CH(CH₂-p-MeOPh)CONHMe | |
| 310 | CONH-S-CH(CH₂OH)CONHMe | |
| 311 | CONHCH₂CH₂CONHMe | |
| 312 | CONH-R-CH(CH₂OH)CONHMe | |
| 313 | CONHCH₂CH₂CH₂CONHMe | |
| 314 | CONH-S-CH(CH₂O-t-Bu)CONHMe | |
| 315 | CONH-S-CH(CH₂CH₂OH)CONHMe | |
| 316 | CONH-R-CH(CH₂O-t-Bu)CONHMe | |
| 317 | CONH-S-(CH(CH₂)₃CH₃)CONHMe | |
| 318 | CONH-CH(Ph)₂ | |
| 319 | CONH(CH₂)₂CO₂Me | |
| 320 | CO-L-proline-NHMe | |
| 321 | CONH(CH₂)₂CO₂H | |
| 322 | CONHCH₂CO(N-piperazinyl) | |
| 323 | CONH-S-CH[(CH₂)₃NHBOC]CO₂Me | |
| 324 | CONHCH₂CO(N-methyl-N-piperazinyl) | |
| 325 | CONH-S-CH[(CH₂)₃NHBOC]CONHMe | |
| 326 | CONHCH₂CO(N-acetyl-N-piperazinyl) | |
| 327 | CONH-S-CH-[(CH₂)₃NH₂]CO₂Me | |
| 328 | CONHCH₂CO-N-morpholino | |
| 329 | CONH-S-CH[(CH₂)₄NH₂]CONH₂ | |
| 330 | CONHCH₂CO-[N-(4-hydroxypiperidinyl)] | |
| 331 | CONH(CH₂)₂Ph | |
| 332 | CO₂H | |
| 333 | CONH(CH₂)₂-(3,4,-dimethoxyphenyl) | |
| 334 | CONHBn | |
| 335 | CONH(CH₂)₂-(N-morpholino) | |
| 336 | CONH-2-pyridyl | |
| 337 | CONH(CH₂)₃-(N-morpholino) | |
| 338 | CONH-Ph | |
| 339 | CONHCH₂CONH-(2-pyridyl) | |
| 340 | CONH-3-pyridyl | |
| 341 | CONHCH₂CONH-(3-pyridyl) | |
| 342 | CONH-4-pyridyl | |
| 343 | CONHCH₂CONH-(4-pyridyl) | |
| 344 | CONH-CH₂CH(Ph)₂ | 600.6 |
| 345 | CONH(CH₂)₂(P-SO₂NH₂-Ph) | 603.6 |

TABLE 4

For the cyclophane:

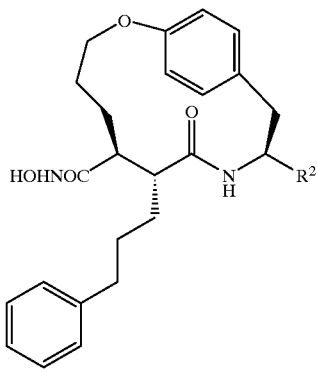

| Ex | R² (CI-MS) | ms |
|---|---|---|
| 350 | CO₂Me | |
| 351 | CONH-cyclopentyl | |
| 352 | CO₂Et | |
| 353 | CONH₂ | |
| 354 | CO₂iPr | |
| 355 | CONHiPr | |
| 356 | CO₂(CH₂)₂OMe | |
| 357 | CONH-tert-butyl | |
| 358 | CO₂(CH₂)₂Ph | |
| 359 | CONMe₂ | |
| 360 | CO₂-tBu | |
| 361 | CONEt₂ | |
| 362 | CO₂CH₂CONHMe | |
| 363 | CONH-3-indazolyl | |
| 364 | CH₂OH | |
| 365 | CONH-adamantyl | |
| 366 | CH₂OCH₂CH₃ | |
| 367 | CONHCH₂(p-SO₂NH₂-Ph) | |
| 368 | CH₂OCH₂CH₂CO₂CH₃ | |
| 369 | CONH(CH₂)₃-1-imidazolyl | |
| 370 | CHOBn | |
| 371 | CONHSO₂NH₂ | |
| 372 | CONH(CH₂)₂-2-pyridyl | |
| 373 | CONHSO₂CH₃ | |
| 374 | CO(N-morpholinyl) | |
| 375 | CONHSO₂Ph | |
| 376 | CO(N-Me-N-piperazinyl) | |
| 377 | CONHSO₂Bn | |
| 378 | CONH(CH₂)₂-(N-Me-N-piperazinyl) | |
| 379 | CONHSO₂-N-Me-imidazolyl | |
| 380 | CONH-cyclopropyl | |
| 381 | CONHSO₂-p-NH₂Ph | |
| 382 | CONH-cyclobutyl | |
| 383 | CONHSO₂-p-MeOPh | |
| 384 | CONHSO₂-p-F-Ph | |
| 385 | CONH-S-CH[CH₂CH(CH₃)₂]CONHMe | |
| 386 | CONH(CH₂)₂NHSO₂Me | |
| 387 | CONH(CH₂)₄NHSO₂Me | |
| 388 | CONH-cyclohexyl | |
| 389 | CONH(CH₂)₆NHSO₂Me | |
| 390 | CONH-2-imidozolyl | |
| 391 | CONH-R-CH[CH₂CH(CH₃)₂]CONHMe | |
| 392 | CH₂SO₂NHCH₃ | |
| 393 | CONH-S-CH[(CH₂)₄NH₂]CONHMe | |
| 394 | CH₂SO₂NHPh | |
| 395 | CONH-S-CH[(CH₂)₃NH₂]CONHMe | |
| 396 | CH₂SO₂NH-[4-NH₂Ph] | |
| 397 | CONH-S-CH[(CH₂)₂NH₂]CONHMe | |
| 398 | 2-imidazolyl | |
| 399 | CONHMe | |
| 400 | 2-oxazoly | |
| 401 | CONHCH₂CONMe₂ | |
| 402 | 2-thiazolyl | |
| 403 | CONHCH₂CONHEt | |
| 404 | 2-benzimidazolyl | |
| 405 | CONHCH₂CONEt₂ | |
| 406 | CONH-R-CH(CH₃)Ph | |
| 407 | CONHCH₂CONH-cyclopropyl | |
| 408 | CONH-S-CH(CH₃)Ph | |
| 409 | CONHCH₂CONH-cyclobutyl | |
| 410 | CONHCH₂CONHMe | |
| 411 | CONHCH₂CONH-cyclopentyl | |
| 412 | CONH-S-CH(CH₃)CONHMe | |
| 413 | CONHCH₂CONH-cyclohexyl | |
| 414 | CONH-R-CH(CH₃)CONHMe | |
| 415 | CONHCH₂CONH-tert-butyl | |
| 416 | CONH-S-CH(2-propyl)CONHMe | |
| 417 | CONH-S-CH(CH₂Ph)CONHMe | |
| 418 | CONH-S-CH(CH₂SH)CONHMe | |
| 419 | CONH-S-CH(CH₂-p-MeOPh)CONHMe | |
| 420 | CONH-S-CH(CH₂OH)CONHMe | |
| 421 | CONHCH₂CH₃CONHMe | |
| 422 | CONH-R-CH(CH₂OH)CONHMe | |
| 423 | CONHCH₂CH₂CH₂CONHMe | |
| 424 | CONH-S-CH(CH₂O-t-Bu)CONHMe | |
| 425 | CONH-S-CH(CH₂CH₂OH)CONHMe | |
| 426 | CONH-R-CH(CH₂O-t-Bu)CONHMe | |
| 427 | CONH-S-(CH(CH₂)₃CH₃)CONHMe | |
| 428 | CONH-CH(Ph)₂ | |
| 429 | CONH(CH₂)₂CO₂Me | |
| 430 | CO-L-proline-NHMe | |
| 431 | CONH(CH₂)₂CO₂H | |
| 432 | CONHCH₂CO(N-piperazinyl) | |
| 433 | CONH-S-CH[(CH₂)₃NHBOC]CO₂Me | |
| 434 | CONHCH₂CO(N-methyl-N-piperazinyl) | |
| 435 | CONH-S-CH[(CH₂)₃NHBOC]CONHMe | |
| 436 | CONHCH₂CO(N-acetyl-N-piperazinyl) | |
| 437 | CONH-S-CH-[(CH₂)₃NH₂]CO₂Me | |
| 438 | CONHCH₂CO-N-morpholino | |
| 439 | CONH-S-CH[(CH₂)₄NH₂]CONH₂ | |
| 440 | CONHCH₂CO-[N-(4-hydroxypiperidinyl)] | |
| 441 | CONH(CH₂)₂Ph | |
| 442 | CO₂H | |
| 443 | CONH(CH₂)₂-(3,4,-dimethoxyphenyl) | |
| 444 | CONHBn | |
| 445 | CONH(CH₂)₂-(N-morpholino) | |
| 446 | CONH-2-pyridyl | |
| 447 | CONH(CH₂)₃-(N-morpholino) | |
| 448 | CONH-Ph | |
| 449 | CONHCH₂CONH-(2-pyridyl) | |
| 450 | CONH-3-pyridyl | |
| 451 | CONHCH₂CONH-(3-pyridyl) | |
| 452 | CONH-4-pyridyl | |
| 453 | CONHCH₂CONH-(4-pyridyl) | |
| 454 | CONH-CH₂CH(Ph)₂ | |
| 455 | CONH(CH₂)₂(P-SO₂NH₂-Ph) | |

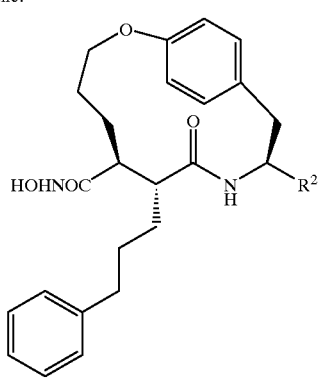

TABLE 5

For the cyclophane:

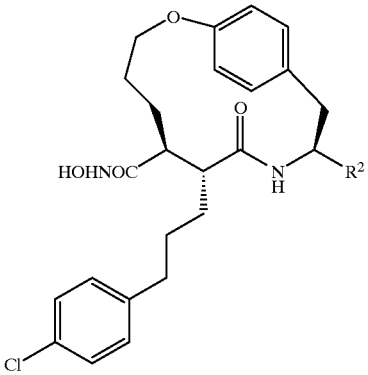

| Ex | R² (CI-MS) | ms |
|---|---|---|
| 470 | CO₂Me | |
| 471 | CONH-cyclopentyl | |
| 472 | CO₂Et | |
| 473 | CONH₂ | |
| 474 | CO₂iPr | |
| 475 | CONHiPr | |
| 476 | CO₂(CH₂)₂OMe | |
| 477 | CONH-tert-butyl | |
| 478 | CO₂(CH₂)₂Ph | |
| 479 | CONMe₂ | |
| 480 | CO₂-tBu | |
| 481 | CONEt₂ | |
| 482 | CO₂CH₂CONHMe | |
| 483 | CONH-3-indazolyl | |
| 484 | CH₂OH | |
| 485 | CONH-adamantyl | |
| 486 | CH₂OCH₂CH₃ | |
| 487 | CONHCH₂(p-SO₂NH₂-Ph) | |
| 488 | CH₂OCH₂CH₂CO₂CH₃ | |
| 489 | CONH(CH₂)₃-1-imidazolyl | |
| 490 | CHOBn | |
| 491 | CONHSO₂NH₂ | |
| 492 | CONH(CH₂)₂-2-pyridyl | |
| 493 | CONHSO₂CH₃ | |
| 494 | CO(N-morpholinyl) | |
| 495 | CONHSO₂Ph | |
| 496 | CO(N-Me-N-piperazinyl) | |
| 497 | CONHSO₂Bn | |
| 498 | CONH(CH₂)₂-(N-Me-N-piperazinyl) | |
| 499 | CONHSO₂-N-Me-imidazolyl | |
| 500 | CONH-cyclopropyl | |
| 501 | CONHSO₂-p-NH₂Ph | |
| 502 | CONH-cyclobutyl | |
| 503 | CONHSO₂-p-MeOPh | |
| 504 | CONHSO₂-p-F-Ph | |
| 505 | CONH-S-CH[CH₂CH(CH₃)₂]CONHMe | |
| 506 | CONH(CH₂)₂NHSO₂Me | |
| 507 | CONH(CH₂)₄NHSO₂Me | |
| 508 | CONH-cyclohexyl | |
| 509 | CONH(CH₂)₆NHSO₂Me | |
| 510 | CONH-2-imidozolyl | |
| 511 | CONH-R-CH[CH₂CH(CH₃)₂]CONHMe | |
| 512 | CH₂SO₂NHCH₃ | |
| 513 | CONH-S-CH[(CH₂)₄NH₂]CONHMe | |
| 514 | CH₂SO₂NHPh | |
| 515 | CONH-S-CH[(CH₂)₃NH₂]CONHMe | |
| 516 | CH₂SO₂NH-[4-NH₂Ph] | |
| 517 | CONH-S-CH[(CH₂)₂NH₂]CONHMe | |
| 518 | 2-imidazolyl | |
| 519 | CONHMe | |
| 520 | 2-oxazoly | |
| 521 | CONHCH₂CONMe₂ | |
| 522 | 2-thiazolyl | |
| 523 | CONHCH₂CONHEt | |
| 524 | 2-benzimidazolyl | |
| 525 | CONHCH₂CONEt₂ | |

TABLE 5-continued

For the cyclophane:

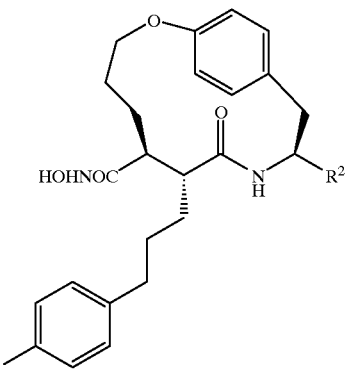

| Ex | R² (CI-MS) | ms |
|---|---|---|
| 526 | CONH-R-CH(CH₃)Ph | |
| 527 | CONHCH₂CONH-cyclopropyl | |
| 528 | CONH-S-CH(CH₃)Ph | |
| 529 | CONHCH₂CONH-cyclobutyl | |
| 530 | CONHCH₂CONHMe | |
| 531 | CONHCH₂CONH-cyclopentyl | |
| 532 | CONH-S-CH(CH₃)CONHMe | |
| 533 | CONHCH₂CONH-cyclohexyl | |
| 534 | CONH-R-CH(CH₃)CONHMe | |
| 535 | CONHCH₂CONH-tert-butyl | |
| 536 | CONH-S-CH(2-propyl)CONHMe | |
| 537 | CONH-S-CH(CH₂Ph)CONHMe | |
| 538 | CONH-S-CH(CH₂SH)CONHMe | |
| 539 | CONH-S-CH(CH₂-p-MeOPh)CONHMe | |
| 540 | CONH-S-CH (CH₂OH)CONHMe | |
| 541 | CONHCH₂CH₂CONHMe | |
| 542 | CONH-R-CH(CH₂OH)CONHMe | |
| 543 | CONHCH₂CH₂CH₂CONHMe | |
| 544 | CONH-S-CH(CH₂O-t-Bu)CONHMe | |
| 545 | CONH-S-CH(CH₂CH₂OH)CONHMe | |
| 546 | CONH-R-CH(CH₂O-t-Bu)CONHMe | |
| 547 | CONH-S-(CH(CH₂)₃CH₃)CONHMe | |
| 548 | CONH-CH(Ph)₂ | |
| 549 | CONH(CH₂)₂CO₂Me | |
| 550 | CO-L-proline-NHMe | |
| 551 | CONH(CH₂)₂CO₂H | |
| 552 | CONHCH₂CO(N-piperazinyl) | |
| 553 | CONH-S-CH[(CH₂)₃NHBOC]CO₂Me | |
| 554 | CONHCH₂CO(N-methyl-N-piperazinyl) | |
| 555 | CONH-S-CH[(CH₂)₃NHBOC]CONHMe | |
| 556 | CONHCH₂CO(N-acetyl-N-piperazinyl) | |
| 557 | CONH-S-CH-[(CH₂)₃NH₂]CO₂Me | |
| 558 | CONHCH₂CO-N-morpholinol | |
| 559 | CONH-S-CH[(CH₂)₄NH₂]CONH₂ | |
| 560 | CONHCH₂CO-[N-(4-hydroxypiperidinyl)] | |
| 561 | CONH(CH₂)₂Ph | |
| 562 | CO₂H | |
| 563 | CONH(CH₂)₂-(3,4,-dimethoxyphenyl) | |
| 564 | CONHBn | |
| 565 | CONH(CH₂)₂-(N-morpholino) | |
| 566 | CONH-2-pryidyl | |
| 567 | CONH(CH₂)₃-(N-morpholino) | |
| 568 | CONH-Ph | |
| 569 | CONHCH₂CONH-(2-pyridyl) | |
| 570 | CONH-3-pyridyl | |
| 571 | CONHCH₂CONH-(3-pyridyl) | |
| 572 | CONH-4-pyridyl | |
| 573 | CONHCH₂CONH-(4-pyridyl) | |
| 574 | CONH-CH₂CH(Ph)₂ | |
| 575 | CONH(CH₂)₂(P-SO₂NH₂-Ph) | |

TABLE 6

For the cyclophane:

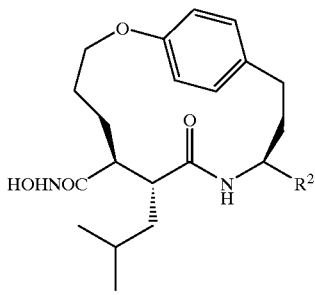

| Ex | R² (CI-MS) | ms |
|---|---|---|
| 600 | CO₂Me | |
| 601 | CONH-cyclopentyl | |
| 602 | CO₂Et | |
| 603 | CONH₂ | |
| 604 | CO₂iPr | |
| 605 | CONHiPr | |
| 606 | CO₂(CH₂)₂OMe | |
| 607 | CONH-tert-butyl | |
| 608 | CO₂(CH₂)₂Ph | |
| 609 | CONMe₂ | |
| 610 | CO₂-tBu | |
| 611 | CONEt₂ | |
| 612 | CO₂CH₂CONHMe | |
| 613 | CONH-3-indazolyl | |
| 614 | CH₂OH | |
| 615 | CONH-adamantyl | |
| 616 | CH₂OCH₂CH₃ | |
| 617 | CONHCH₂(p-SO₂NH₂-Ph) | |
| 618 | CH₂OCH₂CH₂CO₂CH₃ | |
| 619 | CONH(CH₂)₃-1-imidazolyl | |
| 620 | CHOBn | |
| 621 | CONHSO₂NH₂ | |
| 622 | CONH(CH₂)₂-2-pyridyl | |
| 623 | CONHSO₂CH₃ | |
| 624 | CO(N-morpholinyl) | |
| 625 | CONHSO₂Ph | |
| 626 | CO(N-Me-N-piperazinyl) | |
| 627 | CONHSO₂Bn | |
| 628 | CONH(CH₂)₂-(N-Me-N-piperazinyl) | |
| 629 | CONHSO₂-N-Me-imidazolyl | |
| 630 | CONH-cyclopropyl | |
| 631 | CONHSO₂-p-NH₂Ph | |
| 632 | CONH-cyclobutyl | |
| 633 | CONHSO₂-p-MeOPh | |
| 634 | CONHSO₂-p-F-Ph | |
| 635 | CONH-S-CH[CH₂CH(CH₃)₂]CONHMe | |
| 636 | CONH(CH₂)₂NHSO₂Me | |
| 637 | CONH(CH₂)₄NHSO₂Me | |
| 638 | CONH-cyclohexyl | |
| 639 | CONH(CH₂)₆NHSO₂Me | |
| 640 | CONH-2-imidozolyl | |
| 641 | CONH-R-CH[CH₂CH(CH₃)₂]CONHMe | |
| 642 | CH₂SO₂NHCH₃ | |
| 643 | CONH-S-CH[(CH₂)₄NH₂]CONHMe | |
| 644 | CH₂SO₂NHPh | |
| 645 | CONH-S-CH[(CH₂)₃NH₂]CONHMe | |
| 646 | CH₂SO₂NH-[4-NH₂Ph] | |
| 647 | CONH-S-CH[(CH₂)₂NH₂]CONHMe | |
| 648 | 2-imidazolyl | |
| 649 | CONHMe | |
| 650 | 2-oxazoly | |
| 651 | CONHCH₂CONMe₂ | |
| 652 | 2-thiazolyl | |
| 653 | CONHCH₂CONHEt | |
| 654 | 2-benzimidazolyl | |
| 655 | CONHCH₂CONEt₂ | |
| 656 | CONH-R-CH(CH₃)Ph | |
| 657 | CONHCH₂CONH-cyclopropyl | |
| 658 | CONH-S-CH(CH₃)Ph | |
| 659 | CONHCH₂CONH-cyclobutyl | |

TABLE 6-continued

For the cyclophane:

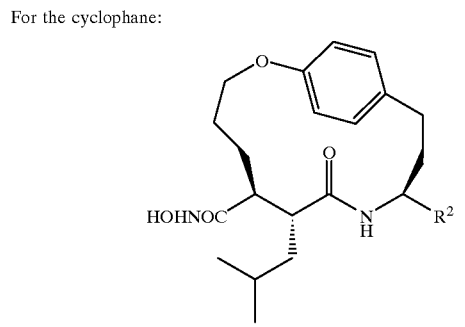

| Ex | R² (CI-MS) | ms |
|---|---|---|
| 660 | CONHCH₂CONHMe | |
| 661 | CONHCH₂CONH-cyclopentyl | |
| 662 | CONH-S-CH(CH₃)CONHMe | |
| 663 | CONHCH₂CONH-cyclohexyl | |
| 664 | CONH-R-CH(CH₃)CONHMe | |
| 665 | CONHCH₂CONH-tert-butyl | |
| 666 | CONH-S-CH(2-propyl)CONHMe | |
| 667 | CONH-S-CH(CH₂Ph)CONHMe | |
| 668 | CONH-S-CH(CH₂SH)CONHMe | |
| 669 | CONH-S-CH(CH₂-p-MeOPh)CONHMe | |
| 670 | CONH-S-CH(CH₂OH)CONHMe | |
| 671 | CONHCH₂CH₂CONHMe | |
| 672 | CONH-R-CH(CH₂OH)CONHMe | |
| 673 | CONHCH₂CH₂CH₂CONHMe | |
| 674 | CONH-S-CH(CH₂O-t-Bu)CONHMe | |
| 675 | CONH-S-CH(CH₂CH₂OH)CONHMe | |
| 676 | CONH-R-CH(CH₂O-t-Bu)CONHMe | |
| 677 | CONH-S-(CH(CH₂)₃CH₃)CONHMe | |
| 678 | CONH-CH(Ph)₂ | |
| 679 | CONH(CH₂)₂CO₂Me | |
| 680 | CO-L-proline-NHMe | |
| 681 | CONH(CH₂)₂CO₂H | |
| 682 | CONHCH₂CO(N-piperazinyl) | |
| 683 | CONH-S-CH[(CH₂)₃NHBOC]CO₂Me | |
| 684 | CONHCH₂CO(N-methyl-N-piperazinyl) | |
| 685 | CONH-S-CH[(CH₂)₃NHBOC]CONHMe | |
| 686 | CONHCH₂CO (N-acetyl-N-piperazinyl) | |
| 687 | CONH-S-CH-[(CH₂)₃NH₂]CO₂Me | |
| 688 | CONHCH₂CO-N-morpholino | |
| 689 | CONH-S-CH[(CH₂)₄NH₂]CONH₂ | |
| 690 | CONHCH₂CO-[N-(4-hydroxypiperidinyl)] | |
| 691 | CONH(CH₂)₂Ph | |
| 692 | CO₂H | |
| 693 | CONH(CH₂)₂-(3,4,-dimethoxyphenyl) | |
| 694 | CONHBn | |
| 695 | CONH(CH₂)₂-(N-morpholino) | |
| 696 | CONH-2-Pyridyl | |
| 697 | CONH(CH₂)₃-(N-morpholino) | |
| 698 | CONH-Ph | |
| 699 | CONHCH₂CONH-(2-pyridyl) | |
| 700 | CONH-3-pyridyl | |
| 701 | CONHCH₂CONH-(3-pyridyl) | |
| 702 | CONH-4-pyridyl | |
| 703 | CONHCH₂CONH-(4-pyridyl) | |
| 704 | CONH-CH₂CH(Ph)₂ | |
| 705 | CONH(CH₂)₂(P-SO₂NH₂-Ph) | |

TABLE 7

For the cyclophane:

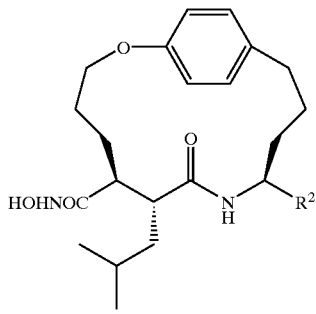

| Ex | R² (CI-MS) | ms |
|---|---|---|
| 710 | CO₂Me | 435 |
| 711 | CONH-cyclopentyl | |
| 712 | CO₂Et | |
| 713 | CONH₂ | |
| 714 | CO₂iPr | |
| 715 | CONHiPr | |
| 716 | CO₂(CH₂)₂OMe | |
| 717 | CONH-tert-butyl | |
| 718 | CO₂(CH₂)₂Ph | |
| 719 | CONMe₂ | |
| 720 | CO₂-tBu | |
| 721 | CONEt₂ | |
| 722 | CO₂CH₂CONHMe | |
| 723 | CONH-3-indazolyl | |
| 724 | CH₂OH | |
| 725 | CONH-adamantyl | |
| 726 | CH₂OCH₂CH₃ | |
| 727 | CONHCH₂(p-SO₂NH₂-Ph) | |
| 728 | CH₂OCH₂CH₂CO₂CH₃ | |
| 729 | CONH(CH₂)₃-1-imidazolyl | |
| 730 | CHOBn | |
| 731 | CONHSO₂NH₂ | |
| 732 | CONH(CH₂)₂-2-pyridyl | |
| 733 | CONHSO₂CH₃ | |
| 734 | CO(N-morpholinyl) | |
| 735 | CONHSO₂Ph | |
| 736 | CO(N-Me-N-piperazinyl) | |
| 737 | CONHSO₂Bn | |
| 738 | CONH(CH₂)₂-(N-Me-N-piperazinyl) | |
| 739 | CONHSO₂-N-Me-piperazinyl) | |
| 740 | CONH-cyclopropyl | |
| 741 | CONHSO₂-p-NH₂Ph | |
| 742 | CONH-cyclobutyl | |
| 743 | CONHSO₂-p-MeOPh | |
| 744 | CONHSO₂-p-F-Ph | |
| 745 | CONH-S-CH[CH₂CH(CH₃)₂]CONHMe | |
| 746 | CONH(CH₂)₂NHSO₂Me | |
| 747 | CONH(CH₂)₄NHSO₂Me | |
| 748 | CONH-cyclohexyl | |
| 749 | CONH(CH₂)₆NHSO₂Me | |
| 750 | CONH-2-imidozolyl | |
| 751 | CONH-R-CH[CH₂CH (CH₃)₂]CONHMe | |
| 752 | CH₂SO₂NHCH₃ | |
| 753 | CONH-S-CH[(CH₂)₄NH₂]CONHMe | |
| 754 | CONH-S-CH₂SO₂NHPh | |
| 755 | CH[(CH₂)₃NH₂]CONHMe | |
| 756 | CH₂SO₂NH-[4-NH₂Ph] | |
| 757 | CONH-S-CH[(CH₂)₂NH₂]CONHMe | |
| 758 | 2-imidazolyl | |
| 759 | CONHMe | 434 |
| 760 | 2-oxazoly | |
| 761 | CONHCH₂CONMe₂ | |
| 762 | 2-thiazolyl | |
| 763 | CONHCH₂CONHEt | |
| 764 | 2-benzimidazolyl | |
| 765 | CONHCH₂CONEt₂ | |
| 766 | CONH-R-CH(CH₃)Ph | |
| 767 | CONHCH₂CONH-cyclopropyl | |
| 768 | CONH-S-CH(CH₃)Ph | |

TABLE 7-continued

For the cyclophane:

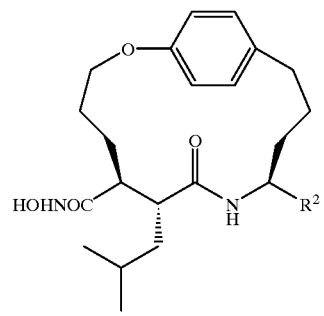

| Ex | R² (CI-MS) | ms |
|---|---|---|
| 769 | CONHCH₂CONH-cyclobutyl | |
| 770 | CONHCH₂CONHMe | |
| 771 | CONHCH₂CONH-cyclopentyl | |
| 772 | CONH-S-CH(CH₃)CONHMe | |
| 773 | CONHCH₂CONH-cyclohexyl | |
| 774 | CONH-R-CH (CH₃)CONHMe | |
| 775 | CONHCH₂CONH-tert-butyl | |
| 776 | CONH-S-CH(2-propyl)CONHMe | |
| 777 | CONH-S-CH(CH₂Ph)CONHMe | |
| 778 | CONH-S-CH(CH₂SH)CONHMe | |
| 779 | CONH-S-CH(CH₂-p-MeOPh)CONHMe | |
| 780 | CONH-S-CH (CH₂OH) CONHMe | |
| 781 | CONHCH₂CH₂CONHMe | |
| 782 | CONH-R-CH(CH₂OH)CONHMe | |
| 783 | CONHCH₂CH₂CH₂CONHMe | |
| 784 | CONH-S-CH(CH₂O-t-Bu)CONHMe | |
| 785 | CONH-S-CH(CH₂CH₂OH)CONHMe | |
| 786 | CONH-R-CH(CH₂O-t-Bu)CONHMe | |
| 787 | CONH-S-(CH(CH₂)₃CH₃)CONHMe | |
| 788 | CONH-CH(Ph)₂ | |
| 789 | CONH(CH₂)₂CO₂Me | |
| 790 | CO-L-proline-NHMe | |
| 791 | CONH(CH₂)₂CO₂H | |
| 792 | CONHCH₂CO(N-piperazinyl) | |
| 793 | CONH-S-CH[(CH₂)₃NHBOC]CO₂Me | |
| 794 | CONHCH₂CO(N-methyl-N-piperazinyl) | |
| 795 | CONH-S-CH[(CH₂)₃NHBOC]CONHMe | |
| 796 | CONHCH₂CO(N-acetyl-N-piperazinyl) | |
| 797 | CONH-S-CH-[(CH₂)₃NH₂]CO₂Me | |
| 798 | CONHCH₂CO-N-morpholino | |
| 799 | CONH-S-(CH₂)₃NH₂]CO₂Me | |
| 800 | CONHCH₂CO-[N-(4-hydroxypiperidinyl)] | |
| 801 | CONH(CH₂)₂Ph | |
| 802 | CO₂H | |
| 803 | CONH(CH₂)₂-(3,4,-dimethoxyphenyl) | |
| 804 | CONHBn | |
| 805 | CONH(CH₂)₂-(N-morpholino) | |
| 806 | CONH-2-pyridyl | |
| 807 | CONH(CH₂)₃-(N-morpholino) | |
| 808 | CONH-Ph | |
| 809 | CONHCH₂CONH-(2-pyridyl) | |
| 810 | CONH-3-pyridyl | |
| 811 | CONHCH₂CONH-3(3-pyridyl) | |
| 812 | CONH-4-pyridyl | |
| 813 | CONHCH₂CONH-(4-pyridyl) | |
| 814 | CONH-CH₂CH(Ph)₂ | |
| 815 | CONH(CH₂)₂(P-SO₂NH₂-Ph) | |

TABLE 8

For the cyclic carbamate:

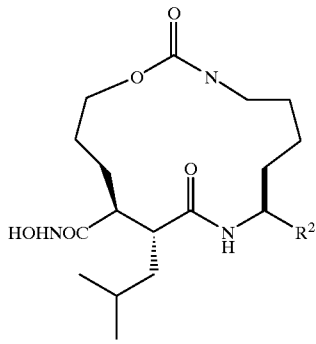

| Ex | R² (CI-MS) | ms |
|---|---|---|
| 820 | CO₂Me | |
| 821 | CONH-cyclopentyl | |
| 822 | CO₂Et | |
| 823 | CONH₂ | |
| 824 | CO₂iPr | |
| 825 | CONHiPr | |
| 826 | CO₂(CH₂)₂OMe | |
| 827 | CONH-tert-butyl | |
| 828 | CO₂(CH₂)₂Ph | |
| 829 | CONMe₂ | |
| 830 | CO₂-tBu | |
| 831 | CONEt₂ | |
| 832 | CO₂CH₂CONHMe | |
| 833 | CONH-3-indazolyl | |
| 834 | CH₂OH | |
| 835 | CONH-adamantyl | |
| 836 | CH₂OCH₂CH₃ | |
| 837 | CONHCH₂(p-SO₂NH₂-Ph) | |
| 838 | CH₂OCH₂CH₂CO₂CH₃ | |
| 839 | CONH(CH₂)₃-1-imidazolyl | |
| 840 | CHOBn | |
| 841 | CONHSO₂NH₂ | |
| 842 | CONH(CH₂)₂-2-pyridyl | |
| 843 | CONHSO₂CH₃ | |
| 844 | CO(N-morpholino) | |
| 845 | CONHSO₂Ph | |
| 846 | CO(N-Me-N-piperazinyl) | |
| 847 | CONHSO₂Bn | |
| 848 | CONH(CH₂)₂-(N-Me-N-piperazinyl) | |
| 849 | CONHSO₂-N-Me-imidazolyl | |
| 850 | CONH-cyclopropyl | |
| 851 | CONHSO₂-p-NH₂Ph | |
| 852 | CONH-cyclobutyl | |
| 853 | CONHSO₂-p-MeOPh | |
| 854 | CONHSO₂-p-F-Ph | |
| 855 | CONH-S-CH[CH₂CH(CH₃)₂]CONHMe | |
| 856 | CONH(CH₂)₂NHSO₂Me | |
| 857 | CONH(CH₂)₄NHSO₂Me | |
| 858 | CONH-(4-hydroxycyclohexyl) | 542.5 |
| 859 | CONH(CH₂)₆NHSO₂Me | |
| 860 | CONH-2-imidozolyl | |
| 861 | CONH-R-CH[CH₂CH(CH₃)₂]CONHMe | |
| 862 | CH₂SO₂NHCH₃ | |
| 863 | CONH-S-CH[(CH₂)₄NH₂]CONHMe | |
| 864 | CH₂SO₂NHPh | |
| 865 | CONH-S-CH[(CH₂)₃NH₂]CONHMe | |
| 866 | CH₂SO₂NH-[4-NH₂Ph] | |
| 867 | CONH-S-CH[(CH₂)₂NH₂]CONHMe | |
| 868 | 2-imidazolyl | |
| 869 | CONHMe | 429.3 |
| 870 | 2-oxazoly | |
| 871 | CONHCH₂CONMe₂ | 500.3 |
| 872 | 2-thiazolyl | |
| 873 | CONHCH₂CONHEt | |
| 874 | 2-benzimidazolyl | |
| 875 | CONHCH₂CONEt₂ | |
| 876 | CONH-R-CH(CH₃)Ph | |
| 877 | CONHCH₂CONH-cyclopropyl | |

TABLE 8-continued

For the cyclic carbamate:

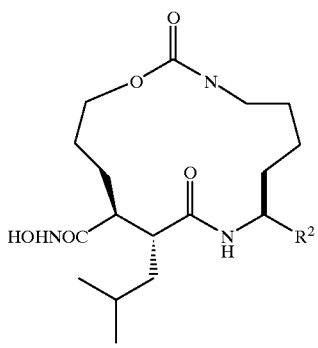

| Ex | R² (CI-MS) | ms |
|---|---|---|
| 878 | CONH-S-CH(CH₃)Ph | |
| 879 | CONHCH₂CONH-cyclobutyl | |
| 880 | CONHCH₂CONHMe | 486.5 |
| 881 | CONHCH₂CONH-cyclopentyl | |
| 882 | CONH-S-CH(CH₃)CONHMe | |
| 883 | CONHCH₂CONH-cyclohexyl | |
| 884 | CONH-R-CH(CH₃)CONHMe | |
| 885 | CONHCH₂CONH-tert-butyl | |
| 886 | CONH-S-CH(2-propyl)CONHMe | |
| 887 | CONH-S-CH(CH₂Ph)CONHMe | |
| 888 | CONH-S-CH(CH₂SH)CONHMe | |
| 889 | CONH-S-CH(CH₂-p-MeOPh)CONHMe | |
| 890 | CONH-S-CH(CH₂OH)CONHMe | |
| 891 | CONHCH₂CH₂CONHMe | |
| 892 | CONH-R-CH(CH₂OH)CONHMe | |
| 893 | CONHCH₂CH₂CH₂CONHMe | |
| 894 | CONH-S-CH(CH₂O-t-Bu)CONHMe | |
| 895 | CONH-S-CH(CH₂CH₂OH)CONHMe | |
| 896 | CONH-R-CH(CH₂O-t-Bu)CONHMe | |
| 897 | CONH-S-(CH(CH₂)₃CH₃)CONHMe | |
| 898 | CO-L-prolinol | 556.5 |
| 899 | CONH(CH₂)₂CO₂Me | |
| 900 | CO-L-proline-NHMe | |
| 901 | CONH(CH₂)₂CO₂H | |
| 902 | CONHCH₂CO(N-piperazinyl) | |
| 903 | CONH-S-CH[(CH₂)₃NHBOC]CO₂Me | |
| 904 | CONHCH₂CO(N-methyl-N-piperazinyl) | 555.5 |
| 905 | CONH-S-CH[(CH₂)₃NHBOC]CONHMe | |
| 906 | CONHCH₂CO(N-ethyl-N-piperazinyl) | 569.6 |
| 907 | CONH-S-CH-[(CH₂)₃NH₂]CO₂Me | |
| 908 | CONHCH₂CO-N-morpholino | 542.5 |
| 909 | CONH-S-CH[(CH₂)₄NH₂]CONH₂ | |
| 910 | CONHCH₂CO-[N-(4-hydroxypiperidinyl)] | 555.7 |
| 911 | CONH(CH₂)₂Ph | |
| 912 | CO₂H | |
| 913 | CONH(CH₂)₂-(3,4,-dimethoxyphenyl) | |
| 914 | CONHBn | |
| 915 | CONH(CH₂)₂-(N-morpholino) | |
| 916 | CONH-2-pryidyl | 496.5 |
| 917 | CONH(CH₂)₃-(N-morpholino) | |
| 918 | CONH-Ph | |
| 919 | CONHCH₂CONH-(2-pyridyl) | 549.5 |
| 920 | CONH-3-pyridyl | |
| 921 | CONHCH₂CONH-(3-pyridyl) | |
| 922 | CONH-4-pyridyl | |
| 923 | CONHCH₂CONH-(4-pyridyl) | |
| 924 | CONH-CH₂CH(Ph)₂ | |
| 925 | CONH-4-(N-ethoxycarbonylpiperidinyl) | 570.5 |
| 926 | CONH-2-(3-methyl)Thiazolyl | 512.4 |
| 927 | CONHCH₂CNH-2-(3,4,5,6-tetrahydropyridinyl) | 553.6 |
| 928 | CONHCH₂CO-2-(3-methyl)Thiazolyl | 569.3 |
| 929 | CONHCH₂-2-pyridyl | 506.5 |

TABLE 9

For the cyclic carbamate:

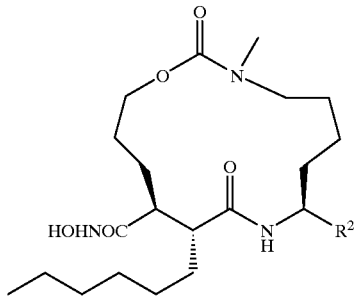

| Ex | R² (CI-MS) | ms |
|---|---|---|
| 930 | CO₂Me | |
| 931 | CONH-cyclopentyl | |
| 932 | CO₂Et | |
| 933 | CONH₂ | |
| 934 | CO₂iPr | |
| 935 | CONHiPr | |
| 936 | CO₂(CH₂)₂OMe | |
| 937 | CONH-tert-butyl | |
| 938 | CO₂(CH₂)₂Ph | |
| 939 | CONMe₂ | |
| 940 | CO₂-tBu | |
| 941 | CONEt₂ | |
| 942 | CO₂CH₂CONHMe | |
| 943 | CONH-3-indazolyl | |
| 944 | CH₂OH | |
| 945 | CONH-adamantyl | |
| 946 | CH₂OCH₂CH₃ | |
| 947 | CONHCH₂(p-SO₂NH₂-Ph) | |
| 948 | CH₂OCH₂CH₂CO₂CH₃ | |
| 949 | CONH(CH₂)₃-1-imidazolyl | |
| 950 | CHOBn | |
| 951 | CONHSO₂NH₂ | |
| 952 | CONH(CH₂)₂-2-pyridyl | |
| 953 | CONHSO₂CH₃ | |
| 954 | CO(N-morpholinyl) | |
| 955 | CONHSO₂Ph | |
| 956 | CO(N-Me-N-piperazinyl) | |
| 957 | CONHSO₂Bn | |
| 958 | CONH(CH₂)₂-(N-Me-N-piperazinyl) | |
| 959 | CONHSO₂-N-Me-imidazolyl | |
| 960 | CONH-cyclopropyl | |
| 961 | CONHSO₂-p-NH₂Ph | |
| 962 | CONH-cyclobutyl | |
| 963 | CONHSO₂-p-MeOPh | |
| 964 | CONHSO₂-p-F-Ph | |
| 965 | CONH-S-CH[CH₂CH(CH₃)₂]CONHMe | |
| 966 | CONH(CH₂)₂NHSO₂Me | |
| 967 | CONH(CH₂)₄NHSO₂Me | |
| 968 | CONH-cyclohexyl | |
| 969 | CONH(CH₂)₆NHSO₂Me | |
| 970 | CONH-2-imidozolyl | |
| 971 | CONH-R-CH[CH₂CH(CH₃)₂]CONHMe | |
| 972 | CH₂SO₂NHCH₃ | |
| 973 | CONH-S-CH[(CH₂)₄NH₂]CONHMe | |
| 974 | CH₂SO₂NHPh | |
| 975 | CONH-S-CH[(CH₂)₃NH₂]CONHMe | |
| 976 | CH₂SO₂NH-[4-NH₂-Ph] | |
| 977 | CONH-S-CH[(CH₂)₂NH₂]CONHMe | |
| 978 | 2-imidazolyl | |
| 979 | CONHMe | |
| 980 | 2-oxazoly | |
| 981 | CONHCH₂CONMe₂ | |
| 982 | 2-thiazolyl | |
| 983 | CONHCH₂CONHEt | |
| 984 | 2-benzimidazolyl | |
| 985 | CONHCH₂CONEt₂ | |
| 986 | CONH-R-CH(CH₃)Ph | |
| 987 | CONHCH₂CONH-cyclopropyl | |
| 988 | CONH-S-CH(CH₃)Ph | |
| 989 | CONHCH₂CONH-cyclobutyl | |

TABLE 9-continued

For the cyclic carbamate:

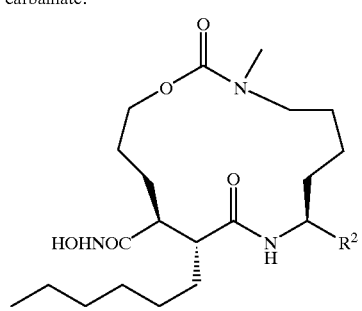

| Ex | R² (CI-MS) | ms |
|---|---|---|
| 990 | CONHCH₂CONHMe | |
| 991 | CONHCH₂CONH-cyclopentyl | |
| 992 | CONH-S-CH(CH₃)CONHMe | |
| 993 | CONHCH₂CONH-cyclohexyl | |
| 994 | CONH-R-CH(CH₃)CONHMe | |
| 995 | CONHCH₂CONH-tert-butyl | |
| 996 | CONH-S-CH(2-propyl)CONHMe | |
| 997 | CONH-S-CH(CH₂Ph)CONHMe | |
| 998 | CONH-S-CH(CH₂SH)CONHMe | |
| 999 | CONH-S-CH(CH₂-p-MeOPh)CONHMe | |
| 1000 | CONH-S-CH(CH₂OH)CONHMe | |
| 1001 | CONHCH₂CH₂CONHMe | |
| 1002 | CONH-R-CH(CH₂OH)CONHMe | |
| 1003 | CONHCH₂CH₂CH₂CONHMe | |
| 1004 | CONH-S-CH(CH₂O-t-Bu)CONHMe | |
| 1005 | CONH-S-CH(CH₂CH₂OH)CONHMe | |
| 1006 | CONH-R-CH(CH₂O-t-Bu)CONHMe | |
| 1007 | CONH-S-(CH(CH₂)₃CH₃)CONHMe | |
| 1008 | CONH-CH(Ph)₂ | |
| 1009 | CONH(CH₂)₂CO₂Me | |
| 1010 | CO-L-proline-NHMe | |
| 1011 | CONH(CH₂)₂CO₂H | |
| 1012 | CONHCH₂CO(N-piperazinyl) | |
| 1013 | CONH-S-CH[(CH₂)₃NHBOC]CO₂Me | |
| 1014 | CONHCH₂CO(N-methyl-N-piperazinyl) | |
| 1015 | CONH-S-CH[(CH₂)₃NHBOC]CONHMe | |
| 1016 | CONHCH₂CO(N-acetyl-N-piperazinyl) | |
| 1017 | CONH-S-CH-[(CH₂)₃NH₂]CO₂Me | |
| 1018 | CONHCH₂CO-N-morpholino | |
| 1019 | CONH-S-CH[(CH₂)₄NH₂]CONH₂ | |
| 1020 | CONHCH₂CO-[N-(4-hydroxypiperidinyl)] | |
| 1021 | CONH(CH₂)₂Ph | |
| 1022 | CO₂H | |
| 1023 | CONH(CH₂)₂-(3,4,-dimethoxyphenyl) | |
| 1024 | CONHBn | |
| 1025 | CONH(CH₂)₂-(N-morpholino) | |
| 1026 | CONH-2-pyridyl | |
| 1027 | CONH(CH₂)₃-(N-morpholino) | |
| 1028 | CONH-Ph | |
| 1029 | CONHCH₂CONH-(2-pyridyl) | |
| 1030 | CONH-3-pyridyl | |
| 1031 | CONHCH₂CONH-(3-pyridyl) | |
| 1032 | CONH-4-pyridyl | |
| 1033 | CONHCH₂CONH-(4-pyridyl) | |
| 1034 | CONH-CH₂CH(Ph)₂ | |
| 1035 | CONH(CH₂)₂(p-SO₂NH₂-Ph) | |

TABLE 10

For the cyclic carbamate:

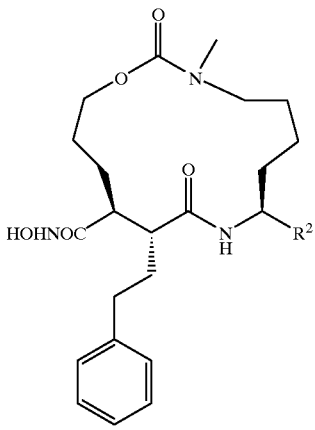

| Ex | R² (CI-MS) | ms |
|---|---|---|
| 1050 | CO₂Me | |
| 1051 | CO₂Et | |
| 1052 | CO₂iPr | |
| 1053 | CO₂(CH₂)₂OMe | |
| 1054 | CO₂(CH₂)₂Ph | |
| 1055 | CO₂-tBu | |
| 1056 | CO₂CH₂CONHMe | |
| 1057 | CH₂OH | |
| 1058 | CH₂OCH₂CH₃ | |
| 1059 | CH₂OCH₂CH₂CO₂CH₃ | |
| 1060 | CHOBn | |
| 1061 | CONH(CH₂)₂-2-pyridyl | |
| 1062 | CO(N-morpholinyl) | |
| 1063 | CO(N-Me-N-piperazinyl) | |
| 1064 | CONH(CH₂)₂-(N-Me-N-piperazinyl) | |
| 1065 | CONH-cyclopentyl | |
| 1066 | CONH₂ | |
| 1067 | CONHiPr | |
| 1068 | CONH-tert-butyl | |
| 1069 | CONMe₂ | |
| 1070 | CONEt₂ | |
| 1071 | CONH-3-indazolyl | |
| 1072 | CONH-adamantyl | |
| 1073 | CONHCH₂(p-SO₂NH₂-Ph) | |
| 1074 | CONH(CH₂)₃-1-imidazolyl | |
| 1075 | CONHSO₂NH₂ | |
| 1076 | CONHSO₂CH₃ | |
| 1077 | CONHSO₂Ph | |
| 1078 | CONHSO₂Bn | |
| 1079 | CONHSO₂-N-Me-imidazolyl | |
| 1080 | CONH-cyclopropyl | |
| 1081 | CONH-cyclobutyl | |
| 1082 | CONHSO₂-p-F-Ph | |
| 1083 | CONH(CH₂)₂NHSO₂Me | |
| 1084 | CONH-cyclohexyl | |
| 1085 | CONH-2-imidozolyl | |
| 1086 | CH₂SO₂NHCH₃ | |
| 1087 | CH₂SO₂NHPh | |
| 1088 | CH₂SO₂NH-[4-NH₂Ph] | |
| 1089 | 2-imidazolyl | |
| 1090 | 2-oxazoly | |
| 1091 | 2-thiazolyl | |
| 1092 | 2-benzimidazolyl | |
| 1093 | CONH-R-CH(CH₃)Ph | |
| 1094 | CONH-S-CH(CH₃)Ph | |
| 1095 | CONHCH₂CONHMe | |
| 1096 | CONH-S-CH(CH₃)CONHMe | |
| 1097 | CONH-R-CH(CH₃)CONHMe | |
| 1098 | CONH-S-CH(2-propyl)CONHMe | |
| 1099 | CONH-S-CH(CH₂SH)CONHMe | |
| 1100 | CONH-S-CH(CH₂OH)CONHMe | |
| 1101 | CONH-R-CH(CH₂OH)CONHMe | |
| 1102 | CONH-S-CH(CH₂O-t-Bu)CONHMe | |
| 1103 | CONH-R-CH(CH₂O-t-Bu)CONHMe | |

TABLE 10-continued

For the cyclic carbamate:

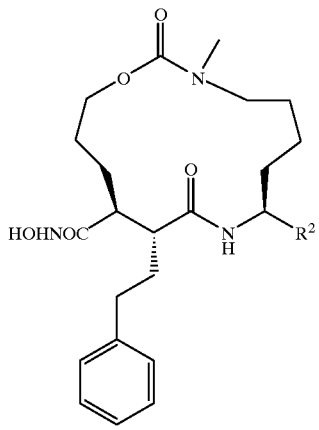

| Ex | R² (CI-MS) | ms |
|---|---|---|
| 1104 | CONH-CH(Ph)₂ | |
| 1105 | CO-L-proline-NHMe | |
| 1106 | CONHCH₂CO(N-piperazinyl) | |
| 1107 | CONHSO₂-p-NH₂Ph | |
| 1108 | CONHSO₂-p-MeOPh | |
| 1109 | CONH-S-CH[CH₂CH(CH3)2]CONHMe | |
| 1110 | CONH(CH₂)₄NHSO₂Me | |
| 1111 | CONH(CH₂)₆NHSO₂Me | |
| 1112 | CONH-R-CH[CH₂CH(CH₃)₂]CONHMe | |
| 1113 | CONH-S-CH[(CH₂)₄NH₂]CONHMe | |
| 1114 | CONH-S-CH[(CH₂)₃NH₂]CONHMe | |
| 1115 | CONH-S-CH[(CH₂)₂NH₂]CONHMe | |
| 1116 | CONHMe | |
| 1117 | CONHCH₂CONMe₂ | |
| 1118 | CONHCH₂CONHEt | |
| 1119 | CONHCH₂CONEt₂ | |
| 1120 | CONHCH₂CONH-cyclopropyl | |
| 1121 | CONHCH₂CONH-cyclobutyl | |
| 1122 | CONHCH₂CONH-cyclopentyl | |
| 1123 | CONHCH₂CONH-cyclohexyl | |
| 1124 | CONHCH₂CONH-tert-butyl | |
| 1125 | CONH-S-CH(CH₂Ph)CONHMe | |
| 1126 | CONH-S-CH(CH₂-p-MeOPh)CONHMe | |
| 1127 | CONHCH₂CH₂CONHMe | |
| 1128 | CONHCH₂CH₂CH₂CONHMe | |
| 1129 | CONH-S-CH(CH₂CH₂OH)CONHMe | |
| 1130 | CONH-S-(CH(CH₂)₃CH3)CONHMe | |
| 1131 | CONH(CH₂)₂CO₂Me | |
| 1132 | CONH(CH₂)₂CO₂H | |
| 1133 | CONH-S-CH[(CH₂)₃NHBOC]CO₂Me | |
| 1134 | CONHCH₂CO(N-methyl-N-piperazinyl) | |
| 1135 | CONHCH₂CO(N-acetyl-N-piperazinyl) | |
| 1136 | CONHCH₂CO-N-morpholino | |
| 1137 | CONHCH₂CO-[N-(4-hydroxypiperidinyl) | |
| 1138 | CO₂H | |
| 1139 | CONHBn | |
| 1140 | CONH-2-pyridyl | |
| 1141 | CONH-Ph | |
| 1142 | CONH-3-pyridyl | |
| 1143 | CONH-4-pyridyl | |
| 1144a | CONH-CH₂CH(Ph)₂ | |
| 1144 | CONH-S-CH[(CH₂)₃NHBOC]CONHMe | |
| 1145 | CONH-S-CH-[(CH₂)₃NH₂]CO₂Me | |
| 1146 | CONH-S-CH[(CH₂)₄NH₂]CONH₂ | |
| 1147 | CONH(CH₂)₂Ph | |
| 1148 | CONH(CH₂)₂-(3,4,-dimethoxyphenyl) | |
| 1149 | CONH(CH₂)₂-(N-morpholino) | |
| 1150 | CONH(CH₂)₃-(N-morpholino) | |
| 1151 | CONHCH₂CONH-(2-pyridyl) | |
| 1152 | CONHCH₂CONH-(3-pyridyl) | |
| 1153 | CONHCH₂CONH-(4-pyridyl) | |
| 1154 | CONH(CH₂)₂(p-SO₂NH₂-Ph) | |

TABLE 11

For the cyclic carbamate:

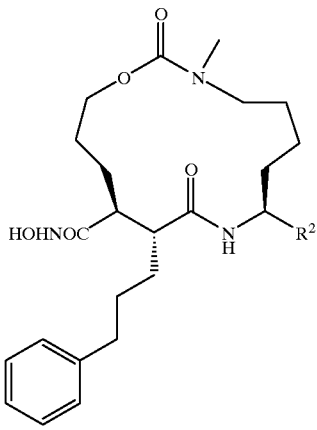

| Ex | R² (CI-MS) | ms |
|---|---|---|
| 1163 | CO₂Me | |
| 1164 | CO₂Et | |
| 1165 | CO₂iPr | |
| 1166 | CO₂(CH₂)₂OMe | |
| 1167 | CO₂(CH₂)₂Ph | |
| 1168 | CO₂-tBu | |
| 1169 | CO₂CH₂CONHMe | |
| 1170 | CH₂OH | |
| 1171 | CH₂OCH₂CH₃ | |
| 1172 | CH₂OCH₂CH₂O₂CH₃ | |
| 1173 | CHOBn | |
| 1174 | CONH(CH₂)₂-2-pyridyl | |
| 1175 | CO(N-morpholinyl) | 47.4 |
| 1176 | CO(N-Me-N-piperazinyl) | 560.4 |
| 1177 | CONH-cyclopentyl | |
| 1178 | CONH₂ | |
| 1179 | CONHiPr | |
| 1180 | CONH-tert-butyl | |
| 1181 | CONMe₂ | |
| 1182 | CONEt₂ | |
| 1183 | CONH-3-indazolyl | |
| 1184 | CONH-adamantyl | |
| 1185 | CONHCH₂(p-SO₂NH₂-Ph) | |
| 1186 | CONH(CH₂)₃-1-imidazolyl | |
| 1187 | CONHSO₂NH₂ | |
| 1188 | CONHSO₂CH₃ | |
| 1189 | CONHSO₂Ph | |
| 1190 | CONHSO₂Bn | |
| 1191 | CONH(CH₂)₂-(N-Me-N-piperazinyl) | |
| 1192 | CONH-cyclopropyl | |
| 1193 | CONH-cyclobutyl | |
| 1194 | CONHSO₂-p-F-Ph | |
| 1195 | CONH(CH₂)₂NHSO₂Me | |
| 1196 | CONH-cyclohexyl | |
| 1197 | CONH-2-imidozolyl | |
| 1198 | CH₂SO₂NHCH₃ | |
| 1199 | CH₂SO₂NHPh | |
| 1200 | CH₂SO₂NH-[4-NH₂Ph) | |
| 1201 | 2-imidazolyl | |
| 1202 | 2-oxazoly | |
| 1203 | 2-thiazolyl | |
| 1204 | 2-benzimidazolyl | |
| 1205 | CONH-R-CH(CH₃)Ph | |
| 1206 | CONH-S-CH(CH₃)Ph | |
| 1207 | CONHCH₂CONHMe | |
| 1208 | CONH-S-CH(CH₃)CONHMe | |
| 1209 | CONH-R-CH(CH₃)CONHMe | |
| 1210 | CONH-S-CH(2-propyl)CONHMe | |
| 1211 | CONH-S-CH(CH₂SH)CONHMe | |
| 1212 | CONH-S-CH(CH₂OH)CONHMe | |
| 1213 | CONH-R-CH(CH₂OH)CONHMe | |
| 1214 | CONH-S-CH(CH₂O-t-Bu)CONHMe | |
| 1215 | CONH-R-CH(CH₂O-t-Bu)CONHMe | |
| 1216 | CONH-CH(Ph)₂ | |

TABLE 11-continued

For the cyclic carbamate:

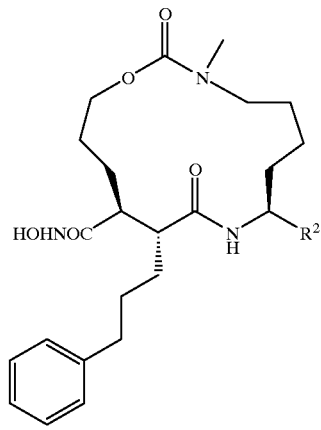

| Ex | R² (CI-MS) | ms |
|---|---|---|
| 1217 | CO-L-proline-NHMe | |
| 1218 | CONHSO₂-N-Me-imidazolyl | |
| 1219 | CONHSO₂-P-NH₂Ph | |
| 1220 | CONHSO₂-p-MeOPh | |
| 1221 | CONH-S-CH[CH₂CH(CH₃)₂]CONHMe | |
| 1222 | CONH(CH₂)₄NHSO₂Me | |
| 1223 | CONH(CH₂)₆NHSO₂Me | |
| 1224 | CONH-R-CH[CH₂CH(CH₃)₂]CONHMe | |
| 1225 | CONH-S-CH-[(CH₂)₄NH₂]CONHMe | |
| 1226 | CONH-S-CH[(CH₂)₃NH₂]CONHMe | |
| 1227 | CONH-S-CH[(CH₂)₂NH₂]CONHMe | |
| 1228 | CONHMe | 491.5 |
| 1229 | CONHCH₂CONMe₂ | |
| 1230 | CONHCH₂CONHEt | |
| 1231 | CONHCH₂CONEt₂ | |
| 1232 | CONHCH₂CONH-cyclopropyl | |
| 1233 | CONHCH₂CONH-cyclobutyl | |
| 1234 | CONHCH₂CONH-cyclopentyl | |
| 1235 | CONHCH₂CONH-cyclohexyl | |
| 1236 | CONHCH₂CONH-tert-butyl | |
| 1237 | CONH-S-CH(CH₂Ph)CONHMe | |
| 1238 | CONH-S-CH(CH₂-p-MeOPh)CONHMe | |
| 1239 | CONHCH₂CH₂CONHMe | |
| 1240 | CONHCH₂CH₂CH₂CONHMe | |
| 1241 | CONH-S-CH(CH₂CH₂OH)CONHMe | |
| 1242 | CONH-S-(CH(CH₂)₃CH₃)CONHMe | |
| 1243 | CONH(CH₂)₂CO₂Me | |
| 1244 | CONH(CH₂)₂CO₂H | |
| 1245 | CONHCH₂CO(N-piperazinyl) | |
| 1246 | CONHCH₂CO(N-methyl-N-piperazinyl) | |
| 1247 | CONHCH₂CO(N-acetyl-N-piperazinyl) | |
| 1248 | CONHCH₂CO-N-morpholinol | |
| 1249 | CONHCH₂CO-[N-(4-hydroxypiperidinyl)] | |
| 1250 | CO₂H | |
| 1251 | CONHBn | |
| 1252 | CONH-2-pyridyl | |
| 1253 | CONH-Ph | |
| 1254 | CONH-3-pyridyl | |
| 1255 | CONH-4-pyridyl | |
| 1256 | CONH-CH₂CH(Ph)₂ | |
| 1256 | CONH-S-CH[(CH₂)₃NHBOC)CO₂Me | |
| 1257 | CONH-S-CH[(CH₂)₃NHBOC]CONHMe | |
| 1258 | CONH-S-CH-(CH₂)₃NH₂]CO₂Me | |
| 1259 | CONH-S-CH[(CH₂)₄NH₂]CONH₂ | |
| 1260 | CONH(CH₂)₂Ph | |
| 1261 | CONH(CH₂)₂-(3,4,-dimethoxyphenyl) | |
| 1262 | CONH(CH₂)₂-(N-morpholino) | |
| 1263 | CONH(CH₂)₃-(N-morpholino) | |
| 1264 | CONHCH₂CONH-(2-pyridyl) | |
| 1265 | CONHCH₂CONH-(3-pyridyl) | |
| 1266 | CONHCH₂CONH-(4-pyridyl) | |
| 1267 | CONH(CH₂)₂(p-SO₂NH₂-Ph) | |

TABLE 12

For the cyclic carbamate:

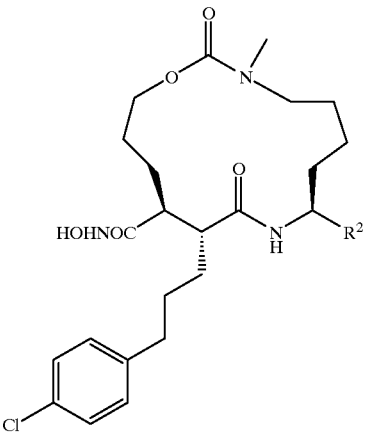

| Ex | R² (CI-MS) |
|---|---|
| 1277 | $CO_2Me$ |
| 1278 | $CO_2Et$ |
| 1279 | $CO_2iPr$ |
| 1280 | $CO_2(CH_2)_2OMe$ |
| 1281 | $CO_2(CH_2)_2Ph$ |
| 1282 | $CO_2$-tBu |
| 1283 | $CO_2CH_2CONHMe$ |
| 1284 | $CH_2OH$ |
| 1285 | $CH_2OCH_2CH_3$ |
| 1286 | $CH_2OCH_2CH_2CO_2CH_3$ |
| 1287 | CHOBn |
| 1288 | $CONH(CH_2)_2$-2-pyridyl |
| 1289 | CO(N-morpholinyl) |
| 1290 | CO(N-Me-N-piperazinyl) |
| 1291 | $CONH(CH_2)_2$-(N-Me-N-piperazinyl) |
| 1292 | CONH-cyclopentyl |
| 1293 | $CONH_2$ |
| 1294 | CONHiPr |
| 1295 | CONH-tert-butyl |
| 1296 | $CONMe_2$ |
| 1297 | $CONEt_2$ |
| 1298 | CONH-3-indazolyl |
| 1299 | CONH-adalnantyl |
| 1300 | $CONHCH_2(p-SO_2NH_2-Ph)$ |
| 1301 | $CONH(CH_2)_3$-1-imidazolyl |
| 1302 | $CONHSO_2NH_2$ |
| 1303 | $CONHSO_2CH_3$ |
| 1304 | $CONHSO_2Ph$ |
| 1305 | $CONHSO_2Bn$ |
| 1306 | $CONHSO_2$-N-Me-imidazolyl |
| 1307 | CONH-cyclopropyl |
| 1308 | CONH-cyclobutyl |
| 1309 | $CONHSO_2$-p-F-Ph |
| 1310 | $CONH(CH_2)_2NHSO_2Me$ |
| 1311 | CONH-cyclohexyl |
| 1312 | CONH-2-imidozolyl |
| 1313 | $CH_2SO_2NHCH_3$ |
| 1314 | $CH_2SO_2NHPh$ |
| 1315 | $CH_2SO_2NH$-[4-$NH_2$Ph] |
| 1316 | 2-imidazolyl |
| 1317 | 2-oxazoly |
| 1318 | 2-thiazolyl |
| 1319 | 2-benzimidazolyl |
| 1320 | CONH-R-CH($CH_3$)Ph |
| 1321 | CONH-S-CH($CH_3$)Ph |
| 1322 | $CONHCH_2CONHMe$ |
| 1323 | CONH-S-CH($CH_3$)CONHMe |
| 1324 | CONH-R-CH($CH_3$)CONHMe |
| 1325 | CONH-S-CH(2-propyl)CONHMe |
| 1326 | CONH-S-CH($CH_2SH$)CONHMe |
| 1327 | CONH-S-CH($CH_2OH$)CONHMe |
| 1328 | CONH-R-CH($CH_2OH$)CONHMe |
| 1329 | CONH-S-CH($CH_2O$-t-Bu)CONHMe |
| 1330 | CONH-R-CH($CH_2O$-t-Bu)CONHMe |

TABLE 12-continued

For the cyclic carbamate:

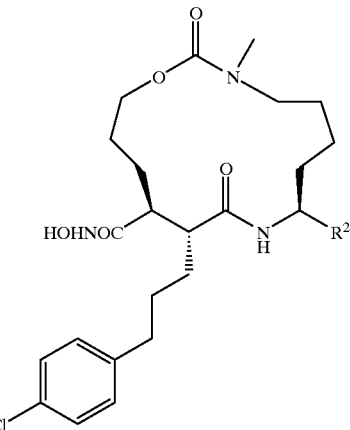

| Ex | R² (CI-MS) |
|---|---|
| 1331 | $CONH-CH(Ph)_2$ |
| 1332 | CO-L-proline-NHMe |
| 1333 | $CONHSO_2$-p-$NH_2$Ph |
| 1334 | $CONHSO_2$-p-MeOPh |
| 1335 | CONH-S-CH[$CH_2CH(CH_3)_2$]CONHMe |
| 1336 | $CONH(CH_2)_4NHSO_2Me$ |
| 1337 | $CONH(CH_2)_6NHSO_2Me$ |
| 1338 | CONH-R-CH[$CH_2CH(CH_3)_2$]CONHMe |
| 1339 | CONH-S-CH[$(CH_2)_4NH_2$]CONHMe |
| 1340 | CONH-S-CH[$(CH_2)_3NH_2$]CONHMe |
| 1341 | CONH-S-CH[$(CH_2)_2NH_2$]CONHMe |
| 1342 | CONHMe |
| 1343 | $CONHCH_2CONMe_2$ |
| 1344 | $CONHCH_2CONHEt$ |
| 1345 | $CONHCH_2CONEt_2$ |
| 1346 | $CONHCH_2CONH$-cyclopropyl |
| 1347 | $CONHCH_2CONH$-cyclobutyl |
| 1348 | $CONHCH_2CONH$-cyclopentyl |
| 1349 | $CONHCH_2CONH$-cyclohexyl |
| 1350 | $CONHCH_2CONH$-tert-butyl |
| 1351 | CONH-S-CH($CH_2Ph$)CONHMe |
| 1352 | CONH-S-CH($CH_2$-p-MeOPh)CONHMe |
| 1353 | $CONHCH_2CH_2CONHMe$ |
| 1354 | $CONHCH_2CH_2CH_2CONHMe$ |
| 1355 | CONH-S-CH($CH_2CH_2OH$)CONHMe |
| 1356 | CONH-S-(CH($CH_2)_3CH_3$)CONHMe |
| 1357 | $CONH(CH_2)_2CO_2Me$ |
| 1358 | $CONH(CH_2)_2CO_2H$ |
| 1359 | $CONHCH_2CO$(N-piperazinyl) |
| 1360 | $CONHCH_2CO$(N-methyl-N-piperazinyl) |
| 1361 | $CONHCH_2CO$(N-acetyl-N-piperazinyl) |
| 1362 | $CONHCH_2CO$-N-morpholino |
| 1363 | $CONHCH_2CO$-[N-(4-hydroxypiperidinyl)] |
| 1364 | $CO_2H$ |
| 1365 | CONHPn |
| 1366 | CONH-2-pryidyl |
| 1367 | CONH-Ph |
| 1368 | CONH-3-pyridyl |
| 1369 | CONH-4-pyridyl |
| 1370 | CONH-S-CH[$(CH_2)_3$NHBOC]$CO_2Me$ |
| 1371 | CONH-S-CH[$(CH_2)_3$NHBOC]CONHMe |
| 1372 | CONH-S-CH-[$(CH_2)_3NH_2$]$CO_2Me$ |
| 1373 | CONH-S-CH[$(CH_2)_4NH_2$]$CONH_2$ |
| 1374 | $CONH(CH_2)_2Ph$ |
| 1375 | $CONH(CH_2)_2$-(3,4,-dimethoxyphenyl) |
| 1376 | $CONH(CH_2)_2$-(N-morpholino) |
| 1377 | $CONH(CH_2)_3$-(N-morpholino) |
| 1378 | $CONHCH_2CONH$-(2-pyridyl) |
| 1379 | $CONHCH_2CONH$-(3-pyridyl) |
| 1380 | $CONHCH_2CONH$-(4-pyridyl) |
| 1381 | $CONH-CH_2CH(Ph)_2$ |
| 1382 | $CONH(CH_2)_2(p-SO_2NH_2-Ph)$ |

TABLE 13

For the lactam:

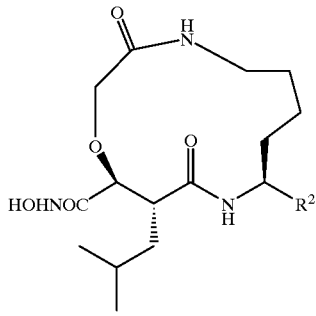

| Ex | R² (CI-MS) | ms |
|---|---|---|
| 1395 | CO₂Me | |
| 1396 | CO₂Et | |
| 1397 | CO₂iPr | |
| 1398 | CO₂(CH₂)₂OMe | |
| 1399 | CO₂(CH₂)₂Ph | |
| 1400 | CO₂-tBu | |
| 1401 | CO₂CH₂CONHMe | |
| 1402 | CH₂OH | |
| 1403 | CH₂OCH₂CH₃ | |
| 1404 | CH₂OCH₂CH₂CO₂CH₃ | |
| 1405 | CHOBn | |
| 1406 | CONH(CH₂)₂-2-pyridyl | |
| 1407 | CO(N-morpholinyl) | |
| 1408 | CO(N-Me-N-piperazinyl) | |
| 1409 | CONH(CH₂)₂-(N-Me-N-piperazinyl) | |
| 1410 | CONH-cyclopropyl | |
| 1411 | CONH-cyclobutyl | |
| 1412 | CONH-cyclopentyl | |
| 1413 | CONH₂ | |
| 1414 | CONHiPr | |
| 1415 | CONH-tert-butyl | |
| 1416 | CONMe₂ | |
| 1417 | CONEt₂ | |
| 1418 | CONH-3-indazolyl | |
| 1419 | CONH-adamantyl | |
| 1420 | CONHCH₂(p-SO₂NH₂-Ph) | |
| 1421 | CONH(CH₂)3-1-imidazolyl | |
| 1422 | CONHSO₂NH₂ | |
| 1423 | CONHSO₂CH₃ | |
| 1424 | CONHSO₂Ph | |
| 1425 | CONHSO₂Bn | |
| 1426 | CONHSO₂-N-Me-imidazolyl | |
| 1427 | CONHSO₂-p-NH₂Ph | |
| 1428 | CONHSO₂-p-MeOPh | |
| 1429 | CONHSO₂-p-F-Ph | |
| 1430 | CONH(CH₂)₂NHSO₂Me | |
| 1431 | CONH-cyclohexyl | |
| 1432 | CONH-2-imidozolyl | |
| 1433 | CH₂SO₂NHCH₃ | |
| 1434 | CH₂SO₂NHPh | |
| 1435 | CH₂SO₂NH-[4-NH₂Ph) | |
| 1436 | 2-imidazolyl | |
| 1437 | 2-oxazoly | |
| 1438 | 2-thiazolyl | |
| 1439 | 2-benzimidazolyl | |
| 1440 | CONH-R-CH(CH₃)Ph | |
| 1441 | CONH-S-CH(CH₃)Ph | |
| 1442 | CONHCH₂CONHMe | 442.4 |
| 1443 | CONH-S-CH(CH₃)CONHMe | 456.4 |
| 1444 | CONH-R-CH(CH₃)CONHMe | |
| 1445 | CONH-S-CH(2-propyl)CONHMe | |
| 1446 | CONH-S-CH(CH₂SH)CONHMe | |
| 1447 | CONH-S-CH(CH₂OH)CONHMe | 472.4 |
| 1448 | CONH-R-CH(CH₂OH)CONHMe | |
| 1449 | CONH-S-CH(CH₂O-t-Bu)CONHMe | |
| 1450 | CONH-R-CH(CH₂O-t-Bu)CONHMe | |
| 1451 | CONH-CH(Ph)₂ | |
| 1452 | CO-L-proline-NHMe | |
| 1453 | CONHCH₂CO(N-piperazinyl) | |

TABLE 13-continued

For the lactam:

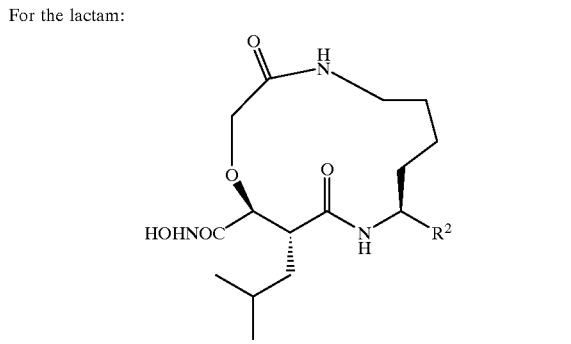

| Ex | R² (CI-MS) | ms |
|---|---|---|
| 1454 | CONHCH₂CO(N-methyl-N-piperazinyl) | |
| 1455 | CONH-S-CH[CH₂CH(CH₃)₂]CONHMe | |
| 1456 | CONH(CH₂)₄NHSO₂Me | |
| 1457 | CONH(CH₂)6NHSO₂Me | |
| 1458 | CONH-R-CH[CH₂CH(CH₃)₂]CONHMe | |
| 1459 | CONH-S-CH[(CH₂)₄NH₂]CONHMe | |
| 1460 | CONH-S-CH[(CH₂)₃NH₂]CONHMe | |
| 1461 | CONH-S-CH[(CH₂)₂NH₂]CONHMe | |
| 1462 | CONHMe | 385.4 |
| 1463 | CONHCH₂CONMe₂ | |
| 1464 | CONHCH₂CONHEt | |
| 1465 | CONHCH₂CONEt₂ | |
| 1466 | CONHCH₂CONH-cyclopropyl | |
| 1467 | CONHCH₂CONH-cyclobutyl | |
| 1468 | CONHCH₂CONH-cyclopentyl | |
| 1469 | CONHCH₂CONH-cyclohexyl | |
| 1470 | CONHCH₂CONH-tert-butyl | |
| 1471 | CONH-S-CH(CH₂Ph)CONHMe | |
| 1472 | CONH-S-CH(CH₂-p-MeOPh)CONHMe | |
| 1473 | CONHCH₂CH₂CONHMe | 456.4 |
| 1474 | CONHCH₂CH₂CONHMe | |
| 1475 | CONH-S-CH(CH₂CH₂OH)CONHMe | |
| 1476 | CONH-S-(CH(CH₂)₃CH₃)CONHMe | |
| 1477 | CONH(CH₂)₂CO₂Me | |
| 1478 | CONH(CH₂)₂CO₂H | |
| 1479 | CONH-S-CH[(CH₂)₃NHBOC)CO₂]Me | |
| 1480 | CONH-S-CH[(CH₂)₃NHBOC]CONHMe | |
| 1481 | CONHCH₂CO(N-acetyl-N-piperazinyl) | |
| 1482 | CONHCH₂CO-N-morpholino | |
| 1483 | CONHCH₂CO-[N-(4-hydroxypiperidinyl)] | |
| 1484 | CO₂H | |
| 1485 | CONHBn | |
| 1486 | CONH-2-pyridyl | |
| 1487 | CONH-Ph | |
| 1488 | CONH-3-pyridyl | |
| 1489 | CONH-4-pyridyl | |
| 1490 | CONH-CH₂CH(Ph)₂ | |
| 1490 | CONH-S-CH-[(CH₂)₃NH₂]CO₂Me | |
| 1491 | CONH-S-CH[(CH₂)₄NH₂]CONH₂ | |
| 1492 | CONH(CH₂)₂Ph | |
| 1493 | CONH(CH₂)₂-(3,4,-dimethoxyphenyl) | |
| 1494 | CONH(CH₂)₂-(N-morpholino) | |
| 1495 | CONH(CH₂)₃-(N-morpholino) | |
| 1496 | CONHCH₂CONH-(2-pyridyl) | |
| 1497 | CONHCH₂CONH-(3-pyridyl) | |
| 1498 | CONHCH₂CONH-(4-pyridyl) | |
| 1499 | CONH(CH₂)₂(p-SO₂NH₂-Ph) | |

TABLE 13

For the lactam:

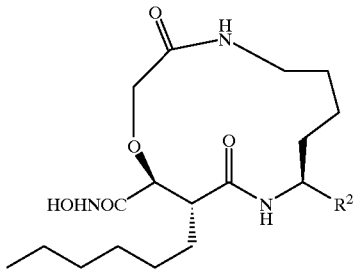

| Ex | R² (CI-MS) | ms |
|---|---|---|
| 1511 | CO₂Me | |
| 1512 | CO₂Et | |
| 1513 | CO₂iPr | |
| 1514 | CO₂(CH₂)₂OMe | |
| 1515 | CO₂(CH₂)₂Ph | |
| 1516 | CO₂-tBu | |
| 1517 | CO₂CH₂CONHMe | |
| 1518 | CH₂OH | |
| 1519 | CH₂OCH₂CH₃ | |
| 1520 | CH₂OCH₂CH₂CO₂CH₃ | |
| 1521 | CHOBn | |
| 1522 | CONH(CH₂)₂-2-pyridyl | |
| 1523 | CO(N-morphoiinyl) | |
| 1524 | CO(N-Me-N-piperazinyl) | |
| 1525 | CONH(CH₂)₂-(N-Me-N-piperazinyl) | |
| 1526 | CONH-cyclopropyl | |
| 1527 | CONH-cyclobutyl | |
| 1528 | CONHSO₂-p-F-Ph | |
| 1529 | CONH-cyclopentyl | |
| 1530 | CONH₂ | |
| 1531 | CONHiPr | |
| 1532 | CONH-tert-butyl | |
| 1533 | CONMe₂ | |
| 1534 | CONEt₂ | |
| 1535 | CONH-3-indazolyl | |
| 1536 | CONH-adamantyl | |
| 1537 | CONHCH₂(p-SO₂NH₂-Ph) | |
| 1538 | CONH(CH₂)₃-1-imidazolyl | |
| 1539 | CONHSO₂NH₂ | |
| 1540 | CONHSO₂CH₃ | |
| 1541 | CONHSO₂Ph | |
| 1542 | CONHSO₂Bn | |
| 1543 | CONHSO₂-N-Me-imidazolyl | |
| 1544 | CONHSO₂-p-NH₂Ph | |
| 1545 | CONHSO₂-p-MeOPh | |
| 1546 | CONH-S-CH[CH₂CH(CH₃)₂]CONHMe | |
| 1547 | CONH(CH₂)₂NHSO₂Me | |
| 1548 | CONH-cyclohexyl | |
| 1549 | CONH-2-imidozolyl | |
| 1550 | CH₂SO₂NHCH₃ | |
| 1551 | CH₂SO₂NHPh | |
| 1552 | CH₂SO₂NH-[4-NH₂Ph] | |
| 1553 | 2-imidazolyl | |
| 1554 | 2-oxazoly | |
| 1555 | 2-thiazolyl | |
| 1556 | 2-benzimidazolyl | |
| 1557 | CONH-R-CH(CH₃)Ph | |
| 1558 | CONH-S-CH(CH₃)Ph | |
| 1559 | CONHCH₂CONHMe | |
| 1560 | CONH-S-CR(CH₃)CONHMe | |
| 1561 | CONH-R-CH(CH₃)CONHMe | |
| 1562 | CONH-S-CH(2-propyl)CONHMe | |
| 1563 | CONH-S-CH(CH₂SH)CONHMe | |
| 1564 | CONH-S-CH(CH₂OH)CONHMe | |
| 1565 | CONH-R-CH(CH₂OH)CONHMe | |
| 1566 | CONH-S-CH(CH₂O-t-Bu)CONHMe | |
| 1567 | CONH-R-CH(CH₂O-t-Bu)CONHMe | |
| 1568 | CONH-CH(Ph)₂ | |
| 1569 | CO-L-proline-NHMe | |
| 1570 | CONHCH₂CO(N-piperazinyl) | |
| 1571 | CONHCH₂CO(N-methyl-N-piperazinyl) | |

TABLE 13-continued

For the lactam:

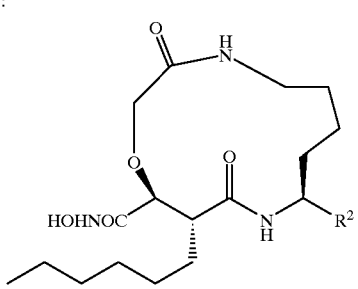

| Ex | R² (CI-MS) | ms |
|---|---|---|
| 1572 | CONHCH₂CO(N-acetyl-N-piperazinyl) | |
| 1573 | CONH(CH₂)₄NHSO₂Me | |
| 1574 | CONH(CH₂)6NHSO₂Me | |
| 1575 | CONH-R-CH[CH₂CH(CH₃)₂]CONHMe | |
| 1576 | CONH-S-CH[(CH₂)₄NH₂]CONHMe | |
| 1577 | CONH-S-CH[(CH₂)₃NH₂]CONHMe | |
| 1578 | CONH-S-CH[(CH₂)₂NH₂]CONHMe | |
| 1579 | CONHMe | |
| 1580 | CONHCH₂CONMe₂ | |
| 1581 | CONHCH₂CONHEt | |
| 1582 | CONHCH₂CONEt₂ | |
| 1583 | CONHCH₂CONH-cyclopropyl | |
| 1584 | CONHCH₂CONH-cyclobutyl | |
| 1585 | CONHCH₂CONH-cyclopentyl | |
| 1586 | CONHCH₂CONH-cyclohexyl | |
| 1587 | CONHCH₂CONH-tert-butyl | |
| 1588 | CONH-S-CH(CH₂Ph)CONHMe | |
| 1589 | CONH-S-CH(CH₂-p-MeOPh)CONHMe | |
| 1590 | CONHCH₂CH₂CONHMe | |
| 1591 | CONHCH₂CH₂CH₂CONHMe | |
| 1592 | CONH-S-CH(CH₂CH₂OH)CONHMe | |
| 1593 | CONH-S-(CH(CH₂)₃CH₃)CONHMe | |
| 1594 | CONH(CH₂)₂CO₂Me | |
| 1595 | CONH(CH₂)₂CO₂H | |
| 1596 | CONH-S-CH[(CH₂)₃NHBOC]CO₂Me | |
| 1597 | CONH-S-CH[(CH₂)₃NHBOC]CONHMe | |
| 1598 | CONH-S-CH-[(CH₂)₃NH₂]CO₂Me | |
| 1599 | CONHCH₂CO-N-morpholino | |
| 1600 | CONHCH₂CO-[N-(4-hydroxypiperidinyl)] | |
| 1601 | CO₂H | |
| 1602 | CONHBn | |
| 1603 | CONH-2-Pyridyl | |
| 1604 | CONH-Ph | |
| 1605 | CONH-3-pyridyl | |
| 1606 | CONH-4-pyridyl | |
| | CONH-CH₂CH(Ph)₂ | |
| 1607 | CONH-S-CH[(CH₂)₄NH₂]CONH₂ | |
| 1608 | CONH(CH₂)₂Ph | |
| 1609 | CONH(CH₂)₂-(3,4,-dimethoxyphenyl) | |
| 1610 | CONH(CH₂)₂-(N-morpholino) | |
| 1611 | CONH(CH₂)₃-(N-morpholino) | |
| 1612 | CONHCH₂CONH-(2-pyridyl) | |
| 1613 | CONHCH₂CONH-(3-pyridyl) | |
| 1614 | CONHCH₂CONH-(4-pyridyl) | |
| | CONH(CH₂)2 (P-SO₂NH₂-Ph) | |

TABLE 14

For the lactam:

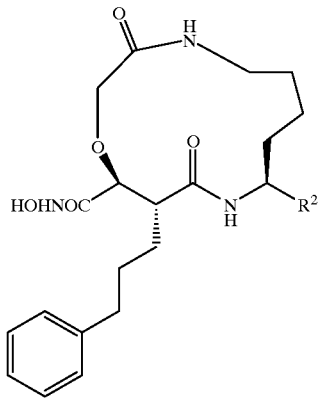

| Ex | R² (CI-MS) | ms |
|---|---|---|
| 1625 | CO₂Me | |
| 1626 | CO₂Et | |
| 1627 | CO₂iPr | |
| 1628 | CO₂(CH₂)₂OMe | |
| 1629 | CO₂(CH₂)₂Ph | |
| 1630 | CO₂-tBu | |
| 1631 | CO₂CH₂CONHMe | |
| 1632 | CH₂OH | |
| 1633 | CH₂OCH₂CH₃ | |
| 1634 | CH₂OCH₂CH₂CO₂CH₃ | |
| 1635 | CHOBn | |
| 1637 | CONH(CH₂)₂-2-pyridyl | |
| 1638 | CO(N-morpholinyl) | |
| 1639 | CO(N-Me-N-piperazinyl) | |
| 1640 | CONH(CH₂)₂-(N-Me-N-piperazinyl) | |
| 1641 | CONH-cyclopropyl | |
| 1642 | CONH-cyclopentyl | |
| 1643 | CONH₂ | |
| 1644 | CONHiPr | |
| 1645 | CONH-tert-butyl | |
| 1646 | CONMe₂ | |
| 1647 | CONEt₂ | |
| 1648 | CONH-3-indazolyl | |
| 1649 | CONH-adamantyl | |
| 1650 | CONHCH₂(p-SO₂NH₂-Ph) | |
| 1651 | CONH(CH₂)₃-1-imidazolyl | |
| 1652 | CONHSO₂NH₂ | |
| 1653 | CONHSO₂CH₃ | |
| 1654 | CONHSO₂Ph | |
| 1655 | CONHSO₂Bn | |
| 1656 | CONHSO₂-N-Me-imidazolyl | |
| 1657 | CONHSO₂-p-NH₂Ph | |
| 1658 | CONH-cyclobutyl | |
| 1659 | CONHSO₂-p-F-Ph | |
| 1660 | CONH(CH₂)₄NHSO₂Me | |
| 1661 | CONH-cyclohexyl | |
| 1662 | CONH-2-imidozolyl | |
| 1663 | CH₂SO₂NHCH₃ | |
| 1664 | CH₂SO₂NHPh | |
| 1665 | CH₂SO₂NH-[4-NH₂Ph] | |
| 1666 | 2-imidazolyl | |
| 1667 | 2-oxazoly | |
| 1668 | 2-thiazolyl | |
| 1669 | 2-benzimidazolyl | |
| 1670 | CONH-R-CH(CH₃)Ph | |
| 1671 | CONH-S-CH(CH₃)Ph | |
| 1672 | CONHCH₂CONHMe | |
| 1673 | CONH-S-CH(CH₃)CONHMe - | |
| 1674 | CONH-R-CH(CH₃)CONHMe - | |
| 1675 | CONH-S-CH(2-propyl)CONHMe | |
| 1676 | CONH-S-CH(CH₂SH)CONHMe | |
| 1677 | CONH-S-CH(CH₂OH)CONHMe | |
| 1678 | CONH-R-CH(CH₂OH)CONHMe | |
| 1679 | CONH-S-CH(CH₂O-t-Bu)CONHMe | |
| 1680 | CONH-R-CH(CH₂O-t-Bu)CONHMe | |

TABLE 14-continued

For the lactam:

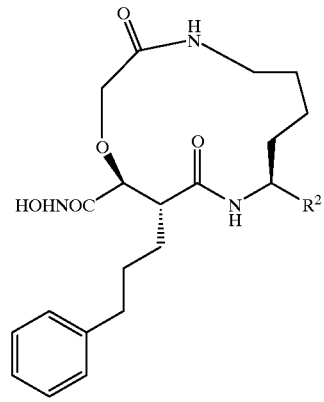

| Ex | R² (CI-MS) | ms |
|---|---|---|
| 1681 | CONH-CH(Ph)₂ | |
| 1682 | CO-L-Proline-NHMe | |
| 1683 | CONHCH₂CO(N-piperazinyl) | |
| 1684 | CONHCH₂CO(N-methyl-N-piperazinyl) | |
| 1685 | CONHCH₂CO(N-acetyl-N-piperazinyl) | |
| 1686 | CONHSO₂-p-MeOPh | |
| 1687 | CONH-S-CHCONH(CH₂)₂NHSO₂Me | |
| 1688 | [CH₂CH(CH₃)₂]CONHMe | |
| 1689 | CONH(CH₂)6NHSO₂Me | |
| 1690 | CONH-R-CH[CH₂CH(CH₃)₂]CONHMe | |
| 1691 | CONH-S-CH[(CH₂)₄NH₂]CONHMe | |
| 1692 | CONH-S-CH[(CH₂)₃NH₂]CONHMe | |
| 1693 | CONH-S-CH[(CH₂)₂NH₂]CONHMe | |
| 1694 | CONHMe | |
| 1695 | CONHCH₂CONMe₂ | |
| 1696 | CONHCH₂CONHEt | |
| 1697 | CONHCH₂CONEt₂ | |
| 1698 | CONHCH₂CONH-cyclopropyl | |
| 1699 | CONHCH₂CONH-cyclobutyl | |
| 1700 | CONHCH₂CONH-cyclopentyl | |
| 1701 | CONHCH₂CONH-cyclohexyl | |
| 1702 | CONHCH₂CONH-tert-butyl | |
| 1703 | CONH-S-CH(CH₂Ph)CONHMe | |
| 1704 | CONH-S-CH(CH₂-p-MeOPh)CONHMe | |
| 1705 | CONHCH₂CH₂CONHMe | |
| 1706 | CONHCH₂CH₂CH₂CONHMe | |
| 1707 | CONH-S-CH(CH₂CH₂OH)CONHMe | |
| 1708 | CONH-S-(CH(CH₂)₃CH₃)CONHMe | |
| 1709 | CONH(CH₂)₂CO₂Me | |
| 1710 | CONH(CH₂)₂CO₂H | |
| 1711 | CONH-S-CH[(CH₂)₃NHBOC]CO₂Me | |
| 1712 | CONH-S-CH[(CH₂)₃NHBOC]CONHMe | |
| 1713 | CONH-S-CH-[(CH₂)₃NH₂]CO₂Me | |
| 1714 | CONHCH₂CO-N-morpholino | |
| 1715 | CONHCH₂CO-[N-(4-hydroxypiperidinyl)] | |
| 1716 | CO₂H | |
| 1717 | CONHBn | |
| 1718 | CONH-2-Pyridyl | |
| 1719 | CONH-Ph | |
| 1720 | CONH-3-pyridyl | |
| 1721 | CONH-4-Pyridyl | |
| 1722 | CONH-CH₂CH(Ph)₂ | |
| 1722 | CONH-S-CH[(CH₂)₄NH₂]CONH₂ | |
| 1723 | CONH(CH₂)₂Ph | |
| 1724 | CONH(CH₂)₂-(3,4,-dimethoxyphenyl) | |
| 1725 | CONH(CH₂)₂-(N-morpholino) | |
| 1726 | CONH(CH₂)₃-(N-morpholino) | |
| 1727 | CONHCH₂CONH-(2-pyridyl) | |
| 1728 | CONHCH₂CONH-(3-pyridyl) | |
| 1729 | CONHCH₂CONH-(4-pyridyl) | |
| 1730 | CONH(CH₂)₂(p-SO₂NH₂-Ph) | |

TABLE 15

For the lactam:

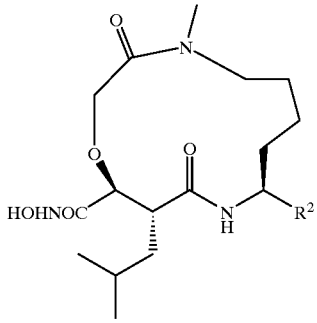

| Ex | R² (CI-MS) | ms |
|---|---|---|
| 1740 | CO₂Me | |
| 1741 | CO₂Et | |
| 1742 | CO₂iPr | |
| 1743 | CO₂(CH₂)₂OMe | |
| 1744 | CO₂(CH₂)₂Ph | |
| 1745 | CO₂-tBu | |
| 1746 | CO₂CH₂CONHMe | |
| 1747 | CH₂OH | |
| 1748 | CH₂OCH₂CH₃ | |
| 1749 | CH₂OCH₂CH₂CO₂CH₃ | |
| 1750 | CHOBn | |
| 1751 | CONH(CH₂)₂-2-Pyridyl | |
| 1752 | CO(N-morpholinyl) | |
| 1753 | CO(N-Me-N-piperazinyl) | |
| 1754 | CONH(CH₂)₂-(N-Me-N-piperazinyl) | |
| 1755 | CONH-cyclopropyl | |
| 1756 | CONH-cyclobutyl | |
| 1757 | CONHSO₂-p-F-Ph | |
| 1758 | CONH-cyclopentyl | |
| 1759 | CONH₂ | |
| 1760 | CONHiPr | |
| 1761 | CONH-tert-butyl | |
| 1762 | CONMe₂ | |
| 1763 | CONEt₂ | |
| 1764 | CONH-3-indazolyl | |
| 1765 | CONH-adamantyl | |
| 1766 | CONHCH₂(p-SO₂NH₂-Ph) | |
| 1767 | CONH(CH₂)₃-1-imidazolyl | |
| 1768 | CONHSO₂NH₂ | |
| 1769 | CONHSO₂CH₃ | |
| 1770 | CONHSO₂Ph | |
| 1771 | CONHSO₂Bn | |
| 1772 | CONHSO₂-N-Me-imidazolyl | |
| 1773 | CONHSO₂-p-NH₂Ph | |
| 1774 | CONHSO₂-p-MeOPh | |
| 1775 | CONH-S-CH[CH₂CH(CH₃)₂CONHMe | |
| 1776 | CONH(CH₂)₂NHSO₂Me | |
| 1777 | CONH-cyclohexyl | |
| 1778 | CONH-2-imidozolyl | |
| 1779 | CH₂SO₂NHCH₃ | |
| 1780 | CH₂SO₂NHPh | |
| 1781 | CH₂SO₂NH-[4-NH₂Ph] | |
| 1782 | 2-imidazolyl | |
| 1783 | 2-oxazoly | |
| 1784 | 2-thiazolyl | |
| 1785 | 2-benzimidazolyl | |
| 1786 | CONH-R-CH(CH₃)Ph | |
| 1787 | CONH-S-CH(CH₃)Ph | |
| 1788 | CONHCH₂CONHMe | |
| 1789 | CONH-S-CH(CH₃)CONHMe | |
| 1790 | CONH-R-CH(CH₃)CONHMe | |
| 1791 | CONH-S-CH(2-propyl)CONHMe | |
| 1792 | CONH-S-CH(CH₂SH)CONHMe | |
| 1793 | CONH-S-CH(CH₂OH)CONHMe | |
| 1794 | CONH-R-CH(CH₂OH)CONHMe | |
| 1795 | CONH-S-CH(CH₂O-t-Bu)CONHMe | |
| 1796 | CONH-R-CH(CH₂O-t-Bu)CONHMe | |
| 1797 | CONH-CH(Ph)₂ | |
| 1798 | CO-L-proiine-NHMe | |

TABLE 15-continued

For the lactam:

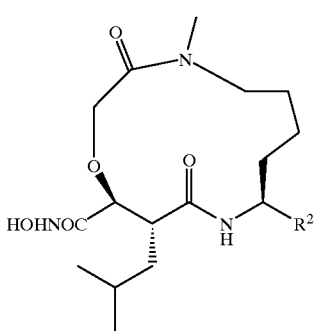

| Ex | R² (CI-MS) | ms |
|---|---|---|
| 1799 | CONHCH₂CO(N-piperazinyl) | |
| 1800 | CONHCH₂CO(N-methyl-N-piperazinyl) | |
| 1801 | CONHCH₂CO(N-acetyl-N-piperazinyl) | |
| 1802 | CONHCH₂CO-N-morpholino | |
| 1803 | CONHCH₂CO-[N-(4-hydroxypiperidinyl)] | |
| 1804 | CONH(CH₂)₄NHSO₂Me | |
| 1805 | CONH(CH₂)6NHSO₂Me | |
| 1806 | CONH-R-CH[CH₂CH(CH₃)₂]CONHMe | |
| 1807 | CONH-S-CH[(CH₂)₄NH₂]CONHMe | |
| 1808 | CONH-S-CH[(CH₂)₃NH₂]CONHMe | |
| 1809 | CONH-S-CH[(CH₂)₂NH₂]CONHMe | |
| 1810 | CONHMe | |
| 1811 | CONHCH₂CONMe₂ | |
| 1812 | CONHCH₂CONHEt | |
| 1813 | CONHCH₂CONEt₂ | |
| 1814 | CONHCH₂CONH-cyclopropyl | |
| 1815 | CONHCH₂CONH-cyclobutyl | |
| 1816 | CONHCH₂CONH-cyclopentyl | |
| 1817 | CONHCH₂CONH-cyclohexyl | |
| 1818 | CONHCH₂CONH-tert-butyl | |
| 1819 | CONH-S-CH(CH₂Ph)CONHMe | |
| 1820 | CONH-S-CH(CH₂-p-MeOPh)CONHMe | |
| 1821 | CONHCH₂CH₂CONHMe | |
| 1822 | CONHCH₂CH₂CH₂CONHMe | |
| 1823 | CONH-S-CH(CH₂CH₂OH)CONHMe | |
| 1824 | CONH-S-(CH(CH₂)₃CH₃)CONHMe | |
| 1825 | CONH(CH₂)₂CO₂Me | |
| 1826 | CONH(CH₂)₂CO₂H | |
| 1827 | CONH-S-CH[(CH₂)₃NHBOC]CO₂Me | |
| 1828 | CONH-S-CH[(CH₂)₃NHBOC]CONHMe | |
| 1829 | CONH-S-CH-[(CH₂)₃NH₂]CO₂Me | |
| 1830 | CONH-S-CH[(CH₂)₄NH₂]CONH₂ | |
| 1831 | CONH(CH₂)₂Ph | |
| 1832 | CO₂H | |
| 1833 | CONHBn | |
| 1834 | CONH-2-pyridyl | |
| 1835 | CONH-Ph | |
| 1836 | CONH-3-pyridyl | |
| 1837 | CONH-4-pyridyl | |
| 1838 | CONH(CH₂)₂-(3,4,-dimethoxyphenyl) | |
| 1838 | CONH-CH₂CH(Ph)₂ | |
| 1839 | CONH(CH₂)₂-(N-morpholino) | |
| 1840 | CONH(CH₂)₃-(N-morpholino) | |
| 1841 | CONHCH₂CONH-(2-pyridyl) | |
| 1842 | CONHCH₂CONH-(3-pyridyl) | |
| 1843 | CONHCH₂CONH-(4-pyridyl) | |
| 1844 | CONH(CH₂)₂(p-SO₂NH₂-Ph) | |

TABLE 16

For the cyclic amine:

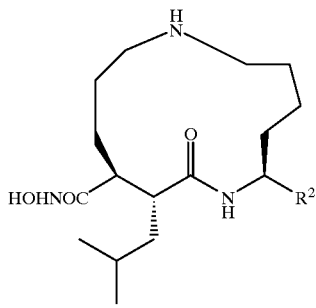

| Ex | R² (CI-MS) | ms |
|---|---|---|
| 1860 | CO₂Me | |
| 1861 | CO₂Et | |
| 1862 | CO₂iPr | |
| 1863 | CO₂(CH₂)₂OMe | |
| 1864 | CO₂(CH₂)₂Ph | |
| 1865 | CO₂-tBu | |
| 1866 | CO₂CH₂CONHMe | |
| 1867 | CH₂OH | |
| 1868 | CH₂OCH₂CH₃ | |
| 1869 | CH₂OCH₂CH₂CO₂CH₃ | |
| 1870 | CHOBn | |
| 1871 | CONH(CH₂)₂-2-pyridyl | |
| 1872 | CO(N-morpholinyl) | |
| 1873 | CO(N-Me-N-piperazinyl) | |
| 1874 | CONH(CH₂)₂-(N-Me-N-piperazinyl) | |
| 1875 | CONH-cyclopropyl | |
| 1876 | CONH-cyclobutyl | |
| 1877 | CONHSO₂-p-F-Ph | |
| 1878 | CONH-cyclopentyl | |
| 1879 | CONH₂ | |
| 1880 | CONHiPr | |
| 1881 | CONH-tert-butyl | |
| 1882 | CONMe₂ | |
| 1883 | CONEt₂ | |
| 1884 | CONH-3-indazolyl | |
| 1885 | CONH-adamantyl | |
| 1886 | CONHCH₂(p-SO₂NH₂-Ph) | |
| 1887 | CONH(CH₂)₃-1-imidazolyl | |
| 1888 | CONHSO₂NH₂ | |
| 1889 | CONHSO₂CH₃ | |
| 1890 | CONHSO₂Ph | |
| 1891 | CONHSO₂Bn | |
| 1892 | CONHSO₂-N-Me-imidazolyl | |
| 1893 | CONHSO₂-p-NH₂Ph | |
| 1894 | CONHSO₂-p-MeOPh | |
| 1895 | CONH-S-CH [CH₂CH(CH₃)₂]CONHMe | |
| 1896 | CONH(CH₂)₂NHSO₂Me | |
| 1897 | CONH-cyclohexyl | |
| 1898 | CONH-2-imidozolyl | |
| 1899 | CH₂SO₂NHCH₃ | |
| 1900 | CH₂SO₂NHPh | |
| 1901 | CH₂SO₂NH-[4-NH₂Ph] | |
| 1902 | 2-imidazolyl | |
| 1903 | 2-oxazoly | |
| 1904 | 2-thiazolyl | |
| 1905 | 2-benzimidazolyl | |
| 1906 | CONH-R-CH(CH₃)Ph | |
| 1907 | CONH-S-CH(CH₃)Ph | |
| 1908 | CONHCH₂CONHME | |
| 1909 | CONH-S-CH(CH₃)CONHMe | |
| 1910 | CONH-R-CH(CH₃)CONHMe | |
| 1911 | CONH-S-CH(2-propyl)CONHMe | |
| 1912 | CONH-S-CH(CH₂SH)CONHMe | |
| 1913 | CONH-S-CH(CH₂OH)CONHMe | |
| 1914 | CONH-R-CH(CH₂OH)CONHMe | |
| 1915 | CONH-S-CH(CH₂O-t-Bu)CONHMe | |
| 1916 | CONH-R-CH(CH₂O-t-Bu)CONHMe | |
| 1917 | CONH-CH(Ph)₂ | |
| 1918 | CO-L-proline-NHMe | |
| 1919 | CONHCH₂CO(N-piperazinyl) | |

TABLE 16-continued

For the cyclic amine:

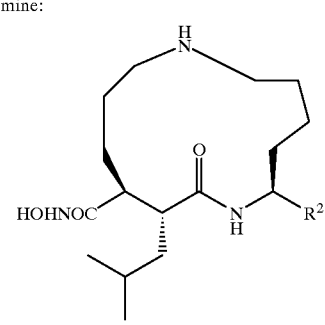

| Ex | R² (CI-MS) | ms |
|---|---|---|
| 1920 | CONHCH₂Co(N-methyl-N-piperazinyl) | |
| 1921 | CONHCH₂Co(N-acetyl-N-piperazinyl) | |
| 1922 | CONHCH₂CO-N-morpholinol | |
| 1923 | CONHCH₂CO-[N-(4-hydroxymorpholinyl)] | |
| 1924 | CONH(CH₂)₄NHSO₂Me | |
| 1925 | CONH(CH₂)₆NHSO₂Me | |
| 1926 | CONH-R-CH[CH₂CH(CH₃)₂]CONHMe | |
| 1927 | CONH-S-CH[(CH₂)₄NH₂]CONHMe | |
| 1928 | CONH-S-CH[(CH₂)₃NH₂]CONHMe | |
| 1929 | CONH-S-CH[(CH₂)₂NH₂]CONHMe | |
| 1930 | CONHMe | 471.4 |
| 1931 | CONHCH₂CONMe₂ | |
| 1932 | CONHCH₂CONHEt | |
| 1933 | CONHCH₂CONEt₂ | |
| 1934 | CONHCH₂CONH-cyclopropyl | |
| 1935 | CONHCH₂CONH-cyclobutyl | |
| 1936 | CONHCH₂CONH-cyclopentyl | |
| 1937 | CH₂CONH-cyclohexyl | |
| 1938 | CONHCH₂CONH-tert-butyl | |
| 1939 | CONH-S-CH(CH₂Ph)CONHMe | |
| 1940 | CONH-S-CH(CH₂-p-MeOPh)CONHMe | |
| 1941 | CONHCH₂CH₂CONHMe | |
| 1942 | CONHCH₂CH₂CH₂CONHMe | |
| 1943 | CONH-S-CH(CH₂CH₂OH)CONHMe | |
| 1944 | CONH-S-(CH(CH₂)₃CH₃)CONHMe | |
| 1945 | CONH(CH₂)₂CO₂Me | |
| 1946 | CONH(CH₂)₂CO₂H | |
| 1947 | CONH-S-CH[(CH₂)₃NHBOC]CO₂Me | |
| 1948 | CONH-S-CH[(CH₂)₃NHBOC]CONHMe | |
| 1949 | CONH-S-CH-[(CH₂)₃NH₂]CO₂Me | |
| 1950 | CONH-S-CH[(CH₂)₄NH₂]CONH₂ | |
| 1951 | CONH(CH₂)₂Ph | |
| 1952 | CO₂H | |
| 1953 | CONHBr | |
| 1954 | CONH-2-pryidyl | |
| 1955 | CONH-Ph | |
| 1956 | CONH-3-pyridyl | |
| 1957 | CONH-4-pyridyl | |
| | CONH-CH₂CH(Ph)₂ | |
| 1958 | CONH(CH₂)₂-(3,4,-dimethoxyphenyl) | |
| 1959 | CONH(CH₂)₂-(N-morpholinyl) | |
| 1960 | CONH(CH₂)₃-(N-morpholino) | |
| 1961 | CONHCH₂CONH-(2-pyridyl) | |
| 1962 | CONHCH₂CONH-(3-pyridyl) | |
| 1963 | CONHCH₂CONH-(4-pyridyl) | |
| | CONH(CH₂)₂-(P-SO₂NH₂-Ph) | |

TABLE 17

For the cyclic sulfonamide:

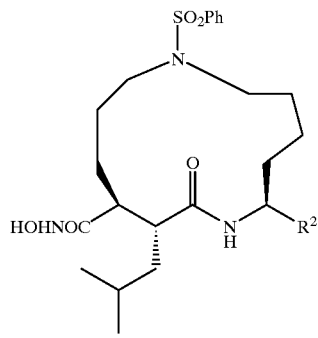

| Ex | R² (CI-MS) | ms |
|---|---|---|
| 1975 | CO₂Me | |
| 1976 | CO₂Et | |
| 1977 | CO₂iPr | |
| 1978 | CO₂(CH₂)₂OMe | |
| 1979 | CO₂(CH₂)₂Ph | |
| 1980 | CO₂-tBu | |
| 1981 | CO₂CH₂CONHMe | |
| 1982 | CH₂OH | |
| 1983 | CH₂OCH₂CH₃ | |
| 1984 | CH₂OCH₂CH₂CO₂CH₃ | |
| 1985 | CHOBn | |
| 1986 | CONH(CH₂)₂-2-pyridyl | |
| 1987 | CO(N-morpholinyl) | |
| 1988 | CO(N-Me-N-piperazinyl) | |
| 1989 | CONH(CH₂)₂-(N-Me-N-piperazinyl) | |
| 1990 | CONH-cyclopropyl | |
| 1991 | CONH-cyclobutyl | |
| 1992 | CONH-cyclopentyl | |
| 1993 | CONH₂ | |
| 1994 | CONHiPr | |
| 1995 | CONH-tert-butyl | |
| 1996 | CONMe₂ | |
| 1997 | CONEt₂ | |
| 1998 | CONH-3-indazolyl | |
| 1999 | CONH-adamantyl | |
| 2000 | CONHCH₂(p-SO₂NH₂-Ph) | |
| 2001 | CONH(CH₂)₃-1-imidazolyl | |
| 2002 | CONHSO₂NH₂ | |
| 2003 | CONHSO₂CH₃ | |
| 2004 | CONHSO₂Ph | |
| 2005 | CONHSO₂Bn | |
| 2006 | CONHSO₂-N-Me-imidazolyl | |
| 2007 | CONHSO₂-p-NH₂Ph | |
| 2008 | CONHSO₂-p-MeOPh | |
| 2009 | CONHSO₂-p-F-Ph | |
| 2010 | CONH(CH₂)₂NHSO₂Me | |
| 2011 | CONH-cyclohexyl | |
| 2012 | CONH-2-imidozolyl | |
| 2013 | CH₂SO₂NHCH₃ | |
| 2014 | CH₂SO₂NHPh | |
| 2015 | CH₂SO₂NH-[4-NH₂PH] | |
| 2016 | 2-imidazolyl | |
| 2017 | 2-oxazoly | |
| 2018 | 2-thiazolyl | |
| 2019 | 2-benzimidazolyl | |
| 2020 | CONH-R-CH(CH₃)Ph | |
| 2021 | CONH-S-CH(CH₃)Ph | |
| 2022 | CONHCH₂CONHMe | |
| 2023 | CONH-S-CH(CH₃)CONHMe | |
| 2024 | CONH-R-CH(CH₃)CONHMe | |
| 2025 | CONH-S-CH(2-propyl)CONHMe | |
| 2026 | CONH-S-CH(CH₂SH)CONHMe | |
| 2027 | CONH-S-CH(CH₂OH)CONHMe | |
| 2028 | CONH-R-CH(CH₂OH)CONHMe | |
| 2029 | CONH-S-CH(CH₂O-t-Bu)CONHMe | |
| 2030 | CONH-R-CH(CH₂O-t-Bu)CONHMe | |
| 2031 | CONH-S-CH[CH₂CH(CH₃)₂]CONHMe | |
| 2032 | CONH(CH₂)₄NHSO₂Me | |

TABLE 17-continued

For the cyclic sulfonamide:

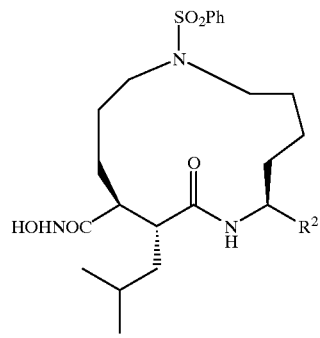

| Ex | R² (CI-MS) | ms |
|---|---|---|
| 2033 | CONH(CH₂)₆NHSO₂ME | |
| 2034 | CONH-R-CH[CH₂CH(CH₃)₂]CONHMe | |
| 2035 | CONH-S-CH[(CH₂)₄NH₂]CONHMe | |
| 2036 | CONH-S-CH[(CH₂)₃NH₂]CONHMe | |
| 2037 | CONH-S-CH[(CH₂)₂NH₂]CONHMe | |
| 2038 | CONHMe | 511.3 |
| 2039 | 2CONMe₂ | |
| 2040 | CONHCH₂CONHEt | |
| 2041 | CONHCH₂CONHEt₂ | |
| 2042 | CONHCH₂CONH-cyclopropyl | |
| 2043 | CONHCH₂CONH-cyclobutyl | |
| 2044 | CONHCH₂CONH-cyclopentyl | |
| 2045 | CONHCH₂CONH-cyclohexyl | |
| 2046 | CONHCH₂CONH-tert-butyl | |
| 2047 | CONH-S-CH(CH₂Ph)CONHMe | |
| 2048 | CONH-S-CH(CH₂-p-MeOPh)CONHMe | |
| 2049 | CONHCH₂CH₂CONHMe | |
| 2050 | CONHCH₂CH₂CH₂CONHMe | |
| 2051 | CONHH-S-CH(CH₂CH₂OH)CONHMe | |
| 2052 | CONH-S-CH(CH₂)₃CH₃)CONHMe | |

TABLE 18

For the cyclic sulfonamide:

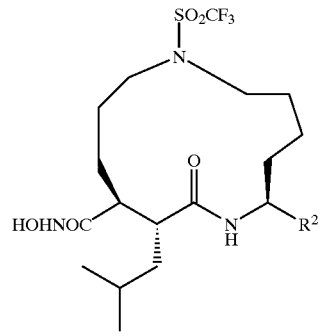

| Ex | R² (CI-MS) | ms |
|---|---|---|
| 2072 | CO₂Me | |
| 2073 | CO₂Et | |
| 2074 | CO₂iPr | |
| 2075 | CO₂(CH₂)₂OMe | |
| 2076 | CO₂(CH₂)₂Ph | |
| 2077 | CO₂-tBu | |
| 2078 | CO₂CH₂CONHMe | |
| 2079 | CH₂OH | |
| 2080 | CH₂OCH₂CH₃ | |
| 2081 | CH₂OCH₂CH₂CO₂CH₃ | |
| 2082 | CHOBn | |
| 2083 | CONH(CH₂)₂-2-pyridyl | |
| 2084 | CO(N-morpholinyl) | |

TABLE 18-continued

For the cyclic sulfonamide:

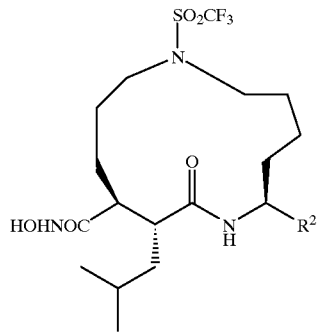

| Ex | R² (CI-MS) | ms |
|---|---|---|
| 2085 | CO(N-Me-N-piperazinyl) | |
| 2086 | CONH(CH₂)₂-(N-Me-N-piperazinyl) | |
| 2087 | CONH-cyclopropyl | |
| 2088 | CONH-cyclobutyl | |
| 2089 | CONH-cyclopentyl | |
| 2090 | CONH₂ | |
| 2091 | CONHiPr | |
| 2092 | CONH-tert-butyl | |
| 2093 | CONMe₂ | |
| 2094 | CONEt₂ | |
| 2095 | CONH-3-indazolyl | |
| 2096 | CONH-adamantyl | |
| 2097 | CONHCH₂(p-SO₂NH₂-Ph) | |
| 2098 | CONH(CH₂)₃-1-imidazolyl | |
| 2099 | CONHSO₂NH₂ | |
| 2100 | CONHSO₂CH₃ | |
| 2101 | CONHSO₂Ph | |
| 2102 | CONHSO₂Bn | |
| 2103 | CONHSO₂-N-Me-imidazolyl | |
| 2104 | CONHSO₂-p-NH₂Ph | |
| 2105 | CONHSO₂-p-MeOPh | |
| 2106 | CONHSO₂-p-F-Ph | |
| 2107 | CONH(CH₂)₂NHSO₂Me | |
| 2108 | CONH-cyclohexyl | |
| 2109 | CONH-2-imidozolyl | |
| 2110 | CH₂SO₂NHCH₃ | |
| 2111 | CH₂SO₂NHPh | |
| 2112 | CH₂SO₂NH-[4-NH₂PH] | |
| 2113 | 2-imidazolyl | |
| 2114 | 2-oxazoly | |
| 2115 | 2-thiazolyl | |
| 2116 | 2-benzimidazolyl | |
| 2117 | CONH-R-CH(CH₃)Ph | |
| 2118 | CONH-S-CH(CH₃)Ph | |
| 2119 | CONHCH₂CONHMe | |
| 2120 | CONH-S-CH(CH₃)CONHMe | |
| 2121 | CONH-R-CH(CH₃)CONHMe | |
| 2122 | CONH-S-CH(2-propyl)CONHMe | |
| 2123 | CONH-S-CH(CH₂SH)CONHMe | |
| 2124 | CONH-S-CH(CH₂OH)CONHMe | |
| 2125 | CONH-R-CH(CH₂OH)CONHMe | |
| 2126 | CONH-S-CH(CH₂O-t-Bu)CONHMe | |
| 2127 | CONH-R-CH(CH₂O-t-Bu)CONHMe | |
| 2128 | CONH-S-CH[CH₂CH(CH₃)₂]CONHMe | |
| 2129 | CONH(CH₂)₄NHSO₂Me | |
| 2130 | CONH(CH₂)₆NHSO₂ME | |
| 2131 | CONH-R-CH[CH₂CH(CH₃)₂]CONHMe | |
| 2132 | CONH-S-CH[(CH₂)₄NH₂]CONHMe | |
| 2133 | CONH-S-CH[(CH₂)₃NH₂]CONHMe | |
| 2134 | CONH-S-CH[(CH₂)₂NH₂]CONHMe | |
| 2135 | CONHMe | 503.3 |
| 2136 | CONHCH₂CONMe₂ | |
| 2137 | CONHCH₂CONHEt | |
| 2138 | CONHCH₂CONHEt₂ | |
| 2139 | CONHCH₂CONH-cyclopropyl | |
| 2140 | CONHCH₂CONH-cyclobutyl | |
| 2141 | CONHCH₂CONH-cyclopentyl | |
| 2142 | CONHCH₂CONH-cyclohexyl | |

TABLE 18-continued

For the cyclic sulfonamide:

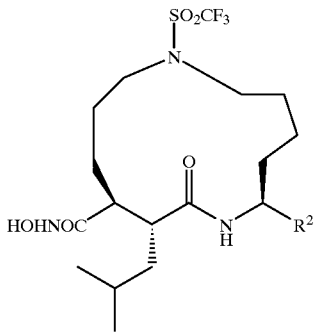

| Ex | R² (CI-MS) | ms |
|---|---|---|
| 2143 | CONHCH₂CONH-tert-butyl | |
| 2144 | CONH-S-CH(CH₂Ph)CONHMe | |
| 2145 | CONH-S-CH(CH₂-p-MeOPh)CONHMe | |
| 2146 | CONHCH₂CH₂CONHMe | |
| 2147 | CONHCH₂CH₂CH₂CONHMe | |
| 2148 | CONHH-S-CH(CH₂CH₂OH)CONHMe | |
| 2149 | CONH-S-CH(CH₂)₃CH₃)CONHMe | |

TABLE 19

For the cyclic sulfonamide:

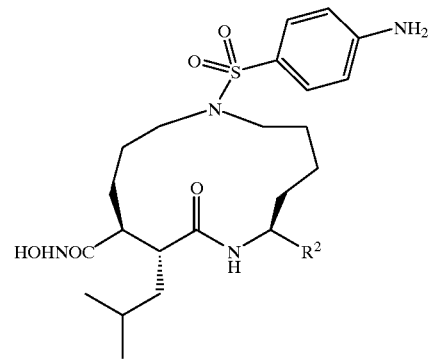

| Ex | R² (CI-MS) | ms |
|---|---|---|
| 2164 | CO₂Me | |
| 2165 | CO₂Et | |
| 2166 | CO₂IPr | |
| 2167 | CO₂(CH₂)₂OMe | |
| 2168 | CO₂(CH₂)₂Ph | |
| 2169 | CO₂-tBu | |
| 2170 | CO₂CH₂CONHMe | |
| 2171 | CH₂OH | |
| 2172 | CH₂OCH₂CH₃ | |
| 2173 | CH₂OCH₂CH₂CO₂CH₃ | |
| 2174 | CHOBn | |
| 2175 | CONH(CH₂)₂-2-pyridyl | |
| 2176 | CO(N-morpholinyl) | |
| 2177 | CO(N-Me-N-piperazinyl) | |
| 2178 | CONH(CH₂)₂-(N-Me-N-piperazinyl) | |
| 2179 | CONH-cyclopropyl | |
| 2180 | CONH-cyclopentyl | |
| 2181 | CONH₂ | |
| 2182 | CONHiPr | |
| 2183 | CONH-tert-butyl | |
| 2184 | CONMe₂ | |
| 2185 | CONEt₂ | |
| 2186 | CONH-3-indazolyl | |
| 2187 | CONH-adamantyl | |
| 2188 | CONHCH₂(p-SO₂NH₂-Ph) | |

TABLE 19-continued

For the cyclic sulfonamide:

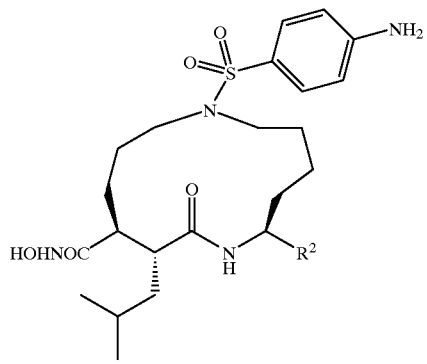

| Ex | R² (CI-MS) | ms |
|---|---|---|
| 2189 | CONH(CH₂)₃-1-imidazolyl | |
| 2190 | CONHSO₂NH₂ | |
| 2191 | CONHSO₂CH₃ | |
| 2192 | CONHSO₂Ph | |
| 2193 | CONHSO₂Bn | |
| 2194 | CONHSO₂-N-Me-imidazolyl | |
| 2195 | CONHSO₂-p-NH₂Ph | |
| 2196 | CONH-cyclobutyl | |
| 2197 | CONHSO₂-p-F-Ph | |
| 2198 | CONH(CH₂)₂NHSO₂Me | |
| 2199 | CONH-cyclohexyl | |
| 2200 | CONH-2-imidozolyl | |
| 2201 | CH₂SO₂NHCH₃ | |
| 2202 | CH₂SO₂NHPh | |
| 2203 | CH₂SO₂NH-[4-NH₂PH] | |
| 2204 | 2-imidazolyl | |
| 2205 | 2-oxazoly | |
| 2206 | 2-thiazolyl | |
| 2207 | 2-benzimidazolyl | |
| 2208 | CONH-R-CH(CH₃)Ph | |
| 2209 | CONH-S-CH(CH₃)Ph | |
| 2210 | CONHCH₂CONHMe | |
| 2211 | CONH-S-CH(CH₃)CONHMe | |
| 2212 | CONH-R-CH(CH₃)CONHMe | |
| 2213 | CONH-S-CH(2-propyl)CONHMe | |
| 2214 | CONH-S-CH(CH₂SH)CONHMe | |
| 2215 | CONH-S-CH(CH₂OH)CONHMe | |
| 2216 | CONH-R-CH(CH₂OH)CONHMe | |
| 2217 | CONH-S-CH(CH₂O-t-Bu)CONHMe | |
| 2218 | CONH-R-CH(CH₂O-t-Pu)CONHMe | |
| 2219 | CONHSO₂-p-MeOph | |
| 2220 | CONH-S-CH[CH₂CH(CH₃)₂]CONHMe | |
| 2221 | CONH(CH₂)₄NHSO₂Me | |
| 2222 | CONH(CH₂)₆NHSO₂ME | |
| 2223 | CONH-R-CH[CH₂CH(CH₃)₂]CONHMe | |
| 2224 | CONH-S-CH[(CH₂)₄NH₂]CONHMe | |
| 2225 | CONH-S-CH[(CH₂)₃NH₂]CONHMe | |
| 2226 | CONH-S-CH[(CH₂)₂NH₂]CONHMe | |
| 2227 | CONHMe | 526.3 |
| 2228 | CONHCH₂CONMe₂ | |
| 2229 | CONHCH₂CONHEt | |
| 2230 | CONHCH₂CONHEt₂ | |
| 2231 | CONHCH₂CONH-cyclopropyl | |
| 2232 | CONHCH₂CONH-cyclobutyl | |
| 2233 | CONHCH₂CONH-cyclopentyl | |
| 2234 | CONHCH₂CONH-cyclohexyl | |
| 2235 | CONHCH₂CONH-tert-butyl | |
| 2236 | CONH-S-CH(CH₂Ph)CONHMe | |
| 2237 | CONH-S-CH(CH₂-p-MeOPh)CONHMe | |
| 2238 | CONHCH₂CH₂CONHMe | |
| 2239 | CONHCH₂CH₂CH₂CONHMe | |
| 2240 | CONHH-S-CH(CH₂CH₂OH)CONHMe | |
| 2241 | CONH-S-CH(CH₂)₃CH₃)CONHMe | |

TABLE 20

For the cyclic sulfonamide:

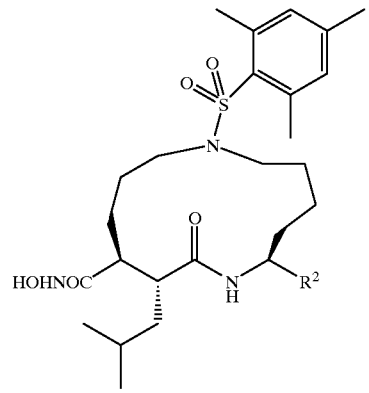

| Ex | R² (CI-MS) | ms |
|---|---|---|
| 2260 | CO₂Me | |
| 2261 | CO₂Et | |
| 2262 | CO₂iPr | |
| 2263 | CO₂(CH₂)₂OMe | |
| 2264 | CO₂(CH₂)₂Ph | |
| 2265 | CO₂-tBu | |
| 2266 | CO₂CH₂CONHMe | |
| 2267 | CH₂OH | |
| 2268 | CH₂OCH₂CH₃ | |
| 2269 | CH₂OCH₂CH₂CO₂CH₃ | |
| 2270 | CHOBn | |
| 2271 | CONH(CH₂)₂-2-pyridyl | |
| 2272 | CO(N-morpholinyl) | |
| 2273 | CO(N-Me-N-piperazinyl) | |
| 2274 | CONH(CH₂)₂-(N-Me-N-piperazinyl) | |
| 2275 | CONH-cyclopropyl | |
| 2276 | CONH-cyclopentyl | |
| 2277 | CONH₂ | |
| 2278 | CONHiPr | |
| 2279 | CONH-tert-butyl | |
| 2280 | CONMe₂ | |
| 2281 | CONEt₂ | |
| 2282 | CONH-3-indazolyl | |
| 2283 | CONH-adamantyl | |
| 2284 | CONHCH₂(p-SO₂NH₂-Ph) | |
| 2285 | CONH(CH₂)₃-1-imidazolyl | |
| 2286 | CONHSO₂NH₂ | |
| 2287 | CONHSO₂CH₃ | |
| 2288 | CONHSO₂Ph | |
| 2289 | CONHSO₂Bn | |
| 2290 | CONHSO₂-N-Me-imidazolyl | |
| 2291 | CONHSO₂-p-NH₂Ph | |
| 2292 | CONH-cyclobutyl | |
| 2293 | CONHSO₂-p-F-Ph | |
| 2294 | CONH(CH₂)₂NHSO₂Me | |
| 2295 | CONH-cyclohexyl | |
| 2296 | CONH-2-inudozolyl | |
| 2297 | CH₂SO₂NHCH₃ | |
| 2298 | CH₂SO₂NHPh | |
| 2299 | CH₂SO₂NH-[4-NH₂PH] | |
| 2300 | 2-imidazolyl | |
| 2301 | 2-oxazoly | |
| 2302 | 2-thiazolyl | |
| 2303 | 2-benzimidazolyl | |
| 2304 | CONH-R-CH(CH₃)Ph | |
| 2305 | CONH-S-CH(CH₃)Ph | |
| 2306 | CONHCH₂CONHMe | |
| 2307 | CONH-S-CH(CH₃)CONHMe | |
| 2308 | CONH-R-CH(CH₃)CONHMe | |
| 2309 | CONH-S-CH(2-propyl)CONHMe | |
| 2310 | CONH-S-CH(CH₂SH)CONHMe | |
| 2311 | CONH-S-CH(CH₂OH)CONHMe | |
| 2312 | CONH-R-CH(CH₂OH)CONHMe | |
| 2313 | CONH-S-CH(CH₂O-t-Bu)CONHMe | |
| 2314 | CONH-R-CH(CH₂O-t-Bu)CONHMe | |
| 2315 | CONHSO₂-p-MeOPh | |

TABLE 20-continued

For the cyclic sulfonamide:

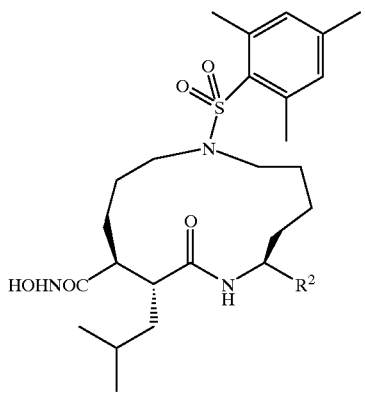

| Ex | R² (CI-MS) | ms |
|---|---|---|
| 2316 | CONH-S-CH[CH₂CH(CH₃)₂]CONHMe | |
| 2317 | CONH(CH₂)₄NHSO₂Me | |
| 2318 | CONH(CH₂)₆NHSO₂ME | |
| 2319 | CONH-R-CH[CH₂CH(CH₃)₂]CONHMe | |
| 2320 | CONH-S-CH[(CH₂)₄NH₂]CONHMe | |
| 2321 | CONH-S-CH[(CH₂)₃NH₂]CONHMe | |
| 2322 | CONH-S-CH[(CH₂)₂NH₂]CONHMe | |
| 2323 | CONHMe | 553.5 |
| 2324 | CONHCH₂CONMe₂ | |
| 2325 | CONHCH₂CONHEt | |
| 2326 | CONHCH₂CONHEt₂ | |
| 2327 | CONHCH₂CONH-cyclopropyl | |
| 2328 | CONHCH₂CONH-cyclobutyl | |
| 2329 | CONHCH₂CONH-cyclopentyl | |
| 2330 | CONHCH₂CONH-cyclohexyl | |
| 2331 | CONHCH₂CONH-tert-butyl | |
| 2332 | CONH-S-CH(CH₂Ph)CONHMe | |
| 2333 | CONH-S-CH(CH₂-p-MeOPh)CONHMe | |
| 2334 | CONHCH₂CH₂CONHMe | |
| 2335 | CONHCH₂CH₂CH₂CONHMe | |
| 2336 | CONHH-S-CH(CH₂CH₂OH)CONHMe | |
| 2337 | CONH-S-CH(CH₂)₃CH₃)CONHMe | |

TABLE 21

For the lactone:

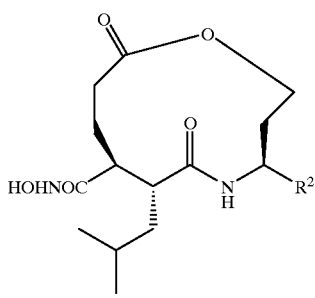

| Ex | R² (CI-MS) | ms |
|---|---|---|
| 2350 | CO₂Me | |
| 2351 | CO₂Et | |
| 2352 | CO₂iPr | |
| 2353 | CO₂(CH₂)₂OMe | |
| 2354 | CO₂(CH₂)₂Ph | |
| 2355 | CO₂-tBu | |
| 2356 | CO₂CH₂CONHMe | |
| 2357 | CH₂OH | |
| 2358 | CH₂OCH₂CH₃ | |
| 2359 | CH₂OCH₂CH₂CO₂CH₃ | |

TABLE 21-continued

For the lactone:

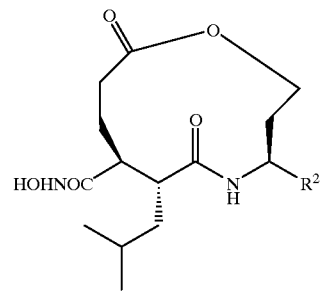

| Ex | R² (CI-MS) | ms |
|---|---|---|
| 2360 | CHOBn | |
| 2361 | CONH(CH₂)₂-2-pyridyl | |
| 2362 | CO(N-morpholinyl) | |
| 2363 | CO(N-Me-N-piperazinyl) | |
| 2364 | CONH(CH₂)₂-(N-Me-N-piperazinyl) | |
| 2365 | CONH-cyclopropyl | |
| 2366 | CONH-cyclobutyl | |
| 2367 | CONHSO₂-P-F-Ph | |
| 2368 | CONH-cyclopentyl | |
| 2369 | CONH₂ | |
| 2370 | CONHiPr | |
| 2371 | CONH-tert-butyl | |
| 2372 | CONMe₂ | |
| 2373 | CONEt₂ | |
| 2374 | CONH-3-indazolyl | |
| 2375 | CONH-adamantyl | |
| 2376 | CONHCH₂(p-SO₂NH₂-Ph) | |
| 2377 | CONH(CH₂)3-1-imidazolyl | |
| 2378 | CONHSO₂NH₂ | |
| 2379 | CONHSO₂CH₃ | |
| 2380 | CONHSO₂Ph | |
| 2381 | CONHSO₂Bn | |
| 2382 | CONHSO₂-N-Me-imidazolyl | |
| 2383 | CONHSO₂-P-NH₂Ph | |
| 2384 | CONHSO₂-p-MeOPh | |
| 2385 | CONH-S-CH[CH₂CH(CH₃)₂]CONHMe | |
| 2386 | CONH(CH₂)₂NHSO₂Me | |
| 2387 | CONH-cyclohexyl | |
| 2388 | CONH-2-imidozolyl | |
| 2389 | CH₂SO₂NHCH₃ | |
| 2390 | CH₂SO₂NHPh | |
| 2391 | CH₂SO₂NH-[4-NH₂PH] | |
| 2392 | 2-imidazolyl | |
| 2393 | 2-oxazoly | |
| 2394 | 2-thiazolyl | |
| 2395 | 2-benzimidazolyl | |
| 2396 | CONH-R-CH(CH3)Ph | |
| 2397 | CONH-S-CH(CH3)Ph | |
| 2398 | CONHCH₂CONHMe | |
| 2399 | CONH-S-CH(CH₃)CONHMe | |
| 2400 | CONH-R-CH(CH₃)CONHMe | |
| 2401 | CONH-S-CH(2-propyl)CONHMe | |
| 2402 | CONH-S-CH(CH₂SH)CONHMe | |
| 2403 | CONH-S-CH(CH₂OH)CONHMe | |
| 2404 | CONH-R-CH(CH₂OH)CONHMe | |
| 2405 | CONH-S-CH(CH₂O-t-Bu)CONHMe | |
| 2406 | CONH-R-CH(CH₂O-t-Bu)CONHMe | |
| 2407 | CONH(CH₂)₄NHSO₂Me | |
| 2408 | CONH(CH₂)₆NHSO₂ME | |
| 2409 | CONH-R-CH[CH₂CH(CH₃)₂] CONHMe | |
| 2410 | CONH-S-CH[(CH₂)₄NH₂]CONHMe | |
| 2411 | CONH-S-CH[(CH₂)₃NH₂]CONHMe | |
| 2412 | CONH-S-CH[(CH₂)₂NH₂]CONHMe | |
| 2413 | CONHMe | 372.3 |
| 2414 | CONHCH₂CONMe₂ | |
| 2415 | CONHCH₂CONHEt | |
| 2416 | CONHCH₂CONHEt₂ | |
| 2417 | CONHCH₂CONH-cyclopropyl | |
| 2418 | CONHCH₂CONH-cyclobutyl | |
| 2419 | CONHCH₂CONH-cyclopentyl | |

TABLE 21-continued

For the lactone:

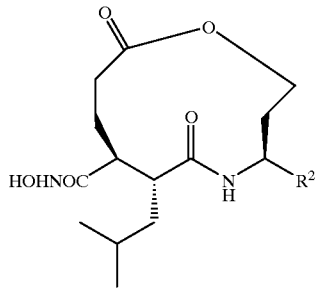

| Ex | R² (CI-MS) | ms |
|---|---|---|
| 2420 | CONHCH₂CONH-cyclohexyl | |
| 2421 | CONHCH₂CONH-tert-butyl | |
| 2422 | CONH-S-CH(CH₂Ph)CONHMe | |
| 2423 | CONH-S-CH(CH₂-p-MeOPh) CONHMe | |
| 2424 | CONHCH₂CH₂CONHMe | |
| 2425 | CONHCH₂CH₂CH₂CONHMe | |
| 2426 | CONHH-S-CH(CH₂CH₂OH)CONHMe | |
| 2427 | CONH-S-CH(CH₂)₃CH₃)CONHMe | |

TABLE 22

For the lactam:

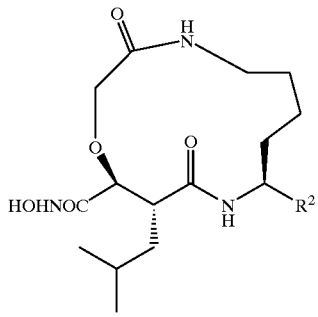

| Ex | R² (CI-MS) | ms |
|---|---|---|
| 2440 | CO₂Me | |
| 2441 | CO₂Et | |
| 2442 | CO₂iPr | |
| 2443 | CO₂(CH₂)₂OMe | |
| 2444 | CO₂(CH₂)₂Ph | |
| 2445 | CO₂-tBu | |
| 2446 | CO₂CH₂CONHMe | |
| 2447 | CH₂OH | |
| 2448 | CH₂OCH₂CH₃ | |
| 2449 | CH₂OCH₂CH₂CO₂CH₃ | |
| 2450 | CHOBn | |
| 2451 | CONH(CH₂)₂-2-pyridyl | |
| 2452 | CO(N-morpholinyl) | |
| 2453 | CO(N-Me-N-piperazinyl) | |
| 2454 | CONH(CH₂)₂-(N-Me-N-piperazinyl) | |
| 2455 | CONH-cyclopropyl | |
| 2456 | CONH-cyclobutyl | |
| 2457 | CONHSO₂-p-F-Ph | |
| 2458 | CONH-cyclopentyl | |
| 2459 | CONH₂ | |
| 2460 | CONHiPr | |
| 2461 | CONH-tert-butyl | |
| 2462 | CONMe₂ | |
| 2463 | CONEt₂ | |
| 2464 | CONH-3-indazolyl | |
| 2465 | CONH-adamantyl | |
| 2466 | CONHCH₂(p-SO₂NH₂-Ph) | |
| 2467 | CONH(CH₂)₃-1-imidazolyl | |

TABLE 22-continued

For the lactam:

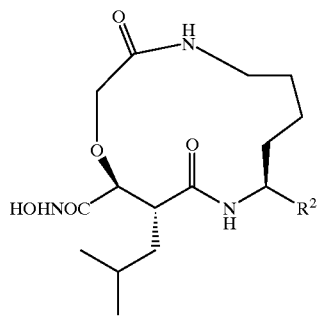

| Ex | R² (CI-MS) | ms |
|---|---|---|
| 2468 | CONHSO₂NH₂ | |
| 2469 | CONHSO₂CH₃ | |
| 2470 | CONHSO₂Ph | |
| 2471 | CONHSO₂Bn | |
| 2472 | CONHSO₂-N-Me-imidazolyl | |
| 2473 | CONHSO₂-p-NH₂Ph | |
| 2474 | CONHSO₂-p-MeOPh | |
| 2475 | CONH-S-CH[CH₂CH(CH₃)₂]CONHMe | |
| 2476 | CONH(CH₂)₂NHSO₂Me | |
| 2477 | CONH-cyclohexyl | |
| 2478 | CONH-2-imidozolyl | |
| 2479 | CH₂SO₂NHCH₃ | |
| 2480 | CH₂SO₂NHPh | |
| 2481 | CH₂SO₂NH-[4-NH₂PH] | |
| 2482 | 2-imidazolyl | |
| 2483 | 2-oxazoly | |
| 2484 | 2-thiazolyl | |
| 2485 | 2-benzimidazolyl | |
| 2486 | CONH-R-CH(CH₃)Ph | |
| 2487 | CONH-S-CH(CH₃)Ph | |
| 2488 | CONHCH₂CONHMe | |
| 2489 | CONH-S-CH(CH₃)CONHMe | |
| 2490 | CONH-R-CH(CH₃)CONHMe | |
| 2491 | CONH-S-CH(2-propyl)CONHMe | |
| 2492 | CONH-S-CH(CH₂SH)CONHMe | |
| 2493 | CONH-S-CH(CH₂OH)CONHMe | |
| 2494 | CONH-R-CH(CH₂OH)CONHMe | |
| 2495 | CONH-S-CH(CH₂O-t-Bu)CONHMe | |
| 2496 | CONH-R-CH(CH₂O-t-Bu)CONHMe | |
| 2497 | CONH(CH₂)₄NHSO₂Me | |
| 2498 | CONH(CH₂)₆NHSO₂ME | |
| 2499 | CONH-R-CH[CH₂CH(CH₃)₂]CONHMe | |
| 2500 | CONH-S-CH[(CH₂₄NH₂]CONHMe | |
| 2501 | CONH-S-CH[(CH₂)₃NH₂]CONHMe | |
| 2502 | CONH-S-CH[(CH₂)₂NH₂]CONHMe | |
| 2503 | CONHCH₂CONHMe | |
| 2504 | CONHCH₂CONMe₂ | |
| 2505 | CONHCH₂CONHEt | |
| 2506 | CONHCH₂CONHEt₂ | |
| 2507 | CONHCH₂CONH-cyclopropyl | |
| 2508 | CONHCH₂CONH-cyclobutyl | |
| 2509 | CONHCH₂CONH-cyclopentyl | |
| 2510 | CONHCH₂CONH-cyclohexyl | |
| 2511 | CONHCH₂CONH-tert-butyl | |
| 2512 | CONH-S-CH(CH₂Ph)CONHMe | |
| 2513 | CONH-S-CH(CH₂-p-MeOPh)CONHMe | |
| 2514 | CONHCH₂CH₂CONHMe | |
| 2515 | CONHCH₂CH₂CH₂CONHMe | |
| 2516 | CONHH-S-CH(CH₂CH₂OH)CONHMe | |
| 2517 | CONH-S-CH(CH₂)₃CH₃)CONHMe | |
| 2518 | CONHMe | 387.3 |
| 2519 | CONHPh | 449.3 |

TABLE 23

For the lactam:

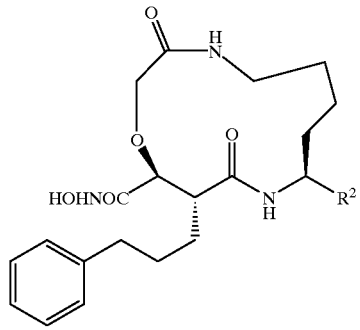

| Ex | R² (CI-MS) | ms |
|---|---|---|
| 2530 | CO₂Me | |
| 2531 | CO₂Et | |
| 2532 | CO₂iPr | |
| 2533 | CO₂(CH₂)₂OMe | |
| 2534 | CO₂(CH₂)₂Ph | |
| 2535 | CO₂-tBu | |
| 2536 | CO₂CH₂CONHMe | |
| 2537 | CH₂OH | |
| 2538 | CH₂OCH₂CH₃ | |
| 2539 | CH₂OCH₂CH₂CO₂CH₃ | |
| 2540 | CHOBn | |
| 2541 | CONH(CH₂)₂-2-pyridyl | |
| 2542 | CO(N-morpholinyl) | |
| 2543 | CO(N-Me-N-piperazinyl) | |
| 2544 | CONH(CH₂)₂-(N-Me-N-piperazinyl) | |
| 2545 | CONH-cyclopropyl | |
| 2546 | CONH-cyclobutyl | |
| 2547 | CONH-cyclopentyl | |
| 2548 | CONH₂ | |
| 2549 | CONHiPr | |
| 2550 | CONH-tert-butyl | |
| 2551 | CONMe₂ | |
| 2552 | CONEt₂ | |
| 2553 | CONH-3-indazolyl | |
| 2554 | CONH-adamantyl | |
| 2555 | CONHCH₂(p-SO₂NH₂-Ph) | |
| 2556 | CONH(CH₂)₃-1-imidazolyl | |
| 2557 | CONHSO₂NH₂ | |
| 2558 | CONHSO₂CH₃ | |
| 2559 | CONHSO₂Ph | |
| 2560 | CONHSO₂Bn | |
| 2561 | CONHSO₂-N-Me-imidazolyl | |
| 2562 | CONHSO₂-p-NH₂Ph | |
| 2563 | CONHSO₂-p-MeOPh | |
| 2564 | CONHSO₂-p-F-Ph | |
| 2565 | CONH(CH₂)₂NHSO₂Me | |
| 2566 | CONH-cyclohexyl | |
| 2567 | CONH-2-imidozolyl | |
| 2568 | CH₂SO₂NHCH₃ | |
| 2569 | CH₂SO₂NHPh | |
| 2570 | CH₂SO₂NH-[4-NH₂PH] | |
| 2571 | 2-imidazolyl | |
| 2572 | 2-oxazoly | |
| 2573 | 2-thiazolyl | |
| 2574 | 2-benzimidazolyl | |
| 2575 | CONH-R-CH(CH₃)Ph | |
| 2576 | CONH-S-CH(CH₃)Ph | |
| 2577 | CONHCH₂CONHMe | |
| 2578 | CONH-S-CH(CH₃)CONHMe | |
| 2579 | CONH-R-CH(CH₃)CONHMe | |
| 2580 | CONH-S-CH(2-propyl)CONHMe | |
| 2581 | CONH-S-CH(CH₂SH)CONHMe | |
| 2582 | CONH-S-CH(CH₂OH)CONHMe | |
| 2583 | CONH-R-CH(CH₂OH)CONHMe | |
| 2584 | CONH-S-CH(CH₂O-t-Bu)CONHMe | |
| 2585 | CONH-R-CH(CH₂O-t-Bu)CONHMe | |
| 2586 | CONH-S-CH[CH₂CH(CH₃)₂]CONHMe | |
| 2587 | CONH(CH₂)₄NHSO₂Me | |
| 2588 | CONH(CH₂)₆NHSO₂ME | |

TABLE 23-continued

For the lactam:

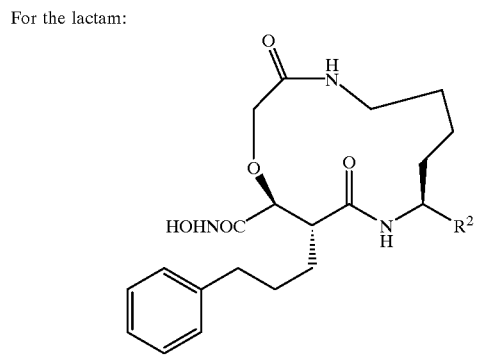

| Ex | R² (CI-MS) | ms |
|---|---|---|
| 2589 | CONH-R-CH[CH₂CH(CH₃)₂]CONHMe | |
| 2590 | CONH-S-CH[(CH₂)₄NH₂]CONHMe | |
| 2591 | CONH-S-CH[(CH₂)₃NH₂]CONHMe | |
| 2592 | CONH-S-CH[(CH₂)₂NH₂]CONHMe | |
| 2593 | CONHCH₂CONHMe | |
| 2594 | CONHCH₂CONMe₂ | |
| 2595 | CONHCH₂CONHEt | |
| 2596 | CONHCH₂CONHEt₂ | |
| 2597 | CONHCH₂CONH-cyclopropyl | |
| 2598 | CONHCH₂CONH-cyclobutyl | |
| 2599 | CONHCH₂CONH-cyclopentyl | |
| 2600 | CONHCH₂CONH-cyclohexyl | |
| 2601 | CONHCH₂CONH-tert-butyl | |
| 2602 | CONH-S-CH(CH₂Ph)CONHMe | |
| 2603 | CONH-S-CH(CH₂-p-MeOPh)CONHMe | |
| 2604 | CONHCH₂CH₂CONHMe | |
| 2605 | CONHCH₂CH₂CH₂CONHMe | |
| 2606 | CONHH-S-CH(CH₂CH₂OH)CONHMe | |
| 2607 | CONH-S-CH(CH₂)₃CH₃)CONHMe | |

TABLE 24

For the lactam:

| Ex | R² (CI-MS) | ms |
|---|---|---|
| 2630 | CO₂Me | |
| 2631 | CO₂Et | |
| 2632 | CO₂iPr | |
| 2633 | CO₂(CH₂)₂OMe | |
| 2634 | CO₂(CH₂)₂Ph | |
| 2635 | CO₂-tBu | |
| 2636 | CO₂CH₂CONHMe | |
| 2637 | CH₂OH | |
| 2638 | CH₂OCH₂CH₃ | |
| 2639 | CH₂OCH₂CH₂CO₂CH₃ | |
| 2640 | CHOBn | |
| 2641 | CONH(CH₂)₂-2-pyridyl | |
| 2642 | CO(N-morpholinyl) | |
| 2643 | CO(N-Me-N-piperazinyl) | |
| 2644 | CONH(CH₂)₂-(N-Me-N-piperazinyl) | |

TABLE 24-continued

For the lactam:

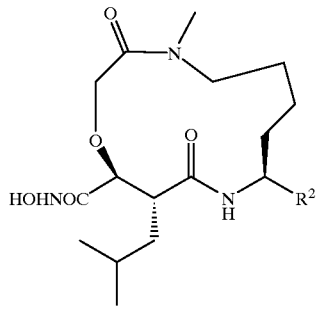

| Ex | R² (CI-MS) | ms |
|---|---|---|
| 2645 | CONH-cyclopropyl | |
| 2646 | CONH-cyclobutyl | |
| 2647 | CONH-cyclopentyl | |
| 2648 | CONH$_2$ | |
| 2649 | CONHiPr | |
| 2650 | CONH-tert-butyl | |
| 2651 | CONMe$_2$ | |
| 2652 | CONEt$_2$ | |
| 2653 | CONH-3-indazolyl | |
| 2654 | CONH-adamantyl | |
| 2655 | CONHCH$_2$(p-SO$_2$NH$_2$-Ph) | |
| 2656 | CONH(CH$_2$)$_3$-1-imidazolyl | |
| 2657 | CONHSO$_2$NH$_2$ | |
| 2658 | CONHSO$_2$CH$_3$ | |
| 2659 | CONHSO$_2$Ph | |
| 2660 | CONHSO$_2$Bn | |
| 2661 | CONHSO$_2$-N-Me-imidazolyl | |
| 2662 | CONHSO$_2$-p-NH$_2$Ph | |
| 2663 | CONHSO$_2$-p-MeOPh | |
| 2664 | CONHSO$_2$-p-F-Ph | |
| 2665 | CONH(CH$_2$)$_2$NHSO$_2$Me | |
| 2666 | CONH-cyclohexyl | |
| 2667 | CONH-2-imidozolyl | |
| 2668 | CH$_2$SO$_2$NHCH$_3$ | |
| 2669 | CH$_2$SO$_2$NHPh | |
| 2670 | CH$_2$SO$_2$NH-[4-NH$_2$PH] | |
| 2671 | 2-imidazolyl | |
| 2672 | 2-oxazoly | |
| 2673 | 2-thiazolyl | |
| 2674 | 2-benzimidazolyl | |
| 2675 | CONH-R-CH(CH$_3$)Ph | |
| 2676 | CONH-S-CH(CH$_3$)Ph | |
| 2677 | CONHCH$_2$CONHMe | |
| 2678 | CONH-S-CH(CH$_3$)CONHMe | |
| 2679 | CONH-R-CH(CH$_3$)CONHMe | |
| 2680 | CONH-S-CH(2-propyl)CONHMe | |
| 2681 | CONH-S-CH(CH$_2$SH)CONHMe | |
| 2682 | CONH-S-CH(CH$_2$OH)CONHMe | |
| 2683 | CONH-R-CH(CH$_2$OH)CONHMe | |
| 2684 | CONH-S-CH(CH$_2$O-t-Bu)CONHMe | |
| 2685 | CONH-R-CH(CH$_2$O-t-Bu)CONHMe | |
| 2686 | CONH-S-CH[CH$_2$CH(CH$_3$)$_2$]CONHMe | |
| 2687 | CONH(CH$_2$)$_4$NHSO$_2$Me | |
| 2688 | CONH(CH$_2$)$_6$NHSO$_2$ME | |
| 2689 | CONH-R-CH[CH$_2$CH(CH$_3$)$_2$]CONHMe | |
| 2690 | CONH-S-CH[(CH$_2$)$_4$NH$_2$]CONHMe | |
| 2691 | CONH-S-CH[(CH$_2$)$_3$NH$_2$]CONHMe | |
| 2692 | CONH-S-CH[(CH$_2$)$_2$NH$_2$]CONHMe | |
| 2693 | CONHCH$_2$CONHMe | |
| 2694 | CONHCH$_2$CONMe$_2$ | |
| 2695 | CONHCH$_2$CONHEt | |
| 2696 | CONHCH$_2$CONHEt$_2$ | |
| 2697 | CONHCH$_2$CONH-cyclopropyl | |
| 2698 | CONHCH$_2$CONH-cyclobutyl | |
| 2699 | CONHCH$_2$CONH-cyclopentyl | |
| 2700 | CONHCH$_2$CONH-cyclohexyl | |
| 2701 | CONHCH$_2$CONH-tert-butyl | |
| 2702 | CONH-S-CH(CH$_2$Ph)CONHMe | |
| 2703 | CONH-S-CH(CH$_2$-p-MeOPh)CONHMe | |
| 2704 | CONHCH$_2$CH$_2$CONHMe | |

TABLE 24-continued

For the lactam:

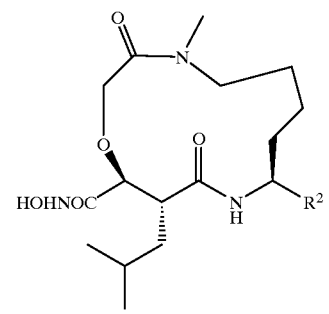

| Ex | R² (CI-MS) | ms |
|---|---|---|
| 2705 | CONHCH$_2$CH$_2$CH$_2$CONHMe | |
| 2706 | CONHH-S-CH(CH$_2$CH$_2$OH)CONHMe | |
| 2707 | CONH-S-CH(CH$_2$)$_3$CH$_3$)CONHMe | |
| 2708 | CONHMe | 401.6 |

TABLE 25

For the lactam:

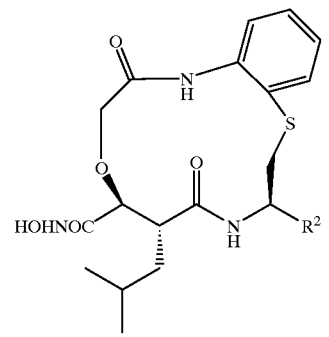

| Ex | R² (CI-MS) | ms |
|---|---|---|
| 2730 | CO$_2$Me | |
| 2731 | CO$_2$Et | |
| 2732 | CO$_2$iPr | |
| 2733 | CO$_2$(CH$_2$)$_2$OMe | |
| 2734 | CO$_2$(CH$_2$)$_2$Ph | |
| 2735 | CO$_2$-tBu | |
| 2736 | CO$_2$CH$_2$CONHMe | |
| 2737 | CH$_2$OH | |
| 2738 | CH$_2$OCH$_2$CH$_3$ | |
| 2739 | CH$_2$OCH$_2$CH$_2$CO$_2$CH$_3$ | |
| 2740 | CHOBn | |
| 2741 | CONH(CH$_2$)$_2$-2-pyridyl | |
| 2742 | CO(N-morpholinyl) | |
| 2743 | CO(N-Me-N-piperazinyl) | |
| 2744 | CONH(CH$_2$)$_2$-(N-Me-N-piperazinyl) | |
| 2745 | CONH-cyclopropyl | |
| 2746 | CONH-cyclobutyl | |
| 2747 | CONH-cyclopentyl | |
| 2748 | CONH$_2$ | |
| 2749 | CONHiPr | |
| 2750 | CONH-tert-butyl | |
| 2751 | CONMe$_2$ | |
| 2752 | CONEt$_2$ | |
| 2753 | CONH-3-indazolyl | |
| 2754 | CONH-adamantyl | |
| 2755 | CONHCH$_2$(p-SO$_2$NH$_2$-Ph) | |
| 2756 | CONH(CH$_2$)$_3$-1-imidazolyl | |
| 2757 | CONHSO$_2$NH$_2$ | |
| 2758 | CONHSO$_2$CH$_3$ | |
| 2759 | CONHSO$_2$Ph | |

TABLE 25-continued

For the lactam:

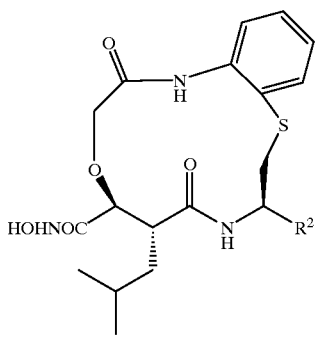

| Ex | R² (CI-MS) | ms |
|---|---|---|
| 2760 | CONHSO₂Bn | |
| 2761 | CONHSO₂-N-Me-imidazolyl | |
| 2762 | CONHSO₂-p-NH₂Ph | |
| 2763 | CONHSO₂-p-MeOPh | |
| 2764 | CONHSO₂-p-F-Ph | |
| 2765 | CONH(CH₂)₂NHSO₂Me | |
| 2766 | CONH-cyclohexyl | |
| 2767 | CONH-2-imidozolyl | |
| 2768 | CH₂SO₂NHCH₃ | |
| 2769 | CH₂SO₂NHPh | |
| 2770 | CH₂SO₂NH-[4-NH₂PH] | |
| 2771 | 2-imidazolyl | |
| 2772 | 2-oxazoly | |
| 2773 | 2-thiazolyl | |
| 2774 | 2-benzimidazolyl | |
| 2775 | CONH-R-CH(CH₃)Ph | |
| 2776 | CONH-S-CH(CH₃)Ph | |
| 2777 | CONHCH₂CONHMe | |
| 2778 | CONH-S-CH(CH₃)CONHMe | |
| 2779 | CONH-R-CH(CH₃)CONHMe | |
| 2780 | CONH-S-CH(2-propyl)CONHMe | |
| 2781 | CONH-S-CH(CH₂SH)CONHMe | |
| 2782 | CONH-S-CH(CH₂OH)CONHMe | |
| 2783 | CONH-R-CH(CH₂OH)CONHMe | |
| 2784 | CONH-S-CH(CH₂O-t-Bu)CONHMe | |
| 2785 | CONH-R-CH(CH₂O-t-Bu)CONHMe | |
| 2786 | CONH-S-CH[CH₂CH(CH₃)₂]CONHMe | |
| 2787 | CONH(CH₂)₄NHSO₂Me | |
| 2789 | CONH(CH₂)₆NHSO₂ME | |
| 2790 | CONH-R-CH[CH₂CH(CH₃)₂]CONHMe | |
| 2791 | CONH-S-CH[(CH₂)₄NH₂]CONHMe | |
| 2792 | CONH-S-CH[(CH₂)₃NH₂]CONHMe | |
| 2793 | CONH-S-CH[(CH₂)₂NH₂]CONHMe | |
| 2794 | CONHCH₂CONHMe | |
| 2795 | CONHCH₂CONMe₂ | |
| 2796 | CONHCH₂CONHEt | |
| 2797 | CONHCH₂CONHEt₂ | |
| 2798 | CONHCH₂CONH-cyclopropyl | |
| 2799 | CONHCH₂CONH-cyclobutyl | |
| 2800 | CONHCH₂CONH-cyclopentyl | |
| 2801 | CONHCH₂CONH-cyclohexyl | |
| 2802 | CONHCH₂CONH-tert-butyl | |
| 2803 | CONH-S-CH(CH₂Ph)CONHMe | |
| 2804 | CONH-S-CH(CH₂-p-MeOPh)CONHMe | |
| 2805 | CONHCH₂CH₂CONHMe | |
| 2806 | CONHCH₂CH₂CH₂CONHMe | |
| 2807 | CONHH-S-CH(CH₂CH₂OH)CONHMe | |
| 2808 | CONH-S-CH(CH₂)₃CH₃)CONHMe | |
| 2809 | CONHMe | 475 |

TABLE 26

For the lactam:

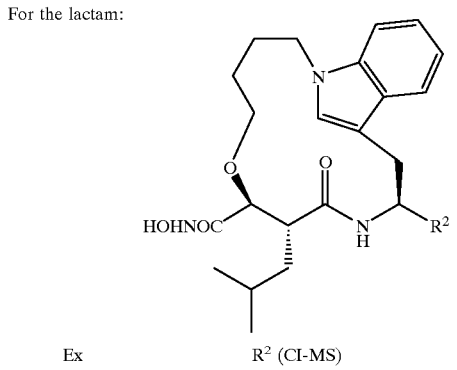

| Ex | R² (CI-MS) | ms |
|---|---|---|
| 2820 | CO₂Me | |
| 2821 | CO₂Et | |
| 2822 | CO₂iPr | |
| 2823 | CO₂(CH₂)₂OMe | |
| 2824 | CO₂(CH₂)₂Ph | |
| 2825 | CO₂-tBu | |
| 2826 | CO₂CH₂CONHMe | |
| 2827 | CH₂OH | |
| 2828 | CH₂OCH₂CH₃ | |
| 2829 | CH₂OCH₂CH₂CO₂CH₃ | |
| 2830 | CHOBn | |
| 2831 | CONH(CH₂)₂-2-pyridyl | |
| 2832 | CO(N-morpholinyl) | |
| 2833 | CO(N-Me-N-piperazinyl) | |
| 2834 | CONH(CH₂)₂-(N-Me-N-piperazinyl) | |
| 2835 | CONH-cyclopropyl | |
| 2836 | CONH-cyclobutyl | |
| 2837 | CONH-cyclopentyl | |
| 2838 | CONH₂ | |
| 2839 | CONHiPr | |
| 2840 | CONH-tert-butyl | |
| 2841 | CONMe₂ | |
| 2842 | CONEt₂ | |
| 2843 | CONH-3-indazolyl | |
| 2844 | CONH-adamantyl | |
| 2845 | CONHCH₂(P-SO₂NH₂-Ph) | |
| 2846 | CONH(CH₂)₃-1-imidazolyl | |
| 2847 | CONHSO₂NH₂ | |
| 2848 | CONHSO₂CH₃ | |
| 2849 | CONHSO₂Ph | |
| 2850 | CONHSO₂Bn | |
| 2851 | CONHSO₂-N-Me-imidazolyl | |
| 2852 | CONHSO₂-p-NH₂Ph | |
| 2853 | CONHSO₂-p-MeOPh | |
| 2854 | CONHSO₂-p-F-Ph | |
| 2855 | CONH(CH₂)₂NHSO₂Me | |
| 2856 | CONH-cyclohexyl | |
| 2857 | CONH-2-imidozolyl | |
| 2858 | CH₂SO₂NHCH₃ | |
| 2859 | CH₂SO₂NHPh | |
| 2860 | CH₂SO₂NH-[4-NH₂PH] | |
| 2861 | 2-imidazolyl | |
| 2862 | 2-oxazoly | |
| 2863 | 2-thiazolyl | |
| 2864 | 2-benzimidazolyl | |
| 2865 | CONH-R-CH(CH₃)Ph | |
| 2866 | CONH-S-CH(CH₃)Ph | |
| 2867 | CONHCH₂CONHMe | |
| 2868 | CONH-S-CH(CH₃)CONHMe | |
| 2869 | CONH-R-CH(CH₃)CONHMe | |
| 2870 | CONH-S-CH(2-propyl)CONHMe | |
| 2871 | CONH-S-CH(CH₂SH)CONHMe | |
| 2872 | CONH-S-CH(CH₂OH)CONHMe | |
| 2873 | CONH-R-CH(CH₂OH)CONHMe | |
| 2874 | CONH-S-CH(CH₂O-t-Bu)CONHMe | |
| 2875 | CONH-R-CH(CH₂O-t-Bu)CONHMe | |
| 2876 | CONH-S-CH[CH₂CH(CH₃)₂]CONHMe | |
| 2877 | CONH(CH₂)₄NHSO₂Me | |
| 2878 | CONH(CH₂)₆NHSO₂ME | |
| 2879 | CONH-R-CH[CH₂CH(CH₃)₂]CONHMe | |

TABLE 27

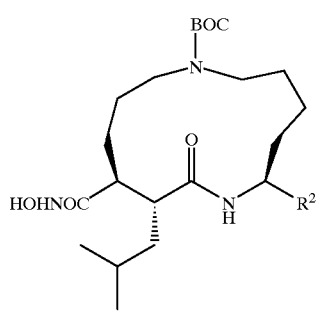

| Ex | R² (CI-MS) | ms |
|---|---|---|
| 2880 | CONHMe | 471.5 |

TABLE 28

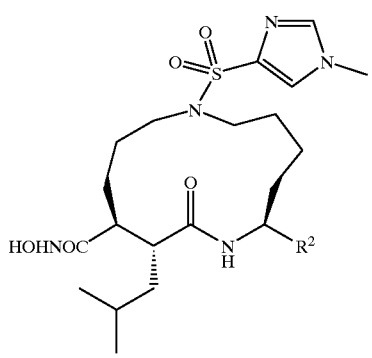

| Ex | R² (CI-MS) | ms |
|---|---|---|
| 2890 | CONHMe | 515.4 |

TABLE 29

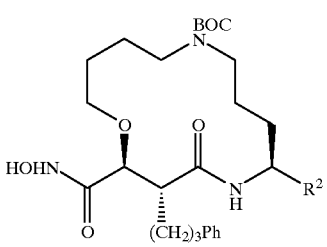

| Ex | R² (CI-MS) | ms |
|---|---|---|
| 2900 | CONHMe | 549.3 |

TABLE 30

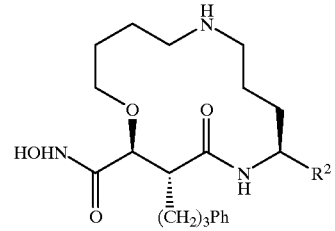

| Ex | R² (CI-MS) | ms |
|---|---|---|
| 2910 | CONHMe | 449.4 |

TABLE 31

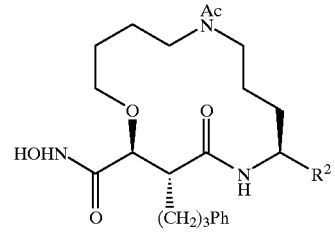

| Ex | R² (CI-MS) | ms |
|---|---|---|
| 2920 | CONHMe | 491.4 |

TABLE 32

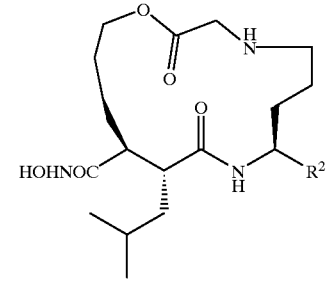

| Ex | R² | MS (ESI) |
|---|---|---|
| 2930 | COHCH₂CON-morphlino | 527.6 |
| 2931 | CONHCH₂CO[N-hydroxypiperidine] | 541.7 |
| 2934 | CONHCH₂CON-(4-methylpiperazino) | 541.3 (M + 1) |
| 2935 | CONHCH(CH₃)CON-morpholino | 564.3 (M + 1 + Na) |
| 2936 | CONHCH(isopropyl)CON-morpholino | 592.2 (M + 1 + Na) |
| 2937 | CONHCH(tert-butyl)CON-morpholino | 606.4 (M + 1 + Na) |
| 2938 | CONHCH₂CH₂CON-morpholino | 564.3 (M + 1 + Na) |
| 2939 | CONHCH₂CH₂OCON-morpholino | 580.3 (M + 1 + Na) |
| 2940 | CONHCH₂CH(OH)Ph | 543.3 (M + 1 + Na) |
| 2941 | CONHCH₂CON-(4-benzylpiperazino) | 617.3 (M + 1) |
| 2942 | CONHCH₂CON-(4-phenylpiperazino) | 603.3 (M + 1) |
| 2943 | CONHCH₂CON-[4-(2-pyridyl)morpholino] | 604.4 (M + 1) |
| 2944 | CONHCH₂CH(S-NHCOOCH₂CH₂-cyclopropane)COOH | 600.3 (M + 1) |
| 2945 | CONHCH₂CON-[4-(1-piperidinyl)- | 609.4 (M + 1) |
| 2946 | CONHCH₂CH(R-CH₃)OCON-morpholino | 572.3 (M + 1) |
| 2947 | CONHCH₂CH(S-CH₃)OCON-morpholino | 572.3 (M + 1) |
| 2948 | CONH-2-thiazole-4-acetic acid | 564.2 (M + 1 + Na) |
| 2949 | CONHCH₂CH(S-NHCOOCH₂CH₂-cyclopropane)CON(CH₃)₂ | 627.3 (M + 1) |
| 2950 | CONHCH₂CH(S-NHCOOCH₂CH₂- | 669.3 (M + 1) |

TABLE 32-continued

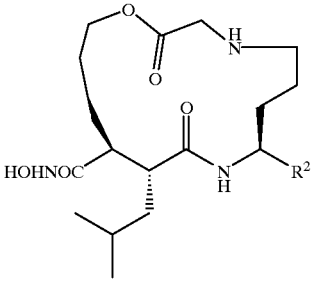

| Ex | R² | MS (ESI) |
|---|---|---|
| | cyclopropane)CON-morpholino | |
| 2951 | CONH-2-thiazole-4-CH₂CON-morpholino | 611.2 (M + 1) |
| 2952 | CONHCH(CH₂OH)CON-morpholino | 558.2 (M + 1) |
| 2953 | CONHCH₂CON-morpholino-3-carboxylic acid | 592.2 (M + 1 + Na) |
| 2954 | CONHCH₂CON-(2,6-dimethylmorpholino) | 556.4 (M + 1) |
| 2955 | CONHCH₂CON-(4-ethycarbonylpiperazino) | 599.4 (M + 1) |
| 2956 | CONHCH₂CON-(4-ethoxycarbonyl-piperidino) | 598.4 (M + 1) |
| 2957 | CONH-[4-(4-morpholinyl)Ph] | 562.3 (M + 1) |
| 2958 | CONHCH₂CONH-[4-(4-morpholinyl)Ph] | 619.4 (M + 1) |
| 2959 | CONHCH₂CON-piperidine-4-carboxylic acid | 592.3 (M + 1 + Na) |
| 2960 | CONHCH₃ | [M + Na]⁺ = 437 |
| 2961 | CONH-Ala-NHCH₃ | [M + Na]⁺ = 508 |
| 2962 | CO2CH₃ | [M + Na]⁺ = 438 |
| 2963 | CONHCH₂CONHCH₃ | [M + Na]⁺ = 494 |
| 2964 | 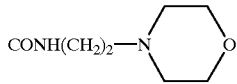 | [M + H]⁺ = 514 |
| 2965 | 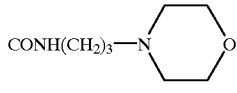 | [M + H]⁺ = 528 |
| 2966 | CONH-Phe-NHCH₃ | [M + Na]⁺ = 584 |
| 2967 | CONH-Leu-NHCH₃ | [M + Na]⁺ = 550 |
| 2968 | CONHCH₂-4-pyridyl | [M + H]⁺ = 492 |
| 2969 | 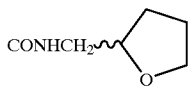 | [M + Na]⁺ = 507 |
| 2970 | CONHC₆H₅ | [M + Na]⁺ = 499 |
| 2971 | CONH-t-butylglycine-NHCH₃ | [M + Na]⁺ = 550 |
| 2972 | CONHCH₂C₆H₅ | [M + Na]⁺ = 513 |
| 2973 | 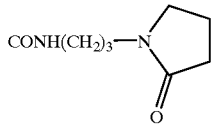 | [M + Na]⁺ = 548 |
| 2974 | 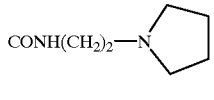 | [M + H]⁺ = 498 |
| 2975 | CONHCH₂-3-pyridyl | [M + H]⁺ = 492 |
| 2976 | CONHCH₂CF₃ | [M + Na]⁺ = 505 |
| 2977 | CONH(CH₂)₂-2-pyridyl | [M + H]⁺ = 506 |
| 2978 | CONH(±)CH(CH₃)CH₂CH₂C₆H₅ | [M + Na]⁺ = 555 |

TABLE 32-continued

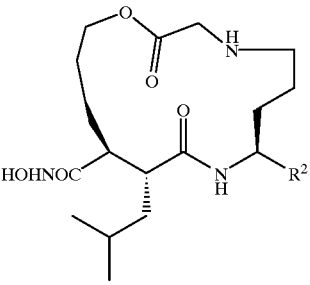

| Ex | R² | MS (ESI) |
|---|---|---|
| 2979 | 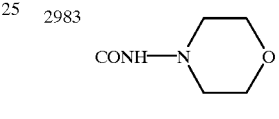 | [M + H]⁺ = 509 |
| 2980 | CONH-Lys(BOC)-NHCH₃ | [M + H]⁺ = 665 |
| 2981 | CONH-Lys-NHCH₃ | [M + H]⁺ = 543 |
| 2982 | CONHCH₂-2-pyridyl | [M + H]⁺ = 492 |
| 2983 | 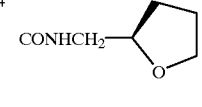 | [M + Na]⁺ = 508 |
| 2984 | 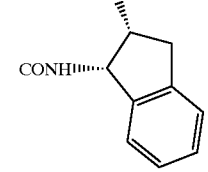 | [M + Na]⁺ = 507 |
| 2985 | 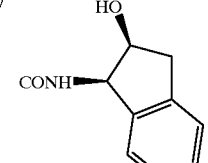 | [M + H]⁺ = 495 |
| 2986 | 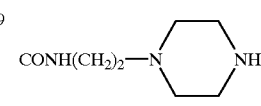 | [M + Na]⁺ = 555 |
| 2987 | 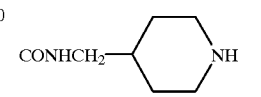 | [M + Na]⁺ = 555 |
| 2988 | CONHCH₂-Ph-4-NH₂ | [M − H]⁻ = 504 |
| 2989 | CONH(CH₂)₂-piperazine-NH | [M + H]⁺ = 513 |
| 2990 | CONHCH₂-piperidine-NH | [M + H]⁺ = 498 |

TABLE 32-continued

[Structure diagram: macrocyclic compound with HOHNOC group, isobutyl side chain, and R² substituent]

| Ex | R² | MS (ESI) |
|---|---|---|
| 2991 | CONH(CH₂)₃-piperidinyl | [M + H]⁺ = 540 |
| 2992 | CONHCH₂-tetrahydrofuranyl | [M + Na]⁺ = 507 |
| 2993 | CONH-Asp(t-Bu)-NHCH₃ | [M + Na]⁺ = 608 |
| 2994 | CONH-Asp-NHCH₃ | [M + Na]⁺ = 552 |
| 2995 | CONH-CH(CH₂-3-pyridyl)-CONHCH₃ | [M + H]⁺ = 563 |
| 2996 | CONHCH(C₆H₅)₂ | [M + Na]⁺ = 589 |
| 2997 | CONHCH₂CO₂C₅H₁₁ | 528.6 |
| 2998 | CONH(Ch₂)₄Ph | 532.7 |
| 2999 | CONH(CH₂)₂-5-methoxy indole | 573.7 |
| 3000 | CONHCH₂CONHCH₂CH(OH)-2,5-dimethoxyphenyl | 637.7 |
| 3001 | CONHCH₂CO₂tBU | 514.6 |
| 3002 | CONHCH(S)(CH₂)₂CO₂tBU(CO₂tBu) | 658.8 |
| 3003 | CONHCH₂CO₂H | 458.5 |
| 3004 | CONH(CH₂)₂Ph | 519.7 |
| 3005 | CONH(CH₂)₂-1-methylpyrrole | 507.6 |
| 3006 | CONH(CH₂)₂NHSO₂Ph | 583.7 |
| 3007 | CONHCH(S)CH₂CO₂C₆H₁₁(CONHCH₃) | 611.7 |
| 3008 | CONHCH(S)CH₂-p-fluorophenyl-(CONHCH₃) | 579.7 |
| 3009 | CONHCH(S)CH₂-p-methoxy Ph(CONHCH-(S-CH₃)Ph) | 681.8 |
| 3010 | CONHCH₂C₆H₁₁ | 496.7 |
| 3011 | CONH(CH₂)₃Ph | 518.7 |
| 3012 | CONH(CH₂)₂CH(Ph)₂ | 594.8 |
| 3013 | CONH(CH₂)₂NH(CH₂)₂-pyrrolidine | 654.7 |
| 3014 | CONHCH(S)CH₂-2'-naphthyl(CONHCH₃) | 611.7 |
| 3015 | CONH-piperidine-4-N-CO₂CH₂CH₃ | 555.7 |
| 3016 | CONH(CH₂)₂-5-methylindole | 557.7 |
| 3017 | CONHCH₂-p-CF₃-phenyl | 558.6 |
| 3018 | CONHCH(S)(CH₂)₂CO₂H(CO₂H) | 546.6 |
| 3019 | CONH-p-Ph-CO₂CH₂CH₂N(C₂H₅)₂ | 733.8 |
| 3020 | CONH(CH₂)₂-6-fluoroindole | 561.7 |
| 3021 | CONH(CH₂)₂-6-methoxyindole | 573.7 |
| 3022 | CONH(CH₂)₂-indole | 543.7 |

TABLE 33

[Structure diagram: macrocyclic compound with PhO₂S, HOHN, and (CH₂)₃Ph substituents and R²]

| Ex | R² (CI-MS) | ms |
|---|---|---|
| 3122 | CONHMe | 589.4 |

TABLE 34

[Structure diagram: macrocyclic compound with N-Ac, HO-NH, and (CH₂)₃Ph substituents and R²]

| Ex | R² (CI-MS) | ms |
|---|---|---|
| 3172 | CONHMe | 491.2 |

TABLE 35

[Structure diagram: macrocyclic compound with HOHN, HO, phenethyl side chain and R²]

| Ex | R² (CI-MS) | ms |
|---|---|---|
| 3222 | CO₂Me | |
| 3224 | CO₂Et | |
| 3225 | CO₂iPr | |
| 3226 | CO₂(CH₂)₂OMe | |
| 3227 | CO₂(CH₂)₂Ph | |
| 3228 | CO₂-tBu | |
| 3229 | CO₂CH₂CONHMe | |
| 3230 | CH₂OH | |
| 3231 | CH₂OCH₂CH₃ | |
| 3232 | CH₂OCH₂CH₂CO₂CH₃ | |
| 3233 | CHOBn | |
| 3234 | CONH(CH₂)₂-2-pyridyl | |

TABLE 35-continued

| Ex | R² (CI-MS) |
|---|---|
| 3235 | CO(N-morpholinyl) |
| 3236 | CO(N-Me-N-piperazinyl) |
| 3237 | CONH(CH₂)₂-(N-Me-N-piperazinyl) |
| 3238 | CONH-cyclopropyl |
| 3239 | CONH-cyclobutyl |
| 3278 | CONH₂ |
| 3279 | CONHiPr |
| 3280 | CONH-tert-butyl |
| 3281 | CONMe₂ |
| 3282 | CONEt₂ |
| 3283 | CONH-3-indazolyl |
| 3284 | CONH-adamantyl |
| 3285 | CONHCH₂(p-SO₂NH₂-Ph) |
| 3286 | CONH(CH₂)₃-1-imidazolyl |
| 3287 | CONHSO₂NH₂ |
| 3288 | CONHSO₂CH₃ |
| 3289 | CONHSO₂Ph |
| 3290 | CONHSO₂Bn |
| 3291 | CONHSO₂-N-Me-imidazolyl |
| 3292 | CONHSO₂-p-NH₂Ph |
| 3293 | CONHSO₂-p-MeOPh |
| 3294 | CONH-S-CH[CH₂CH(CH₃)2]CONHMe |
| 3295 | CONH(CH₂)₄NHSO₂Me |
| 3296 | CONH(CH₂)₆NHSO₂Me |
| 3297 | CONH-R-CH[CH₂CH (CH₃) 2 ]CONHMe |
| 3298 | CONH-S-CH[(CH₂)₄NH₂]CONHMe |
| 3299 | CONH-S-CH[(CH₂)₃NH₂]CONHMe |
| 3300 | CONH-S-CH[(CH₂)₂NH₂]CONHMe |
| 3301 | CONHMe |
| 3302 | CONHCH₂CONMe₂ |
| 3303 | CONHCH₂CONHEt |
| 3304 | CONHCH₂CONEt₂ |
| 3305 | CONHCH₂CONH-cyclopropyl |
| 3306 | CONHCH₂CONH-cyclobutyl |
| 3307 | CONHCH₂CONH-cyclopentyl |
| 3308 | CONHCH₂CONH-cyclohexyl |
| 3309 | CONHCH₂CONH-tert-butyl |
| 3310 | CONH-S-CH(CH₂Ph)CONHMe |
| 3311 | CONH-S-CH(CH₂-p-MeOPh)CONHMe |
| 3312 | CONHCH₂CH₂CONHMe |
| 3313 | CONHCH₂CH₂CH₂CONHMe |
| 3314 | CONH-S-CH(CH₂CH₂OH)CONHMe |
| 3315 | CONH-S-(CH(CH₂)₃CH₃)CONHMe |
| 3316 | CONH(CH₂)₂CO₂Me |
| 3317 | CONH(CH₂)₂CO2H |
| 3318 | CONH-S-CH[(CH₂)₃NHBOC]CO₂Me |
| 3319 | CONH-S-CH[(CH₂)₃NHBOC]CONHMe |
| 3320 | CONH-S-CH-[(CH₂)₃NH₂]CO₂Me |
| 3321 | CONH-S-CH[(CH₂)₄NH₂]CONH₂ |
| 3322 | CONH(CH₂)₂Ph |
| 3323 | CONH(CH₂)₂-(3,4,-dimethoxyphenyl) |
| 3324 | CONH(CH₂)₂-(N-morpholino) |
| 3325 | CONH(CH₂)₃-(N-morpholino) |
| 3326 | CONHCH₂CONH-(2-pyridyl) |
| 3327 | CONHCH₂CONH-(3-pyridyl) |
| 3328 | CONHCH₂CONH-(4-pyridyl) |
| 3329 | CONH(CH₂)₂(P-SO₂NH₂-Ph) |
| 3240 | CONHSO₂-P-F-Ph |
| 3241 | CONH(CH₂)₂NHSO₂Me |
| 3242 | CONH-cyclohexyl |
| 3243 | CONH-2-imidozolyl |
| 3244 | CH₂SO₂NHCH₃ |
| 3245 | CH₂SO₂NHPh |
| 3246 | CH₂SO₂NH-[4-NH₂Ph] |
| 3247 | 2-imidazolyl |
| 3248 | 2-oxazoly |
| 3249 | 2-thiazolyl |
| 3250 | 2-benzimidazolyl |
| 3251 | CONH-R-CH(CH₃)Ph |
| 3252 | CONH-S-CH(CH₃)Ph |
| 3253 | CONHCH₂CONHMe |
| 3254 | CONH-S-CH(CH₃)CONHMe |
| 3255 | CONH-R-CH(CH₃)CONHMe |
| 3256 | CONH-S-CH(2-propyl)CONHMe |
| 3257 | CONH-S-CH(CH₂SH)CONHMe |
| 3258 | CONH-S-CH(CH₂OH)CONHMe |
| 3259 | CONH-R-CH(CH₂OH)CONHMe |
| 3260 | CONH-S-CH(CH₂O-t-Bu)CONHMe |
| 3261 | CONH-R-CH(CH₂O-t-Bu)CONHMe |
| 3262 | CONH-CH(Ph)2 |
| 3263 | CO-L-proline-NHMe |
| 3264 | CONHCH₂CO(N-piperazinyl) |
| 3265 | CONHCH₂CO(N-methyl-N-piperazinyl) |
| 3266 | CONHCH₂CO(N-acetyl-N-piperazinyl) |
| 3267 | CONHCH₂CO-N-morpholino |
| 3268 | CONHCH₂CO-[N-(4-hydroxypiperidinyl)] |
| 3269 | CO₂H |
| 3270 | CONHBn |
| 3271 | CONH-2-pyridyl |
| 3272 | CONH-Ph |
| 3273 | CONH-3-pyridyl |
| 3274 | CONH-4-pyridyl |
| 3275 | CONH-CH₂CH(Ph)₂ |
| 3277 | CONH-cyclopentyl |

Utility

The compounds of formula I possess metalloproteinase and aggrecanase and TNF inhibitory activity. The MMP-3 inhibitory activity of the compounds of the present invention is demonstrated using assays of MMP-3 activity, for example, using the assay described below for assaying inhibitors of MMP-3 activity. The compounds of the present invention are bioavailable in vivo as demonstrated, for example, using the ex vivo assay described below. The compounds of formula I have the ability to suppress/inhibit cartilage degradation in vivo, for example, as demonstrated using the animal model of acute cartilage degradation described below.

The compounds provided by this invention are also useful as standards and reagents in determining the ability of a potential pharmaceutical to inhibit MPs. These would be provided in commercial kits comprising a compound of this invention.

Metalloproteinases have also been implicated in the degradation of basement membrances to allow infiltration of cancer cells into the circulation and subsequent penetration into other tissues leading to tumor metastasis. (Stetler-Stevenson, Cancer and Metastasis Reviews, 9, 289–303, 1990.) The compounds of the present invention should be useful for the prevention and treatment of invasive tumors by inhibition of this aspect of metastasis.

The compounds of the present invention would also have utility for the prevention and treatment of osteopenia associated with matrixmetalloproteinase-mediated breakdown of cartilage and bone which occurs in osteoporosis patients.

Compounds which inhibit the production or action of TNF and/or Aggrecanase and/or MP's are potentially useful for the treatment or prophylaxis of various inflammatory, infectious, immunological or malignant diseases. These include, but are not limited to inflammation, fever, cardiovascular effects, hemorrhage, coagulation and acute phase response, an acute infection, septic shock, haemodynamic shock and sepsis syndrome, post ischaemic reperfusion injury, malaria, Crohn's disease, mycobacterial infection, meningitis, psoriasis, periodontits, gingivitis, congestive heart failure, fibrotic disease, cachexia, and aneroxia, graft rejection, cancer, corneal ulceration or tumor invasion by secondary metastases, autoimmune disease, skin inflammatory diseases, multiple osteo and rheumatoid arthritis, multiple sclerosis, radiation damage, HIV, and hyperoxic alveolar injury.

The compounds of the present invention have been shown to inhibit TNF production in lipopolysacharride stimulated mice, for example, using the assay for TNF Induction in Mice and in human whole blood asdescribed below.

The compounds of the present invention have been shown to inhibit aggrecanase a key enzyme in cartilage breakdown as determined by the aggrecanase assay described below.

As used herein "$\mu$g" denotes microgram, "mg" denotes milligram, "g" denotes gram, "$\mu$L" denotes microliter, "mL" denotes milliliter, "L" denotes liter, "nM" denotes nanomolar, "$\mu$E" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 1 mM for the inhibition of MMP-3.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanase time of incubation and amount of product loaded for Western analysis were optimized for use of this assay in screening putative aggrecanase inhibitors Aggrecanase is generated by stimulation of cartilage slices with interleukin-1 (IL-1), tumor necrosis factor alpha (TNF$\partial$) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media. (Tortorella, M. D. et. al. Trans. Ortho. Res. Soc. 20, 341, 1995). Therefore, in order to accumulate BNC aggrecanase in culture media, cartilage is first depleted of endogenous aggrecan by stimulation with 500 ng/ml human recombinant IL-$\beta$ for 6 days with media changes every 2 days. Cartilage is then stimulated for an additional 8 days without media change to allow accumulation of soluble, active aggrecanase in the culture media. In order to decrease the amounts of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, C E, et al., Biochem J 306:799–804, 1995). This antibody recognizes aggrecan fragments with the N-terminus, 374ARGSVIL . . . , generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 uM for aggrecanase.

To evaluate inhibition of aggrecanase, compounds are prepared as 10 mM stocks in DMSO, water or other solvents and diluted to appropriate concentrations in water. Drug (50 ul) is added to 50 ul of aggrecanase-containing media and 50 ul of 2 mg/ml aggrecan substrate and brought to a final volume of 200 ul in 0.2 M Tris, pH 7.6, containing 0.4 M NaCl and 40 mM CaCl2. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 ul of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

Bisacetylated Substance P/MMP-3 Fluorescent Assay

A high capacity enzymatic assay was developed to detect potential inhibitors of MMP-3. The assay uses a derivative of a peptide substrate, substance P (Arg-Pro-Lys-Pro-Gln-Gln-Phe-Phe-Gly-Leu-Met), which is cleaved by MMP-3 exclusively at the glutamine-phenylalanine bond. In order to adapt this assay for high throughput screening, we have developed a fluorimetric method of product detection. The production of the hydrolysis product, substance P 7–11, is measured by reaction with fluorescamine, a fluorogenic compound which reacts with the primary amine of this fragment. The substance P substrate is bisacetylated to block the primary amines of the intact substrate. Thus, the resulting fluorescence represents generation of product (7–11 peptide) formed upon cleavage by MMP-3, and is quantitated using a standard curve prepared with known concentrations of 7–11 peptide. Kinetic studies using the bisacetylated substrate yield the following parameters for MMP-3: Km=769+/−52 uM; Vmax=0.090+/−0.003 nmoles 7–11 peptide/min.

To evaluate inhibition of MMP-3, compounds were prepared at a concentration of 10 mM in 100% methanol, and then further diluted to a 20× molar stock. Five microliters of each drug stock was added to the assay in the presence of 20 nM truncated MMP-3 in 67.5 mM tricine (pH 7.5), 10 mM $CaCl_2$, 40 mM NaCl, and 0.005% Brij 35 in a final volume of 100 microliters. Bisacetylated substance P (1000 mM) was added, and the assay was run for 1 hour at 25° C. The reaction was quenched with EDTA (20 mM) and product was detected fluorometrically following addition of fluorescamine (0.075 mg/ml). Fluorescence of each sample was converted to an amount of product formed using a substance P 7–11 standard curve. Under these conditions, the assay is linear with respect to MMP-3 amount up to 10 pmoles. Inhibition of MMP-3 was determined by comparing the amount of product generated in the presence and absence of compound.

Selected compounds of the present invention were tested and shown to have activity in the above assay.

Ex vivo Assay for Bioavailability of MMP-3 Inhibitors

Blood was collected by cardiac puncture from rats at different times after dosing I.V., I.P., or P.O. with compound in order to determine the levels of inhibitor present. Plasma was extracted with 10% TCA in 95% methanol, and placed on ice for 10 minutes. The plasma was then centrifuged for 15 minutes at 14,000 rpm in an Eppendorf microcentrifuge. The supernatant was removed, recentrifuged, and the resulting supernatant was diluted 1:10 in 50 mM tricine, pH 8.5. The pH of the sample was adjusted to 7.5, and then assayed in the MMP-3 substance P fluorescent enzymatic assay. Plasma from naive rats was extracted by the same method and used as a negative control. This plasma was also used to prepare a spiked plasma curve of the compound of interest. Known concentrations of the compound were added to control plasma, the plasma was extracted by the same method, and then assayed in the MMP-3 enzymatic assay. A standard curve was prepared that related percent inhbition in the MMP-3 assay to the concentration of drug added in the spiked samples. Based on the percent inhibition in the presence of plasma from dosed rats, the concentration of compound was determined using the standard curve.

Acute Cartilage Degradation Rat Model

A novel in vivo model of acute cartilage degradation in rats has been characterized as a method to determine the proteoglycan content in the synovial fluid after the induction of cartilage degradation. Experimental groups exhibit increased levels of proteoglycan content in their synovial fluid versus control rats. The criteria to demonstrate a compound's activity in this model, is the ability to inhibit the demonstration of cartilage degradation, as measured by increased proteoglycan content in the synovial fluid of rats after compound administration. Indomethacin, a non-steroidal anti-inflammatory drug is inactive in this model. Indomethacin administration does not inhibit the demonstration of cartilage degradation in experimental animals. In contrast, administration of a compound of this invention significantly inhibited the demonstration of cartilage degradation in this model.

TNF Human Whole Blood Assay

Blood is drawn from normal donors into tubes containing 143 USP units of heparin/10 ml. 225 ul of blood is plated directly into sterile polypropylene tubes. Compounds are diluted in DMSO/serum free media and added to the blood samples so the final concentration of compounds are 50,10, 5,1,0.5,0.1, and 0.01 uM. The final concentration of DMSO does not exceed 0.5%. Compounds are preincubated for 15 minutes before the addition of 100 ng/ml LPS. Plates are incubated for 5 hours in an atmosphere of 5% CO2 in air. At the end of 5 hours, 750 ul of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the IC50 value.

TNF Induction in Mice

Test compounds are administered to mice either I.P. or P.O. at time zero. Immediately following compound administration, mice receive an I.P. injection of 20 mg of D-galactosamine plus 10 $\mu$g of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action, MMP-3, in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulcose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed:
1. A compound of formula I:

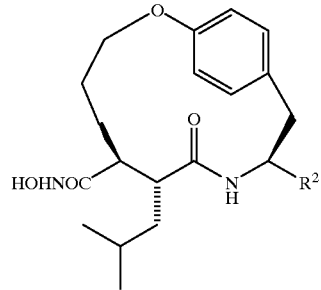

or pharmaceutically acceptable salts or prodrug forms thereof, wherein;

$R^2$ is selected from H, —$CO_2R^5$, —$CONR^6R^5$, —$CONR^6$($OR^5$), -alkyl, -alkylaryl, -alkylheteroaryl, -alkylheterocyclic, -aryl, heteroaryl or -heterocyclic which is substituted with one or more substituents selected from:
hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, lower alkylthio, arylthio, phenylthio, carboxy, sulfonamido, carboxamido, or carboalkoxy;

$R^5$ is selected from:
—$(CHR^1Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
—$C(R^7R^8)_m CONR^7R^8$,
—$C(R^7R^8)_m$-heteroaryl,
—$C(R^7R^8)_m$-heterocyclic;

$R^6$ is selected from:
H, alkyl-, —($C_1$–$C_6$)alkyl-aryl, —($C_1$–$C_6$)alkyl-heteroaryl, —($C_1$–$C_6$)alkyl-heterocyclic, —($C_1$–$C_6$)alkyl-acyl;

Alternatively, $R^5$ and $R^6$ may form a 3 to 8 membered ring optionally unsaturated containing from 1 to 3 heteroatoms selected from —O—, —$NR^6$—, —S(O)p, or an acyl group, optionally fused to an aryl ring;

$R^7$ and $R^8$ may be selected independently from:
  H, $R^{11}$, or form a 3 to 7 membered substituted ring with 0–3 unsaturations,
  wherein the substituent is selected from;
    hydrogen, $C_1$–$C_5$ alkyl, hydroxy, halo, alkoxy, amino, mono-alkylamino, di-alkylamino, acylamino, thio, thioalkyl, carboxy, carboamido or aryl, optionally containing —O—, —S(O)p, —$NR^6$, optionally fused to a substituted aryl ring,
    wherein the substituent is selected from;
      hydrogen, $C_1$–$C_5$ alkyl, hydroxy, halo, alkoxy, amino, mono-alkylamino, di-alkylamino, acylamino, thio, thioalkyl, carboxy, carboxamido or aryl;

$R^9$ is H, alkyl, cycloalkyl, 5 or 6 membered ring optionally containing from 1 to 2 N, O or S(O)p, optionally substituted with —OH, —O—($C_1$–$C_6$)alkyl, —O-acyl-alkyl, $NHR^{10}$, or aryl;

$R^{10}$ is H or an optionally substituted alkyl group;

$R^{11}$ is selected from:
  H,
  —($C_0$–$C_6$)alkyl-S(O)p-($C_1$–$C_6$)alkyl,
  —($C_0$–$C_6$)alkyl-O—($C_1$–$C_6$)alkyl,
  —($C_0$–$C_6$)alkyl-S(O)p-($C_0$–$C_6$)alkyl-aryl,
  —($C_0$–$C_6$)alkyl-O—($C_0$–$C_6$)alkyl-aryl,
  alkyl of from 1 to 20 carbon atoms which may be branched, cyclic and unsaturated alkyl groups, substituted alkyl
  wherein the substituent is selected from;
    hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
  —($C_0$–$C_8$)alkyl-aryl,
  —($C_0$–$C_8$)alkyl-substituted aryl,
  —($C_0$–$C_8$)aryl-($C_1$–$C_4$)alkyl-aryl,
  —($C_1$–$C_8$)alkyl-biaryl,
  —($C_0$–$C_8$)alkyl-S(O)p-($C_0$–$C_8$)alkyl-aryl,
  —($C_0$–$C_8$)alkyl-S(O)p-($C_0$–$C_8$)alkyl-substituted aryl,
  —($C_1$–$C_4$)alkyl-aryl-($C_0$–$C_8$)alkyl-aryl-[S(O)p-($C_0$–$C_8$)alkyl],
  —($C_0$–$C_8$)alkyl-S(O)p-($C_0$–$C_8$)alkyl-biaryl,
  —($C_0$–$C_8$)alkyl-O—($C_0$–$C_8$)alkyl-aryl,
  —($C_0$–$C_8$)alkyl-S(O)p-($C_0$–$C_8$)alkyl-substituted aryl,
  —($C_1$–$C_4$)alkyl-aryl-($C_0$–$C_8$)alkyl-aryl-[O—($C_0$–$C_8$)alkyl],
  —($C_0$–$C_8$)alkyl-O—($C_0$–$C_8$)alkyl-biaryl,
  —($C_0$–$C_8$)alkyl-O—($C_0$–$C_8$)alkyl-substituted aryl,
  wherein the substituent is selected from;
    hydrogen, $C_1$–$C_5$ alkyl, hydroxy, halo, alkoxy, amino, mono-alkylamino, di-alkylamino, acylamino, thio, thioalkyl, carboxy, carboamido or aryl;

m is an integer from 0 to 5;
n is an integer from 1 to 5;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O or S.

2. A compound of claim 1 wherein:

$R^2$ is selected from H, —$CO_2R^5$, —$CONR^6R^5$, —$CONR^6(OR^5)$, -alkyl, -alkylaryl, -alkylheteroaryl, -alkylheterocyclic, -aryl, -heteroaryl or -heterocyclic which is substituted with one or more substituents selected from:
  hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, lower alkylthio, arylthio, phenylthio, carboxy, sulfonamido, carboxamido, or carboalkoxy;

$R^5$ is selected from:
  —$(CHR^{11}Y)_n$—$R^9$, —$C(R^7R^8)_n$—W—$C(R^7R^8)_m$—$R^9$,
  —$C(R^7R^8)_m$—$R^9$, —$C(R^7R^8)_m$-aryl,
  —$C(R^7R^8)_m CONR^7R^8$,
  —$C(R^7R^8)_m$-heteroaryl,
  —$C(R^7R^8)_m$-heterocyclic;

$R^6$ is selected from:
  H, alkyl-, —($C_1$–$C_6$)alkyl-aryl,
  —($C_1$–$C_6$)alkyl-heteroaryl,
  —($C_1$–$C_6$)alkyl-heterocyclic,
  —($C_1$–$C_6$)alkyl-acyl;

$R^7$ and $R^8$ may be selected independently from:
  H, $R^{11}$, or form a 3 to 7 membered substituted ring with 0–3 unsaturations,
  wherein the substituent is selected from;
    hydrogen, $C_1$–$C_5$ alkyl, hydroxy, halo, alkoxy, amino, mono-alkylamino, di-alkylamino, acylamino, thio, thioalkyl, carboxy, carboamido or aryl,
  optionally containing —O—, —S(O)p, —$NR^6$, optionally fused to a substituted aryl ring,
    wherein the substituent is selected from;
      hydrogen, $C_1$–$C_5$ alkyl, hydroxy, halo, alkoxy, amino, mono-alkylamino, di-alkylamino, acylamino, thio, thioalkyl, carboxy, carboxamido or aryl;

$R^9$ is H, alkyl, cycloalkyl, 5 or 6 membered ring optionally containing from 1 to 2 N, O or S(O)p, optionally substituted with —OH, —O—($C_1$–$C_6$)alkyl, —O-acyl-alkyl, $NHR^{10}$, or aryl;

$R^{10}$ is H or an optionally substituted alkyl group;

$R^{11}$ is selected from:
  H,
  —($C_0$–$C_6$)alkyl-S(O)p-($C_1$–$C_6$)alkyl,
  —($C_0$–$C_6$)alkyl-O—($C_1$–$C_6$)alkyl,
  —($C_0$–$C_6$)alkyl-S(O)p-($C_0$–$C_6$)alkyl-aryl,
  —($C_0$–$C_6$)alkyl-O—($C_0$–$C_6$)alkyl-aryl,
  alkyl of from 1 to 20 carbon atoms which may be branched, cyclic and unsaturated alkyl groups, substituted alkyl
  wherein the substituent is selected from;
    hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
  —($C_0$–$C_8$)alkyl-aryl,
  —($C_0$–$C_8$)alkyl-substituted aryl, —($C_0$–$C_8$)aryl-($C_1$–$C_4$)alkyl-aryl,
—($C_1$–$C_8$)alkyl-biaryl,
—($C_0$–$C_8$)alkyl-S(O)p-($C_0$–$C_8$)alkyl-aryl,
—($C_0$–$C_8$)alkyl-S(O)p-($C_0$–$C_8$)alkyl-substituted aryl,
—($C_1$–$C_4$)alkyl-aryl-($C_0$–$C_8$)alkyl-aryl-[S(O)p-($C_0$–$C_8$)alkyl],
—($C_0$–$C_8$)alkyl-S(O)p-($C_0$–$C_8$)alkyl-biaryl,
—($C_0$–$C_8$)alkyl-O—($C_0$–$C_8$)alkyl-aryl,
—($C_0$–$C_8$)alkyl-S(O)p-($C_0$–$C_8$)alkyl-substituted aryl,
—($C_1$–$C_4$)alkyl-aryl-($C_0$–$C_8$)alkyl-aryl-[O—($C_0$–$C_8$)alkyl],
—($C_0$–$C_8$)alkyl-O—($C_0$–$C_8$)alkyl-biaryl,
—($C_0$–$C_8$)alkyl-O—($C_0$–$C_8$)alkyl-substituted aryl,
wherein the substituent is selected from;
   hydrogen, $C_1$–$C_5$ alkyl, hydroxy, halo, alkoxy, amino, mono-alkylamino, di-alkylamino, acylamino, thio, thioalkyl, carboxy, carboamido or aryl;
m is an integer from 0 to 5;
n is an integer from 1 to 5;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O or S.

3. A compound of claim 2 wherein:
$R^2$ is selected from H, —$CO_2R^5$, —$CONR^6R^5$, —$CONR^6$($OR^5$), -alkyl, -alkylaryl, -alkylheteroaryl, -alkylheterocyclic, -aryl, -heteroaryl or -heterocyclic;
$R^5$ is selected from:
   —$(CHR^{11}Y)_n$—$R^9$, —$C(R^7R^8)_n$—W—$C(R^7R^8)_m$—$R^9$,
   —$C(R^7R^8)_m$—$R^9$, —$C(R^7R^8)_m$-aryl,
   —$C(R^7R^8)_m CONR^7R^8$,
   —$C(R^7R^8)_m$-heteroaryl,
   —$C(R^7R^8)_m$-heterocyclic;
$R^6$ is selected from:
   H, alkyl-, —($C_1$–$C_6$)alkyl-aryl,
   —($C_1$–$C_6$)alkyl-heteroaryl,
   —($C_1$–$C_6$)alkyl-heterocyclic,
   —($C_1$–$C_6$)alkyl-acyl;
$R^7$ and $R^8$ may be selected independently from:
   H, $R^{11}$, or form a 3 to 7 membered substituted ring with 0–3 unsaturations,
   wherein the substituent is selected from;
      hydrogen, $C_1$–$C_5$ alkyl, hydroxy, halo, alkoxy, amino, mono-alkylamino, di-alkylamino, acylamino, thio, thioalkyl, carboxy, carboamido or aryl,
   optionally containing —O—, —S(O)p, —$NR^6$, optionally fused to a substituted aryl ring,
   wherein the substituent is selected from;
      hydrogen, $C_1$–$C_5$ alkyl, hydroxy, halo, alkoxy, amino, mono-alkylamino, di-alkylamino, acylamino, thio, thioalkyl, carboxy, carboxamido or aryl;
$R^9$ is H, alkyl, cycloalkyl, 5 or 6 membered ring optionally containing from 1 to 2 N, 0 or S(O)p, optionally substituted with —OH, —O—($C_1$–$C_6$)alkyl, —O-acyl-alkyl, $NHR^{10}$, or aryl;
$R^{10}$ is H or an optionally substituted alkyl group;
$R^{11}$ is selected from:
   H,
   —($C_0$–$C_6$)alkyl-S(O)p-($C_1$–$C_6$)alkyl,
   —($C_0$–$C_6$)alkyl-O—($C_1$–$C_6$)alkyl,
   —($C_0$–$C_6$)alkyl-S(O)p-($C_0$–$C_6$)alkyl-aryl,
   —($C_0$–$C_6$)alkyl-O—($C_0$–$C_6$)alkyl-aryl,
   alkyl of from 1 to 20 carbon atoms may be branched, cyclic and unsaturated alkyl groups, substituted alkyl
   wherein the substituent is selected from;
      hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
   —($C_0$–$C_8$)alkyl-aryl,
   —($C_0$–$C_8$)alkyl-substituted aryl,
   —($C_0$–$C_8$)aryl-($C_1$–$C_4$)alkyl-aryl,
   —($C_1$–$C_8$)alkyl-biaryl,
   —($C_0$–$C_8$)alkyl-S(O)p-($C_0$–$C_8$)alkyl-aryl,
   —($C_0$–$C_8$)alkyl-S(O)p-($C_0$–$C_8$)alkyl-substituted aryl,
   —($C_1$–$C_4$)alkyl-aryl-($C_0$–$C_8$)alkyl-aryl-[S(O)p-($C_0$–$C_8$)alkyl],
   —($C_0$–$C_8$)alkyl-S(O)p-($C_0$–$C_8$)alkyl-biaryl,
   —($C_0$–$C_8$)alkyl-O—($C_0$–$C_8$)alkyl-aryl,
   —($C_0$–$C_8$)alkyl-S(O)p-($C_0$–$C_8$)alkyl-substituted aryl,
   —($C_1$–$C_4$)alkyl-aryl-($C_0$–$C_8$)alkyl-aryl-[O—($C_0$–$C_8$)alkyl],
   —($C_0$–$C_8$)alkyl-O—($C_0$–$C_8$)alkyl-biaryl,
   —($C_0$–$C_8$)alkyl-O—($C_0$–$C_8$)alkyl-substituted aryl,
   wherein the substituent is selected from;
      hydrogen, $C_1$–$C_5$ alkyl, hydroxy, halo, alkoxy, amino, mono-alkylamino, di-alkylamino, acylamino, thio, thioalkyl, carboxy, carboamido or aryl;
m is an integer from 0 to 5;
n is an integer from 1 to 5;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O or S.

4. A compound of claim 3 wherein:
$R^2$ is selected from H, —$CO_2R^5$, —$CONR^6R^5$, —$CONR^6$($OR^5$), -alkyl, -alkylaryl, -alkylheteroaryl, -alkylheterocyclic, -aryl, -heteroaryl or -heterocyclic;
$R^5$ is selected from:
   —$(CHR^{11}Y)_n$—$R^9$, —$C(R^7R^8)_n$—W—$C(R^7R^8)_m$—$R^9$,
   —$C(R^7R^8)_m$—$R^9$, —$C(R^7R^8)_m$-aryl,
   —$C(R^7R^8)_m CONR^7R^8$,
   —$C(R^7R^8)_m$-heteroaryl,
   —$C(R^7R^8)_m$-heterocyclic;
$R^6$ is selected from:
   H, alkyl-, —($C_1$–$C_6$)alkyl-aryl,
   —($C_1$–$C_6$)alkyl-heteroaryl,
   —($C_1$–$C_6$)alkyl-heterocyclic,
   —($C_1$–$C_6$)alkyl-acyl;
$R^7$ and $R^8$ may be selected independently from:
   H, $R^{11}$, or form a 3 to 7 membered substituted ring with 0–3 unsaturations,
   wherein the substituent is selected from;
      hydrogen, $C_1$–$C_5$ alkyl, hydroxy, halo, alkoxy, amino, mono-alkylamino, di-alkylamino, acylamino, thio, thioalkyl, carboxy, carboamido or aryl;

$R^9$ is H, alkyl, cycloalkyl, 5 or 6 membered ring optionally containing from 1 to 2 N, O or S(O)p, optionally substituted with —OH, —O—$(C_1$–$C_6)$alkyl, —O-acyl-alkyl, $NHR^{10}$, or aryl;

$R^{10}$ is H or an optionally substituted alkyl group;

$R^{11}$ is selected from:
H,
—$(C_0$–$C_6)$alkyl-S(O)p-$(C_1$–$C_6)$alkyl,
—$(C_0$–$C_6)$alkyl-O—$(C_1$–$C_6)$alkyl,
—$(C_0$–$C_6)$alkyl-S(O)p-$(C_0$–$C_6)$alkyl-aryl,
—$(C_0$–$C_6)$alkyl-O—$(C_0$–$C_6)$alkyl-aryl,
alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0$–$C_8)$alkyl-aryl,
—$(C_0$–$C_8)$alkyl-substituted aryl,
—$(C_0$–$C_8)$aryl-$(C_1$–$C_4)$alkyl-aryl,
—$(C_1$–$C_8)$alkyl-biaryl,
—$(C_0$–$C_8)$alkyl-S(O)p-$(C_0$–$C_8)$alkyl-aryl,
—$(C_0$–$C_8)$alkyl-S(O)p-$(C_0$–$C_8)$alkyl-substituted aryl,
—$(C_1$–$C_4)$alkyl-aryl-$(C_0$–$C_8)$alkyl-aryl-[S(O)p-$(C_0$–$C_8)$alkyl],
—$(C_0$–$C_8)$alkyl-S(O)p-$(C_0$–$C_8)$alkyl-biaryl,
—$(C_0$–$C_8)$alkyl-O—$(C_0$–$C_8)$alkyl-aryl,
—$(C_0$–$C_8)$alkyl-S(O)p-$(C_0$–$C_8)$alkyl-substituted aryl,
—$(C_1$–$C_4)$alkyl-aryl-$(C_0$–$C_8)$alkyl-aryl-[O—$(C_0$–$C_8)$alkyl],
—$(C_0$–$C_8)$alkyl-O—$(C_0$–$C_8)$alkyl-biaryl,
—$(C_0$–$C_8)$alkyl-O—$(C_0$–$C_8)$alkyl-substituted aryl,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl;

m is an integer from 0 to 5;
n is an integer from 1 to 5;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O or S.

5. A compound of claim 4 wherein:
$R^2$ is selected from:
H, —$CO_2R^5$, —$CONR^6R^5$, —$CONR^6(OR^5)$, -alkyl, -alkylaryl, -alkylheteroaryl, -alkylheterocyclic, -aryl, -heteroaryl or -heterocyclic;

$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
—$C(R^7R^8)_m CONR^7R^8$,
—$C(R^7R^8)_m$-heteroaryl,
—$C(R^7R^8)_m$-heterocyclic;

$R^6$ is selected from:
H, alkyl-, —$(C_1$–$C_6)$alkyl-aryl,
—$(C_1$–$C_6)$alkyl-heteroaryl,
—$(C_1$–$C_6)$alkyl-heterocyclic,
—$(C_1$–$C_6)$alkyl-acyl;

$R^7$ and $R^8$ may be selected independently from:
H, $R^{11}$, or form a 3 to 7 membered substituted ring with 0–3 unsaturations,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl;

$R^9$ is H, alkyl, cycloalkyl, 5 or 6 membered ring optionally containing from 1 to 2 N, 0 or S(O)p, optionally substituted with —OH, —O—$(C_1$–$C_6)$alkyl, —O-acyl-alkyl, $NHR^{10}$, or aryl;

$R^{10}$ is H or an optionally substituted alkyl group;

$R^{11}$ is selected from:
H,
—$(C_0$–$C_6)$alkyl-S(O)p-$(C_1$–$C_6)$alkyl,
—$(C_0$–$C_6)$alkyl-O—$(C_1$–$C_6)$alkyl,
—$(C_0$–$C_6)$alkyl-S(O)p-$(C_0$–$C_6)$alkyl-aryl,
—$(C_0$–$C_6)$alkyl-O—$(C_0$–$C_6)$alkyl-aryl,
alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0$–$C_8)$alkyl-aryl,
—$(C_0$–$C_8)$alkyl-substituted aryl,
—$(C_0$–$C_8)$aryl-$(C_1$–$C_4)$alkyl-aryl,
—$(C_1$–$C_8)$alkyl-biaryl,
—$(C_0$–$C_8)$alkyl-S(O)p-$(C_0$–$C_8)$alkyl-aryl,
—$(C_0$–$C_8)$alkyl-S(O)p-$(C_0$–$C_8)$alkyl-substituted aryl,
—$(C_1$–$C_4)$alkyl-aryl-$(C_0$–$C_8)$alkyl-aryl-[S(O)p-$(C_0$–$C_8)$alkyl],
—$(C_0$–$C_8)$alkyl-S(O)p-$(C_0$–$C_8)$alkyl-biaryl,
—$(C_0$–$C_8)$alkyl-O—$(C_0$–$C_8)$alkyl-aryl,
—$(C_0$–$C_8)$alkyl-S(O)p-$(C_0$–$C_8)$alkyl-substituted aryl,
—$(C_1$–$C_4)$alkyl-aryl-$(C_0$–$C_8)$alkyl-aryl-[O—$(C_0$–$C_8)$alkyl],
—$(C_0$–$C_8)$alkyl-O—$(C_0$–$C_8)$alkyl-biaryl,
—$(C_0$–$C_8)$alkyl-O—$(C_0$–$C_8)$alkyl-substituted aryl,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl;

m is an integer from 0 to 5;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—, [a peptide bond mimic], a 5 membered heterocyclic ring saturated, unsaturated or partially unsaturated containing from 1 to 4 heteroatoms selected from N, O or S.

6. A compound of claim 5 wherein:
$R^2$ is selected from:
H, —$CO_2R^5$, —$CONR^6R^5$, —$CONR^6(OR^5)$, -alkyl, -alkylaryl, -alkylheteroaryl, -alkylheterocyclic, -aryl, -heteroaryl or -heterocyclic;

$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$,—$C(R^7R^8)_m$-aryl,
—$C(R^7R^8)_m CONR^7R^8$,
—$C(R^7R^8)_m$-heteroaryl,
—$C(R^7R^8)_m$-heterocyclic;

$R^6$ is selected from:
H, alkyl-, —$(C_1-C_6)$alkyl-aryl,
—$(C_1-C_6)$alkyl-heteroaryl,
—$(C_1-C_6)$alkyl-heterocyclic,
—$(C_1-C_6)$alkyl-acyl;

$R^7$ and $R^8$ may be selected independently from:
H, $R^{11}$, or form a 3 to 7 membered substituted ring with 0–3 unsaturations,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;

$R^9$ is H, alkyl, cycloalkyl, 5 or 6 membered ring optionally containing from 1 to 2 N, O or S(O)p, optionally substituted with —OH, —O—$(C_1-C_6)$alkyl, —O-acyl-alkyl, $NHR^{10}$, or aryl;

$R^{10}$ is H or an optionally substituted alkyl group;

$R^{11}$ is selected from:
H,
—$(C_0-C_6)$alkyl-S(O)p-$(C_1-C_6)$alkyl,
—$(C_0-C_6)$alkyl-O—$(C_1-C_6)$alkyl,
—$(C_0-C_6)$alkyl-S(O)p-$(C_0-C_6)$alkyl-aryl,
—$(C_0-C_6)$alkyl-O—$(C_0-C_6)$alkyl-aryl,
alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0-C_8)$alkyl-aryl,
—$(C_0-C_8)$alkyl-substituted aryl,
—$(C_0-C_8)$aryl-$(C_1-C_4)$alkyl-aryl,
—$(C_1-C_8)$alkyl-biaryl,
—$(C_0-C_8)$alkyl-S(O)p-$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[S(O)p-$(C_0-C_8)$alkyl],
—$(C_0-C_8)$alkyl-S(O)p-$(C_0-C_8)$alkyl-biaryl,
—$(C_0-C_8)$alkyl-O—$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[O—$(C_0-C_8)$alkyl],
—$(C_0-C_8)$alkyl-O—$(C_0-C_8)$alkyl-biaryl,
—$(C_0-C_8)$alkyl-O—$(C_0-C_8)$alkyl-substituted aryl,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;
m is an integer from 0 to 3;
n is an integer from 1 to 3;
p can be 0, 1 or 2;
W is —O—, S(O)p or $NR^{10}$;

Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O or S.

7. A compound of claim 5 wherein:
$R^2$ is selected from:
H, —$CO_2R^5$, —$CONR^6R^5$, —$CONR^6(OR^5)$, -alkyl, -alkylaryl, -alkylheteroaryl, -alkylheterocyclic, -aryl, -heteroaryl or -heterocyclic;

$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$,—$C(R^7R^8)_m$-aryl,
—$C(R^7R^8)_m CONR^7R^8$, $R^6$ is selected from:
H, alkyl-, —$(C_1-C_6)$alkyl-aryl,
—$(C_1-C_6)$alkyl-heteroaryl,
—$(C_1-C_6)$alkyl-heterocyclic,
—$(C_1-C_6)$alkyl-acyl;

$R^7$ and $R^8$ may be selected independently from:
H, $R^{11}$, or form a 3 to 7 membered substituted ring with 0–3 unsaturations,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;

$R^9$ is H, alkyl, cycloalkyl, 5 or 6 membered ring optionally containing from 1 to 2 N, O or S(O)p, optionally substituted with —OH, —O—$(C_1-C_6)$alkyl, —O-acyl-alkyl, $NHR^{10}$, or aryl;

$R^{10}$ is H or an optionally substituted alkyl group;

$R^{11}$ is selected from:
H,
—$(C_0-C_6)$alkyl-S(O)p-$(C_1-C_6)$alkyl,
—$(C_0-C_6)$alkyl-O—$(C_1-C_6)$alkyl,
—$(C_0-C_6)$alkyl-S(O)p-$(C_0-C_6)$alkyl-aryl,
—$(C_0-C_6)$alkyl-O—$(C_0-C_6)$alkyl-aryl,
alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0-C_8)$alkyl-aryl,
—$(C_0-C_8)$alkyl-substituted aryl,
—$(C_0-C_8)$aryl-$(C_1-C_4)$alkyl-aryl,
—$(C_1-C_8)$alkyl-biaryl,
—$(C_0-C_8)$alkyl-S(O)p-$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[S(O)p-$(C_0-C_8)$alkyl],
—$(C_0-C_8)$alkyl-S(O)p-$(C_0-C_8)$alkyl-biaryl,
—$(C_0-C_8)$alkyl-O—$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[O—$(C_0-C_8)$alkyl],
—$(C_0-C_8)$alkyl-O—$(C_0-C_8)$alkyl-biaryl,
—$(C_0-C_8)$alkyl-O—$(C_0-C_8)$alkyl-substituted aryl,
wherein the substituent is selected from;

hydrogen, $C_1$–$C_5$ alkyl, hydroxy, halo, alkoxy, amino, mono-alkylamino, di-alkylamino, acylamino, thio, thioalkyl, carboxy, carboamido or aryl;

m is an integer from 0 to 3;

n is an integer from 1 to 3;

p can be 0, 1 or 2;

W is —O—, S(O)p or $NR^{10}$;

Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O or S.

8. A compound of claim 7 wherein:

$R^2$ is selected from:
H, —$CO_2R^5$, —$CONR^6R^5$, —$CONR^6(OR^5)$, -alkyl, -alkylaryl, -alkylheteroaryl, -alkylheterocyclic, -aryl, -heteroaryl or -heterocyclic;

$R^5$ is selected from:
—$(CHR^{11}Y)_n$—$R^9$, —$C(R^7R^8)_n$—W—$C(R^7R^8)_m$—$R^9$, —$C(R^7R^8)_m$—$R^9$, —$C(R^7R^8)_m$-aryl, —$C(R^7R^8)_m CONR^7R^8$, $R^6$ is selected from:
H, alkyl-, —$(C_1$–$C_6)$alkyl-aryl, —$(C_1$–$C_6)$alkyl-heteroaryl, $R^7$ and $R^8$ may be selected independently from:
H, $R^{11}$, or form a 3 to 7 membered substituted ring with 0–3 unsaturations,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl;

$R^9$ is H, alkyl, cycloalkyl, 5 or 6 membered ring optionally containing from 1 to 2 N, O or S(O)p, optionally substituted with —OH, —O—$(C_1$–$C_6)$alkyl, —O-acyl-alkyl, $NHR^{10}$, or aryl;

$R^{10}$ is H or an optionally substituted alkyl group;

$R^{11}$ is selected from:
H,
—$(C_0$–$C_6)$alkyl-S(O)p-$(C_1$–$C_6)$alkyl,
—$(C_0$–$C_6)$alkyl-O—$(C_1$–$C_6)$alkyl,
—$(C_0$–$C_6)$alkyl-S(O)p-$(C_0$–$C_6)$alkyl-aryl,
—$(C_0$–$C_6)$alkyl-O—$(C_0$–$C_6)$alkyl-aryl,
alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0$–$C_8)$alkyl-aryl,
—$(C_0$–$C_8)$alkyl-substituted aryl,
—$(C_0$–$C_8)$aryl-$(C_1$–$C_4)$alkyl-aryl,
—$(C_1$–$C_8)$alkyl-biaryl,
—$(C_0$–$C_8)$alkyl-S(O)p-$(C_0$–$C_8)$alkyl-aryl,
—$(C_0$–$C_8)$alkyl-S(O)p-$(C_0$–$C_8)$alkyl-substituted aryl,
—$(C_1$–$C_4)$alkyl-aryl-$(C_0$–$C_8)$alkyl-aryl-[S(O)p-$(C_0$–$C_8)$alkyl],
—$(C_0$–$C_8)$alkyl-S(O)p-$(C_0$–$C_8)$alkyl-biaryl,
—$(C_0$–$C_8)$alkyl-O—$(C_0$–$C_8)$alkyl-aryl,
—$(C_0$–$C_8)$alkyl-S(O)p-$(C_0$–$C_8)$alkyl-substituted aryl,
—$(C_1$–$C_4)$alkyl-aryl-$(C_0$–$C_8)$alkyl-aryl-[O—$(C_0$–$C_8)$alkyl],
—$(C_0$–$C_8)$alkyl-O—$(C_0$–$C_8)$alkyl-biaryl,
—$(C_0$–$C_8)$alkyl-O—$(C_0$–$C_8)$alkyl-substituted aryl,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl;

m is an integer from 0 to 3;

n is an integer from 1 to 3;

p can be 0, 1 or 2;

W is —O—, S(O)p or $NR^{10}$;

Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O or S.

9. A compound of claim 8 wherein:

$R^2$ is selected from:
H, —$CO_2R^5$, —$CONR^6R^5$, —$CONR^6(OR^5)$, -alkyl, -alkylaryl, -alkylheteroaryl, -alkylheterocyclic, -aryl, -heteroaryl or -heterocyclic;

$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
—$C(R^7R^8)_m CONR^7R^8$, $R^6$ is selected from:
H, alkyl-, —$(C_1$–$C_6)$alkyl-aryl,
—$(C_1$–$C_6)$alkyl-heteroaryl, $R^7$ and $R^8$ may be selected independently from:
H, $R^{11}$, or form a 3 to 7 membered substituted ring with 0–3 unsaturations,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl;

$R^9$ is H, alkyl, cycloalkyl, 5 or 6 membered ring optionally containing from 1 to 2 N, O or S(O)p, optionally substituted with —OH, —O—$(C_1$–$C_6)$alkyl, —O-acyl-alkyl, $NHR^{10}$, or aryl;

$R^{10}$ is H or an optionally substituted alkyl group;

$R^{11}$ is selected from:
H,
—$(C_0$–$C_6)$alkyl-S(O)p-$(C_1$–$C_6)$alkyl,
—$(C_0$–$C_6)$alkyl-O—$(C_1$–$C_6)$alkyl,
—$(C_0$–$C_6)$alkyl-S(O)p-$(C_0$–$C_6)$alkyl-aryl,
—$(C_0$–$C_6)$alkyl-O—$(C_0$–$C_6)$alkyl-aryl,
alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0$–$C_8)$alkyl-aryl,
—$(C_0$–$C_8)$alkyl-substituted aryl,
—$(C_0$–$C_8)$aryl-$(C_1$–$C_4)$alkyl-aryl, —$(C_1-C_8)$alkyl-biaryl,
—$(C_0-C_8)$alkyl-S(O)p-$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[S(O)p-$(C_0-C_8)$alkyl],
—$(C_0-C_8)$alkyl-S(O)p-$(C_0-C_8)$alkyl-biaryl,
—$(C_0-C_8)$alkyl-O—$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[O—$(C_0-C_8)$alkyl],
—$(C_0-C_8)$alkyl-O—$(C_0-C_8)$alkyl-biaryl,
—$(C_0-C_8)$alkyl-O—$(C_0-C_8)$alkyl-substituted aryl,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;

m is an integer from 0 to 3;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O or S.

10. A compound of claim 9 wherein:
$R^2$ is selected from:
H, —$CO_2R^5$, —$CONR^6R^5$, —$CONR^6(OR^5)$, -alkyl, -alkylaryl;
$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
—$C(R^7R^8)_m CONR^7R^8$,
$R^6$ is selected from:
H, alkyl-, —$(C_1-C_6)$alkyl-aryl,
—$(C_1-C_6)$alkyl-heteroaryl,
$R^7$ and $R^8$ may be selected independently from:
H, $R^{11}$, or form a 3 to 7 membered substituted ring with 0–3 unsaturations,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;
$R^9$ is H, alkyl, cycloalkyl, 5 or 6 membered ring optionally containing from 1 to 2 N, O or S(O)p, optionally substituted with —OH, —O—$(C_1-C_6)$alkyl, —O-acyl-alkyl, $NHR^{10}$, or aryl;
$R^{10}$ is H or an optionally substituted alkyl group;
$R^{11}$ is selected from:
H,
—$(C_0-C_6)$alkyl-S(O)p-$(C_1-C_6)$alkyl,
—$(C_0-C_6)$alkyl-O—$(C_1-C_6)$alkyl,
—$(C_0-C_6)$alkyl-S(O)p-$(C_0-C_6)$alkyl-aryl,
—$(C_0-C_6)$alkyl-O—$(C_0-C_6)$alkyl-aryl, alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0-C_8)$alkyl-aryl,
—$(C_0-C_8)$alkyl-substituted aryl,
—$(C_0-C_8)$aryl-$(C_1-C_4)$alkyl-aryl,
—$(C_1-C_8)$alkyl-biaryl,
—$(C_0-C_8)$alkyl-S(O)p-$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[S(O)p-$(C_0-C_8)$alkyl],
—$(C_0-C_8)$alkyl-S(O)p-$(C_0-C_8)$alkyl-biaryl,
—$(C_0-C_8)$alkyl-O—$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[O—$(C_0-C_8)$alkyl],
—$(C_0-C_8)$alkyl-O—$(C_0-C_8)$alkyl-biaryl,
—$(C_0-C_8)$alkyl-O—$(C_0-C_8)$alkyl-substituted aryl,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;

m is an integer from 0 to 3;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O or S.

11. A compound of claim 10 wherein:
$R^2$ is selected from:
H, —$CO_2R^5$, —$CONR^6R^5$, —$CONR^6(OR^5)$, -alkyl, -alkylaryl;
$R^5$ is selected from:
—$(CHR^{11}Y)_n$—$R^9$, —$C(R^7R_8)_n$—W—$C(R^7R^8)_m$—$R^9$,
—$C(R^7R^8)_m$—$R^9$, —$C(R^7R^8)_m$-aryl,
$R^6$ is selected from:
H, alkyl-, —$[(C_1-C_6)$alkyl-aryl,
—$(C_1-C_6)$alkyl-heteroaryl,
$R^7$ and $R^8$ may be selected independently from:
H, $R^{11}$, or form a 3 to 7 membered substituted ring with 0–3 unsaturations,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;
$R^9$ is H, alkyl, cycloalkyl, 5 or 6 membered ring optionally containing from 1 to 2 N, O or S(O)p, optionally substituted with —OH, —O—$(C_1-C_6)$alkyl —O-acyl-alkyl, $NHR^{10}$, or aryl;
$R^{10}$ is H or optionally substituted alkyl group;
$R^{11}$ is selected from: H,
—$(C_0-C_6)$alkyl-S(O)p-$(C_1-C_6)$alkyl,
—$(C_0-C_6)$alkyl-O—$(C_1-C_6)$alkyl,
—$(C_0-C_6)$alkyl-S(O)p-$(C_0-C_6)$alkyl-aryl,
—$(C_0-C_6)$alkyl-O—$(C_0-C_6)$alkyl-aryl,
alkyl of from 1 to 20 carbon atoms which include branched, cyclic and unsaturated alkyl groups, substituted alkyl
wherein the substituent is selected from;
hydrogen, halo, hydroxy, alkoxy, aryloxy, phenoxy, amino, mono-alkylamino, di-alkylamino, acylamino, acetamido, benzamido, arylamino, guanidino, N-methyl imidazoly, imidazoly, indolyl, mercapto, alkylthio, arylthio, phenylthio, carboxy, carboxamido, carbo alkoxy, or sulfonamido,
—$(C_0-C_8)$alkyl-aryl,
—$(C_0-C_8)$alkyl-substituted aryl,
—$(C_0-C_8)$aryl-$(C_1-C_4)$alkyl-aryl,
—$(C_1-C_8)$alkyl-biaryl,
—$(C_0-C_8)$alkyl-S(O)p-$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$aklyl-aryl-[S(O)p-$(C_0-C_8)$alkyl],
—$(C_0-C_8)$alkyl-S(O)p-$(C_0-C_8)$alkyl-biaryl,
—$(C_0-C_8)$alkyl-O—$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[O—$(C_0-C_8)$alkyl],
—$(C_0-C_8)$alkyl-O—$(C_0-C_8)$alkyl-biaryl,
—$(C_0-C_8)$alkyl-O—$(C_0-C_8)$alkyl-substituted aryl,
wherein the substituent is selected from;
hydrogen, $C_1-C_5$, alkyl, hydroxy, halo, alkoxy, amino, mono-alkylamino, di-alkylamino, acylamino, thio, thioalky, carboxy, carboxamido or aryl;
m is an integer from 0 to 3;
n is an integer from 1 to 3;
p can be 0, 1 or 2;
W is —O—, S(O)p or $NR^{10}$;
Y is selected from —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O, or S.

12. A compound of claim 11 wherein:
$R^2$ is selected from:
H, —$CO_2R^5$, —$CONR^6R^5$, —$CONR^6(OR^5)$, -alkyl, -alkylaryl;
$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
$R^6$ is selected from:
H, alkyl-, —$(C_1-C_6)$alkyl-aryl,
$R^7$ and $R^8$ may be selected independently from:
H, $R^{11}$, or form a 3 to 7 membered substituted ring with 0–3 unsaturations,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;
$R^9$ is H, alkyl, cycloalkyl, 5 or 6 membered ring optionally containing from 1 to 2 N, O or S(O)p, optionally substituted with —OH, —O—$(C_1-C_6)$alkyl, —O-acyl-alkyl, $NHR^{10}$, or aryl;
$R^{10}$ is H or an optionally substituted alkyl group;
$R^{11}$ is selected from:
H,
—$(C_0-C_6)$alkyl-S(O)p-$(C_1-C_6)$alkyl,
—$(C_0-C_6)$alkyl-O—$(C_1-C_6)$alkyl,
—$(C_0-C_6)$alkyl-S(O)p-$(C_0-C_6)$alkyl-aryl,
—$(C_0-C_6)$alkyl-O—$(C_0-C_6)$alkyl-aryl,
alkyl of from 1 to 20 carbon atoms which may be branched, cyclic and unsaturated alkyl groups, substituted alkyl wherein the substituent is selected from;
hydrogen, halo, hydroxy, alkoxy, aryloxy, phenoxy, amino, mono- alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0-C_8)$alkyl-aryl,
—$(C_0-C_8)$alkyl-substituted aryl,
—$(C_0-C_8)$aryl-$(C_1-C_4)$alkyl-aryl,
—$(C_0-C_8)$alkyl-biaryl,
—$(C_0-C_8)$alkyl-S(O)p-$(C_0-C_8)$alkyl-aryl,
—$(C_0-C_8)$alkyl-S(O)p-$(C_0-C_8)$alkyl-substituted aryl,
—$(C_1-C_4)$alky-aryl-$(C_{0-C8})$alkyl-aryl-[S(O)p-$(C_0-C_8)$alkyl],
—$(C_0-C_8)$alkyl-S(O)p-$(C_0-C_8)$alkyl-biaryl,
—$(C_0-C_8)$alkyl-O—$(C_0-C_8)$alkyl-aryl,
—$(C_0-C_8)$alkyl-S(O)p-$(C_0-C_8)$alkyl-substituted aryl,
—$(C_0-C_4)$alkyl-aryl-$(C_0-C_8)$alkyl-aryl-[O—$(C_0-C_8)$alkyl],
—$(C_0-C_8)$alkyl-O—$(C_0-C_8)$alkyl-biaryl,
—$(C_0-C_8)$alkyl-O—$(C_0-C_8)$alkyl-substituted aryl,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;
m is an integer from 0 to 3;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N,O or S.

13. A compound of claim 12 wherein:
$R^2$ is selected from:
H, —$CO_2R^5$, —$CONR^6R^5$, —$CONN^6(OR^5)$, -alkyl, -alkylaryl;
$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
$R^6$ is selected from:
H, alkyl-, —$(C_1-C_6)$alkyl-aryl,
$R^7$ and $R^8$ may be selected independently from:
H, $R^{11}$, or form a 3 to 7 membered substituted ring with 0–3 unsaturations,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;
$R^9$ is H, alkyl, cycloalkyl, 5 or 6 membered ring optionally containing from 1 to 2 N, O or S(O)p;
$R^{10}$ is H or an optionally substituted alkyl group;
$R^{11}$ is selected from:
H,
—$(C_0-C_6)$alkyl-S(O)p-$(C_1-C_6)$alkyl,
—$(C_0-C_6)$alkyl-O—$(C_1-C_6)$alkyl,
—$(C_0-C_6)$alkyl-S(O)p-$(C_0-C_6)$alkyl-aryl,
—$(C_0-C_6)$alkyl-O—$(C_0-C_6)$alkyl-aryl,
alkyl of from 1 to 20 carbon atoms which may be branched, cyclic and unsaturated alkyl groups, substituted alkyl wherein the substituent is selected from;
hydrogen, halo, hydroxy, alkoxy, aryloxy, phenoxy, amino, mono- alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0–C_8)$alkyl-aryl,
—$(C_0–C_8)$alkyl-substituted aryl,
—$(C_0–C_8)$aryl-$(C_1–C_4)$alkyl-aryl,
—$(C_0–C_8)$alkyl-biaryl,
—$(C_0–C_8)$alkyl-S(O)p-$(C_0C_8)$alkyl-aryl,
—$(C_0–C_8)$alkyl-S(O)p-$(C_0–C_8)$alkyl-substituted aryl,
—$(C_1–C_4)$alkyl-aryl-$(C_0–C_8)$alkyl-aryl-[S(O)p-$(C_0–C_8)$alkyl],
—$(C_0–C_8)$alkyl-S(O)p-$(C_0–C_8)$alkyl-biaryl,
—$(C_0–C_8)$alkyl-O—$(C_0–C_8)$alkyl-aryl,
—$(C_0–C_8)$alkyl-S(O)p-$(C_0–C_8)$alkyl-substituted aryl,
—$(C_1–C_4)$alkyl-aryl-$(C_0–C_8)$alkyl-aryl-[O—$(C_0–C_8)$alkyl],
—$(C_0–C_8)$alkyl-O—$(C_0–C_8)$alkyl-biaryl,
—$(C_0–C_8)$alkyl-O—$(C_0–C_8)$alkyl-substituted aryl,
wherein the substituent is selected from;
hydrogen, $C_1–C_5$ alkyl, hydroxy, halo, alkoxy, amino, mono-alkylamino, di-alkylamino, acylamino, thio, thioalkyl, carboxy, carboamido or aryl;
m is an integer from 0 to 3;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O or S.

14. A compound of claim 13 wherein:
$R^2$ is selected from:
H, —$CO_2R^5$, —$CONR^6R^5$, —$CONR^6(OR^5)$, -alkyl, -alkylaryl;
$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
$R^6$ is selected from:
H, alkyl-, —$(C_1–C_6)$alkyl-aryl,
$R^7$ and $R^8$ may be selected independently from:
H, $R^{11}$, or form a 3 to 7 membered substituted ring with 0–3 unsaturations,
wherein the substituent is selected from;
hydrogen, $C_1–C_5$ alkyl, hydroxy, halo, alkoxy, amino, mono-alkylamino, di-alkylamino, acylamino, thio, thioalkyl, carboxy, carboamido or aryl;
$R^9$ is H, alkyl, 5 or 6 membered ring optionally containing from 1 to 2 N, O or S(O)p;
$R^{10}$ is H or an optionally substituted alkyl group;
$R^{11}$ is selected from:
H,
—$(C_0–C_6)$alkyl-S(O)p-$(C_1–C_6)$alkyl,
—$(C_0–C_6)$alkyl-O—$(C_1–C_6)$alkyl,
—$(C_0–C_6)$alkyl-S(O)p-$(C_0–C_6)$alkyl-aryl,
—$(C_0–C_6)$alkyl-O—$(C_0–C_6)$alkyl-aryl,
alkyl of from 1 to 20 carbon atoms which may be branched, cyclic and unsaturated alkyl groups, substituted alkyl wherein the substituent is selected from;
hydrogen, halo, hydroxy, alkoxy, aryloxy, phenoxy, amino, mono- alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0–C_8)$alkyl-aryl,
—$(C_0–C_8)$alkyl-substituted aryl,
—$(C_0–C_8)$alkyl-$(C_1C_4)$alkyl-aryl,
—$(C_1–C_8)$alkyl-biaryl,
—$(C_0–C_8)$alkyl-S(O)p-$(C_0–C_8)$alkyl-aryl,
—$(C_0–C_8)$alkyl-S(O)p-$(C_0–C_8)$alkyl-substituted aryl,
—$(C_1–C_4)$alkyl-aryl-$(C_0–C_8)$alkyl-aryl-[S(O)p-$(C_0–C_8)$alkyl],
—$(C_0–C_8)$alkyl-S(O)p-$(C_0–C_8)$alkyl-biaryl,
—$(C_0–C_8)$alkyl-O—$(C_0–C_8)$alkyl-aryl,
—$(C_0–C_8)$alkyl-S(O)p-$(C_0–C_8)$alkyl-substituted aryl,
—$(C_1–C_4)$alkyl-aryl-$(C_0–C_8)$alkyl-aryl-[O—$(C_0–C_8)$alkyl],
—$(C_0–C_8)$alkyl-O—$(C_0–C_8)$alkyl-biaryl,
—$(C_0–C_8)$alkyl-O—$(C_0–C_8)$alkyl-substituted aryl,
wherein the substituent is selected from;
hydrogen, $C_1–C_5$ alkyl, hydroxy, halo, alkoxy, amino, mono-alkylamino, di-alkylamino, acylamino, thio, thioalkyl, carboxy, carboamido or aryl;
m is an integer from 0 to 3;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—,—$NR^{10}SO_2$, a 5 membered heterocyclic ring saturated, unsaturated or partially unsaturated containing from 1 to 4 heteroatoms selected from N, O or S.

15. A compound of claim 14 wherein:
$R^2$ is selected from:
H, —$CO_2R^5$, —$CONR^6R^5$, —$CONR^6(OR^5)$, -alkyl, -alkylaryl;
$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
$R^6$ is selected from:
H, alkyl-, —$(C_1–C_6)$alkyl-aryl,
$R^7$ and $R^8$ may be selected independently from:
H, $R^{11}$, or form a 3 to 7 membered substituted ring with 0–2 unsaturations,
wherein the substituent is selected from;
hydrogen, $C_1–C_5$ alkyl, hydroxy, halo, alkoxy, amino, mono-alkylamino, di-alkylamino, acylamino, thio, thioalkyl, carboxy, carboamido or aryl;
$R^9$ is H, alkyl, 5 or 6 membered ring optionally containing from 1 to 2 N, O or S(O)p;
$R^{10}$ is H or an optionally substituted alkyl group;
$R^{11}$ is selected from:
H,
—$(C_0–C_6)$alkyl-S(O)p-$(C_1–C_6)$alkyl,
—$(C_0–C_6)$alkyl-O—$(C_1–C_6)$alkyl,
—$(C_0–C_6)$alkyl-S(O)p-$(C_0–C_6)$alkyl-aryl,
—$(C_0–C_6)$alkyl-O—$(C_0–C_6)$alkyl-aryl,
alkyl of from 1 to 20 carbon atoms which may be branched, cyclic and unsaturated alkyl groups, substituted alkyl wherein the substituent is selected from;
hydrogen, halo, hydroxy, alkoxy, aryloxy, phenoxy, amino, mono- alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0–C_8)$alkyl-aryl,
—$(C_0–C_8)$alkyl-substituted aryl,
—$(C_0–C_8)$aryl-$(C_1–C_4)$alkyl-aryl,
—$(C_1–C_8)$alkyl-biaryl,
—$(C_0–C_8)$alkyl-S(O)p-$(C_0–C_8)$alkyl-aryl,
—$(C_0–C_8)$alkyl-S(O)p-$(C_0–C_8)$alkyl-substituted aryl,
—$(C_1–C_4)$alkyl-aryl-$(C_0–C_8)$alkyl-aryl-[S(O)p-$(C_0–C_8)$alkyl],
—$(C_0–C_8)$alkyl-S(O)p-$(C_0C_8)$alkyl-biaryl,
—$(C_0–C_8)$alkyl-O—$(C_0–C_8)$alkyl-aryl,
—$(C_0–C_8)$alkyl-S(O)p-$(C_0–C_8)$alkyl-substituted aryl,
—$(C_1–C_4)$alkyl-aryl-$(C_0–C_8)$alkyl-aryl-[O—$(C_0–C_8)$alkyl],
—$(C_0–C_8)$alkyl-O—$(C_0–C_8)$alkyl-bairyl,
—$(C_0–C_8)$alkyl-O—$(C_0–C_8)$alkyl-substituted aryl,
wherein the substituent is selected from;
hydrogen, $C_1–C_5$ alkyl, hydroxy, halo, alkoxy, amino, mono-alkylamino, di-alkylamino, acylamino, thio, thioalkyl, carboxy, carboamido or aryl;
m is an integer from 0 to 3;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O or S.

16. A compound of claim 15 wherein:
$R^2$ is selected from:
H, —$CO_2R^5$, —$CONR^6R^5$, —$CONR^6(OR^5)$;
$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
$R^6$ is selected from:
H, alkyl-, —$(C_1–C_6)$alkyl-aryl,
$R^7$ and $R^8$ may be selected independently from:
H, $R^{11}$, or form a 3 to 7 membered substituted ring with 0–2 unsaturations,
wherein the substituent is selected from;
hydrogen, $C_1–C_5$ alkyl, hydroxy, halo, alkoxy, amino, mono-alkylamino, di-alkylamino, acylamino, thio, thioalkyl, carboxy, carboamido or aryl;
$R^9$ is H, alkyl, 5 or 6 membered ring optionally containing from 1 to 2 N, O or S(O)p;
$R^{10}$ is H or an optionally substituted alkyl group;
$R^{11}$ is selected from:
H,
—$(C_0–C_6)$alkyl-S(O)p-$(C_1–C_6)$alkyl,
—$(C_0–C_6)$alkyl-O—$(C_1–C_6)$alkyl,
—$(C_0–C_6)$alkyl-S(O)p-$(C_0–C_6)$alkyl-aryl,
—$(C_0–C_6)$alkyl-O—$(C_0–C_6)$alkyl-aryl,
alkyl of from 1 to 20 carbon atoms which may be branched, cyclic and unsaturated alkyl groups, substituted alkyl wherein the substituent is selected from;
hydrogen, halo, hydroxy, alkoxy, aryloxy, phenoxy, amino, mono- alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0–C_8)$alkyl-aryl,
—$(C_0–C_8)$alkyl-substituted aryl,
—$(C_0–C_8)$aryl-$(C_1–C_4)$alkyl-aryl,
—$(C_1–C_8)$alkyl-biaryl,
—$(C_0–C_8)$alkyl-S(O)p-$(C_0–C_8)$alkyl-aryl,
—$(C_0–C_8)$alkyl-S(O)p-$(C_0–C_8)$alkyl-substituted aryl,
—$(C_1–C_4)$alkyl-aryl-$(C_0–C_8)$alkyl-aryl-[S(O)p-$(C_0–C_8)$aklyl],
—$(C_0–C_8)$alkyl-S(O)p-$(C_0–C_8)$alkyl-biaryl,
—$(C_0–C_8)$alkyl-O—$(C_0–C_8)$alkyl-aryl,
—$(C_0–C_8)$alkyl-S(O)p-$(C_0–C_8)$alkyl-substituted aryl,
—$(C_1–C_4)$alkyl-aryl-$(C_0–C_8)$alkyl-aryl-[O—$(C_0–C_8)$alkyl],
—$(C_0–C_8)$alkyl-O—$(C_0–C_8)$alkyl-biaryl,
—$(C_0–C_8)$alkyl-O—$(C_0–C_8)$alkyl-substituted aryl,
wherein the substituent is selected from;
hydrogen, $C_1–C_5$ alkyl, hydroxy, halo, alkoxy, amino, mono-alkylamino, di-alkylamino, acylamino, thio, thioalkyl, carboxy, carboamido or aryl;
m is an integer from 0 to 3;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—, a 5 membered heterocyclic ring saturated, unsaturated or partially unsaturated containing from 1 to 4 heteroatoms selected from N, O or S.

17. A compound of claim 16 wherein:
$R^2$ is selected from:
H, —$CO_2R^5$, —$CONR^6R^5$, —$CONR^6(OR^5)$;
$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
$R^6$ is selected from:
H, alkyl-, —$(C_1–C_6)$alkyl-aryl,
$R^7$ and $R^8$ may be selected independently from:
H, $R^{11}$, or form a 3 to 7 membered substituted ring with 0–2 unsaturations,
wherein the substituent is selected from;
hydrogen, $C_1–C_5$ alkyl, hydroxy, halo, alkoxy, amino, mono-alkylamino, di-alkylamino, acylamino, thio, thioalkyl, carboxy, carboamido or aryl;
$R^9$ is H, alkyl, 5 or 6 membered ring optionally containing from 1 to 2 N, O or S(O)p;
$R^{10}$ is H or an optionally substituted alkyl group;
$R^{11}$ is selected from:
H,
—$(C_0–C_6)$alkyl-S(O)p-$(C_1–C_6)$alkyl,
—$(C_0–C_6)$alkyl-O—$(C_1–C_6)$alkyl,
—$(C_0–C_6)$alkyl-S(O)p-$(C_0–C_6)$alkyl-aryl,
—$(C_0–C_6)$alkyl-O—$(C_0–C_6)$alkyl-aryl,
alkyl of from 1 to 20 carbon atoms which may be branched, cyclic and unsaturated alkyl groups, substituted alkyl wherein the substituent is selected from:
hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0-C_8)$alkyl-aryl,
—$(C_0-C_8)$alkyl-substituted aryl,
—$(C_0-C_8)$aryl-$(C_1-C_4)$alkyl-aryl,
—$(C_1-C_8)$alkyl-biaryl,
—$(C_0-C_8)$alkyl-S(O)p-$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[S(O)p-$(C_0-C_8)$alkyl],
—$(C_0-C_8)$alkyl-S(O)p-$(C_0-C_8)$alkyl-biaryl,
—$(C_0-C_8)$alkyl-O—$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[O—$(C_0-C_8)$alkyl],
—$(C_0-C_8)$alkyl-O—$(C_0-C_8)$alkyl-biaryl,
—$(C_0-C_8)$alkyl-O—$(C_0-C_8)$alkyl-substituted aryl,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;
m is an integer from 0 to 3;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—.
18. A compound of claim 17 wherein:
$R^2$ is selected from:
H, —$CO_2R^5$, —$CONR^6R^5$, —$CONR^6(OR^5)$;
$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$, —$C(R^7R^8)_m$-aryl,
$R^6$ is selected from:
H, alkyl-, —$(C_1-C_6)$alkyl-aryl,
$R^7$ and $R^8$ may be selected independently from:
H, $R^{11}$;
$R^9$ is H, alkyl, 5 or 6 membered ring optionally containing from 1 to 2 N, O or S(O)p;
$R^{10}$ is H or an optionally substituted alkyl group;
$R^{11}$ is selected from:
H,
—$(C_0-C_6)$alkyl-S(O)p-$(C_1-C_6)$alkyl,
—$(C_0-C_6)$alkyl-O—$(C_1-C_6)$alkyl,
—$(C_0-C_6)$alkyl-S(O)p-$(C_0-C_6)$alkyl-aryl,
—$(C_0-C_6)$alkyl-O—$(C_0-C_6)$alkyl-aryl,
alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, henoxy, amino, mono- alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0-C_8)$alkyl-aryl,
—$(C_0-C_8)$alkyl-substituted aryl,
—$(C_0-C_8)$aryl-$(C_1-C_4)$alkyl-aryl,
—$(C_1-C_8)$alkyl-biaryl,
—$(C_0-C_8)$alkyl-S(O)p-$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[S(O)p-$(C_0-C_8)$alkyl],
—$(C_0-C_8)$alkyl-S(O)p-$(C_0-C_8)$alkyl-biaryl,
—$(C_0-C_8)$alkyl-O—$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[O—$(C_0-C_8)$alkyl],
—$(C_0-C_8)$alkyl-O—$(C_0-C_8)$alkyl-biaryl,
—$(C_0-C_8)$alkyl-O—$(C_0-C_8)$alkyl-substituted aryl,
wherein the substituent is selected from;
hydrogen, $C_1-C_5$ alkyl, hydroxy, halo, alkoxy, amino, mono-alkylamino, di-alkylamino, acylamino, thio, thioalkyl, carboxy, carboamido or aryl;
m is an integer from 0 to 3;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—.
19. A compound of claim 18 wherein:
$R^2$ is selected form:
H, —$CONR^6R^5$, —$CONR^6(OR^5)$;
$R^5$ is selected from:
—$(CHR^{11}Y)_n$—$R^9$, —$C(R^7R^8)_n$—W—$C(R^7R^8)_m$—$R^9$,
—$C(R^7R^8)_m$—$R^9$, —$C(R^7R^8)_m$—aryl,
$R^6$ is selected from:
H, alkyl-, —$(C_1-C_6)$alkyl-aryl,
$R^7$ and $R^8$ may be selected independently from:
H, $R^{11}$;
$R^9$ is H, alkyl, 5 or 6 membered ring optionally containing from 1 to 2 N, O or S(O)p;
$R^{10}$ is H or an optionally substituted alkyl group;
$R^{11}$ is selected from:
H,
—$(C_0-C_6)$alkyl-S(O)p-$(C_1-C_6)$alkyl,
—$(C_0-C_6)$alkyl-O—$(C_1-C_6)$alkyl,
—$(C_0-C_6)$alkyl-S(O)p-$(C_0-C_6)$alkyl-aryl,
—$(C_0-C_6)$alkyl-O—$(C_0-C_6)$alkyl-aryl,
alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, phenoxy, amino, mono- alkylamino, di-alkylamino, acylamino acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—$(C_0-C_8)$alkyl-aryl,
—$(C_0-C_8)$alkyl-substituted aryl,
—$(C_0-C_8)$aryl-$(C_1-C_4)$alkyl-aryl,
—$(C_1-C_8)$alkyl-biaryl,
—$(C_0-C_8)$alkyl-S(O)p-$(C_0-C_8)$alkyl-aryl,
—$(C_0-C_8)$alkyl-S(O)p-$(C_0-C_8)$alkyl-substituted aryl,
—$(C_1-C_4)$alkyl-aryl-$(C_0-C_8)$alkyl-aryl-[S(O)p-$(C_0-C_8)$alkyl], —($C_0$–$C_8$)alkyl-S(O)p-($C_0$–$C_8$)alkyl-biaryl,
—($C_0$–$C_8$)alkyl-O—($C_0$–$C_8$)alkyl-aryl,
—($C_0$–$C_8$)alkyl-S(O)p-($C_0C_8$)alkyl-substituted aryl,
—($C_1$–$C_4$)alkyl-aryl-($C_0C_8$)alkyl-aryl-[O—($C_0$–$C_8$)alkyl],
—($C_0$–$C_8$)alkyl-O—($C_0$–$C_8$)alkyl-biaryl,
—($C_0$–$C_8$)alkyl-O—($C_0$–$C_8$)alkyl-substituted aryl,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl;

m is an integer from 0 to 3;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—.

20. A compound of claim 19 wherein:
$R^2$ is selected from:
H, —$CONR^6R^5$, —$CONR^6(OR^5)$;
$R^5$ is selected from:
—$(CHR^{11}Y)_n$—$R^9$,
$R^6$ is selected from:
H, alkyl-, —($C_1$–$C_6$)alkyl-aryl,
$R^7$ and $R^8$ may be selected independently from:
H, $R^{11}$;
$R^9$ is H, alkyl, 5 or 6 membered ring optionally containing from 1 to 2 N, O or S(O)p;
$R^{10}$ is H or an optionally substituted alkyl group;
$R^{11}$ is selected from:
H,
—($C_0$–$C_6$)alkyl-S(O)p-($C_1$–$C_6$)alkyl,
—($C_0$–$C_6$)alkyl-O—($C_1$–$C_6$)alkyl,
—($C_0$–$C_6$)alkyl-S(O)p-($C_0$–$C_6$)alkyl-aryl,
—($C_0$–$C_6$)alkyl-O—($C_0$–$C_6$)alkyl-aryl,
alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—($C_0$–$C_8$)alkyl-aryl,
—($C_0$–$C_8$)-substituted aryl,
—($C_0$–$C_8$)aryl-($C_1$–$C_4$)alkyl-aryl,
—($C_1$–$C_8$)alkyl-biaryl,
—($C_0$–$C_8$)alkyl-S(O)p-($C_0$–$C_8$)alkyl-aryl,
—($C_0$–$C_8$)alkyl-S(O)p-($C_0$–$C_8$)alkyl-substituted aryl,
—($C_1$–$C_4$)alkyl-aryl-($C_0$–$C_8$)alkyl-aryl-[S(O)p-($C_0$–$C_8$)alkyl],
—($C_0$–$C_8$)alkyl-S(O)p-($C_0$–$C_8$)alkyl-biaryl,
—($C_0$–$C_8$)alkyl-O—($C_0$–$C_8$)alkyl-aryl,
—($C_0$–$C_8$)alkyl-S(O)p-($C_0$–$C_8$)alkyl-substituted aryl,
—($C_1$–$C_4$)alkyl-aryl-($C_0$–$C_8$)alkyl-aryl-[O—($C_0$–$C_8$)alkyl],
—($C_0$–$C_8$)alkyl-O—($C_0$–$C_8$)alkyl-biaryl,
—($C_0$–$C_8$)alkyl-O—($C_0$–$C_8$)alkyl-substituted aryl,
wherein the substituent is selected from;
hydrogen, $C_1$–$C_5$ alkyl, hydroxy, halo, alkoxy, amino, mono-alkylamino, di-alkylamino, acylamino, thio, thioalkyl, carboxy, carboamido or aryl;

m is an integer from 0 to 3;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—.

21. A compound of claim 20 wherein:
$R^2$ is selected from:
H, —$CONR^6R^5$, —$CONR^6(OR^5)$;
$R^5$ is selected from:
—$(CHR^{11}Y)_n$—$R^9$,
$R^6$ is selected from:
H, alkyl-, —($C_1$–$C_6$)alkyl-aryl,
$R^7$ and $R^8$ may be selected independently from:
H, $R^{11}$;
$R^9$ is H, alkyl, 5 or 6 membered ring optionally containing from 1 to 2 N, O or S(O)p;
$R^{10}$ is H or an optionally substituted alkyl group;
$R^{11}$ is selected from:
H,
—($C_0$–$C_6$)alkyl-S(O)p-($C_1$–$C_6$)alkyl,
—($C_0$–$C_6$)alkyl-O—($C_1$–$C_6$)alkyl,
—($C_0$–$C_6$)alkyl-S(O)p-($C_0$–$C_6$)alkyl-aryl,
—($C_0$–$C_6$)alkyl-O—($C_0$–$C_6$)alkyl-aryl, alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—($C_0$–$C_8$)alkyl-aryl,
—($C_0$–$C_8$)aryl-($C_1$–$C_4$)alkyl-aryl,
—($C_1$–$C_8$)alkyl-biaryl
—($C_0$–$C_8$)alkyl-S(O)p-($C_0$–$C_8$)alkyl-aryl,
—($C_1$–$C_4$)alkyl-aryl-($C_0$–$C_8$)alkyl-aryl-[S(O)p-($C_0$–$C_8$)alkyl],
—($C_0$–$C_8$)alkyl-S(O)p-($C_0$–$C_8$)alkyl-biaryl,
—($C_0$–$C_8$)-O—($C_0$–$C_8$)alkyl-aryl,
—($C_1$–$C_4$)alkyl-aryl-($C_0$–$C_8$)alkyl-aryl-[O—($C_0$–$C_8$)alkyl],
—($C_0$–$C_8$)-O—($C_0$–$C_8$)alkyl-biaryl, m is an integer from 0 to 3;
n is an integer from 1 to 3;
p can be 0, 1 or 2;
W is —O—, S(O)p or $NR^{10}$;
Y is selected from: —$CONR^{10}$—, —$NR^{10}CO$—, —$SO_2NR^{10}$—, —$NR^{10}SO_2$—.

22. A compound of claim 21 wherein:
$R^2$ is selected from:
H, —$CONR^6R^5$, —$CONR^6(OR^5)$;
$R^5$ is selected from:
—$(CHR^{11}Y)_n$—$R^9$,
$R^6$ is selected from:
H, alkyl-, —($C_1$–$C_6$)alkyl-aryl,
$R^7$ and $R^8$ may be selected independently from:
H, $R^{11}$;
$R^9$ is H, alkyl, 5 or 6 membered ring optionally containing from 1 to 2 N, O or S(O)p;
$R^{10}$ is H or an optionally substituted alkyl group;

R$^{11}$ is selected from:
H,
—(C$_0$–C$_6$)alkyl-S(O)p-(C$_1$–C$_6$)alkyl,
—(C$_0$–C$_6$)alkyl-O—(C$_1$–C$_6$)alkyl,
—(C$_0$–C$_6$)alkyl-S(O)p-(C$_0$–C$_6$)alkyl-aryl,
—(C$_0$–C$_6$)alkyl-O—(C$_0$–C$_6$)alkyl-aryl,
alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, phenoxy, amino, mono-alkylamino, di-alkylamino, acylamino, acetamido, benzamido, arylamino, guanidino, N-methyl imidazolyl, imidazolyl, indolyl, mercapto, alkylthio, arylthio, phenylthio, carboxy, carboxamido, carbo alkoxy, or sulfonamido,
—(C$_0$–C$_8$)alkyl-aryl,
—(C$_0$–C$_8$)aryl-(C$_1$–C$_4$)alkyl-aryl,
—(C$_0$–C$_8$)alkyl-S(O)p-(C$_0$–C$_8$)alkyl-aryl,
—(C$_1$–C$_4$)alkyl-aryl-(C$_0$–C$_8$)alkyl-aryl-[S(O)p-(C$_0$–C$_8$)alkyl],
—(C$_0$–C$_8$)alkyl-O—(C$_0$–C$_8$)alkyl-aryl,
—(C$_1$–C$_4$)alkyl-aryl-(C$_0$–C$_8$)alkyl-aryl-[O—(C$_0$–C$_8$)alkyl],
m is an integer from 0 to 3;
n is an integer from 1 to 3;
p can be 0, 1 or 2;
W is —O—, S(O)p or NR$^{10}$;
Y is selected from: —CONR$^{10}$—, —NR$^{10}$CO—, —SO$_2$NR$^{10}$—, —NR$^{10}$SO$_2$—.

23. A compound of claim 22 wherein:
R$^2$ is selected from:
H, —CONR$^6$R$^5$, —CONR$^6$(OR$^5$);
R$^5$ is selected from:
—(CHR$^{11}$Y)$_n$—R$^9$,
R$^6$ is selected from:
H, alkyl-, —(C$_1$–C$_6$)alkyl-aryl,
R$^7$ and R$^8$ may be selected independently from:
H, R$^{11}$;
R$^9$ is H, alkyl, 5 or 6 membered ring optionally containing from 1 to 2 N, O or S(O)p;
R$^{10}$ is H or an optionally substituted alkyl group;
R$^{11}$ is selected from:
H,
—(C$_0$–C$_6$)alkyl-S(O)p-(C$_1$–C$_6$)alkyl,
—(C$_0$–C$_6$)alkyl-O—(C$_1$–C$_6$)alkyl,
—(C$_0$–C$_6$)alkyl-S(O)p-(C$_0$–C$_6$)alkyl-aryl,
—(C$_0$–C$_6$)alkyl-O—(C$_0$–C$_6$)alkyl-aryl,
alkyl of from 1 to 20 carbon atoms which may be branched, cyclic and unsaturated alkyl groups, substituted alkyl
wherein the substituent is selected from;
hydrogen, halo, hydroxy, alkoxy, aryloxy, phenoxy, amino, mono-alkylamino, di-alkylamino, acylamino, acetamido, benzamido, arylamino, guanidino, N-methyl imidazoly, imidazolyl, indolyl, mercapto, alkylthio, arylthio, phenylthio, carboxy, carboxamido, carbo alkoxy, or sulfonamido,
m is an integer from 0 to 3;
n is an integer from 1 to 3;
p can be 0, 1 or 2;
W is —O—, S(O)p or NR$^{10}$;
Y is selected from: —CONR$^{10}$—, —NR$^{10}$CO—, —SO$_2$NR$^{10}$—, —NR$^{10}$SO$_2$—.

24. A compound of claim 23 wherein:
R$^2$ is selected from:
H, —CONR$^6$R$^5$, —CONR$^6$(OR$^5$);
R$^5$ is selected from:
—(CHR$^{11}$Y)$_n$—R$^9$,
R$^6$ is selected from:
H, alkyl-, —(C$_1$–C$_6$)alkyl-aryl,
R$^7$ and R$^8$ may be selected independently from:
H, R$^{11}$;
R$^9$ is H, alkyl, 5 or 6 membered ring optionally containing from 1 to 2 N, O or S(O)p;
R$^{10}$ is H or an optionally substituted alkyl group;
R$^{11}$ is selected from:
H,
—(C$_0$–C$_6$)alkyl-S(O)p-(C$_1$–C$_6$)alkyl,
—(C$_0$–C$_6$)alkyl-O-(C$_1$–C$_6$)alkyl,
—(C$_0$–C$_6$)alkyl-S-(O)p-(C$_0$–C$_6$)alkyl-aryl,
—(C$_0$–C$_6$)alkyl-O-(C$_0$–C$_6$)alkyl-aryl,
alkyl of from 1 to 20 carbon atoms which may be branched,
cyclic and unsaturated alkyl groups,
m is an integer from 0 to 3;
n is an integer from 1 to 3;
p can be 0, 1 or 2;
W is —O—, S(O)p or NR$^{10}$;
Y is selected from: —CONR$^{10}$—, —NR$^{10}$CO—, —SO$_2$NR$^{10}$—, —NR$^{10}$SO$_2$—.

25. A compound of claim 1 selected from the group consisting of:

2S,5R,6S-3-aza-4-oxo-10-oxa-5-isobutyl-2-(N-methylcarboxamido)-(10)paracyclophane-6-N-hydroxycarboxamide;
2S,5R,6S-3-aza-4-oxo-10-oxa-5-isobutyl-2-(carboxymethyl)-(10) paracyclophane-6-N-hydroxycarboxamide;
2S,5R,6S-3-aza-4-oxo-10-oxa-5-isobutyl-2-(N-benzylcarboxamido)-(10)paracyclophane-6-N-hydroxycarboxamide;
2S,5R,6S-3-aza-4-oxo-10-oxa-5-isobutyl-2-(hydroxymethyl)-(10)paracyclophane-6-N-hydroxycarboxamide;
2S,5R,6S-3-aza-4-oxo-10-oxa-5-isobutyl-2-(L-alanine-N-methylamide)-(10)paracyclophane-6-N-hydroxycarboxamide;
2S,5R,6S-3-aza-4-oxo-10-oxa-5-isobutyl-2-[L-(O)-methyl)tyrosine-N-methylamide]-(10)paracyclophane-6-N-hydroxycarboxamide;
2S,5R,6S-3-aza-4-oxo-10-oxa-5-isobutyl-2-[L-(O-tert-butyl)serine-N-methylamide]-(10)paracyclophane-6-N-hydroxycarboxamide;
2S,5R,6S-3-aza-4-oxo-10-oxa-5-isobutyl-2-(L-serine-N-methylamide)-(10paracyclophane-6-N-hydroxycarboxamide;
2S,5R,6S-3-aza-4-oxo-10-oxa-5-isobutyl-2-(glycine-N-methylamide)-(10)paracyclophane-6-N-hydroxycarboxamide;
2S,5R,6S-3-aza-4-oxo-10-oxa-5-isobutyl-2-(D-alanine-N-methylamido)-(10)paracyclophane-6-N-hydroxycarboxamide;
2S,5R,6S-3-aza-4-oxo-10-oxa-5-isobutyl-2-(L-valine-N-methylcarboxamido)-(10)paracyclophane-6-N-hydroxycarboxamide;

2S,5R,6S-3-aza-4-oxo-10-oxa-5-isobutyl-2-(beta-alanine-N-methylcarboxamido)-(10)paracyclophane-6-N-hydroxycarboxamide;

2S,5R,6S-3-aza-4-oxo-10-oxa-5-isobutyl-2-(D-alanine-N-methylamide)-(10)paracyclophane-6-N-hydroxycarboxamide;

2S,5R,6S-3-aza-4-oxo-10-oxa-5-isobutyl-2-(beta-alanine-N-methylamide)-(10)paracyclophane-6-N-hydroxycarboxamide;

2S,5R,6S-3-aza-4-oxo-10-oxa-5-isobutyl-2-[D-(O-tert-butyl)serine-N-methylamide]-(10)paracyclophane-6-N-hydroxycarboxamide;

2S,5R,6S-3-aza-4-oxo-10-oxa-5-isobutyl-2-(D-serine-N-methylamide)-(10)paracyclophane-6-N-hydroxycarboxamide;

2S,5R,6S-3-aza-4-oxo-10-oxa-5-isobutyl-2-(L-lysine-N-methylamide)-(10)paracyclophane-6-N-hydroxycarboxamide;

2S,5R,6S-3-aza-4-oxo-10-oxa-5-isobutyl-2-(L-valine-N-methylamide)-(10)paracyclophane-6-N-hydroxycarboxamide;

2S,5R,6S-3-aza-4-oxo-10-oxa-5-isobutyl-2-[(2-pyridyl)ethylcarboxamido]-(10)paracyclophane-6-N-hydroxycarboxamide trifluoroacetate;

2S,5R,6S-3-aza-4-oxo-10-oxa-5-isobutyl-2-[(4-methyl)piperazinylcarboxamido]-(10)paracyclophane-6-N-hydroxycarboxamide;

2S,5R,6S-3-aza-4-oxo-10-oxa-5-isobutyl-2-(2-benzimidazolyl)-(10)paracyclophane-6-N-bydorxycarboxamide;

2S,5R,6S-3-aza-4-oxo-10-oxa-5-isobutyl-2-[(2-imidazolyl)carboxamido]-(10)paracyclophane-6-N-hydroxycarboxamide;

2S,5R,6S-3-aza-4-oxo-10-oxa-5-isobutyl-2-[(2-benzimidazolyl)methylcarboxamido]-(10)paracyclophane-6-N-hydroxycarboxamide;

2S,5R,6S-3-aza-4-oxo-10-oxa-5-isobutyl-2-[(3-imidazolyl)propylcarboxamido]-(10)paracyclophane-6-N-hydroxycarboxamide;

2S,5R,6S-3-aza-4-oxo-10-oxa-5-isobutyl-2-[2-(4-aminosulfonylphenyl)ethylcarboxamido]-(10)paracyclophane-6-N-hydroxycarboxamide;

2S,5R,6S-3-aza-4-oxo-10-oxa-5-isobutyl-2-(glycine-N,N-dimethylamide)-(10)paracyclophane-6-N-hydroxycarboxamide;

2S,5R,6S-3-aza-4-oxo-10-oxa-5-isobutyl-2-(1-adamantylcarboxamido)-(10)paracyclophane-6-N-hydroxycarboxamide;

2S,5R,6S-3-aza-4-oxo-10-oxa-5-isobutyl-2-[(4-aminoindazolyl)carboxamido]-(10)paracyclophane-6-N-hydroxycarboxamide;

2S,5R,6S-3-aza-4-oxo-10-oxa-5-isobutyl-2-(N,N-diethylcarboxamido)-(10)paracyclophane-6-N-hydroxycarboxamide;

2S,5R,6S-3-aza-4-oxo-10-oxa-5-isobutyl-2-(N-isopropylcarboxamido)-(10)paracyclophane-6-N-hydroxycarboxamide;

2S,5R,6S-3-aza-4-oxo-10-oxa-5-isobutyl-2-(N-cyclopropylcarboxamido)-(10)paracyclophane-6-N-hydroxycarboxamide;

2S,5R,6S-3-aza-4-oxo-10-oxa-5-isobutyl-2-(N-tert-butylcarboxamido)-(10)paracyclophane-6-N-hydroxycarboxamide;

2S,5R,6S-3-aza-4-oxo-10-oxa-5-isobutyl-2-[glycine-(N-isopropyl)amide]-(10)paracyclophane-6-N-hydroxycarboxamide;

2S,5R,6S-3-aza-4-oxo-10-oxa-5-isobutyl-2-[glycine-(N-ethyl)amide]-(10)paracyclophane-6-N-hydroxycarboxamide;

2S,5R,6S-3-aza-4-oxo-10-oxa-5-isobutyl-2-[glycine-(N-cyclopropyl)amide]-(10)paracyclophane-6-N-hydroxycarboxamide;

2S,5R,6S-3-aza-4-oxo-10-oxa-5-isobutyl-2-[glycine-(N-tert-butyl)amide]-(10)paracyclophane-6-N-hydroxycarboxamide;

2S,5R,6S-3-aza-4-oxo-10-oxa-5-isobutyl-2-[glycine-(N-cyclobutyl)amide]-(10)paracyclophane-6-N-hydroxycarlooxamide;

2S,5R,6S-3-aza-4-oxo-10-oxa-5-isobutyl-2-[glycine-(N-morpholino)amide]-[10]paracyclophane-6-N-hydroxycarboxamide;

2S,5R,6S-3-aza-4-oxo-10-oxa-5-isobutyl-2-[glycine-(N-2-hydroxydimethylethyl)amide]-[10]paracyclophane-6-N-hydroxycarboxamide;

2S,5R,6S-3-aza-4-oxo-10-oxa-5-isobutyl-2-[glycine-(N-ethylmethylpropyl)amide]-[10]paracyclophane-6-N-hydroxycarboxamide 2S,5R,6S-3-aza-4-oxo-10-oxa-5-isobutyl-2-[glycine-(N-dimethylpropyl)amide]-[10]paracyclophane-6-N-hydroxycarboxamide;

2S,5R,6S-3-aza-4-oxo-10-oxa-5-isobutyl-2-[glycine-(N-(di-2-hydroxymethyl)ethylamide]-(10)paracyclophane-6-N-hydroxycarboxamide;

2S,5R,6S-3-aza-4-oxo-10-oxa-5-isobutyl-2-[glycine-(4-hydroxypiperidine)amide]-(10)paracyclophane-6-N-hydroxycarboxamide;

2S,5R,6S-3-aza-4-oxo-10-oxa-5-isobutyl-2-(2-benzimidazolecarboxamido)-(10)paracyclophane-6-N-hydroxycarboxamide;

2S,5R,6S-3-aza-4-oxo-10-oxa-5-isobutyl-2-[S-(methyl)-2-phenylmethylcarboxamido]-(10)paracyclophane-6-N-hydroxycarboxamide.

26. A pharmaceutical composition comprising a pharmaceutically acceptable carrier and a therapeutically effective amount of a compound of claim 1.

27. A pharmaceutical composition comprising a pharmaceutically acceptable carrier and a therapeutically effective amount of a compound of claim 2.

28. A pharmaceutical composition comprising a pharmaceutically acceptable carrier and a therapeutically effective amount of a compound of claim 3.

29. A pharmaceutical composition comprising a pharmaceutically acceptable carrier and a therapeutically effective amount of a compound of claim 4.

30. A pharmaceutical composition comprising a pharmaceutically acceptable carrier and a therapeutically effective amount of a compound of claim 5.

31. A pharmaceutical composition comprising a pharmaceutically acceptable carrier and a therapeutically effective amount of a compound of claim 6.

32. A pharmaceutical composition comprising a pharmaceutically acceptable carrier and a therapeutically effective amount of a compound of claim 7.

33. A pharmaceutical composition comprising a pharmaceutically acceptable carrier and a therapeutically effective amount of a compound of claim 8.

34. A pharmaceutical composition comprising a pharmaceutically acceptable carrier and a therapeutically effective amount of a compound of claim 9.

35. A pharmaceutical composition comprising a pharmaceutically acceptable carrier and a therapeutically effective amount of a compound of claim 10.

36. A pharmaceutical composition comprising a pharmaceutically acceptable carrier and a therapeutically effective amount of a compound of claim 11.

37. A pharmaceutical composition comprising a pharmaceutically acceptable carrier and a therapeutically effective amount of a compound of claim 12.

38. A pharmaceutical composition comprising a pharmaceutically acceptable carrier and a therapeutically effective amount of a compound of claim 13.

39. A pharmaceutical composition comprising a pharmaceutically acceptable carrier and a therapeutically effective amount of a compound of claim 14.

40. A pharmaceutical composition comprising a pharmaceutically acceptable carrier and a therapeutically effective amount of a compound of claim 15.

41. A pharmaceutical composition comprising a pharmaceutically acceptable carrier and a therapeutically effective amount of a compound of claim 16.

42. A pharmaceutical composition comprising a pharmaceutically acceptable carrier and a therapeutically effective amount of a compound of claim 17.

43. A pharmaceutical composition comprising a pharmaceutically acceptable carrier and a therapeutically effective amount of a compound of claim 18.

44. A pharmaceutical composition comprising a pharmaceutically acceptable carrier and a therapeutically effective amount of a compound of claim 19.

45. A pharmaceutical composition comprising a pharmaceutically acceptable carrier and a therapeutically effective amount of a compound of claim 20.

46. A pharmaceutical composition comprising a pharmaceutically acceptable carrier and a therapeutically effective amount of a compound of claim 21.

47. A pharmaceutical composition comprising a pharmaceutically acceptable carrier and a therapeutically effective amount of a compound of claim 22.

48. A pharmaceutical composition comprising a pharmaceutically acceptable carrier and a therapeutically effective amount of a compound of claim 23.

49. A pharmaceutical composition comprising a pharmaceutically acceptable carrier and a therapeutically effective amount of a compound of claim 24.

50. A pharmaceutical composition comprising a pharmaceutically acceptable carrier and a therapeutically effective amount of a compound of claim 25.

* * * * *